United States Patent
Liu et al.

(10) Patent No.: US 10,604,504 B2
(45) Date of Patent: Mar. 31, 2020

(54) INDOLE CARBOXAMIDE COMPOUNDS

(71) Applicant: BRISTOL-MYERS SQUIBB COMPANY, Princeton, NJ (US)

(72) Inventors: Qingjie Liu, Newtown, PA (US); Scott Hunter Watterson, Pennington, NJ (US); John E. Macor, Washington Crossing, PA (US); Khehyong Ngu, Pennington, NJ (US); Saleem Ahmad, Wall, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/396,879

(22) Filed: Apr. 29, 2019

(65) Prior Publication Data
US 2019/0248760 A1    Aug. 15, 2019

Related U.S. Application Data

(63) Continuation of application No. 15/886,192, filed on Feb. 1, 2018, now Pat. No. 10,329,274, which is a continuation of application No. 15/608,340, filed on May 30, 2017, now Pat. No. 9,920,031, which is a continuation of application No. 14/921,347, filed on Oct. 23, 2015, now Pat. No. 9,688,629.

(60) Provisional application No. 62/068,225, filed on Oct. 24, 2014.

(51) Int. Cl.
| | |
|---|---|
| *A61K 31/436* | (2006.01) |
| *A61P 35/04* | (2006.01) |
| *C07D 401/10* | (2006.01) |
| *C07D 403/12* | (2006.01) |
| *C07D 401/04* | (2006.01) |
| *C07D 401/06* | (2006.01) |
| *C07D 401/12* | (2006.01) |
| *C07D 403/04* | (2006.01) |
| *C07D 403/10* | (2006.01) |
| *C07D 413/04* | (2006.01) |
| *C07D 417/04* | (2006.01) |
| *C07D 471/04* | (2006.01) |
| *C07D 487/04* | (2006.01) |
| *C07D 487/10* | (2006.01) |
| *C07D 209/18* | (2006.01) |
| *A61P 29/00* | (2006.01) |
| *A61P 37/00* | (2006.01) |
| *C07D 209/08* | (2006.01) |

(52) U.S. Cl.
CPC ........... *C07D 401/10* (2013.01); *A61P 29/00* (2018.01); *A61P 37/00* (2018.01); *C07D 209/08* (2013.01); *C07D 209/18* (2013.01); *C07D 401/04* (2013.01); *C07D 401/06* (2013.01); *C07D 401/12* (2013.01); *C07D 403/04* (2013.01); *C07D 403/10* (2013.01); *C07D 403/12* (2013.01); *C07D 413/04* (2013.01); *C07D 417/04* (2013.01); *C07D 471/04* (2013.01); *C07D 487/04* (2013.01); *C07D 487/10* (2013.01)

(58) Field of Classification Search
CPC .. C07D 401/10; C07D 209/08; C07D 209/18; C07D 487/10; C07D 487/04; C07D 471/04; C07D 417/04; C07D 413/04; C07D 403/10; C07D 403/04; C07D 401/12; C07D 401/06; C07D 401/04; C07D 403/12; A61P 37/00; A61P 29/00; A61K 31/454; A61K 31/4045
See application file for complete search history.

(56) References Cited

U.S. PATENT DOCUMENTS

| | | |
|---|---|---|
| 5,604,236 A | 2/1997 | Jakubowski et al. |
| 7,514,444 B2 | 4/2009 | Honigberg et al. |

(Continued)

FOREIGN PATENT DOCUMENTS

| | | |
|---|---|---|
| CN | 101475571 | 7/2009 |
| WO | WO 2005/005429 | 1/2005 |

(Continued)

OTHER PUBLICATIONS

Lou, Y., et al., "Bruton's Tyrosine Kinase Inhibitors: Approaches to Potent and Selective Inhibition, Preclinical and Clinical Evaluation for Inflammatory Diseases and B Cell Malignancies," J. Med. Chem., 2012, 55 (10), pp. 4539-4550.

(Continued)

*Primary Examiner* — Daniel M Podgorski
(74) *Attorney, Agent, or Firm* — Gary Greenblatt

(57) ABSTRACT

Disclosed are compounds of Formula (I):

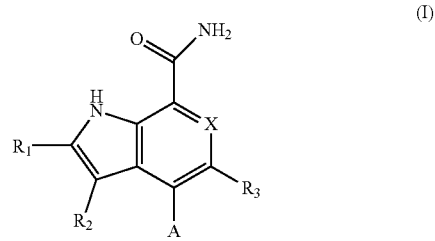

or a salt thereof, wherein: X is $CR_4$ or N; $R_1$, $R_2$, $R_3$, $R_4$, and A are defined herein. Also disclosed are methods of using such compounds as inhibitors of Bruton's tyrosine kinase (Btk), and pharmaceutical compositions comprising such compounds. These compounds are useful in treating, preventing, or slowing the progression of diseases or disorders in a variety of therapeutic areas, such as autoimmune diseases and vascular disease.

14 Claims, No Drawings

(56) References Cited

U.S. PATENT DOCUMENTS

| | | |
|---|---|---|
| 8,084,620 B2 | 12/2011 | Liu et al. |
| 8,088,781 B2 | 1/2012 | Honigberg et al. |
| 8,188,272 B2 | 5/2012 | Liu et al. |
| 8,354,406 B2 | 1/2013 | Deng et al. |
| 8,362,065 B2 | 1/2013 | Liu et al. |
| 8,476,430 B2 | 7/2013 | Liu et al. |
| 8,586,751 B2 | 11/2013 | DeLucca et al. |
| 8,735,403 B2 | 5/2014 | Honigberg et al. |
| 8,846,673 B2 | 9/2014 | Duan et al. |
| 2006/0084650 A1 | 4/2006 | Dong et al. |
| 2008/0045536 A1 | 2/2008 | Vaccaro et al. |
| 2009/0275570 A1 | 11/2009 | Daly et al. |
| 2009/0281131 A1 | 11/2009 | Gopalan et al. |
| 2012/0136023 A1 | 5/2012 | Bell et al. |
| 2014/0378475 A1 | 12/2014 | Batt et al. |
| 2015/0005279 A1 | 1/2015 | Bonafoux et al. |

FOREIGN PATENT DOCUMENTS

| | | |
|---|---|---|
| WO | WO 2005/014599 | 2/2005 |
| WO | WO 2005/047290 | 5/2005 |
| WO | WO2006034317 A2 | 3/2006 |
| WO | WO 2006/053121 | 5/2006 |
| WO | WO 2006/064355 | 6/2006 |
| WO | WO 2006/099075 | 9/2006 |
| WO | WO 2007/038314 | 4/2007 |
| WO | WO 2007/061764 | 5/2007 |
| WO | WO 2008/032171 | 3/2008 |
| WO | WO 2008/033858 | 3/2008 |
| WO | WO 2008/132500 | 11/2008 |
| WO | WO 2008/144253 | 11/2008 |
| WO | WO 2009/075830 | 6/2009 |
| WO | WO 2009/102498 | 8/2009 |
| WO | WO 2009/141627 | 11/2009 |
| WO | WO 2010/015636 | 2/2010 |
| WO | WO 2011/159857 | 12/2011 |
| WO | WO 2012/059232 | 5/2012 |
| WO | WO 2012/156334 | 11/2012 |
| WO | WO 2013/157022 | 10/2013 |
| WO | WO2013185084 A1 | 12/2013 |
| WO | WO 2014/210087 | 12/2014 |
| WO | WO 2014/210255 | 12/2014 |

OTHER PUBLICATIONS

Clayden, J. et al, "The Challenge of Atropisomerism in Drug Discovery," Angew. Chem. Int. Ed. (2009) 48, pp. 6398-6401.

International Search Report Application No. PCT/US2015/057055 completed Nov. 26, 2015.

Laplante, Steven R., et al., "Assessing Atropisomer Axial Chirality in Drug Discovery and Development," J. Med. Chem. 54, 7005-7022 (2011).

Potashman, Michele H., et al., "Covalent Modifiers: An Orthogonal Approach to Drug Design," J. Med. Chem. (2009), vol. 52(5), pp. 1231-1246.

Singh, Juswinder, et al., "Targeted Covalent Drugs of the Kinase Family," Targeted Covalent Drugs of the Kinase Family, Current Opinion in Chemical Biology (2010), vol. 14, pp. 475-480.

Zhang, Jianming, et al. "Targeting Cancer with Small Molecule Kinase Inhibitors," Nature Reviews Cancer, (2009), vol. 9, pp. 28-39.

Honigberg, Lee, A., et al. "The Bruton Tyrosine Kinase Inhibitor PCI-32765 Blocks B-cell Activation and is Efficacious in Models of Autoimmune Disease and B-cell Malignancy," Proc. Nat. Acad. Sci., (2010), vol. 107, 29, pp. 13075-13080.

Mah, Robert, et al. "Drug Discovery Consideration in the Development of Covalent Inhibitors," Bioorg. Med. Chem Lett., (2014), vol. 24, pp. 33-39 (Available online Oct. 10, 2013).

INDOLE CARBOXAMIDE COMPOUNDS

CROSS-REFERENCE TO RELATED APPLICATIONS

This application is a continuation application of U.S. Ser. No. 15/886,192, filed Feb. 1, 2018, which is a continuation application of U.S. Ser. No. 15/608,340, filed Mary 30, 2017, which is a continuation application of U.S. Ser. No. 14/921,347, filed Oct. 23, 2015, which claims priority to U.S. Provisional Application Ser. No. 62/068,225, filed Oct. 24, 2014, each of which is incorporated herein it its entirety.

DESCRIPTION

The present invention generally relates to indole carboxamide compounds useful as kinase inhibitors, including the modulation of Bruton's tyrosine kinase (Btk) and other Tec family kinases such as Itk. Provided herein are indole carboxamide compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including Btk and other Tec family kinases such as Itk, in a mammal.

Protein kinases, the largest family of human enzymes, encompass well over 500 proteins. Btk is a member of the Tec family of tyrosine kinases, and is a regulator of early B-cell development, as well as mature B-cell activation, signaling, and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium signal upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to *Staphylococcus*-induced arthritis.

A large body of evidence supports the role of B-cells and the humoral immune system in the pathogenesis of autoimmune and/or inflammatory diseases. Protein-based therapeutics such as rituximab, developed to deplete B-cells, represent an important approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, allergic rhinitis, multiple sclerosis (MS), transplant rejection, type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, Btk has been reported to play a role in controlling B-cell survival in certain B-cell cancers. For example, Btk has been shown to be important for the survival of BCR-Abl-positive B-cell acute lymphoblastic leukemia cells. Thus inhibition of Btk activity can be useful for the treatment of B-cell lymphoma and leukemia.

In view of the numerous conditions that are contemplated to benefit by treatment involving modulation of protein kinases, it is immediately apparent that new compounds capable of modulating protein kinases such as Btk and methods of using these compounds should provide substantial therapeutic benefits to a wide variety of patients.

U.S. Pat. Nos. 8,084,620 and 8,685,969 disclose tricyclic carboxamide compounds useful as kinase inhibitors, including the modulation of Btk and other Tec family kinases.

There still remains a need for compounds useful as Btk inhibitors. Applicants have found potent compounds that have activity as Btk inhibitors. These compounds are provided to be useful as pharmaceuticals with desirable stability, bioavailability, therapeutic index, and toxicity values that are important to this utility.

SUMMARY OF THE INVENTION

The present invention provides indole carboxamide compounds, including salts, solvates, and prodrugs thereof, that are useful as inhibitors of Btk and are useful for the treatment of proliferative diseases, allergic diseases, autoimmune diseases and inflammatory diseases.

The present invention also provides pharmaceutical compositions comprising a pharmaceutically acceptable carrier and at least one of the compounds of Formula (I) or salts, solvates, and prodrugs thereof.

The present invention also provides a method of inhibiting Btk activity comprising administering to a mammal in need thereof at least one of the compounds of Formula (I) or salts, solvates, and prodrugs thereof.

The present invention also provides a method for treating allergic disorders and/or autoimmune and/or inflammatory diseases, comprising administering to a mammal in need thereof at least one of the compounds of Formula (I) or salts, solvates, and prodrugs thereof.

The present invention also provides a method for treating proliferative diseases, such as cancer, comprising administering to a mammal in need thereof at least one of the compounds of Formula (I) or salts, solvates, and prodrugs thereof.

The present invention also provides a method of treating a disease or disorder associated with Btk activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment or prophylaxis of Btk related conditions, such as proliferative diseases, allergic diseases, autoimmune diseases and inflammatory diseases.

The present invention also provides the use of at least one of the compounds of Formula (I) or salts, solvates, and prodrugs thereof, for the manufacture of a medicament for treatment of cancer.

The compounds of Formula (I) and compositions comprising the compounds of Formula (I) may be used in treating, preventing, or curing various Btk related conditions. Pharmaceutical compositions comprising these compounds are useful in treating, preventing, or slowing the progression of diseases or disorders in a variety of therapeutic areas, such as proliferative diseases, allergic diseases, autoimmune diseases and inflammatory diseases.

These and other features of the invention will be set forth in expanded form as the disclosure continues.

DETAILED DESCRIPTION

The first aspect of the present invention provides at least one compound of Formula (I):

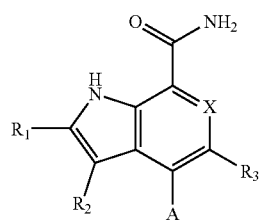

(I)

or a salt thereof, wherein:
X is CR$_4$ or N;
A is:
(i)

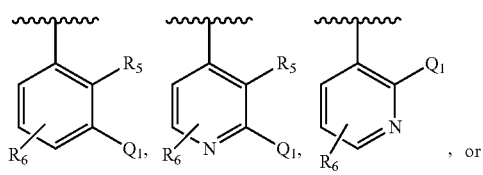

, or

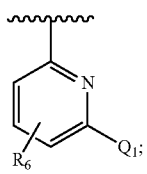

(ii)

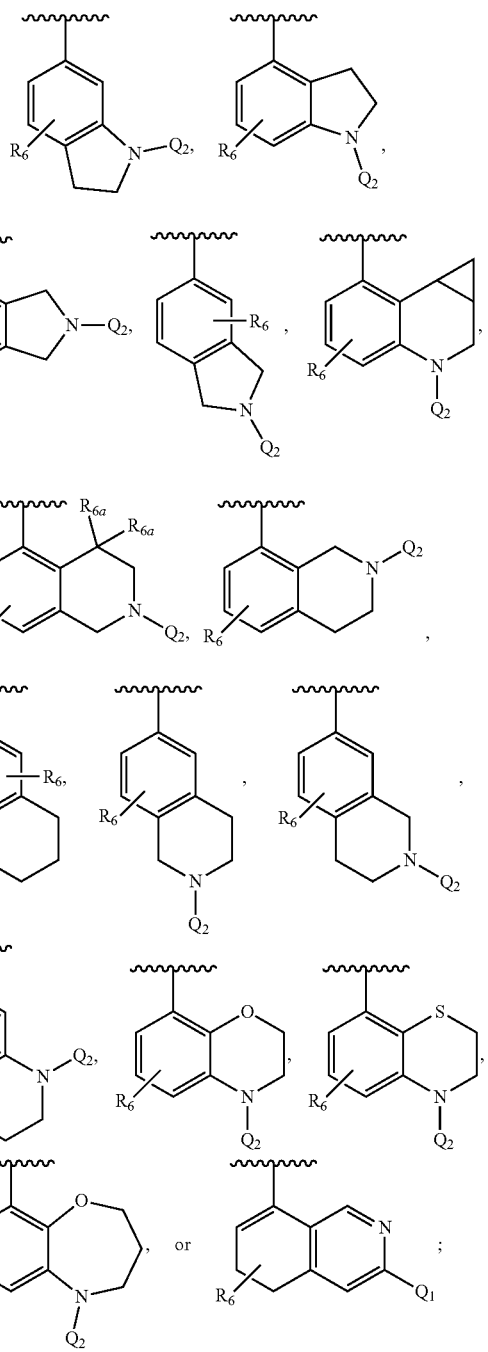

(iii)

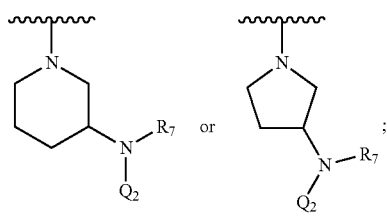

;

(iv)

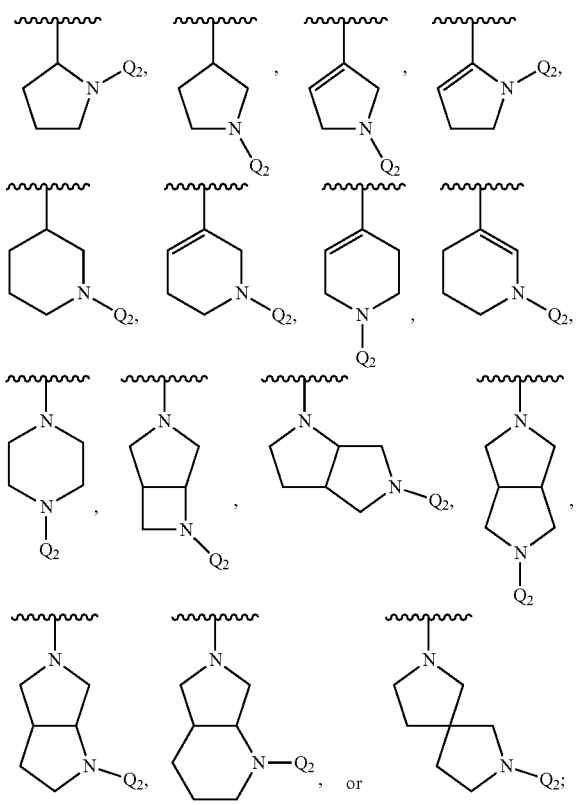

(v)

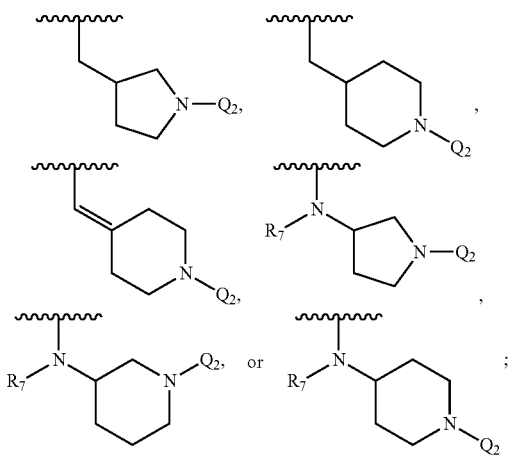

or (vi) —CHR$_8$(pyridinyl) wherein each pyridinyl is substituted with R$_6$ and R$_9$;

Q$_1$ is —NR$_7$Q$_2$, —CR$_{10}$R$_{10}$NR$_7$Q$_2$, —C(O)NR$_7$(C$_{1-4}$ alkyl substituted with zero or 1 R$_{11}$), —CH=CH$_2$, —CH=C (CN)S(O)$_2$CH$_3$, —S(O)$_2$CH=CR$_{10}$R$_{10}$, —NR$_7$(dichlorotriazinyl), —NR$_7$(quinazolin-4-yl substituted with zero or 1 R$_{11}$), 3-methylenepyrrolidin-2-on-1-yl, or a cyclic group selected from 1H-pyrrol-2(5H)-on-1-yl, isoindolin-1-on-2-yl, quinazolin-4(3H)-on-3-yl, and quinazoline-2,4 (1H, 3H)-dion-3-yl, each cyclic group substituted with zero to two substituents independently selected from F, Cl, —CH$_3$, —CN, and —OCH$_3$;

Q$_2$ is —CN, —C(O)(C$_{1-4}$ alkyl substituted with zero or 1 R$_{11}$), —C(O)(C$_{3-6}$ cycloalkyl substituted with zero or 1 R$_{11}$), —C(O)(C$_{5-6}$ cycloalkenyl), —C(O) CR$_{10}$=CR$_{10}$R$_{10}$, —C(O)C(R$_{10}$)=CHCH$_2$N(CH$_3$)$_2$, —C(O)C≡CR$_7$, —C(O)C≡C(C$_{1-3}$ hydroxyalkyl), —C(O)C≡C(phenyl), —C(O)C≡CSi(CH$_3$)$_3$, or —S(O)$_2$CH=CHR$_{10}$;

R$_1$ is H, —CH$_3$, —CF$_3$, or phenyl substituted with zero or 1 R$_{12}$;

R$_2$ is H, —CH$_3$, cyclopropyl, or phenyl substituted with zero or 1 R$_{12}$, provided that zero or one of R$_1$ and R$_2$ is phenyl substituted with zero or 1 R$_{12}$;

R$_3$ is H, F, Cl, I, —CN, or —CH$_3$;

R$_4$ is H, F, —OH, —O(C$_{1-4}$ alkyl), —O(C$_{1-4}$ alkyl)-O—(C$_{1-2}$ alkyl), —O(CH$_2$)$_{1-3}$(phenyl), —O(CH$_2$)$_{1-3}$(methoxyphenyl), or —O(CH$_2$)$_{1-3}$(morpholinyl);

R$_5$ is H, F, Cl, or —CH$_3$;

R$_6$ is H, F, Cl, —CF$_3$, or C$_{1-3}$ alkoxy;

each R$_{6a}$ is independently H or F;

R$_7$, at each occurrence, is independently H, C$_{1-4}$ alkyl, or cyclopropyl;

R$_8$ is H or C$_{1-4}$ alkyl;

R$_9$ is —CH=CH$_2$, —CH=CHCH$_2$N(CH$_3$)$_2$, —C≡CH, or —C≡CCH$_3$;

R$_{10}$, at each occurrence, is independently H or —CH$_3$;

R$_{11}$ is F, Cl, —CN, —CF$_3$, or C$_{1-3}$ alkoxy; and

R$_{12}$ is F, Cl, —CN, —CF$_3$, or C$_{1-3}$ alkoxy.

The second aspect of the present invention provides at least one compound of Formula (I) in which X is CR$_4$, having the structure of Formula (Ia):

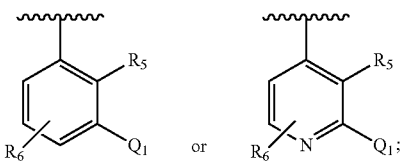

(Ia)

or a salt thereof, wherein:

A is:

(i)

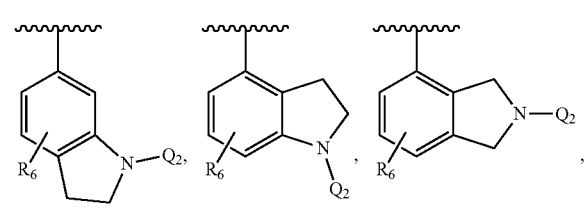

(ii)

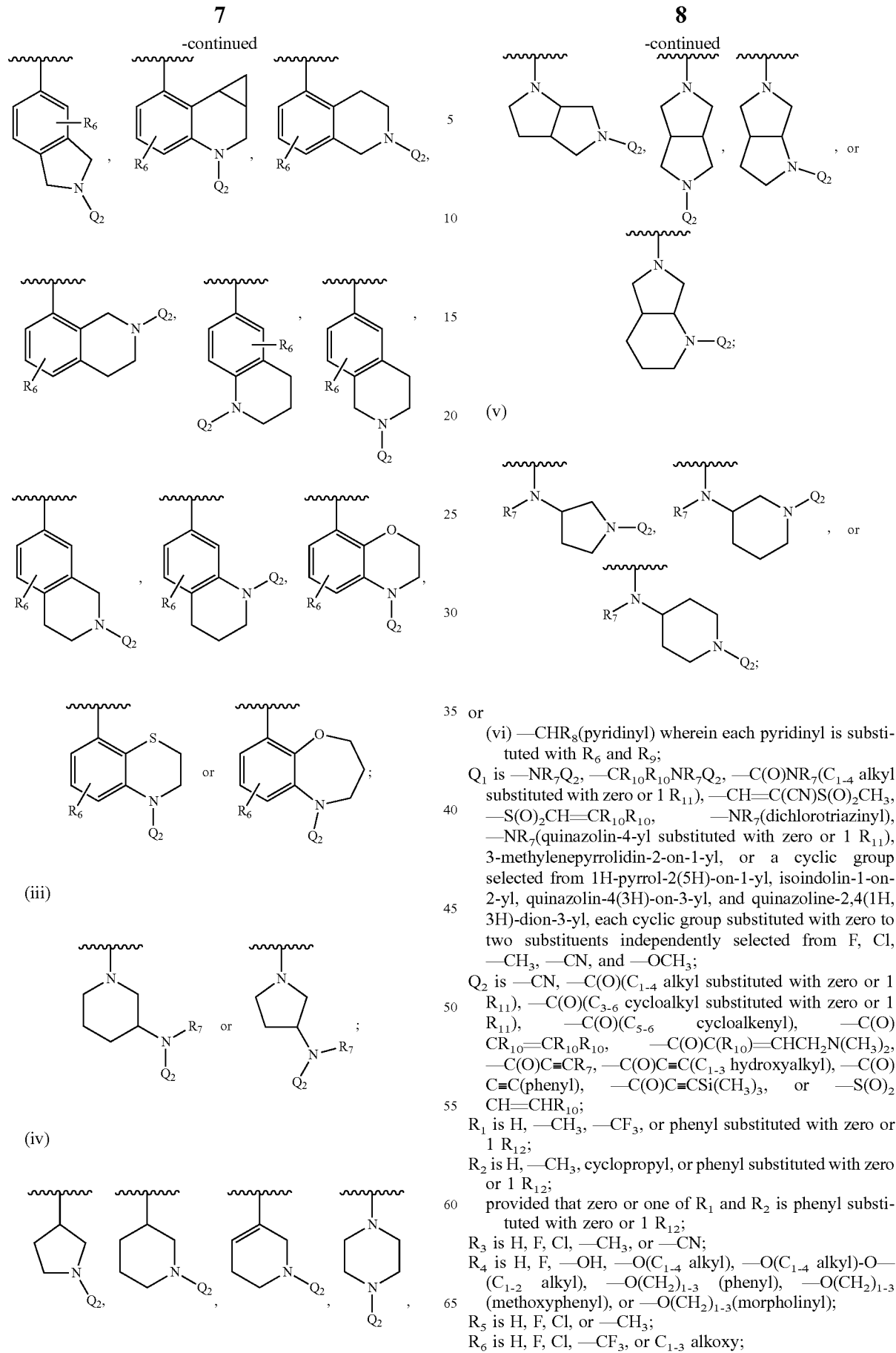

or (vi) —CHR₈(pyridinyl) wherein each pyridinyl is substituted with R₆ and R₉;

Q₁ is —NR₇Q₂, —CR₁₀R₁₀NR₇Q₂, —C(O)NR₇(C₁₋₄ alkyl substituted with zero or 1 R₁₁), —CH=C(CN)S(O)₂CH₃, —S(O)₂CH=CR₁₀R₁₀, —NR₇(dichlorotriazinyl), —NR₇(quinazolin-4-yl substituted with zero or 1 R₁₁), 3-methylenepyrrolidin-2-on-1-yl, or a cyclic group selected from 1H-pyrrol-2(5H)-on-1-yl, isoindolin-1-on-2-yl, quinazolin-4(3H)-on-3-yl, and quinazoline-2,4(1H,3H)-dion-3-yl, each cyclic group substituted with zero to two substituents independently selected from F, Cl, —CH₃, —CN, and —OCH₃;

Q₂ is —CN, —C(O)(C₁₋₄ alkyl substituted with zero or 1 R₁₁), —C(O)(C₃₋₆ cycloalkyl substituted with zero or 1 R₁₁), —C(O)(C₅₋₆ cycloalkenyl), —C(O)CR₁₀=CR₁₀R₁₀, —C(O)C(R₁₀)=CHCH₂N(CH₃)₂, —C(O)C≡CR₇, —C(O)C≡C(C₁₋₃ hydroxyalkyl), —C(O)C≡C(phenyl), —C(O)C≡CSi(CH₃)₃, or —S(O)₂CH=CHR₁₀;

R₁ is H, —CH₃, —CF₃, or phenyl substituted with zero or 1 R₁₂;

R₂ is H, —CH₃, cyclopropyl, or phenyl substituted with zero or 1 R₁₂;

provided that zero or one of R₁ and R₂ is phenyl substituted with zero or 1 R₁₂;

R₃ is H, F, Cl, —CH₃, or —CN;

R₄ is H, F, —OH, —O(C₁₋₄ alkyl), —O(C₁₋₄ alkyl)-O—(C₁₋₂ alkyl), —O(CH₂)₁₋₃ (phenyl), —O(CH₂)₁₋₃ (methoxyphenyl), or —O(CH₂)₁₋₃(morpholinyl);

R₅ is H, F, Cl, or —CH₃;

R₆ is H, F, Cl, —CF₃, or C₁₋₃ alkoxy;

$R_7$, at each occurrence, is independently H, $C_{1-4}$ alkyl, or cyclopropyl;
$R_8$ is H or $C_{1-4}$ alkyl;
$R_9$ is —CH=CH$_2$, —CH=CHCH$_2$N(CH$_3$)$_2$, —C≡CH, or —C≡CCH$_3$;
$R_{10}$, at each occurrence, is independently H or —CH$_3$;
$R_{11}$ is F, Cl, —CN, —CF$_3$, or $C_{1-3}$ alkoxy; and
$R_{12}$ is F, Cl, —CN, —CF$_3$, or $C_{1-3}$ alkoxy.

One embodiment provides a compound of Formula (I) or a salt thereof, wherein: X is CR$_4$; and $R_1$, $R_2$, $R_3$, $R_4$, and A are defined in the first aspect.

One embodiment provides a compound of Formula (I) or a salt thereof, wherein: X is N; and $R_1$, $R_2$, $R_3$, and A are defined in the first aspect.

One embodiment provides a compound of Formula (I) or a salt thereof, wherein: $Q_1$ is —NR$_7$Q$_2$, —CR$_{10}$R$_{10}$NR$_7$Q$_2$, —C(O)NR$_7$(C$_{1-4}$ alkyl substituted with zero or 1 R$_{11}$), —CH=CH$_2$, —CH=C(CN)S(O)$_2$CH$_3$, —S(O)$_2$CH=CR$_{10}$R$_{10}$, —NR$_7$(dichlorotriazinyl), —NR$_7$(quinazolin-4-yl substituted with zero or 1 R$_{11}$), 3-methylenepyrrolidin-2-on-1-yl, or a cyclic group selected from 1H-pyrrol-2(5H)-on-1-yl, isoindolin-1-on-2-yl, quinazolin-4(3H)-on-3-yl, and quinazoline-2,4(1H, 3H)-dion-3-yl, each cyclic group substituted with zero to two substituents independently selected from F, Cl, —CH$_3$, —CN, and —OCH$_3$.

One embodiment provides a compound of Formula (I) or a salt thereof, wherein: $Q_1$ is —NR$_7$Q$_2$, —CR$_{10}$R$_{10}$NR$_7$Q$_2$, —S(O)$_2$CH=CR$_{10}$R$_{10}$, —NR$_7$(dichlorotriazinyl), 1H-pyrrol-2(5H)-on-1-yl, or 3-methylenepyrrolidin-2-on-1-yl; $Q_2$ is —CN, —C(O)(C$_{5-6}$ cycloalkenyl), —C(O)CH=CHR$_{10}$, —C(O)CR$_{10}$=CH$_2$, —C(O)CR$_{10}$=CHCH$_2$N(CH$_3$)$_2$, —C(O)C≡CR$_7$, —C(O)C≡C(C$_{1-3}$ hydroxyalkyl), —C(O)C≡C(phenyl), —C(O)C≡CSi(CH$_3$)$_3$, or —S(O)$_2$CH=CH$_2$; $R_3$ is H, F, or Cl; $R_4$, when present, is H or F; and X, $R_1$, $R_2$, $R_5$, $R_6$, $R_7$, $R_8$, $R_9$, $R_{10}$, and A are defined in either the first aspect or the second aspect. Included in this embodiment are compounds in which X is CR$_4$.

One embodiment provides a compound of Formula (I) or a salt thereof, wherein: $Q_1$ is —NR$_7$Q$_2$ or —S(O)$_2$CH=CH$_2$; $Q_2$ is —C(O)CH=CH$_2$, —C(O)CH=CHCH$_2$N(CH$_3$)$_2$, —C(O)C≡CR$_7$, —C(O)C≡C(phenyl), —C(O)C≡C(C$_{1-3}$ hydroxyalkyl), —C(O)C≡CSi(CH$_3$)$_3$, or —S(O)$_2$CH=CH$_2$; $R_3$ is H, F, or Cl; $R_4$, when present, is H or F; and X, $R_1$, $R_2$, $R_5$, $R_6$, $R_7$, $R_8$, $R_9$, $R_{10}$, and A are defined in either the first aspect or the second aspect. Included in this embodiment are compounds in which X is CR$_4$.

One embodiment provides a compound of Formula (I) or a salt thereof, wherein A is

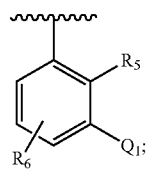

$Q_1$ is —NR$_7$Q$_2$ or —S(O)$_2$CH=CH$_2$; $Q_2$ is —C(O)CH=CH$_2$, —C(O)CH=CHCH$_2$N(CH$_3$)$_2$, —C(O)C≡CR$_7$, —C(O)C≡C(phenyl), —C(O)C≡C(C$_{1-3}$ hydroxyalkyl), —C(O)C≡CSi(CH$_3$)$_3$, or —S(O)$_2$CH=CH$_2$; $R_1$ is H, —CH$_3$, —CF$_3$, or phenyl substituted with zero or 1 R$_{12}$; and $R_2$ is H, —CH$_3$, cyclopropyl, or phenyl substituted with zero or 1 R$_{12}$; provided that zero or one of $R_1$ and $R_2$ is phenyl substituted with zero or 1 R$_{12}$ and further provided that at least one of $R_1$ and $R_2$ is —CH$_3$; $R_3$ is H, F, or Cl; $R_4$, when present, is H or F; $R_5$ is H, —CH$_3$, F or Cl; $R_6$ is H, F, Cl, —CF$_3$ or $C_{1-3}$ alkoxy; and $R_7$ and $R_{12}$ are defined in either the first aspect or the second aspect. Included in this embodiment are compounds in which X is CR$_4$.

One embodiment provides a compound of Formula (I) or a salt thereof, wherein A is:

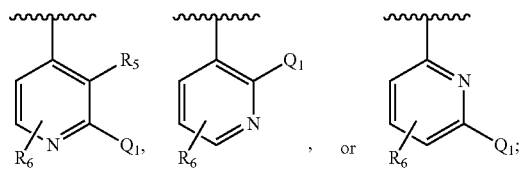

$Q_1$ is —CH=CH$_2$, —NR$_7$Q$_2$, or —S(O)$_2$CH=CH$_2$; $Q_2$ is —C(O)CH=CH$_2$, —C(O)CH=CHCH$_2$N(CH$_3$)$_2$, —C(O)C≡CR$_7$, —C(O)C≡C(phenyl), —C(O)C≡C(C$_{1-3}$ hydroxyalkyl), —C(O)C≡CSi(CH$_3$)$_3$, or —S(O)$_2$CH=CH$_2$; $R_1$ is H, —CH$_3$, —CF$_3$, or phenyl substituted with zero or 1 R$_{12}$; and $R_2$ is H, —CH$_3$, cyclopropyl, or phenyl substituted with zero or 1 R$_{12}$; provided that zero or one of $R_1$ and $R_2$ is phenyl substituted with zero or 1 R$_{12}$ and further provided that at least one of $R_1$ and $R_2$ is —CH$_3$; $R_3$ is H, F, or Cl; $R_4$, when present, is H or F; $R_5$ is H, —CH$_3$, F or Cl; $R_6$ is H, F, Cl, —CF$_3$ or $C_{1-3}$ alkoxy; and $R_7$ and $R_{12}$ are defined in either the first aspect or the second aspect. Included in this embodiment are compounds in which X is CR$_4$.

One embodiment provides a compound of Formula (I) or a salt thereof, wherein A is:

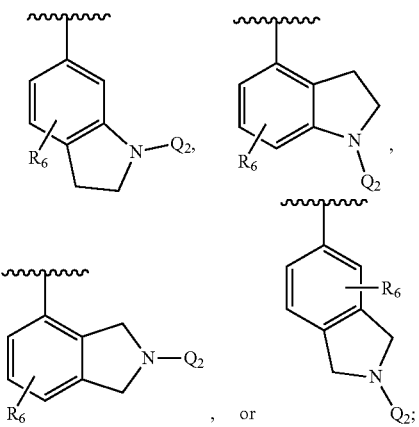

$Q_2$ is —C(O)CH=CH$_2$, —C(O)CH=CHCH$_2$N(CH$_3$)$_2$, —C(O)C≡CR$_7$, —C(O)C≡C(phenyl), —C(O)C≡C(C$_{1-3}$ hydroxyalkyl), —C(O)C≡CSi(CH$_3$)$_3$, or —S(O)$_2$CH=CH$_2$; $R_1$ is H, —CH$_3$, —CF$_3$, or phenyl substituted with zero or 1 R$_{12}$; and $R_2$ is H, —CH$_3$, cyclopropyl, or phenyl substituted with zero or 1 R$_{12}$; provided that zero or one of $R_1$ and $R_2$ is phenyl substituted with zero or 1 R$_{12}$ and further provided that at least one of $R_1$ and $R_2$ is —CH$_3$; $R_3$ is H, F, or Cl; $R_4$, when present, is H or F; $R_6$ is H, F, Cl, —CF$_3$ or $C_{1-3}$ alkoxy; and $R_7$ and $R_{12}$ are defined in either the first aspect or the second aspect. Included in this embodiment are compounds in which X is CR$_4$.

One embodiment provides a compound of Formula (I) or a salt thereof, wherein A is:

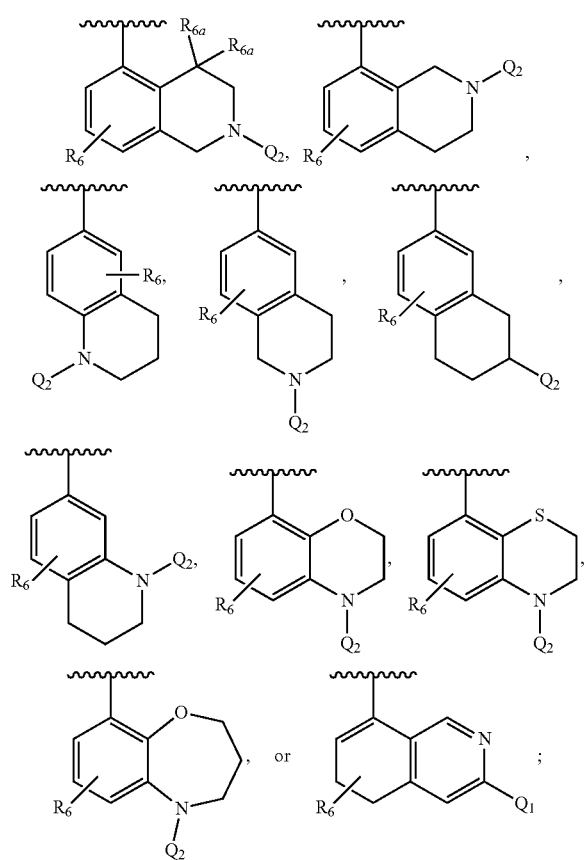

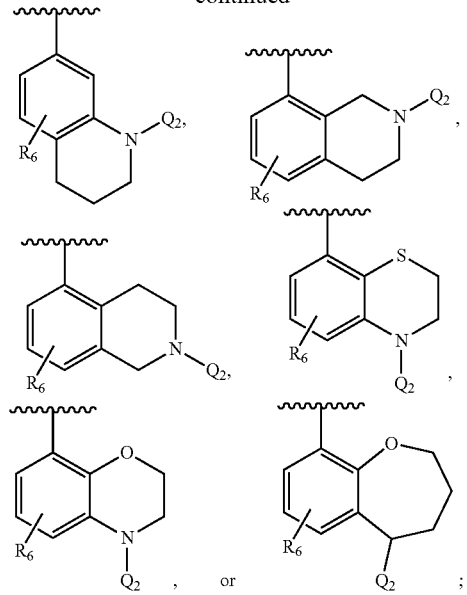

$Q_1$ is —CH=CH$_2$, —NR$_7$Q$_2$, or —S(O)$_2$CH=CH$_2$; $Q_2$ is —C(O)CH=CH$_2$, —C(O)CH=CHCH$_2$N(CH$_3$)$_2$, —C(O)C≡CR$_7$, —C(O)C≡C(phenyl), —C(O)C≡C(C$_{1-3}$ hydroxyalkyl), —C(O)C≡CSi(CH$_3$)$_3$, or —S(O)$_2$CH=CH$_2$; $Q_2$ is —C(O)CH=CH$_2$, —C(O)CH=CHCH$_2$N(CH$_3$)$_2$, —C(O)C≡CR$_7$, —C(O)C≡C(phenyl), —C(O)C≡C(C$_{1-3}$ hydroxyalkyl), —C(O)C≡CSi(CH$_3$)$_3$, or —S(O)$_2$CH=CH$_2$; $R_1$ is H, —CH$_3$, —CF$_3$, or phenyl substituted with zero or 1 R$_{12}$; and R$_2$ is H, —CH$_3$, cyclopropyl, or phenyl substituted with zero or 1 R$_{12}$; provided that zero or one of R$_1$ and R$_2$ is phenyl substituted with zero or 1 R$_{12}$ and further provided that at least one of R$_1$ and R$_2$ is —CH$_3$; R$_3$ is H, F, or Cl; R$_4$ is H or F; R$_6$ is H, F, Cl, —CF$_3$ or C$_{1-3}$ alkoxy; R$_{6a}$ is defined in the first aspect; and R$_7$ and R$_{12}$ are defined in either the first aspect or the second aspect.

One embodiment provides a compound of Formula (I) or a salt thereof, wherein A is:

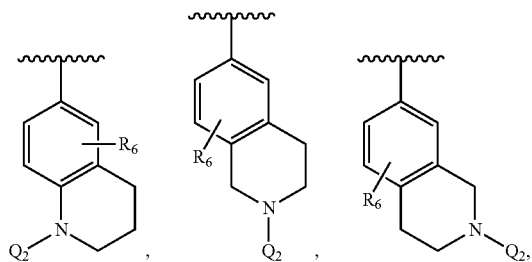

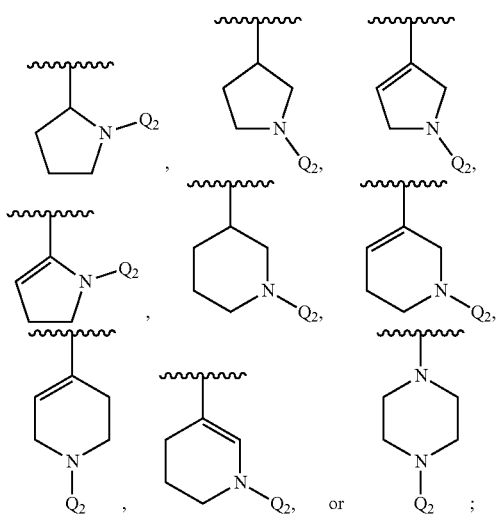

$Q_2$ is —C(O)CH=CH$_2$, —C(O)CH=CHCH$_2$N(CH$_3$)$_2$, —C(O)C≡CR$_7$, —C(O)C≡C(phenyl), —C(O)C≡C(C$_{1-3}$ hydroxyalkyl), —C(O)C≡CSi(CH$_3$)$_3$, or —S(O)$_2$CH=CH$_2$; R$_1$ is H, —CH$_3$, —CF$_3$, or phenyl substituted with zero or 1 R$_{12}$; and R$_2$ is H, —CH$_3$, cyclopropyl, or phenyl substituted with zero or 1 R$_{12}$; provided that zero or one of R$_1$ and R$_2$ is phenyl substituted with zero or 1 R$_{12}$ and further provided that at least one of R$_1$ and R$_2$ is —CH$_3$; R$_3$ is H, F, or Cl; R$_4$ is H or F; R$_6$ is H, F, Cl, —CF$_3$ or C$_{1-3}$ alkoxy; and R$_7$ and R$_{12}$ are defined in either the first aspect or the second aspect.

One embodiment provides a compound of Formula (I) or a salt thereof, wherein A is:

$Q_2$ is —C(O)CH=CH$_2$, —C(O)CH=CHCH$_2$N(CH$_3$)$_2$, —C(O)C≡CR$_7$, —C(O)C≡C(phenyl), —C(O)C≡C(C$_{1-3}$ hydroxyalkyl), —C(O)C≡CSi(CH$_3$)$_3$, or —S(O)$_2$CH=CH$_2$; R$_1$ is H, —CH$_3$, —CF$_3$, or phenyl substituted with zero or 1 R$_{12}$; and R$_2$ is H, —CH$_3$, cyclopropyl, or phenyl substituted with zero or 1 R$_{12}$; provided that zero or one of R$_1$ and $R_2$ is phenyl substituted with zero or 1 $R_{12}$ and further provided that at least one of $R_1$ and $R_2$ is —$CH_3$; $R_3$ is H, F, or Cl; $R_4$ is H or F; each $R_7$ is independently H, $C_{1-4}$ alkyl, or cyclopropyl; and $R_{12}$ is defined in either the first aspect or the second aspect.

One embodiment provides a compound of Formula (I) or a salt thereof, wherein A is:

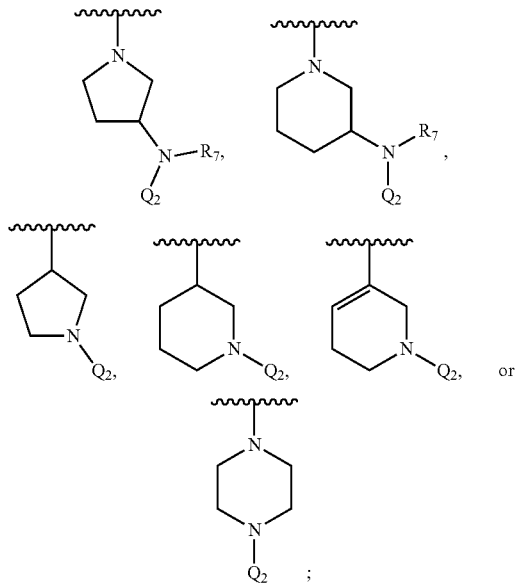

$Q_2$ is —$C(O)CH\!=\!CH_2$, —$C(O)CH\!=\!CHCH_2N(CH_3)_2$, —$C(O)C\!\equiv\!CR_7$, —$C(O)C\!\equiv\!C(phenyl)$, —$C(O)C\!\equiv\!C(C_{1-3}$ hydroxyalkyl), —$C(O)C\!\equiv\!CSi(CH_3)_3$, or —$S(O)_2CH\!=\!CH_2$; $R_1$ is H, —$CH_3$, —$CF_3$, or phenyl substituted with zero or 1 $R_{12}$; and $R_2$ is H, —$CH_3$, cyclopropyl, or phenyl substituted with zero or 1 $R_{12}$; provided that zero or one of $R_1$ and $R_2$ is phenyl substituted with zero or 1 $R_{12}$ and further provided that at least one of $R_1$ and $R_2$ is —$CH_3$; $R_3$ is H, F, or Cl; $R_4$ is H or F; each $R_7$ is independently H, $C_{1-4}$ alkyl, or cyclopropyl; and $R_{12}$ is defined in either the first aspect or the second aspect.

One embodiment provides a compound of Formula (I) or a salt thereof, wherein A is:

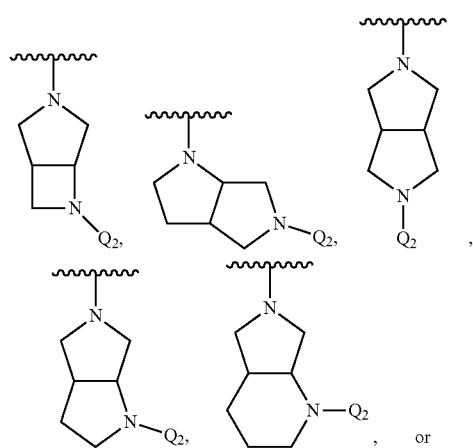

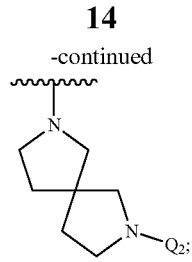

$Q_2$ is —$C(O)CH\!=\!CH_2$, —$C(O)CH\!=\!CHCH_2N(CH_3)_2$, —$C(O)C\!\equiv\!CR_7$, —$C(O)C\!\equiv\!C(phenyl)$, —$C(O)C\!\equiv\!C(C_{1-3}$ hydroxyalkyl), —$C(O)C\!\equiv\!CSi(CH_3)_3$, or —$S(O)_2CH\!=\!CH_2$; $R_1$ is H, —$CH_3$, —$CF_3$, or phenyl substituted with zero or 1 $R_{12}$; and $R_2$ is H, —$CH_3$, cyclopropyl, or phenyl substituted with zero or 1 $R_{12}$; provided that zero or one of $R_1$ and $R_2$ is phenyl substituted with zero or 1 $R_{12}$ and further provided that at least one of $R_1$ and $R_2$ is —$CH_3$; $R_3$ is H, F, or Cl; $R_4$ is H or F; and $R_7$ and $R_{12}$ are defined in either the first aspect or the second aspect.

One embodiment provides a compound of Formula (I) or a salt thereof, wherein A is:

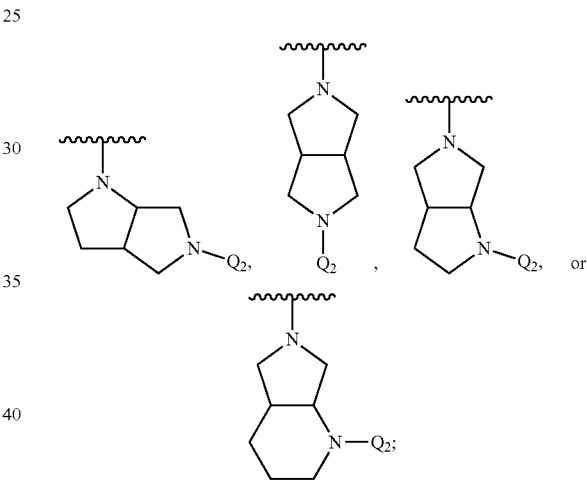

$Q_2$ is —$C(O)CH\!=\!CH_2$, —$C(O)CH\!=\!CHCH_2N(CH_3)_2$, —$C(O)C\!\equiv\!CR_7$, —$C(O)C\!\equiv\!C(phenyl)$, —$C(O)C\!\equiv\!C(C_{1-3}$ hydroxyalkyl), —$C(O)C\!\equiv\!CSi(CH_3)_3$, or —$S(O)_2CH\!=\!CH_2$; $R_1$ is H, —$CH_3$, —$CF_3$, or phenyl substituted with zero or 1 $R_{12}$; and $R_2$ is H, —$CH_3$, cyclopropyl, or phenyl substituted with zero or 1 $R_{12}$; provided that zero or one of $R_1$ and $R_2$ is phenyl substituted with zero or 1 $R_{12}$ and further provided that at least one of $R_1$ and $R_2$ is —$CH_3$; $R_3$ is H, F, or Cl; $R_4$ is H or F; and $R_7$ and $R_{12}$ are defined in either the first aspect or the second aspect.

One embodiment provides a compound of Formula (I) or a salt thereof, wherein A is:

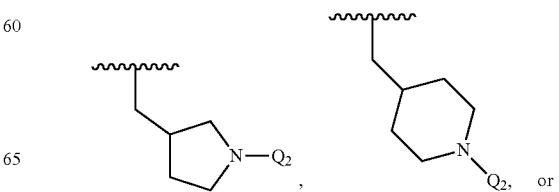

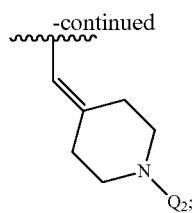

$Q_2$ is —C(O)CH=CH$_2$, —C(O)CH=CHCH$_2$N(CH$_3$)$_2$, —C(O)C≡CR$_7$, —C(O)C≡C(phenyl), —C(O)C≡C(C$_{1-3}$ hydroxyalkyl), —C(O)C≡CSi(CH$_3$)$_3$, or —S(O)$_2$CH=CH$_2$; R$_1$ is H, —CH$_3$, —CF$_3$, or phenyl substituted with zero or 1 R$_{12}$; and R$_2$ is H, —CH$_3$, cyclopropyl, or phenyl substituted with zero or 1 R$_{12}$; provided that zero or one of R$_1$ and R$_2$ is phenyl substituted with zero or 1 R$_{12}$ and further provided that at least one of R$_1$ and R$_2$ is —CH$_3$; R$_3$ is H, F, or Cl; R$_4$ is H or F; and R$_7$ and R$_{12}$ are defined in either the first aspect or the second aspect.

One embodiment provides a compound of Formula (I) or a salt thereof, wherein A is:

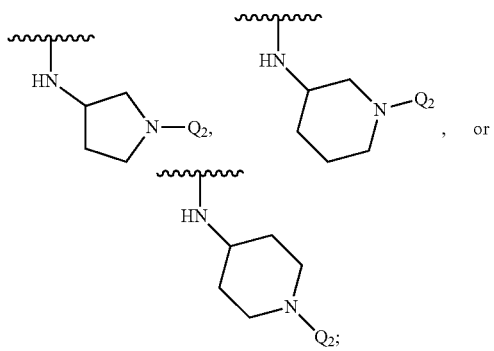

$Q_2$ is —C(O)CH=CH$_2$, —C(O)CH=CHCH$_2$N(CH$_3$)$_2$, —C(O)C≡CR$_7$, —C(O)C≡C(phenyl), —C(O)C≡C(C$_{1-3}$ hydroxyalkyl), —C(O)C≡CSi(CH$_3$)$_3$, or —S(O)$_2$CH=CH$_2$; R$_1$ is H, —CH$_3$, —CF$_3$, or phenyl substituted with zero or 1 R$_{12}$; and R$_2$ is H, —CH$_3$, cyclopropyl, or phenyl substituted with zero or 1 R$_{12}$; provided that zero or one of R$_1$ and R$_2$ is phenyl substituted with zero or 1 R$_{12}$ and further provided that at least one of R$_1$ and R$_2$ is —CH$_3$; R$_3$ is H, F, or Cl; R$_4$ is H or F; and R$_7$ and R$_{12}$ are defined in either the first aspect or the second aspect.

One embodiment provides a compound of Formula (I) or a salt thereof, wherein A is:

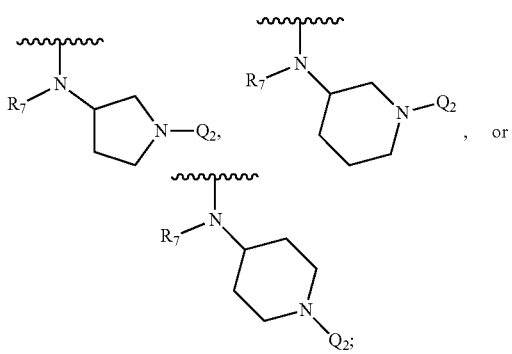

$Q_2$ is —C(O)CH=CH$_2$, —C(O)CH=CHCH$_2$N(CH$_3$)$_2$, —C(O)C≡CR$_7$, —C(O)C≡C(phenyl), —C(O)C≡C(C$_{1-3}$ hydroxyalkyl), —C(O)C≡CSi(CH$_3$)$_3$, or —S(O)$_2$CH=CH$_2$; R$_1$ is H, —CH$_3$, —CF$_3$, or phenyl substituted with zero or 1 R$_{12}$; and R$_2$ is H, —CH$_3$, cyclopropyl, or phenyl substituted with zero or 1 R$_{12}$; provided that zero or one of R$_1$ and R$_2$ is phenyl substituted with zero or 1 R$_{12}$ and further provided that at least one of R$_1$ and R$_2$ is —CH$_3$; R$_3$ is H, F, or Cl; R$_4$ is H or F; each R$_7$ is independently C$_{1-4}$ alkyl or cyclopropyl; and R$_{12}$ is defined in either the first aspect or the second aspect.

One embodiment provides a compound of Formula (I) or a salt thereof, wherein A is —CHR$_8$(pyridinyl) wherein each pyridinyl is substituted with R$_6$ and R$_9$; R$_1$ is H, —CH$_3$, —CF$_3$, or phenyl substituted with zero or 1 R$_{12}$; and R$_2$ is H, —CH$_3$, cyclopropyl, or phenyl substituted with zero or 1 R$_{12}$; provided that zero or one of R$_1$ and R$_2$ is phenyl substituted with zero or 1 R$_{12}$ and further provided that at least one of R$_1$ and R$_2$ is —CH$_3$; R$_3$ is H, F, or Cl; R$_4$ is H or F; R$_6$ is H; R$_8$ is H or C$_{1-4}$ alkyl; R$_9$ is —CH=CH$_2$, —CH=CHCH$_2$N(CH$_3$)$_2$, —C≡CH, or —C≡CCH$_3$; and R$_{12}$ is defined in either the first aspect or the second aspect.

One embodiment provides a compound of Formula (I) or a salt thereof, wherein R$_1$ is H, —CH$_3$, —CF$_3$, or phenyl substituted with zero or 1 R$_{12}$; and R$_2$ is H, —CH$_3$, cyclopropyl, or phenyl substituted with zero or 1 R$_{12}$; provided that zero or one of R$_1$ and R$_2$ is phenyl substituted with zero or 1 R$_{12}$ and further provided that at least one of R$_1$ and R$_2$ is —CH$_3$; and R$_3$, R$_4$, R$_{12}$ and A are defined in either the first aspect or the second aspect.

One embodiment provides a compound of Formula (I) or a salt thereof, wherein R$_1$ is H, —CF$_3$ or —CH$_3$; and R$_2$ is H or —CH$_3$: provided that one of R$_1$ and R$_2$ is —CH$_3$ or —CF$_3$ and the other of R$_1$ and R$_2$ is H; and R$_3$, R$_4$, and A are defined in either the first aspect or the second aspect. Included in this embodiment are compounds in which R$_1$ is —CH$_3$ and R$_2$ is H. Also included in this embodiment are compounds in which R$_1$ is H and R$_2$ is —CH$_3$.

One embodiment provides a compound of Formula (I) or a salt thereof, wherein R$_1$ is —CH$_3$; R$_2$ is —CH$_3$; and R$_3$, R$_4$, and A are defined in either the first aspect or the second aspect.

One embodiment provides a compound of Formula (I) or a salt thereof, wherein R$_1$ is —CF$_3$; R$_2$ is —CH$_3$; and R$_3$, R$_4$, and A are defined in either the first aspect or the second aspect.

One embodiment provides a compound of Formula (I) or a salt thereof, wherein R$_1$ is —CH$_3$; R$_2$ is cyclopropyl; and R$_3$, R$_4$, and A are defined in either the first aspect or the second aspect.

One embodiment provides a compound of Formula (I) or a salt thereof, wherein R$_1$ is 4-fluorophenyl; R$_2$ is —CH$_3$; and R$_3$, R$_4$, and A are defined in either the first aspect or the second aspect.

One embodiment provides a compound of Formula (I) or a salt thereof, wherein R$_1$ is —CH$_3$; R$_2$ is 4-fluorophenyl; and R$_3$, R$_4$, and A are defined in either the first aspect or the second aspect.

One embodiment provides a compound of Formula (I) or a salt thereof, wherein R$_3$ is H, F, Cl, I, —CN, or —CH$_3$; and R$_1$, R$_2$, R$_4$, and A are defined in either the first aspect or the second aspect. Included in this embodiment are compounds in which R$_3$ is H or F. Also included in this embodiment are compounds in which R$_1$ is H, —CH$_3$, —CF$_3$, or phenyl substituted with zero or 1 R$_{12}$; and R$_2$ is H, —CH$_3$, cyclopropyl, or phenyl substituted with zero or 1 R$_{12}$; provided that zero or one of R$_1$ and R$_2$ is phenyl substituted with zero or 1 R$_{12}$ and further provided that at least one of R$_1$ and R$_2$ is —CH$_3$.

One embodiment provides a compound of Formula (I) or a salt thereof, wherein $R_3$ is H, F, or Cl; and $R_1$, $R_2$, $R_4$, and A are defined in either the first aspect or the second aspect. Included in this embodiment are compounds in which $R_3$ is H or F. Also included in this embodiment are compounds in which $R_1$ is H, —CH$_3$, —CF$_3$, or phenyl substituted with zero or 1 $R_{12}$; and $R_2$ is H, —CH$_3$, cyclopropyl, or phenyl substituted with zero or 1 $R_{12}$; provided that zero or one of $R_1$ and $R_2$ is phenyl substituted with zero or 1 $R_{12}$ and further provided that at least one of $R_1$ and $R_2$ is —CH$_3$.

One embodiment provides a compound of Formula (I) or a salt thereof, wherein $R_3$ is F, Cl, or I; and $R_1$, $R_2$, $R_4$, and A are defined in either the first aspect or the second aspect. Included in this embodiment are compounds in which $R_3$ is F or Cl. Also included in this embodiment are compounds in which $R_3$ is F.

One embodiment provides a compound of Formula (I) or a salt thereof, wherein $R_4$ is H, F, —OH, —O(C$_{1-2}$ alkyl), —OCH$_2$CH$_2$OCH$_3$, —OCH$_2$(phenyl), —OCH$_2$(methoxyphenyl), or —OCH$_2$(morpholinyl); and $R_1$, $R_2$, $R_3$, and A are defined in either the first aspect or the second aspect. Included in this embodiment are compounds in which $R_4$ is H or F. Also included in this embodiment are compounds in which $R_1$ is H, —CH$_3$, —CF$_3$, or phenyl substituted with zero or 1 $R_{12}$; and $R_2$ is H, —CH$_3$, cyclopropyl, or phenyl substituted with zero or 1 $R_{12}$; provided that zero or one of $R_1$ and $R_2$ is phenyl substituted with zero or 1 $R_{12}$ and further provided that at least one of $R_1$ and $R_2$ is —CH$_3$; and $R_3$ is H or F.

One embodiment provides a compound of Formula (I) or a salt thereof, wherein A is

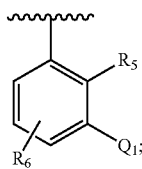

$R_5$ is H, F, or —CH$_3$; and $R_1$, $R_2$, $R_3$, $R_4$, and $R_6$ are defined in either the first aspect or the second aspect. Included in this embodiment are compounds in which $R_6$ is H. Also included in this embodiment are compounds in which $R_1$ is H, —CH$_3$, —CF$_3$, or phenyl substituted with zero or 1 $R_{12}$; and $R_2$ is H, —CH$_3$, cyclopropyl, or phenyl substituted with zero or 1 $R_{12}$; provided that zero or one of $R_1$ and $R_2$ is phenyl substituted with zero or 1 $R_2$ and further provided that at least one of $R_1$ and $R_2$ is —CH$_3$; $R_3$ is H or F; $R_4$ is H or F; $R_6$ is H; and $R_{12}$ is defined in either the first aspect or the second aspect.

One embodiment provides a compound of Formula (I) or a salt thereof, wherein $R_6$ is H or F; and $R_1$, $R_2$, $R_3$, $R_4$, $R_5$, and A are defined in either the first aspect or the second aspect. Included in this embodiment are compounds in which $R_6$ is H. Also included are compounds in which $R_1$ is H, —CH$_3$, —CF$_3$, or phenyl substituted with zero or 1 $R_{12}$; and $R_2$ is H, —CH$_3$, cyclopropyl, or phenyl substituted with zero or 1 $R_{12}$; provided that zero or one of $R_1$ and $R_2$ is phenyl substituted with zero or 1 $R_{12}$ and further provided that at least one of $R_1$ and $R_2$ is —CH$_3$; $R_3$ is H or F; $R_4$ is H or F; $R_5$ is H, F, or —CH$_3$; $R_6$ is H or F; and $R_{12}$ is defined in either the first aspect or the second aspect.

One embodiment provides a compound of Formula (I) or a salt thereof, wherein $R_7$, at each occurrence, is independently H or C$_{1-2}$ alkyl; and $R_1$, $R_2$, $R_3$, $R_4$, and A are defined in either the first aspect or the second aspect.

One embodiment provides a compound of Formula (I) or a salt thereof, wherein A is —CHR$_8$(pyridinyl) wherein each pyridinyl is substituted with $R_6$ and $R_9$; $R_8$ is H or —CH$_3$; and $R_1$, $R_2$, $R_3$, $R_4$, $R_6$, and $R_9$ are defined in either the first aspect or the second aspect. Included in this embodiment are compounds in which $R_1$ is H, —CH$_3$, —CF$_3$, or phenyl substituted with zero or 1 $R_{12}$; and $R_2$ is H, —CH$_3$, cyclopropyl, or phenyl substituted with zero or 1 $R_{12}$; provided that zero or one of $R_1$ and $R_2$ is phenyl substituted with zero or 1 $R_{12}$ and further provided that at least one of $R_1$ and $R_2$ is —CH$_3$; $R_3$ is H or F; $R_4$ is H or F; $R_5$ is H, F, or —CH$_3$; $R_6$ is H; $R_9$ is —CH=CH$_2$ or —C≡CCH$_3$; and $R_{12}$ is defined in either the first aspect or the second aspect.

One embodiment provides a compound of Formula (I) or a salt thereof, wherein A is —CHR$_8$(pyridinyl) wherein each pyridinyl is substituted with $R_6$ and $R_9$; $R_9$ is —CH=CH$_2$, —C≡CH, or —C≡CCH$_3$; and $R_1$, $R_2$, $R_3$, $R_4$, $R_6$, and $R_8$ are defined in either the first aspect or the second aspect. Included in this embodiment are compounds in which $R_9$ is —CH=CH$_2$ or —C≡CCH$_3$.

One embodiment provides a compound of Formula (I) or a salt thereof, wherein $R_{11}$ is F, Cl, —CN, —CF$_3$, or C$_{1-3}$ alkoxy; and $R_1$, $R_2$, $R_3$, $R_4$, and A are defined in either the first aspect or the second aspect. Included in this embodiment are compounds in which $R_{11}$ is F or —CN.

One embodiment provides a compound of Formula (I) or a salt thereof, wherein $R_1$ is H, —CH$_3$, —CF$_3$, or phenyl substituted with zero or 1 $R_{12}$; and $R_2$ is H, —CH$_3$, cyclopropyl, or phenyl substituted with zero or 1 $R_{12}$; provided that zero or one of $R_1$ and $R_2$ is phenyl substituted with zero or 1 $R_{12}$ and further provided that at least one of $R_1$ and $R_2$ is —CH$_3$; $R_3$ is H, F, or Cl; $R_4$ is H, F, —OH, —O(C$_{1-2}$ alkyl), —OCH$_2$CH$_2$OCH$_3$, —OCH$_2$(phenyl), —OCH$_2$(methoxyphenyl), or —OCH$_2$CH$_2$(morpholinyl); $R_5$ is H, F, or —CH$_3$; $R_6$ is H or F; $R_7$ is H or C$_{1-3}$ alkyl; $R_8$ is H or —CH$_3$; $R_9$ is —CH=CH$_2$ or —C≡CCH$_3$; $Q_1$ is —N(CH$_3$)C(O)CH=CH$_2$, —N(CH$_3$)S(O)$_2$CH=CH$_2$, —C(O)NHCH$_2$CN, —C(CH$_3$)$_2$NHS(O)$_2$CH=CH$_2$, —CH$_2$NHC(O)CH=CH$_2$, —CH$_2$NHS(O)$_2$CH=CH$_2$, —NHC(O)CH$_2$CN, —NHC(O)CH$_2$CH$_3$, —NHC(O)CH=CH$_2$, —NHC(O)C(CH$_3$)=CH$_2$, —NHC(O)CH=C(CH$_3$)$_2$, —NHC(O)CH=CHCH$_3$, —NHC(O)CH=CHCH$_2$N(CH$_3$)$_2$, —NHC(O)(cyclohexenyl), —NHC(O)(cyclopropyl), —NHC(O)(cyanocyclopropyl), —NHS(O)$_2$CH=CH$_2$, —S(O)$_2$CH=CH$_2$, —CH=C(CN)S(O)$_2$CH$_3$, —NH(dichlorotriazinyl), —NH(fluoroquinazolin-4-yl), 3-methylenepyrrolidin-2-on-1-yl, or a cyclic group selected from 1H-pyrrol-2(5H)-on-1-yl, isoindolin-1-on-2-yl, quinazolin-4(3H)-on-3-yl, and quinazoline-2,4(1H, 3H)-dion-3-yl, each cyclic group substituted with zero to two substituents independently selected from F, Cl, —CH$_3$, —CN, and —OCH$_3$; $Q_2$ is —CN, —C(O)CH=CH$_2$, —S(O)$_2$CH=CH$_2$, —C(O)CH=CHCH$_2$N(CH$_3$)$_2$, —C(O)C≡CH, —C(O)C≡CCH$_3$, —C(O)C≡CCH$_2$CH$_3$, —C(O)C≡CCH$_2$CH$_2$CH$_3$, —C(O)C≡C(CH$_3$)$_2$OH, —C(O)C≡CSi(CH$_3$)$_3$, —C(O)C≡C(cyclopropyl), or —C(O)C≡C(phenyl); and A and $R_{12}$ are defined in either the first aspect or the second aspect.

One embodiment provides a compound of Formula (I) or a salt thereof, wherein A is:

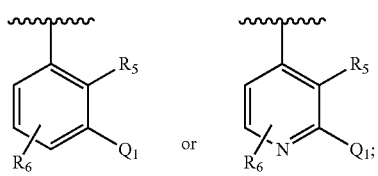

R₁ is H, —CH₃, —CF₃, or 4-fluorophenyl; and R₂ is H, —CH₃, cyclopropyl, or 4-fluorophenyl; provided that zero or one of R₁ and R₂ is 4-fluorophenyl and further provided that at least one of R₁ and R₂ is —CH₃; R₃ is H, F, or Cl; R₄ is H, F, —OH, —O(C$_{1-2}$ alkyl), —OCH₂CH₂OCH₃, —OCH₂(phenyl), or —OCH₂(morpholinyl); R₅ is H, F, or —CH₃; R₆ is H; and Q₁ is —N(CH₃)C(O)CH=CH₂, —N(CH₃)S(O)₂CH=CH₂, —C(O)NHCH₂CN, —C(CH₃)₂NHS(O)₂CH=CH₂, —CH₂NHC(O)CH=CH₂, —CH₂NHS(O)₂CH=CH₂, —NHC(O)CH₂CN, —NHC(O)CH₂CH₃, —NHC(O)CH=CH₂, —NHC(O)C(CH₃)=CH₂, —NHC(O)CH=C(CH₃)₂, —NHC(O)CH=CHCH₃, —NHC(O)CH=CHCH₂N(CH₃)₂, —NHC(O)(cyclohexenyl), —NHC(O)(cyclopropyl), —NHC(O)(cyanocyclopropyl), —NHS(O)₂CH=CH₂, —S(O)₂CH=CH₂, —CH=C(CN)S(O)₂CH₃, —NH(dichlorotriazinyl), —NH(fluoroquinazolin-4-yl), 3-methylenepyrrolidin-2-on-1-yl, or a cyclic group selected from 1H-pyrrol-2(5H)-on-1-yl, isoindolin-1-on-2-yl, quinazolin-4(3H)-on-3-yl, and quinazoline-2,4(1H, 3H)-dion-3-yl, each cyclic group substituted with zero to two substituents independently selected from F, Cl, —CH₃, —CN, and —OCH₃. Included in this embodiment are compounds in which A is

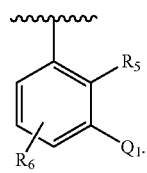

One embodiment provides a compound of Formula (I) or a salt thereof, wherein A is:

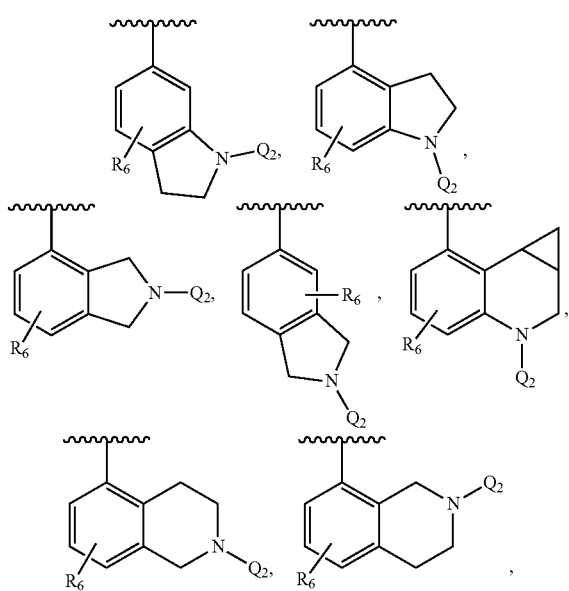

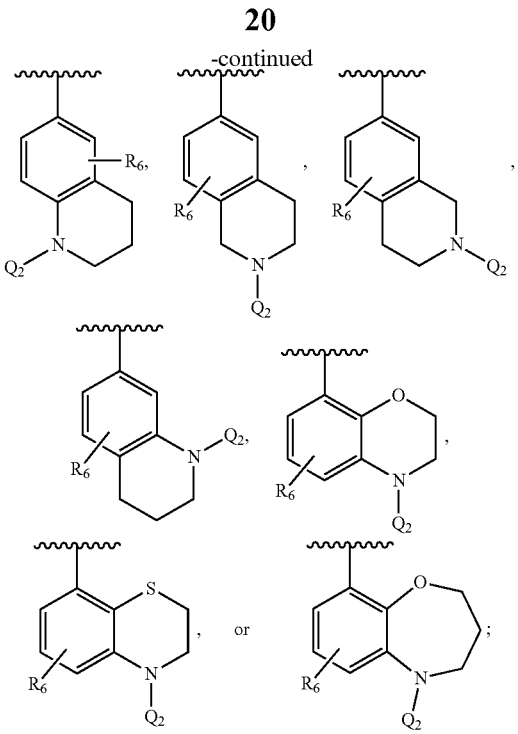

R₁ is H, —CH₃, —CF₃, or 4-fluorophenyl; and R₂ is H, —CH₃, cyclopropyl, or 4-fluorophenyl; provided that zero or one of R₁ and R₂ is 4-fluorophenyl and further provided that at least one of R₁ and R₂ is —CH₃; R₃ is H or F; R₄ is H or F; R₆ is H or F; and Q₂ is —CN, —C(O)CH=CH₂, —C(O)C≡CCH₃, or —S(O)₂CH=CH₂. Included in this embodiment are compounds in which R₃ is F.

One embodiment provides a compound of Formula (I) or a salt thereof, wherein A is:

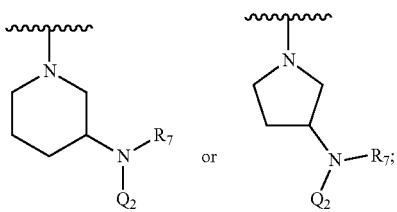

R₁ is H, —CH₃, —CF₃, or 4-fluorophenyl; and R₂ is H, —CH₃, cyclopropyl, or 4-fluorophenyl; provided that zero or one of R₁ and R₂ is 4-fluorophenyl and further provided that at least one of R₁ and R₂ is —CH₃; R₃ is H or F; R₄ is H or F; R₇ is H, —CH₃, or —CH₂CH₃; and Q₂ is —CN, —C(O)CH=CH₂, —C(O)C≡CH, —C(O)C≡CCH₃, —C(O)C≡CCH₂CH₃, —C(O)C≡CCH₂CH₂CH₃, —C(O)C≡C(CH₃)₂(OH), —C(O)C≡CSi(CH₃)₃, —C(O)C≡C(cyclopropyl), —C(O)C≡C(phenyl), or —S(O)₂CH=CH₂.

One embodiment provides a compound of Formula (I) or a salt thereof, wherein A is:

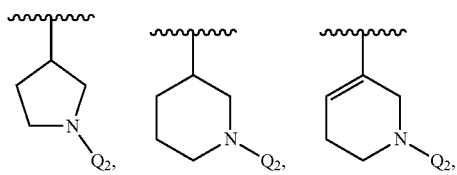

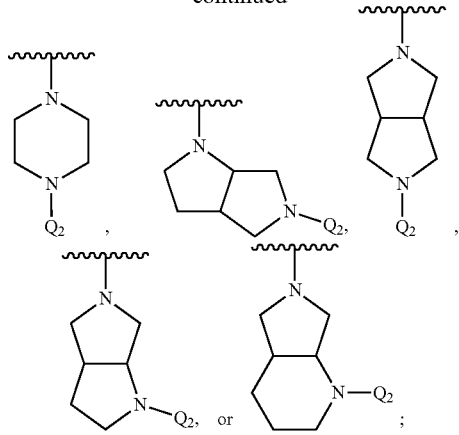

$R_1$ is H, —$CH_3$, —$CF_3$, or 4-fluorophenyl; and $R_2$ is H, —$CH_3$, cyclopropyl, or 4-fluorophenyl; provided that zero or one of $R_1$ and $R_2$ is 4-fluorophenyl and further provided that at least one of $R_1$ and $R_2$ is —$CH_3$; $R_3$ is H or F; $R_4$ is H or F; and $Q_2$ is —CN, —C(O)CH=$CH_2$, —C(O)C≡$CCH_3$, or —S(O)$_2$CH=$CH_2$. Included in this embodiment are compounds in which A is:

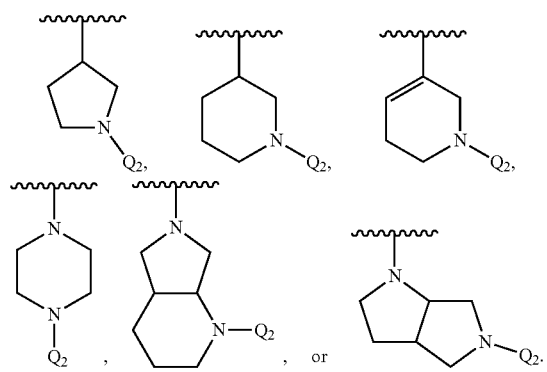

One embodiment provides a compound of Formula (I) or a salt thereof, wherein A is:

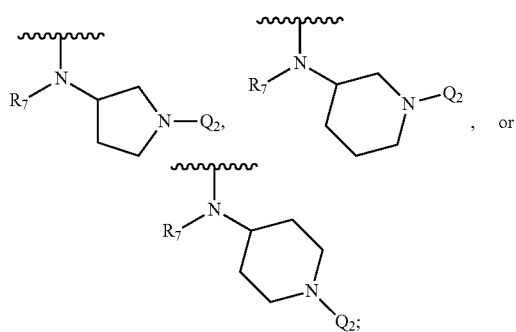

$R_1$ is H, —$CH_3$, —$CF_3$, or 4-fluorophenyl; and $R_2$ is H, —$CH_3$, cyclopropyl, or 4-fluorophenyl; provided that zero or one of $R_1$ and $R_2$ is 4-fluorophenyl and further provided that at least one of $R_1$ and $R_2$ is —$CH_3$; $R_3$ is H or F; $R_4$ is H or F; $R_7$ is H; and $Q_2$ is —CN, —C(O)CH=$CH_2$, —C(O)≡CH, —C(O)C≡$CCH_3$, —C(O)CH=CHCH$_2$N(CH$_3$)$_2$, or —S(O)$_2$CH=$CH_2$.

One embodiment provides a compound of Formula (I) or a salt thereof, wherein A is —CHR$_8$(pyridinyl) wherein each pyridinyl is substituted with R$_6$ and R$_9$; R$_1$ is H, —CH$_3$, —CF$_3$, or 4-fluorophenyl; and R$_2$ is H, —CH$_3$, cyclopropyl, or 4-fluorophenyl; provided that zero or one of R$_1$ and R$_2$ is 4-fluorophenyl and further provided that at least one of R$_1$ and R$_2$ is —CH$_3$; R$_3$ is F; R$_4$ is H or F; R$_6$ is H; R$_8$ is H or —CH$_3$; and R$_9$ is —CH=CH$_2$ or —C≡CCH$_3$.

One embodiment provides a compound of Formula (I) or a salt thereof, wherein: X is N; R$_1$ is —CH$_3$; R$_2$ is —CH$_3$; R$_3$ is H, —CN, or —CH$_3$; A is

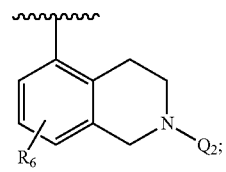

and $Q_2$ is —C(O)C=CH$_2$.

A compound that inhibits an enzyme by reacting with the enzyme to form a covalent bond can offer advantages over a compound that does not form such a covalent bond. (See, for example, Liu, Q. et al., Chem. Biol., 20:146 (2013); Barf, T. et al., J. Med. Chem., 55:6243 (2012); Kalgutkar, A. et al., Expert Opin. Drug Discov., 7:561 (2012); and Garuti, L. et al., Curr. Med. Chem., 18:2981 (2011); and references cited therein). A compound that does not form a covalent bond can dissociate from the enzyme, releasing the enzyme from the inhibition resulting from its binding. Such reversible inhibition may require a relatively high and continuous concentration of the inhibitory compound to drive the binding equilibrium toward sufficient enzyme occupancy by the inhibitor to achieve useful enzyme inhibition. A higher concentration of the compound could require administration of a higher dose of the compound to a mammal in need of such inhibition, and at a higher concentration the inhibitor could have undesired effects due to inhibition of other, non-targeted enzymes. Such off-target inhibition could include toxicity. Additionally, more frequent dosing may be required since the inhibitory compound, after dissociation from the target enzyme, can be removed from the body by metabolism and/or elimination, lowering the concentration available to achieve inhibition of the target enzyme.

In contrast, an inhibitor that forms a covalent bond with its target enzyme irreversibly inhibits the enzyme. The irreversible inhibition would result from either slow or negligible dissociation of the inhibitor, since such dissociation would require breaking a covalent bond. If the affinity of such a covalent inhibitor for its target enzyme is sufficiently great relative to affinities for other, off-target enzymes, a significantly lower concentration of the inhibitor can result in useful inhibition relative to a concentration required for reversible inhibition. The lower concentration could reduce the likelihood of undesired off-target inhibition and potential toxicity. Also, since the covalent inhibitor can bind essentially irreversibly to the target enzyme, the free (non-bound) concentration of the inhibitor can become extremely low as non-bound inhibitor is removed from the body by metabolism and/or elimination, even while useful enzyme inhibition is maintained. This can reduce the likelihood of undesired effects. Additionally, since the enzyme can be irreversibly inhibited, less frequent dosing may be required to achieve useful inhibition.

Certain reactive functional groups can be attached to a compound with good affinity for the target enzyme, which will allow formation of covalent bond with a functional group in the target enzyme. For example, an electrophilic group such as a vinylic or acetylenic group attached to an electron-withdrawing group such as a ketone, amide, sulfone, sulfonamide, or an electron-withdrawing heterocyclic ring such as a pyridyl ring can react with a nucleophilic group present in the target enzyme, such as the thiol or thiolate group of a cysteine residue, to form a covalent bond. Such a reaction can be essentially irreversible under normal physiological conditions. In order for such a reaction to be achieved, the inhibitor compound must bind to the target enzyme and present the attached electrophilic group in a correct spatial orientation to allow favorable interaction with the attacking nucleophile. If the orientation is not correct, the covalent bond may not easily form, and the desired irreversible inhibition may not be achieved. In this case, the compound would behave like a reversible inhibitor and the benefits of irreversible inhibition may not be realized. Also, if the orientation of the electrophile on the bound inhibitor is not suitable for reaction with the nucleophilic group of the target enzyme, the inhibitor will be capable of dissociation from the target enzyme, resulting in a higher concentration of the inhibitor and a greater likelihood that the reactive electrophilic group can react with other, non-target nucleophiles and cause undesired effects such as toxicity.

One embodiment provides a compound of Formula (I) or a salt thereof, wherein said compound covalently bonds to the Btk enzyme.

One embodiment provides a compound of Formula (I) or a salt thereof, wherein $Q_1$ is —$NR_7Q_2$, —$CR_{10}R_{10}NR_7Q_2$, —CH=C(CN)S(O)$_2$CH$_3$, or —S(O)$_2$CH=$CR_{10}R_{10}$; $Q_2$ is —C(O)$CR_{10}$=$CR_{10}R_{10}$, —C(O)C($R_{10}$)=CHCH$_2$N(CH$_3$)$_2$, —C(O)C≡$CR_7$, —C(O)C≡C($C_{1-3}$ hydroxyalkyl), —C(O)C≡C(phenyl), —C(O)C≡CSi(CH$_3$)$_3$, or —S(O)$_2$CH=CH$R_{10}$; and $R_1$, $R_2$, $R_3$, $R_4$, A, $R_7$, $R_9$, and $R_{10}$ are defined in the first embodiment. Included in this embodiment are compounds in which $R_3$ is H, F, or Cl; $R_4$ is H, F, —OH, —O($C_{1-2}$ alkyl), —OCH$_2$CH$_2$OCH$_3$, —OCH$_2$(phenyl), —OCH$_2$(methoxyphenyl), or —OCH$_2$CH$_2$(morpholinyl); $R_5$ is H, F, or —CH$_3$; $R_6$ is H or F; $R_7$ is H or $C_{1-3}$ alkyl; $R_8$ is H or —CH$_3$; and $R_9$ is —CH=CH$_2$ or —C≡CCH$_3$.

One embodiment provides a compound of Formula (I) or a salt thereof, wherein $Q_1$ is —N(CH$_3$)C(O)CH=CH$_2$, —N(CH$_3$)S(O)$_2$CH=CH$_2$, —C(CH$_3$)$_2$NHS(O)$_2$CH=CH$_2$, —CH$_2$NHC(O)CH=CH$_2$, —CH$_2$NHS(O)$_2$CH=CH$_2$, —NHC(O)CH=CH$_2$, —NHC(O)C(CH$_3$)=CH$_2$, —NHC(O)CH=C(CH$_3$)$_2$, —NHC(O)CH=CHCH$_3$, —NHC(O)CH=CHCH$_2$N(CH$_3$)$_2$, —NHC(O)(cyclohexenyl), —NHS(O)$_2$CH=CH$_2$, —S(O)$_2$CH=CH$_2$, or —CH=C(CN)S(O)$_2$CH$_3$; and $Q_2$ is —C(O)CH=CH$_2$, —S(O)$_2$CH=CH$_2$, —C(O)CH=CHCH$_2$N(CH$_3$)$_2$, —C(O)C≡CH, —C(O)C≡CCH$_3$, —C(O)C≡CCH$_2$CH$_3$, —C(O)C≡CCH$_2$CH$_2$CH$_3$, —C(O)C≡C(CH$_3$)$_2$OH, —C(O)C≡CSi(CH$_3$)$_3$, —C(O)C≡C(cyclopropyl), or —C(O)C≡C(phenyl); and $R_1$, $R_2$, $R_3$, $R_4$, and A are defined in the first embodiment. Included in this embodiment are compounds in which $R_3$ is H, F, or Cl; $R_4$ is H, F, —OH, —O($C_{1-2}$ alkyl), —OCH$_2$CH$_2$OCH$_3$, —OCH$_2$(phenyl), —OCH$_2$(methoxyphenyl), or —OCH$_2$CH$_2$(morpholinyl); $R_5$ is H, F, or —CH$_3$; $R_6$ is H or F; $R_7$ is H or $C_{1-3}$ alkyl; $R_8$ is H or —CH$_3$; and $R_9$ is —CH=CH$_2$ or —C≡CCH$_3$.

One embodiment provides a compound of Formula (I) or a salt thereof, wherein said compound is 4-(3-acrylamido-2-methylphenyl)-3-methyl-1H-indole-7-carboxamide (1); 2,3-dimethyl-4-(3-(vinylsulfonyl)phenyl)-1H-indole-7-carboxamide (2); 5-fluoro-2,3-dimethyl-4-(3-(N-methylacrylamido)phenyl)-1H-indole-7-carboxamide (3); 2,3-dimethyl-4-(3-(vinylsulfonamido)phenyl)-1H-indole-7-carboxamide (4); 4-(3-acrylamido-2-methylphenyl)-2,3-dimethyl-1H-indole-7-carboxamide (5); (E)-4-(3-(but-2-enamido)-2-methylphenyl)-2,3-dimethyl-1H-indole-7-carboxamide (6); 4-(3-acrylamido-2-methylphenyl)-2-methyl-1H-indole-7-carboxamide (7); (E)-4-(3-(but-2-enamido)-2-methylphenyl)-2-methyl-1H-indole-7-carboxamide (8); (E)-4-(3-(but-2-enamido)-2-methylphenyl)-3-methyl-1H-indole-7-carboxamide (9); 2,3-dimethyl-4-(2-methyl-3-(3-methylbut-2-enamido)phenyl)-1H-indole-7-carboxamide (10); 2-methyl-4-(2-methyl-3-(3-methylbut-2-enamido)phenyl)-1H-indole-7-carboxamide (11); 3-methyl-4-(2-methyl-3-(3-methylbut-2-enamido)phenyl)-1H-indole-7-carboxamide (12); 2,3-dimethyl-4-(2-methyl-3-propionamidophenyl)-1H-indole-7-carboxamide (13); 4-(3-(cyclopropanecarboxamido)-2-methylphenyl)-2,3-dimethyl-1H-indole-7-carboxamide (14); 4-(3-(1-cyanocyclopropanecarboxamido)-2-methylphenyl)-2,3-dimethyl-1H-indole-7-carboxamide (15); (E)-4-(3-(4-(dimethylamino)but-2-enamido)-2-methylphenyl)-2,3-dimethyl-1H-indole-7-carboxamide (16); 4-(3-methacrylamido-2-methylphenyl)-2,3-dimethyl-1H-indole-7-carboxamide (17); 4-(3-(cyclohex-1-enecarboxamido)-2-methylphenyl)-2,3-dimethyl-1H-indole-7-carboxamide (18); 4-(3-(2-cyanoacetamido)-2-methylphenyl)-3-methyl-1H-indole-7-carboxamide (19); 2,3-dimethyl-4-(2-methyl-3-(N-methylacrylamido)phenyl)-1H-indole-7-carboxamide (20); 4-(3-((cyanomethyl)carbamoyl)-2-methylphenyl)-2,3-dimethyl-1H-indole-7-carboxamide (21); 4-(3-acrylamidophenyl)-2,3-dimethyl-1H-indole-7-carboxamide (22); 2,3-dimethyl-4-(2-methyl-3-(N-methylvinylsulfonamido)phenyl)-1H-indole-7-carboxamide (23); 3-methyl-4-(2-methyl-3-(N-methylvinylsulfonamido)phenyl)-1H-indole-7-carboxamide (24); 2,3-dimethyl-4-(3-(N-methylvinylsulfonamido)phenyl)-1H-indole-7-carboxamide (25); 5-fluoro-2,3-dimethyl-4-(3-(N-methylvinylsulfonamido)phenyl)-1H-indole-7-carboxamide (26); 5-chloro-2,3-dimethyl-4-(3-(N-methylvinylsulfonamido)phenyl)-1H-indole-7-carboxamide (27); 3-methyl-4-(3-(N-methylvinylsulfonamido)phenyl)-1H-indole-7-carboxamide (28); 2,3-dimethyl-4-(3-(N-methylacrylamido)phenyl)-1H-indole-7-carboxamide (29); 3-methyl-4-(3-(N-methylacrylamido)phenyl)-1H-indole-7-carboxamide (30); 3-methyl-4-(2-methyl-3-(vinylsulfonamido)phenyl)-1H-indole-7-carboxamide (31); 4-(2-fluoro-3-(N-methylacrylamido)phenyl)-2,3-dimethyl-1H-indole-7-carboxamide (32); 3-methyl-4-(3-(vinylsulfonamido)phenyl)-1H-indole-7-carboxamide (33); 2,3-dimethyl-4-(2-methyl-3-(vinylsulfonamido)phenyl)-1H-indole-7-carboxamide (34); 2,3-dimethyl-4-(2-methyl-3-(3-methylene-2-oxopyrrolidin-1-yl)phenyl)-1H-indole-7-carboxamide (35); 2,3-dimethyl-4-(3-(3-methylene-2-oxopyrrolidin-1-yl)phenyl)-1H-indole-7-carboxamide (36); 5-fluoro-2,3-dimethyl-4-(3-(3-methyl-2-oxo-2,5-dihydro-1H-pyrrol-1-yl)phenyl)-1H-indole-7-carboxamide (37); 4-(1-acryloylindolin-6-yl)-2,3-dimethyl-1H-indole-7-carboxamide (38); 2,3-dimethyl-4-(1-(vinylsulfonyl)indolin-6-yl)-1H-indole-7-carboxamide (39); 2,3-dimethyl-4-(3-(vinylsulfonamidomethyl)phenyl)-1H-indole-7-carboxamide (40); 4-(3-(acrylamidomethyl)phenyl)-2,3-dimethyl-1H-indole-7-carboxamide (41); 2,3-dimethyl-4-(3-(2-(vinylsulfonamido)propan-2-yl)phenyl)-1H-indole-7-carboxamide (42); 4-(2-acrylamidopyridin-4-yl)-2,3-dimethyl-1H-indole-7-carboxamide (43); 4-(2-acrylamidopyridin-4-yl)-2-methyl-1H-indole-7-carboxamide (44); 4-(3-acrylamido-2-methylphenyl)-1H- indole-7-carboxamide (45); 4-(2-methyl-3-(N-methylacrylamido)phenyl)-1H-indole-7-carboxamide (46); 2,3-dimethyl-4-(2-methyl-3-(6-methyl-1-oxoisoindolin-2-yl)phenyl)-1H-indole-7-carboxamide (47); 4-(3-(6-fluoro-1-oxoisoindolin-2-yl)-2-methylphenyl)-2,3-dimethyl-1H-indole-7-carboxamide (48); 2,3-dimethyl-4-(2-methyl-3-(4-oxoquinazolin-3(4H)-yl)phenyl)-1H-indole-7-carboxamide (49); 4-(3-(6-fluoro-4-oxoquinazolin-3(4H)-yl)-2-methylphenyl)-2,3-dimethyl-1H-indole-7-carboxamide (50); 4-(3-((5-fluoroquinazolin-4-yl)amino)-2-methylphenyl)-2,3-dimethyl-1H-indole-7-carboxamide (51); 4-(3-(6-fluoro-4-oxoquinazolin-3(4H)-yl)-2-methylphenyl)-1H-indole-7-carboxamide (52); 4-(3-(7-fluoro-4-oxoquinazolin-3(4H)-yl)-2-methylphenyl)-1H-indole-7-carboxamide (53); 4-(3-(8-fluoro-4-oxoquinazolin-3(4H)-yl)-2-methylphenyl)-1H-indole-7-carboxamide (54); 4-(3-(6-chloro-4-oxoquinazolin-3(4H)-yl)-2-methylphenyl)-1H-indole-7-carboxamide (55); 4-(3-(8-methoxy-4-oxoquinazolin-3(4H)-yl)-2-methylphenyl)-1H-indole-7-carboxamide (56); 4-(3-(6-fluoro-1-oxoisoindolin-2-yl)-2-methylphenyl)-1H-indole-7-carboxamide (57); 4-(3-(6-cyano-1-oxoisoindolin-2-yl)-2-methylphenyl)-1H-indole-7-carboxamide (58); 3-methyl-4-(2-methyl-3-(4-oxoquinazolin-3(4H)-yl)phenyl)-1H-indole-7-carboxamide (59); 2-methyl-4-(2-methyl-3-(4-oxoquinazolin-3(4H)-yl)phenyl)-1H-indole-7-carboxamide (60); 6-((4-methoxybenzyl)oxy)-2,3-dimethyl-4-(2-methyl-3-(4-oxoquinazolin-3(4H)-yl)phenyl)-1H-indole-7-carboxamide (61); 4-(3-(8-fluoro-4-oxoquinazolin-3(4H)-yl)-2-methylphenyl)-6-((4-methoxybenzyl)oxy)-2,3-dimethyl-1H-indole-7-carboxamide (62); 4-(3-(6-cyano-1-oxoisoindolin-2-yl)-2-methylphenyl)-6-((4-methoxybenzyl)oxy)-2,3-dimethyl-1H-indole-7-carboxamide (63); 4-(3-(6-fluoro-4-oxoquinazolin-3(4H)-yl)-2-methylphenyl)-6-((4-methoxybenzyl)oxy)-2,3-dimethyl-1H-indole-7-carboxamide (64); 4-(3-(7-fluoro-4-oxoquinazolin-3 (4H)-yl)-2-methylphenyl)-6-((4-methoxybenzyl)oxy)-2,3-dimethyl-1H-indole-7-carboxamide (65); 4-(3-(8-methoxy-4-oxoquinazolin-3(4H)-yl)-2-methylphenyl)-6-((4-methoxybenzyl)oxy)-2,3-dimethyl-1H-indole-7-carboxamide (66); 4-(3-(8-fluoro-1-methyl-2,4-dioxo-1,2-dihydroquinazolin-3(4H)-yl)-2-methylphenyl)-2,3-dimethyl-1H-indole-7-carboxamide (67); 2,3-dimethyl-4-(2-methyl-3-(1-methyl-2,4-dioxo-1,2-dihydroquinazolin-3(4H)-yl)phenyl)-1H-indole-7-carboxamide (68); 4-(2-methyl-3-(4-oxoquinazolin-3(4H)-yl)phenyl)-1H-indole-7-carboxamide (69); 4-(3-(2-cyano-2-(methylsulfonyl)vinyl)phenyl)-2,3-dimethyl-1H-indole-7-carboxamide (70); 6-hydroxy-2,3-dimethyl-4-(2-methyl-3-(4-oxoquinazolin-3 (4H)-yl)phenyl)-1H-indole-7-carboxamide (71); 6-ethoxy-2,3-dimethyl-4-(2-methyl-3-(4-oxoquinazolin-3(4H)-yl) phenyl)-1H-indole-7-carboxamide (72); 6-methoxy-2,3-dimethyl-4-(2-methyl-3-(4-oxoquinazolin-3(4H)-yl) phenyl)-1H-indole-7-carboxamide (73); 6-(benzyloxy)-2,3-dimethyl-4-(2-methyl-3-(4-oxoquinazolin-3 (4H)-yl) phenyl)-1H-indole-7-carboxamide (74); 2,3-dimethyl-4-(2-methyl-3-(4-oxoquinazolin-3 (4H)-yl)phenyl)-6-(2-morpholinoethoxy)-1H-indole-7-carboxamide (75); 6-(2-methoxyethoxy)-2,3-dimethyl-4-(2-methyl-3-(4-oxoquinazolin-3 (4H)-yl)phenyl)-1H-indole-7-carboxamide (76); 4-(3-((4,6-dichloro-1,3,5-triazin-2-yl)amino)-2-methylphenyl)-2,3-dimethyl-1H-indole-7-carboxamide (77); (RS)-2,3-dimethyl-4-(3-(N-methylacrylamido)piperidin-1-yl)-1H-indole-7-carboxamide (78); 4-((1-acryloylpiperidin-4-yl)amino)-2,3-dimethyl-1H-indole-7-carboxamide (79); 4-(1-acryloylpiperidin-3-yl)-2,3-dimethyl-1H-indole-7-carboxamide (80); (R)-4-(3-acrylamidopiperidin-1-yl)-2,3-dimethyl-1H-indole-7-carboxamide (81); 4-(3-acrylamidopyrrolidin-1-yl)-2,3-dimethyl-1H-indole-7-carboxamide (82); 4-(3-acrylamidopiperidin-1-yl)-2,3-dimethyl-1H-indole-7-carboxamide (83); (S)-4-(3-acrylamidopiperidin-1-yl)-2,3-dimethyl-1H-indole-7-carboxamide (84); (R)-4-(3-acrylamidopyrrolidin-1-yl)-2,3-dimethyl-1H-indole-7-carboxamide (85); 4-((1-acryloylpyrrolidin-3-yl)amino)-2,3-dimethyl-1H-indole-7-carboxamide (86); (R)-4-((1-acryloylpyrrolidin-3-yl)amino)-2,3-dimethyl-1H-indole-7-carboxamide (87); (S)-4-((1-acryloylpyrrolidin-3-yl)amino)-5-fluoro-2,3-dimethyl-1H-indole-7-carboxamide (88); (S)-4-(3-acrylamidopiperidin-1-yl)-5-fluoro-2,3-dimethyl-1H-indole-7-carboxamide (89); 4-(1-acryloylpyrrolidin-3-yl)-2,3-dimethyl-1H-indole-7-carboxamide (90); 4-((1-acryloylpiperidin-3-yl)amino)-2,3-dimethyl-1H-indole-7-carboxamide (91); 4-((1-acryloylpiperidin-4-yl)amino)-5-fluoro-2,3-dimethyl-1H-indole-7-carboxamide (92); 4-(1-acryloylpiperidin-3-yl)-3-methyl-1H-indole-7-carboxamide (93); (S)-4-((1-acryloylpyrrolidin-3-yl)(methyl)amino)-2,3-dimethyl-1H-indole-7-carboxamide (94); (RS)-4-(2-acryloyl-1,2,3,4-tetrahydroisoquinolin-5-yl)-5-fluoro-2,3-dimethyl-H-inindole-7-carboxamide (95); (S)-4-((1-acryloylpyrrolidin-3-yl)(methyl)amino)-5-fluoro-2,3-dimethyl-1H-indole-7-carboxamide (96); 4-(1-acryloyl-1,2,3,4-tetrahydroquinolin-6-yl)-5-fluoro-2,3-dimethyl-1H-indole-7-carboxamide (97); cis-4-(5-acryloylhexahydropyrrolo [3,4-c]pyrrol-2(1H)-yl)-5-fluoro-2,3-dimethyl-1H-indole-7-carboxamide (98); 4-(1-acryloyl-1,2,3,4-tetrahydroquinolin-7-yl)-5-fluoro-2,3-dimethyl-1H-indole-7-carboxamide (99); (S)-4-(3-acrylamidopyrrolidin-1-yl)-5-fluoro-2,3-dimethyl-1H-indole-7-carboxamide (100); 4-(2-acryloylisoindolin-5-yl)-5-fluoro-2,3-dimethyl-1H-indole-7-carboxamide (101); (RS)-4-(4-acryloyl-3,4-dihydro-2H-benzo[b][1,4]oxazin-8-yl)-5-fluoro-2,3-dimethyl-1H-indole-7-carboxamide (102); (RS)-2,3-dimethyl-4-((1-propioloylpyrrolidin-3-yl)amino)-1H-indole-7-carboxamide (103); (RS)-4-(1-(but-2-ynoyl)piperidin-3-yl)-3-methyl-1H-indole-7-carboxamide (104); 2,3-dimethyl-4-(3-(N-methylpropiolamido)piperidin-1-yl)-1H-indole-7-carboxamide (105); 2,3-dimethyl-4-((1-propioloylpiperidin-3-yl)amino)-1H-indole-7-carboxamide (106); 4-((1-(but-2-ynoyl)piperidin-4-yl)amino)-2,3-dimethyl-1H-indole-7-carboxamide (107); 2,3-dimethyl-4-(3-(N-methylbut-2-ynamido)piperidin-1-yl)-1H-indole-7-carboxamide (108); (S)-2,3-dimethyl-4-(3-(3-phenylpropiolamido)piperidin-1-yl)-1H-indole-7-carboxamide (109); (S)-2,3-dimethyl-4-(3-(3-(trimethylsilyl)propiolamido)piperidin-1-yl)-1H-indole-7-carboxamide (110); (S)-4-(3-(4-hydroxy-4-methylpent-2-ynamido)piperidin-1-yl)-2,3-dimethyl-1H-indole-7-carboxamide (111); (S)-2,3-dimethyl-4-(3-(pent-2-ynamido) piperidin-1-yl)-1H-indole-7-carboxamide (112); (S)-4-(3-(hex-2-ynamido)piperidin-1-yl)-2,3-dimethyl-1H-indole-7-carboxamide (113); 2,3-dimethyl-4-((1-propioloylpiperidin-4-yl)amino)-1H-indole-7-carboxamide (114); (S)-2,3-dimethyl-4-(3-propiolamidopiperidin-1-yl)-1H-indole-7-carboxamide (115); (S)-4-(3-(but-2-ynamido) piperidin-1-yl)-2,3-dimethyl-1H-indole-7-carboxamide (116); (R)-2,3-dimethyl-4-(3-propiolamidopiperidin-1-yl)-1H-indole-7-carboxamide (117); (R)-4-(3-(but-2-ynamido) piperidin-1-yl)-2,3-dimethyl-1H-indole-7-carboxamide (118); (R)-2,3-dimethyl-4-(3-propiolamidopyrrolidin-1-yl)-1H-indole-7-carboxamide (119); (R)-4-(3-(but-2-ynamido) pyrrolidin-1-yl)-2,3-dimethyl-1H-indole-7-carboxamide (120); 4-((1-(but-2-ynoyl)pyrrolidin-3-yl)amino)-2,3-dimethyl-1H-indole-7-carboxamide (121); 4-((1-(but-2-ynoyl) piperidin-4-yl)amino)-5-fluoro-2,3-dimethyl-1H-indole-7-carboxamide (122); (S)-4-(3-(but-2-ynamido)piperidin-1-yl)-5-fluoro-2,3-dimethyl-1H-indole-7-carboxamide (123);

(S,E)-4-((1-(4-(dimethylamino)but-2-enoyl)pyrrolidin-3-yl)amino)-2,3-dimethyl-1H-indole-7-carboxamide (124); (S)-5-fluoro-2,3-dimethyl-4-(3-(N-methylbut-2-ynamido)piperidin-1-yl)-1H-indole-7-carboxamide (125); (S)-5-fluoro-2,3-dimethyl-4-(3-(pent-2-ynamido)piperidin-1-yl)-1H-indole-7-carboxamide (126); (S)-5-fluoro-2,3-dimethyl-4-(3-(N-methylpent-2-ynamido)piperidin-1-yl)-1H-indole-7-carboxamide (127); (S)-5-fluoro-4-(3-(hex-2-ynamido)piperidin-1-yl)-2,3-dimethyl-1H-indole-7-carboxamide (128); 4-(2-(but-2-ynoyl)-1,2,3,4-tetrahydroisoquinolin-5-yl)-5-fluoro-2,3-dimethyl-1H-indole-7-carboxamide (129); (S)-4-(3-(N-ethylbut-2-ynamido)piperidin-1-yl)-5-fluoro-2,3-dimethyl-1H-indole-7-carboxamide (130); 4-(2-acryloyl-1,2,3,4-tetrahydroisoquinolin-7-yl)-5-fluoro-2,3-dimethyl-1H-indole-7-carboxamide (131); (RS)-4-(2-acryloylisoindolin-4-yl)-5-fluoro-2,3-dimethyl-1H-indole-7-carboxamide (132); (RS)-4-(2-(but-2-ynoyl)isoindolin-4-yl)-5-fluoro-2,3-dimethyl-1H-indole-7-carboxamide (133); 4-(2-(but-2-ynoyl)-1,2,3,4-tetrahydroisoquinolin-7-yl)-5-fluoro-2,3-dimethyl-1H-indole-7-carboxamide (134); (S)-4-(3-(but-2-ynamido)pyrrolidin-1-yl)-5-fluoro-2,3-dimethyl-1H-indole-7-carboxamide (135); (S)-4-(3-(3-cyclopropylpropiolamido)piperidin-1-yl)-5-fluoro-2,3-dimethyl-1H-indole-7-carboxamide (136); 4-(2-(but-2-ynoyl)isoindolin-5-yl)-5-fluoro-2,3-dimethyl-1H-indole-7-carboxamide (137); (RS)-2,3-dimethyl-4-(3-(N-methylvinylsulfonamido)piperidin-1-yl)-1H-indole-7-carboxamide (138); 2,3-dimethyl-4-(3-(vinylsulfonamido)piperidin-1-yl)-1H-indole-7-carboxamide (139); 2,3-dimethyl-4-(3-(vinylsulfonamido)pyrrolidin-1-yl)-1H-indole-7-carboxamide (140); (S)-2,3-dimethyl-4-(3-(vinylsulfonamido)piperidin-1-yl)-1H-indole-7-carboxamide (141); (R)-2,3-dimethyl-4-(3-(vinylsulfonamido)pyrrolidin-1-yl)-1H-indole-7-carboxamide (142); (R)-2,3-dimethyl-4-(3-(vinylsulfonamido)piperidin-1-yl)-1H-indole-7-carboxamide (143); 2,3-dimethyl-4-((1-(vinylsulfonyl)pyrrolidin-3-yl)amino)-1H-indole-7-carboxamide (144); 2,3-dimethyl-4-(4-(vinylsulfonyl)piperazin-1-yl)-1H-indole-7-carboxamide (145); (S)-5-fluoro-2,3-dimethyl-4-(3-(vinylsulfonamido)piperidin-1-yl)-1H-indole-7-carboxamide (146); (S)-4-((1-cyanopyrrolidin-3-yl)amino)-5-fluoro-2,3-dimethyl-1H-indole-7-carboxamide (147); 4-(1-cyanopiperidin-3-yl)-2,3-dimethyl-1H-indole-7-carboxamide (148); 4-(1-cyanopyrrolidin-3-yl)-2,3-dimethyl-1H-indole-7-carboxamide (149); (S)-4-(3-cyanamidopiperidin-1-yl)-5-fluoro-2,3-dimethyl-1H-indole-7-carboxamide (150); 4-((1-cyanopiperidin-4-yl)amino)-5-fluoro-2,3-dimethyl-1H-indole-7-carboxamide (151); 4-(2-cyano-1,2,3,4-tetrahydroisoquinolin-5-yl)-5-fluoro-2,3-dimethyl-1H-indole-7-carboxamide (152); 4-(2-acryloyl-1,2,3,4-tetrahydroisoquinolin-5-yl)-5-fluoro-2,3-dimethyl-1H-indole-7-carboxamide, single enantiomers (153 and 154); 4-(4-acryloyl-3,4-dihydro-2H-benzo[b][1,4]oxazin-8-yl)-5-fluoro-2,3-dimethyl-1H-indole-7-carboxamide, single enantiomers (155 and 156); 4-(2-cyano-1,2,3,4-tetrahydroisoquinolin-5-yl)-5-fluoro-2,3-dimethyl-1H-indole-7-carboxamide, single enantiomers (157 and 158); cis-4-(1-acryloylhexahydro-1H-pyrrolo[3,4-b]pyridin-6(2H)-yl)-5-fluoro-2,3-dimethyl-1H-indole-7-carboxamide, single enantiomers (159 and 160); cis-4-(3-acryloyl-1a,2,3,7b-tetrahydro-1H-cyclopropa[c]quinolin-7-yl)-5-fluoro-2,3-dimethyl-1H-indole-7-carboxamide, single diastereomers (161 through 164); 4-(5-acryloylhexahydropyrrolo[3,4-b]pyrrol-1(2H)-yl)-5-fluoro-2,3-dimethyl-1H-indole-7-carboxamide, single enantiomers (165 and 166); 4-(1-acryloylhexahydropyrrolo[3,4-b]pyrrol-5(1H)-yl)-5-fluoro-2,3-dimethyl-1H-indole-7-carboxamide, single enantiomers (167 and 168); 4-(2-acryloyl-4-fluoro-1,2,3,4-tetrahydroisoquinolin-5-yl)-5-fluoro-2,3-dimethyl-1H-indole-7-carboxamide, single diastereomers (169 through 172); cis-4-(1-(but-2-ynoyl)hexahydro-1H-pyrrolo[3,4-b]pyridin-6(2H)-yl)-5-fluoro-2,3-dimethyl-1H-indole-7-carboxamide, single enantiomers (173 and 174); 4-(5-(but-2-ynoyl)hexahydropyrrolo[3,4-b]pyrrol-1(2H)-yl)-5-fluoro-2,3-dimethyl-1H-indole-7-carboxamide, single enantiomers (175 and 176); 4-(1-(but-2-ynoyl)hexahydropyrrolo[3,4-b]pyrrol-5(1H)-yl)-5-fluoro-2,3-dimethyl-1H-indole-7-carboxamide, single enantiomers (177 and 178); cis-4-(1-cyanohexahydro-1H-pyrrolo[3,4-b]pyridin-6(2H)-yl)-5-fluoro-2,3-dimethyl-1H-indole-7-carboxamide, single enantiomers (179 and 180); 5-fluoro-2,3-dimethyl-4-((6-vinylpyridin-3-yl)methyl)-1H-indole-7-carboxamide (181); 5-fluoro-2,3-dimethyl-4-((6-(prop-1-yn-1-yl)pyridin-3-yl)methyl)-1H-indole-7-carboxamide (182); 5-fluoro-2,3-dimethyl-4-(1-(6-vinylpyridin-3-yl)ethyl)-1H-indole-7-carboxamide, single enantiomers (183 and 184); 5-fluoro-2,3-dimethyl-4-((2-vinylpyridin-4-yl)methyl)-1H-indole-7-carboxamide (185); (RS)-4-(5-acryloyl-2,3,4,5-tetrahydrobenzo[b][1,4]oxazepin-9-yl)-5-fluoro-2,3-dimethyl-1H-indole-7-carboxamide (186); 4-(5-acryloyl-2,3,4,5-tetrahydrobenzo[b][1,4]oxazepin-9-yl)-5-fluoro-2,3-dimethyl-1H-indole-7-carboxamide, single enantiomers (187 and 188); (RS)-4-(2-acryloyl-7-fluoro-1,2,3,4-tetrahydroisoquinolin-5-yl)-5-fluoro-2,3-dimethyl-1H-indole-7-carboxamide (189); 4-(2-acryloyl-7-fluoro-1,2,3,4-tetrahydroisoquinolin-5-yl)-5-fluoro-2,3-dimethyl-1H-indole-7-carboxamide, single enantiomers (190 and 191); 4-(2-acryloyl-1,2,3,4-tetrahydroisoquinolin-6-yl)-5-fluoro-2,3-dimethyl-1H-indole-7-carboxamide (192); (RS)-4-(1-acryloylindolin-4-yl)-5-fluoro-2,3-dimethyl-1H-indole-7-carboxamide (193); (RS)-4-(4-acryloyl-3,4-dihydro-2H-benzo[b][1,4]thiazin-8-yl)-5-fluoro-2,3-dimethyl-1H-indole-7-carboxamide (194); 4-(4-acryloyl-3,4-dihydro-2H-benzo[b][1,4]thiazin-8-yl)-5-fluoro-2,3-dimethyl-1H-indole-7-carboxamide, single enantiomers (195 and 196); (RS)-4-(2-acryloyl-1,2,3,4-tetrahydroisoquinolin-5-yl)-5-fluoro-3-methyl-2-(trifluoromethyl)-1H-indole-7-carboxamide (197); 4-(2-acryloyl-1,2,3,4-tetrahydroisoquinolin-5-yl)-5-fluoro-3-methyl-2-(trifluoromethyl)-1H-indole-7-carboxamide, single enantiomers (198 and 199); (S)-4-(3-(N-cyclopropylbut-2-ynamido)piperidin-1-yl)-5-fluoro-2,3-dimethyl-1H-indole-7-carboxamide (200); 4-(4-(but-2-ynoyl)piperazin-1-yl)-5-fluoro-2,3-dimethyl-1H-indole-7-carboxamide (201); 4-(4-acryloylpiperazin-1-yl)-5-fluoro-2,3-dimethyl-1H-indole-7-carboxamide (202); 4-(2-(but-2-ynoyl)-1,2,3,4-tetrahydroisoquinolin-6-yl)-5-fluoro-2,3-dimethyl-1H-indole-7-carboxamide (203); (RS)-4-(2-acryloyl-1,2,3,4-tetrahydroisoquinolin-8-yl)-5-fluoro-2,3-dimethyl-1H-indole-7-carboxamide (204); 4-(2-acryloyl-1,2,3,4-tetrahydroisoquinolin-8-yl)-5-fluoro-2,3-dimethyl-1H-indole-7-carboxamide, single enantiomers (205 and 206); 4-(1-acryloylindolin-6-yl)-5-fluoro-2,3-dimethyl-1H-indole-7-carboxamide (207); 4-(2-acryloyl-1,2,3,4-tetrahydroisoquinolin-5-yl)-6-fluoro-2,3-dimethyl-1H-indole-7-carboxamide (208); (RS)-4-(2-acryloyl-1,2,3,4-tetrahydroisoquinolin-5-yl)-3-cyclopropyl-5-fluoro-2-methyl-1H-indole-7-carboxamide (209); 4-(2-acryloyl-1,2,3,4-tetrahydroisoquinolin-5-yl)-3-cyclopropyl-5-fluoro-2-methyl-1H-indole-7-carboxamide, single enantiomers (210 and 211); (RS)-4-(2-acryloyl-1,2,3,4-tetrahydroisoquinolin-5-yl)-5-fluoro-3-(4-fluorophenyl)-2-methyl-1H-indole-7-carboxamide (212); 4-(2-acryloyl-1,2,3,4-tetrahydroisoquinolin-5-yl)-5-fluoro-3-(4-fluorophenyl)-2-methyl-1H-indole-7-carboxamide, single enantiomers (213 and 214);

(RS)-4-(2-acryloyl-1,2,3,4-tetrahydroisoquinolin-5-yl)-5-fluoro-2-(4-fluorophenyl)-3-methyl-1H-indole-7-carboxamide (215); 4-(1-acryloyl-1,2,5,6-tetrahydropyridin-3-yl)-5-fluoro-2,3-dimethyl-1H-indole-7-carboxamide (216); (RS)-4-(1-acryloylpiperidin-3-yl)-5-fluoro-2,3-dimethyl-1H-indole-7-carboxamide (217); 4-(1-acryloylpiperidin-3-yl)-5-fluoro-2,3-dimethyl-1H-indole-7-carboxamide, single enantiomers (218 and 219); (RS)-4-(1-(but-2-ynoyl) piperidin-3-yl)-5-fluoro-2,3-dimethyl-1H-indole-7-carboxamide (220); 5-fluoro-2,3-dimethyl-4-((6-vinylpyridin-2-yl) methyl)-1H-indole-7-carboxamide (221); 5-fluoro-4-((5-fluoro-6-vinylpyridin-3-yl)methyl)-2,3-dimethyl-1H-indole-7-carboxamide (222); (S)-4-(3-(but-2-ynamido) piperidin-1-yl)-5-fluoro-2,3-dimethyl-1H-indole-7-carboxamide (223); 4-(2-acryloyl-1,2,3,4-tetrahydroisoquinolin-5-yl)-5-iodo-2,3-dimethyl-1H-indole-7-carboxamide (224); 4-(2-acryloyl-1,2,3,4-tetrahydroisoquinolin-5-yl)-2,3-dimethyl-1H-pyrrolo[2,3-c]pyridine-7-carboxamide (225); 4-(2-acryloyl-1,2,3,4-tetrahydroisoquinolin-5-yl)-2,3,5-trimethyl-1H-pyrrolo[2,3-c]pyridine-7-carboxamide (226); 4-(2-acryloyl-1,2,3,4-tetrahydroisoquinolin-5-yl)-2,3,5-trimethyl-1H-pyrrolo[2,3-c]pyridine-7-carboxamide (227 and 228); 4-(2-acryloyl-1,2,3,4-tetrahydroisoquinolin-5-yl)-5-cyano-2,3-dimethyl-1H-indole-7-carboxamide (229); 4-((1-acryloylpiperidin-4-yl) methyl)-5-fluoro-3-methyl-2-(trifluoromethyl)-1H-indole-7-carboxamide (230); 4-(2-acryloyl-4,4-difluoro-1,2,3,4-tetrahydroisoquinolin-5-yl)-5-fluoro-2,3-dimethyl-1H-indole-7-carboxamide (231 and 232); 4-(1-acryloyl-1,4,5,6-tetrahydropyridin-3-yl)-5-fluoro-2,3-dimethyl-1H-indole-7-carboxamide (233); 4-(1-acryloyl-2,5-dihydro-1H-pyrrol-3-yl)-5-fluoro-2,3-dimethyl-1H-indole-7-carboxamide (234); 4-(1-acryloyl-2,5-dihydro-1H-pyrrol-2-yl)-5-fluoro-2,3-dimethyl-1H-indole-7-carboxamide (235); 4-(1-acryloyl-1,2,3,6-tetrahydropyridin-4-yl)-5-fluoro-2,3-dimethyl-1H-indole-7-carboxamide (236); 4-(1-acryloyl-2,5-dihydro-1H-pyrrol-3-yl)-5-fluoro-3-methyl-2-(trifluoromethyl)-1H-indole-7-carboxamide (237); 4-(1-(but-2-ynoyl)-2,5-dihydro-1H-pyrrol-3-yl)-5-fluoro-2,3-dimethyl-1H-indole-7-carboxamide (238); 4-(2-acryloyl-1,2,3,4-tetrahydroisoquinolin-5-yl)-5-chloro-2,3-dimethyl-1H-indole-7-carboxamide, racemate (239); 4-(2-acryloyl-1,2,3,4-tetrahydroisoquinolin-5-yl)-5-chloro-2,3-dimethyl-1H-indole-7-carboxamide, atropisomer A (240); 4-(2-acryloyl-1,2,3,4-tetrahydroisoquinolin-5-yl)-2,3-dimethyl-1H-indole-7-carboxamide (241); (S)-5-fluoro-2,3-dimethyl-4-(3-propiolamidopiperidin-1-yl)-1H-indole-7-carboxamide (242); (R)-4-(3-(but-2-ynamido)piperidin-1-yl)-5-fluoro-2,3-dimethyl-1H-indole-7-carboxamide (243); 4-(6-acryloyl-3,6-diazabicyclo[3.2.0]heptan-3-yl)-5-fluoro-2,3-dimethyl-1H-indole-7-carboxamide (244); 4-(6-(but-2-ynoyl)-3,6-diazabicyclo[3.2.0]heptan-3-yl)-5-fluoro-2,3-dimethyl-1H-indole-7-carboxamide (245); 4-(7-acryloyl-2,7-diazaspiro[4.4]nonan-2-yl)-5-fluoro-2,3-dimethyl-1H-indole-7-carboxamide (246); 4-(7-(but-2-ynoyl)-2,7-diazaspiro[4.4]nonan-2-yl)-5-fluoro-2,3-dimethyl-1H-indole-7-carboxamide (247); 5-fluoro-2,3-dimethyl-4-(2-vinylpyridin-3-yl)-1H-indole-7-carboxamide (248); 5-fluoro-3-methyl-2-(trifluoromethyl)-4-((6-vinylpyridin-3-yl)methyl)-1H-indole-7-carboxamide (249); 4-(1-acryloylpyrrolidin-3-yl)-5-fluoro-3-methyl-2-(trifluoromethyl)-1H-indole-7-carboxamide (250); 4-(1-acryloylpyrrolidin-2-yl)-5-fluoro-2,3-dimethyl-1H-indole-7-carboxamide (251); 4-(1-acryloylpyrrolidin-3-yl)-5-fluoro-2,3-dimethyl-1H-indole-7-carboxamide (252); 5-fluoro-2,3-dimethyl-4-(3-vinyl-5,6-dihydroisoquinolin-8-yl)-1H-indole-7-carboxamide (253); 4-(1-(but-2-ynoyl)-2,5-dihydro-1H-pyrrol-3-yl)-5-fluoro-3-methyl-2-(trifluoromethyl)-1H-indole-7-carboxamide (254); 4-(1-acryloyloctahydro-6H-pyrrolo[3,4-b]pyridin-6-yl)-5-fluoro-3-methyl-2-(trifluoromethyl)-1H-indole-7-carboxamide (255); 4-(1-(but-2-ynoyl)octahydro-6H-pyrrolo[3,4-b]pyridin-6-yl)-5-fluoro-3-methyl-2-(trifluoromethyl)-1H-indole-7-carboxamide (256); 4-((1-acryloylpiperidin-4-ylidene)methyl)-5-fluoro-2,3-dimethyl-1H-indole-7-carboxamide (257); 4-((1-acryloylpiperidin-4-yl)methyl)-5-fluoro-2,3-dimethyl-1H-indole-7-carboxamide (258); 4-((1-acryloylpyrrolidin-3-yl)methyl)-5-fluoro-2,3-dimethyl-1H-indole-7-carboxamide (259); 4-((1-(but-2-ynoyl)piperidin-4-yl)methyl)-5-fluoro-2,3-dimethyl-1H-indole-7-carboxamide (260); 4-((1-(but-2-ynoyl)piperidin-4-ylidene) methyl)-5-fluoro-2,3-dimethyl-1H-indole-7-carboxamide (261); 4-((1-(but-2-ynoyl) pyrrolidin-3-yl)methyl)-5-fluoro-2,3-dimethyl-1H-indole-7-carboxamide (262); 5-fluoro-4-(3-fluoro-2-vinylpyridin-4-yl)-2,3-dimethyl-1H-indole-7-carboxamide (263); 4-(2-acryloyl-1,2,3,4-tetrahydroisoquinolin-5-yl)-5-chloro-2,3-dimethyl-1H-indole-7-carboxamide, atropisomer B (264); or 4-(2-(but-2-ynoyl)-1,2,3,4-tetrahydroisoquinolin-5-yl)-5-chloro-2,3-dimethyl-1H-indole-7-carboxamide (265).

One embodiment provides a compound of Formula (I) or a salt thereof, wherein said compound is 4-(3-acrylamido-2-methylphenyl)-3-methyl-1H-indole-7-carboxamide (1); 2,3-dimethyl-4-(3-(vinylsulfonyl)phenyl)-1H-indole-7-carboxamide (2); 5-fluoro-2,3-dimethyl-4-(3-(N-methylacrylamido)phenyl)-1H-indole-7-carboxamide (3); 2,3-dimethyl-4-(3-(vinylsulfonamido)phenyl)-1H-indole-7-carboxamide (4); 4-(3-acrylamido-2-methylphenyl)-2,3-dimethyl-1H-indole-7-carboxamide (5); 4-(3-acrylamido-2-methylphenyl)-2-methyl-1H-indole-7-carboxamide (7); (E)-4-(3-(4-(dimethylamino)but-2-enamido)-2-methylphenyl)-2,3-dimethyl-1H-indole-7-carboxamide (16); 2,3-dimethyl-4-(2-methyl-3-(N-methylacrylamido)phenyl)-1H-indole-7-carboxamide (20); 4-(3-acrylamidophenyl)-2,3-dimethyl-1H-indole-7-carboxamide (22); 2,3-dimethyl-4-(2-methyl-3-(N-methylvinylsulfonamido)phenyl)-1H-indole-7-carboxamide (23); 3-methyl-4-(2-methyl-3-(N-methylvinylsulfonamido)phenyl)-1H-indole-7-carboxamide (24); 2,3-dimethyl-4-(3-(N-methylvinylsulfonamido)phenyl)-1H-indole-7-carboxamide (25); 5-fluoro-2,3-dimethyl-4-(3-(N-methylvinylsulfonamido) phenyl)-1H-indole-7-carboxamide (26); 5-chloro-2,3-dimethyl-4-(3-(N-methylvinylsulfonamido)phenyl)-1H-indole-7-carboxamide (27); 3-methyl-4-(3-(N-methylvinylsulfonamido)phenyl)-1H-indole-7-carboxamide (28); 2,3-dimethyl-4-(3-(N-methylacrylamido)phenyl)-1H-indole-7-carboxamide (29); 3-methyl-4-(3-(N-methylacrylamido)phenyl)-1H-indole-7-carboxamide (30); 3-methyl-4-(2-methyl-3-(vinylsulfonamido)phenyl)-1H-indole-7-carboxamide (31); 4-(2-fluoro-3-(N-methylacrylamido)phenyl)-2,3-dimethyl-1H-indole-7-carboxamide (32); 3-methyl-4-(3-(vinylsulfonamido) phenyl)-1H-indole-7-carboxamide (33); 2,3-dimethyl-4-(2-methyl-3-(vinylsulfonamido)phenyl)-1H-indole-7-carboxamide (34); 4-(1-acryloylindolin-6-yl)-2,3-dimethyl-1H-indole-7-carboxamide (38); 2,3-dimethyl-4-(1-(vinylsulfonyl)indolin-6-yl)-1H-indole-7-carboxamide (39); (RS)-2,3-dimethyl-4-(3-(N-methylacrylamido) piperidin-1-yl)-1H-indole-7-carboxamide (78); 4-((1-acryloylpiperidin-4-yl)amino)-2,3-dimethyl-1H-indole-7-carboxamide (79); 4-(1-acryloylpiperidin-3-yl)-2,3-dimethyl-1H-indole-7-carboxamide (80); 4-(3-acrylamidopyrrolidin-1-yl)-2,3-dimethyl-1H-indole-7-carboxamide (82); 4-(3-acrylamidopiperidin-1-yl)-2,3-dimethyl-1H-indole-7-carboxamide (83); 4-((1-acryloylpyrrolidin-3-yl)amino)-2,3-dimethyl-1H-indole-7-carboxamide (86); (S)-4-((1-acryloylpyrrolidin-3-yl)

amino)-5-fluoro-2,3-dimethyl-1H-indole-7-carboxamide (88); (S)-4-(3-acrylamidopiperidin-1-yl)-5-fluoro-2,3-dimethyl-1H-indole-7-carboxamide (89); 4-((1-acryloylpiperidin-4-yl)amino)-5-fluoro-2,3-dimethyl-1H-indole-7-carboxamide (92); 4-(1-acryloylpiperidin-3-yl)-3-methyl-1H-indole-7-carboxamide (93); (S)-4-((1-acryloylpyrrolidin-3-yl)(methyl)amino)-2,3-dimethyl-1H-indole-7-carboxamide (94); (RS)-4-(2-acryloyl-1,2,3,4-tetrahydroisoquinolin-5-yl)-5-fluoro-2,3-dimethyl-1H-indole-7-carboxamide (95); (S)-4-((1-acryloylpyrrolidin-3-yl)(methyl)amino)-5-fluoro-2,3-dimethyl-1H-indole-7-carboxamide (96); 4-(1-acryloyl-1,2,3,4-tetrahydroquinolin-6-yl)-5-fluoro-2,3-dimethyl-1H-indole-7-carboxamide (97); cis-4-(5-acryloylhexahydropyrrolo[3,4-c]pyrrol-2(1H)-yl)-5-fluoro-2,3-dimethyl-1H-indole-7-carboxamide (98); 4-(1-acryloyl-1,2,3,4-tetrahydroquinolin-7-yl)-5-fluoro-2,3-dimethyl-1H-indole-7-carboxamide (99); (S)-4-(3-acrylamidopyrrolidin-1-yl)-5-fluoro-2,3-dimethyl-1H-indole-7-carboxamide (100); (RS)-4-(4-acryloyl-3,4-dihydro-2H-benzo[b][1,4]oxazin-8-yl)-5-fluoro-2,3-dimethyl-1H-indole-7-carboxamide (102); (RS)-2,3-dimethyl-4-((1-propioloylpyrrolidin-3-yl)amino)-1H-indole-7-carboxamide (103); 2,3-dimethyl-4-(3-(N-methylpropiolamido)piperidin-1-yl)-1H-indole-7-carboxamide (105); 2,3-dimethyl-4-(3-(N-methylbut-2-ynamido) piperidin-1-yl)-1H-indole-7-carboxamide (108); (S)-2,3-dimethyl-4-(3-(3-phenylpropiolamido)piperidin-1-yl)-1H-indole-7-carboxamide (109); (S)-2,3-dimethyl-4-(3-(3-(trimethylsilyl)propiolamido)piperidin-1-yl)-1H-indole-7-carboxamide (110); (S)-4-(3-(4-hydroxy-4-methylpent-2-ynamido)piperidin-1-yl)-2,3-dimethyl-1H-indole-7-carboxamide (111); (S)-2,3-dimethyl-4-(3-(pent-2-ynamido)piperidin-1-yl)-1H-indole-7-carboxamide (112); (S)-4-(3-(hex-2-ynamido)piperidin-1-yl)-2,3-dimethyl-1H-indole-7-carboxamide (113); 2,3-dimethyl-4-((1-propioloylpiperidin-4-yl)amino)-1H-indole-7-carboxamide (114); (S)-2,3-dimethyl-4-(3-propiolamidopiperidin-1-yl)-1H-indole-7-carboxamide (115); (S)-4-(3-(but-2-ynamido)piperidin-1-yl)-2,3-dimethyl-1H-indole-7-carboxamide (116); (R)-2,3-dimethyl-4-(3-propiolamidopiperidin-1-yl)-1H-indole-7-carboxamide (117); (R)-4-(3-(but-2-ynamido)piperidin-1-yl)-2,3-dimethyl-1H-indole-7-carboxamide (118); (R)-2,3-dimethyl-4-(3-propiolamidopyrrolidin-1-yl)-1H-indole-7-carboxamide (119); (R)-4-(3-(but-2-ynamido)pyrrolidin-1-yl)-2,3-dimethyl-1H-indole-7-carboxamide (120); (S)-4-(3-(but-2-ynamido)piperidin-1-yl)-5-fluoro-2,3-dimethyl-1H-indole-7-carboxamide (123); (S)-5-fluoro-2,3-dimethyl-4-(3-(N-methylbut-2-ynamido) piperidin-1-yl)-1H-indole-7-carboxamide (125); (S)-5-fluoro-2,3-dimethyl-4-(3-(pent-2-ynamido)piperidin-1-yl)-1H-indole-7-carboxamide (126); (S)-5-fluoro-2,3-dimethyl-4-(3-(N-methylpent-2-ynamido)piperidin-1-yl)-1H-indole-7-carboxamide (127); (S)-5-fluoro-4-(3-(hex-2-ynamido)piperidin-1-yl)-2,3-dimethyl-1H-indole-7-carboxamide (128); (S)-4-(3-(N-ethylbut-2-ynamido)piperidin-1-yl)-5-fluoro-2,3-dimethyl-1H-indole-7-carboxamide (130); 4-(2-acryloyl-1,2,3,4-tetrahydroisoquinolin-7-yl)-5-fluoro-2,3-dimethyl-1H-indole-7-carboxamide (131); (RS)-4-(2-acryloylisoindolin-4-yl)-5-fluoro-2,3-dimethyl-1H-indole-7-carboxamide (132); (S)-4-(3-(but-2-ynamido)pyrrolidin-1-yl)-5-fluoro-2,3-dimethyl-1H-indole-7-carboxamide (135); (S)-4-(3-(3-cyclopropylpropiolamido)piperidin-1-yl)-5-fluoro-2,3-dimethyl-1H-indole-7-carboxamide (136); (RS)-2,3-dimethyl-4-(3-(N-methylvinylsulfonamido)piperidin-1-yl)-1H-indole-7-carboxamide (138); 2,3-dimethyl-4-(3-(vinylsulfonamido)piperidin-1-yl)-1H-indole-7-carboxamide (139); 2,3-dimethyl-4-(3-(vinylsulfonamido)pyrrolidin-1-yl)-1H-indole-7-carboxamide (140); (S)-2,3-dimethyl-4-(3-(vinylsulfonamido)piperidin-1-yl)-1H-indole-7-carboxamide (141); (R)-2,3-dimethyl-4-(3-(vinylsulfonamido)pyrrolidin-1-yl)-1H-indole-7-carboxamide (142); (R)-2,3-dimethyl-4-(3-(vinylsulfonamido) piperidin-1-yl)-1H-indole-7-carboxamide (143); 2,3-dimethyl-4-((1-(vinylsulfonyl)pyrrolidin-3-yl)amino)-1H-indole-7-carboxamide (144); 2,3-dimethyl-4-(4-(vinylsulfonyl)piperazin-1-yl)-1H-indole-7-carboxamide (145); (S)-5-fluoro-2,3-dimethyl-4-(3-(vinylsulfonamido)piperidin-1-yl)-1H-indole-7-carboxamide (146); (S)-4-((1-cyanopyrrolidin-3-yl)amino)-5-fluoro-2,3-dimethyl-1H-indole-7-carboxamide (147); (S)-4-(3-cyanamidopiperidin-1-yl)-5-fluoro-2,3-dimethyl-1H-indole-7-carboxamide (150); 4-(2-acryloyl-1,2,3,4-tetrahydroisoquinolin-5-yl)-5-fluoro-2,3-dimethyl-1H-indole-7-carboxamide, single enantiomers (153 and 154); 4-(4-acryloyl-3,4-dihydro-2H-benzo[b][1,4]oxazin-8-yl)-5-fluoro-2,3-dimethyl-1H-indole-7-carboxamide, single enantiomers (155 and 156); cis-4-(1-acryloylhexahydro-1H-pyrrolo[3,4-b]pyridin-6(2H)-yl)-5-fluoro-2,3-dimethyl-1H-indole-7-carboxamide, single enantiomers (159 and 160); cis-4-(3-acryloyl-1a,2,3,7b-tetrahydro-1H-cyclopropa[c]quinolin-7-yl)-5-fluoro-2,3-dimethyl-1H-indole-7-carboxamide, single diastereomers (161 and 164); 4-(5-acryloylhexahydropyrrolo[3,4-b]pyrrol-1(2H)-yl)-5-fluoro-2,3-dimethyl-1H-indole-7-carboxamide, single enantiomers (165 and 166); 4-(1-acryloylhexahydropyrrolo[3,4-b]pyrrol-5(1H)-yl)-5-fluoro-2,3-dimethyl-1H-indole-7-carboxamide, single enantiomers (167 and 168); 4-(2-acryloyl-4-fluoro-1,2,3,4-tetrahydroisoquinolin-5-yl)-5-fluoro-2,3-dimethyl-1H-indole-7-carboxamide, single diastereomers (170 through 172); cis-4-(1-(but-2-ynoyl)hexahydro-1H-pyrrolo[3,4-b]pyridin-6(2H)-yl)-5-fluoro-2,3-dimethyl-1H-indole-7-carboxamide, single enantiomers (173 and 174); 4-(1-(but-2-ynoyl) hexahydropyrrolo[3,4-b]pyrrol-5(1H)-yl)-5-fluoro-2,3-dimethyl-1H-indole-7-carboxamide, single enantiomers (177 and 178); 5-fluoro-2,3-dimethyl-4-((6-vinylpyridin-3-yl)methyl)-1H-indole-7-carboxamide (181); 5-fluoro-2,3-dimethyl-4-((6-(prop-1-yn-1-yl)pyridin-3-yl)methyl)-1H-indole-7-carboxamide (182); 5-fluoro-2,3-dimethyl-4-(1-(6-vinylpyridin-3-yl)ethyl)-1H-indole-7-carboxamide, single enantiomers (183 and 184); 5-fluoro-2,3-dimethyl-4-((2-vinylpyridin-4-yl)methyl)-1H-indole-7-carboxamide (185); (RS)-4-(5-acryloyl-2,3,4,5-tetrahydrobenzo[b][1,4]oxazepin-9-yl)-5-fluoro-2,3-dimethyl-1H-indole-7-carboxamide (186); 4-(5-acryloyl-2,3,4,5-tetrahydrobenzo[b][1,4]oxazepin-9-yl)-5-fluoro-2,3-dimethyl-1H-indole-7-carboxamide, single enantiomer (188); (RS)-4-(2-acryloyl-7-fluoro-1,2,3,4-tetrahydroisoquinolin-5-yl)-5-fluoro-2,3-dimethyl-1H-indole-7-carboxamide (189); 4-(2-acryloyl-7-fluoro-1,2,3,4-tetrahydroisoquinolin-5-yl)-5-fluoro-2,3-dimethyl-1H-indole-7-carboxamide, single enantiomer (191); (RS)-4-(1-acryloylindolin-4-yl)-5-fluoro-2,3-dimethyl-1H-indole-7-carboxamide (193); (RS)-4-(4-acryloyl-3,4-dihydro-2H-benzo[b][1,4]thiazin-8-yl)-5-fluoro-2,3-dimethyl-1H-indole-7-carboxamide (194); 4-(4-acryloyl-3,4-dihydro-2H-benzo[b][1,4]thiazin-8-yl)-5-fluoro-2,3-dimethyl-1H-indole-7-carboxamide, single enantiomers (195 and 196); (RS)-4-(2-acryloyl-1,2,3,4-tetrahydroisoquinolin-5-yl)-5-fluoro-3-methyl-2-(trifluoromethyl)-1H-indole-7-carboxamide (197); 4-(2-acryloyl-1,2,3,4-tetrahydroisoquinolin-5-yl)-5-fluoro-3-methyl-2-(trifluoromethyl)-1H-indole-7-carboxamide, single enantiomer (199); (S)-4-(3-(N-cyclopropylbut-2-ynamido)piperidin-1-yl)-5-fluoro-2,3-dimethyl-1H-indole-7-carboxamide (200); (RS)-4-(2-acryloyl-1,2,3,4-tetrahydroisoquinolin-8-yl)-5-fluoro-2,3- dimethyl-1H-indole-7-carboxamide (204); 4-(2-acryloyl-1,2,3,4-tetrahydroisoquinolin-8-yl)-5-fluoro-2,3-dimethyl-1H-indole-7-carboxamide, single enantiomer (206); 4-(1-acryloylindolin-6-yl)-5-fluoro-2,3-dimethyl-1H-indole-7-carboxamide (207); 4-(2-acryloyl-1,2,3,4-tetrahydroisoquinolin-5-yl)-6-fluoro-2,3-dimethyl-1H-indole-7-carboxamide (208); (RS)-4-(2-acryloyl-1,2,3,4-tetrahydroisoquinolin-5-yl)-3-cyclopropyl-5-fluoro-2-methyl-1H-indole-7-carboxamide (209); 4-(2-acryloyl-1,2,3,4-tetrahydroisoquinolin-5-yl)-3-cyclopropyl-5-fluoro-2-methyl-1H-indole-7-carboxamide, single enantiomer (211); (RS)-4-(2-acryloyl-1,2,3,4-tetrahydroisoquinolin-5-yl)-5-fluoro-3-(4-fluorophenyl)-2-methyl-1H-indole-7-carboxamide (212); 4-(2-acryloyl-1,2,3,4-tetrahydroisoquinolin-5-yl)-5-fluoro-3-(4-fluorophenyl)-2-methyl-1H-indole-7-carboxamide, single enantiomer (213); (RS)-4-(2-acryloyl-1,2,3,4-tetrahydroisoquinolin-5-yl)-5-fluoro-2-(4-fluorophenyl)-3-methyl-1H-indole-7-carboxamide (215); 4-(1-acryloyl-1,2,5,6-tetrahydropyridin-3-yl)-5-fluoro-2,3-dimethyl-1H-indole-7-carboxamide (216); (RS)-4-(1-acryloylpiperidin-3-yl)-5-fluoro-2,3-dimethyl-1H-indole-7-carboxamide (217); or 4-(1-acryloylpiperidin-3-yl)-5-fluoro-2,3-dimethyl-1H-indole-7-carboxamide, single enantiomer (219).

One embodiment provides a compound of Formula (I) or a salt thereof, wherein $R_3$ is F and said compound is 5-fluoro-2,3-dimethyl-4-(3-(N-methylacrylamido)phenyl)-1H-indole-7-carboxamide (3); 5-fluoro-2,3-dimethyl-4-(3-(N-methylvinylsulfonamido) phenyl)-1H-indole-7-carboxamide (26); 5-fluoro-2,3-dimethyl-4-(3-(3-methyl-2-oxo-2,5-dihydro-1H-pyrrol-1-yl)phenyl)-1H-indole-7-carboxamide (37); (S)-4-((1-acryloylpyrrolidin-3-yl)amino)-5-fluoro-2,3-dimethyl-1H-indole-7-carboxamide (88); (S)-4-(3-acrylamidopiperidin-1-yl)-5-fluoro-2,3-dimethyl-1H-indole-7-carboxamide (89); 4-((1-acryloylpiperidin-4-yl)amino)-5-fluoro-2,3-dimethyl-1H-indole-7-carboxamide (92); (RS)-4-(2-acryloyl-1,2,3,4-tetrahydroisoquinolin-5-yl)-5-fluoro-2,3-dimethyl-1H-indole-7-carboxamide (95); (S)-4-((1-acryloylpyrrolidin-3-yl)(methyl)amino)-5-fluoro-2,3-dimethyl-1H-indole-7-carboxamide (96); 4-(1-acryloyl-1,2,3,4-tetrahydroquinolin-6-yl)-5-fluoro-2,3-dimethyl-1H-indole-7-carboxamide (97); cis-4-(5-acryloylhexahydropyrrolo[3,4-c]pyrrol-2(1H)-yl)-5-fluoro-2,3-dimethyl-1H-indole-7-carboxamide (98); 4-(1-acryloyl-1,2,3,4-tetrahydroquinolin-7-yl)-5-fluoro-2,3-dimethyl-1H-indole-7-carboxamide (99); (S)-4-(3-acrylamidopyrrolidin-1-yl)-5-fluoro-2,3-dimethyl-1H-indole-7-carboxamide (100); 4-(2-acryloylisoindolin-5-yl)-5-fluoro-2,3-dimethyl-1H-indole-7-carboxamide (101); (RS)-4-(4-acryloyl-3,4-dihydro-2H-benzo[b][1,4]oxazin-8-yl)-5-fluoro-2,3-dimethyl-1H-indole-7-carboxamide (102); 4-((1-(but-2-ynoyl)piperidin-4-yl)amino)-5-fluoro-2,3-dimethyl-1H-indole-7-carboxamide (122); (S)-4-(3-(but-2-ynamido)piperidin-1-yl)-5-fluoro-2,3-dimethyl-1H-indole-7-carboxamide (123); (S)-5-fluoro-2,3-dimethyl-4-(3-(N-methylbut-2-ynamido)piperidin-1-yl)-1H-indole-7-carboxamide (125); (S)-5-fluoro-2,3-dimethyl-4-(3-(pent-2-ynamido) piperidin-1-yl)-1H-indole-7-carboxamide (126); (S)-5-fluoro-2,3-dimethyl-4-(3-(N-methylpent-2-ynamido) piperidin-1-yl)-1H-indole-7-carboxamide (127); (S)-5-fluoro-4-(3-(hex-2-ynamido)piperidin-1-yl)-2,3-dimethyl-1H-indole-7-carboxamide (128); 4-(2-(but-2-ynoyl)-1,2,3,4-tetrahydroisoquinolin-5-yl)-5-fluoro-2,3-dimethyl-1H-indole-7-carboxamide (129); (S)-4-(3-(N-ethylbut-2-ynamido)piperidin-1-yl)-5-fluoro-2,3-dimethyl-1H-indole-7-carboxamide (130); 4-(2-acryloyl-1,2,3,4-tetrahydroisoquinolin-7-yl)-5-fluoro-2,3-dimethyl-1H-indole-7-carboxamide (131); (RS)-4-(2-acryloylisoindolin-4-yl)-5-fluoro-2,3-dimethyl-1H-indole-7-carboxamide (132); (RS)-4-(2-(but-2-ynoyl)isoindolin-4-yl)-5-fluoro-2,3-dimethyl-1H-indole-7-carboxamide (133); 4-(2-(but-2-ynoyl)-1,2,3,4-tetrahydroisoquinolin-7-yl)-5-fluoro-2,3-dimethyl-1H-indole-7-carboxamide (134); (S)-4-(3-(but-2-ynamido)pyrrolidin-1-yl)-5-fluoro-2,3-dimethyl-1H-indole-7-carboxamide (135); (S)-4-(3-(3-cyclopropylpropiolamido)piperidin-1-yl)-5-fluoro-2,3-dimethyl-1H-indole-7-carboxamide (136); 4-(2-(but-2-ynoyl)isoindolin-5-yl)-5-fluoro-2,3-dimethyl-1H-indole-7-carboxamide (137); (S)-5-fluoro-2,3-dimethyl-4-(3-(vinylsulfonamido)piperidin-1-yl)-1H-indole-7-carboxamide (146); (S)-4-((1-cyanopyrrolidin-3-yl)amino)-5-fluoro-2,3-dimethyl-1H-indole-7-carboxamide (147); (S)-4-(3-cyanamidopiperidin-1-yl)-5-fluoro-2,3-dimethyl-1H-indole-7-carboxamide (150); 4-((1-cyanopiperidin-4-yl)amino)-5-fluoro-2,3-dimethyl-1H-indole-7-carboxamide (151); 4-(2-cyano-1,2,3,4-tetrahydroisoquinolin-5-yl)-5-fluoro-2,3-dimethyl-1H-indole-7-carboxamide (152); 4-(2-acryloyl-1,2,3,4-tetrahydroisoquinolin-5-yl)-5-fluoro-2,3-dimethyl-1H-indole-7-carboxamide, single enantiomers (153 and 154); 4-(4-acryloyl-3,4-dihydro-2H-benzo[b][1,4]oxazin-8-yl)-5-fluoro-2,3-dimethyl-1H-indole-7-carboxamide, single enantiomers (155 and 156); 4-(2-cyano-1,2,3,4-tetrahydroisoquinolin-5-yl)-5-fluoro-2,3-dimethyl-1H-indole-7-carboxamide, single enantiomers (157 and 158); cis-4-(1-acryloylhexahydro-1H-pyrrolo[3,4-b]pyridin-6(2H)-yl)-5-fluoro-2,3-dimethyl-1H-indole-7-carboxamide, single enantiomers (159 and 160); cis-4-(3-acryloyl-1a,2,3,7b-tetrahydro-1H-cyclopropa[c]quinolin-7-yl)-5-fluoro-2,3-dimethyl-1H-indole-7-carboxamide, single diastereomers (161 through 164); 4-(5-acryloylhexahydropyrrolo [3,4-b]pyrrol-1(2H)-yl)-5-fluoro-2,3-dimethyl-1H-indole-7-carboxamide, single enantiomers (165 and 166); 4-(1-acryloylhexahydropyrrolo[3,4-b]pyrrol-5(1H)-yl)-5-fluoro-2,3-dimethyl-1H-indole-7-carboxamide, single enantiomers (167 and 168); 4-(2-acryloyl-4-fluoro-1,2,3,4-tetrahydroisoquinolin-5-yl)-5-fluoro-2,3-dimethyl-1H-indole-7-carboxamide, single diastereomers (169 through 172); cis-4-(1-(but-2-ynoyl)hexahydro-1H-pyrrolo[3,4-b]pyridin-6(2H)-yl)-5-fluoro-2,3-dimethyl-1H-indole-7-carboxamide, single enantiomers (173 and 174); 4-(5-(but-2-ynoyl)hexahydropyrrolo[3,4-b]pyrrol-1(2H)-yl)-5-fluoro-2,3-dimethyl-1H-indole-7-carboxamide, single enantiomers (175 and 176); 4-(1-(but-2-ynoyl)hexahydropyrrolo[3,4-b]pyrrol-5(1H)-yl)-5-fluoro-2,3-dimethyl-1H-indole-7-carboxamide, single enantiomers (177 and 178); cis-4-(1-cyanohexahydro-1H-pyrrolo[3,4-b]pyridin-6(2H)-yl)-5-fluoro-2,3-dimethyl-1H-indole-7-carboxamide, single enantiomers (179 and 180); 5-fluoro-2,3-dimethyl-4-((6-vinylpyridin-3-yl)methyl)-1H-indole-7-carboxamide (181); 5-fluoro-2,3-dimethyl-4-((6-(prop-1-yn-1-yl)pyridin-3-yl)methyl)-1H-indole-7-carboxamide (182); 5-fluoro-2,3-dimethyl-4-(1-(6-vinylpyridin-3-yl)ethyl)-1H-indole-7-carboxamide, single enantiomers (183 and 184); 5-fluoro-2,3-dimethyl-4-((2-vinylpyridin-4-yl)methyl)-1H-indole-7-carboxamide (185); (RS)-4-(5-acryloyl-2,3,4,5-tetrahydrobenzo[b][1,4]oxazepin-9-yl)-5-fluoro-2,3-dimethyl-1H-indole-7-carboxamide (186); 4-(5-acryloyl-2,3,4,5-tetrahydrobenzo[b][1,4]oxazepin-9-yl)-5-fluoro-2,3-dimethyl-1H-indole-7-carboxamide, single enantiomers (187 and 188); (RS)-4-(2-acryloyl-7-fluoro-1,2,3,4-tetrahydroisoquinolin-5-yl)-5-fluoro-2,3-dimethyl-1H-indole-7-carboxamide (189); 4-(2-acryloyl-7-fluoro-1,2,3,4-tetrahydroisoquinolin-5-yl)-5-fluoro-2,3-dimethyl-1H-indole-7-carboxamide, single enantiomers (190 and 191); 4-(2-acryloyl-1,2,3,4-tetrahydroisoquinolin-6-yl)-5-fluoro- 2,3-dimethyl-1H-indole-7-carboxamide (192); (RS)-4-(1-acryloylindolin-4-yl)-5-fluoro-2,3-dimethyl-1H-indole-7-carboxamide (193); (RS)-4-(4-acryloyl-3,4-dihydro-2H-benzo[b][1,4]thiazin-8-yl)-5-fluoro-2,3-dimethyl-1H-indole-7-carboxamide (194); 4-(4-acryloyl-3,4-dihydro-2H-benzo[b][1,4]thiazin-8-yl)-5-fluoro-2,3-dimethyl-1H-indole-7-carboxamide, single enantiomers (195 and 196); (RS)-4-(2-acryloyl-1,2,3,4-tetrahydroisoquinolin-5-yl)-5-fluoro-3-methyl-2-(trifluoromethyl)-1H-indole-7-carboxamide (197); 4-(2-acryloyl-1,2,3,4-tetrahydroisoquinolin-5-yl)-5-fluoro-3-methyl-2-(trifluoromethyl)-1H-indole-7-carboxamide, single enantiomers (198 and 199); (S)-4-(3-(N-cyclopropylbut-2-ynamido)piperidin-1-yl)-5-fluoro-2,3-dimethyl-1H-indole-7-carboxamide (200); 4-(4-(but-2-ynoyl)piperazin-1-yl)-5-fluoro-2,3-dimethyl-1H-indole-7-carboxamide (201); 4-(4-acryloylpiperazin-1-yl)-5-fluoro-2,3-dimethyl-1H-indole-7-carboxamide (202); 4-(2-(but-2-ynoyl)-1,2,3,4-tetrahydroisoquinolin-6-yl)-5-fluoro-2,3-dimethyl-1H-indole-7-carboxamide (203); (RS)-4-(2-acryloyl-1,2,3,4-tetrahydroisoquinolin-8-yl)-5-fluoro-2,3-dimethyl-1H-indole-7-carboxamide (204); 4-(2-acryloyl-1,2,3,4-tetrahydroisoquinolin-8-yl)-5-fluoro-2,3-dimethyl-1H-indole-7-carboxamide, single enantiomers (205 and 206); or 4-(1-acryloylindolin-6-yl)-5-fluoro-2,3-dimethyl-1H-indole-7-carboxamide (207); One embodiment provides a compound of Formula (I) or a salt thereof, wherein $R_3$ is F and said compound is (RS)-4-(2-acryloyl-1,2,3,4-tetrahydroisoquinolin-5-yl)-5-fluoro-3-(4-fluorophenyl)-2-methyl-1H-indole-7-carboxamide (212); 4-(2-acryloyl-1,2,3,4-tetrahydroisoquinolin-5-yl)-5-fluoro-3-(4-fluorophenyl)-2-methyl-1H-indole-7-carboxamide, single enantiomers (213 and 214); (RS)-4-(2-acryloyl-1,2,3,4-tetrahydroisoquinolin-5-yl)-5-fluoro-2-(4-fluorophenyl)-3-methyl-1H-indole-7-carboxamide (215); 4-(1-acryloyl-1,2,5,6-tetrahydropyridin-3-yl)-5-fluoro-2,3-dimethyl-1H-indole-7-carboxamide (216); (RS)-4-(1-acryloylpiperidin-3-yl)-5-fluoro-2,3-dimethyl-1H-indole-7-carboxamide (217); 4-(1-acryloylpiperidin-3-yl)-5-fluoro-2,3-dimethyl-1H-indole-7-carboxamide, single enantiomers (218 and 219); (RS)-4-(1-(but-2-ynoyl)piperidin-3-yl)-5-fluoro-2,3-dimethyl-1H-indole-7-carboxamide (220); 5-fluoro-2,3-dimethyl-4-((6-vinylpyridin-2-yl)methyl)-1H-indole-7-carboxamide (221); or 5-fluoro-4-((5-fluoro-6-vinylpyridin-3-yl)methyl)-2,3-dimethyl-1H-indole-7-carboxamide (222).

One embodiment provides a compound of Formula (I) or a salt thereof, wherein $R_3$ is F and said compound is (S)-4-(3-(but-2-ynamido)piperidin-1-yl)-5-fluoro-2,3-dimethyl-1H-indole-7-carboxamide (223); 4-((1-acryloylpiperidin-4-yl)methyl)-5-fluoro-3-methyl-2-(trifluoromethyl)-1H-indole-7-carboxamide (230); 4-(2-acryloyl-4,4-difluoro-1,2,3,4-tetrahydroisoquinolin-5-yl)-5-fluoro-2,3-dimethyl-1H-indole-7-carboxamide (231 and 232); 4-(1-acryloyl-1,4,5,6-tetrahydropyridin-3-yl)-5-fluoro-2,3-dimethyl-1H-indole-7-carboxamide (233); 4-(1-acryloyl-2,5-dihydro-1H-pyrrol-3-yl)-5-fluoro-2,3-dimethyl-1H-indole-7-carboxamide (234); 4-(1-acryloyl-2,5-dihydro-1H-pyrrol-2-yl)-5-fluoro-2,3-dimethyl-1H-indole-7-carboxamide (235); 4-(1-acryloyl-1,2,3,6-tetrahydropyridin-4-yl)-5-fluoro-2,3-dimethyl-1H-indole-7-carboxamide (236); 4-(1-acryloyl-2,5-dihydro-1H-pyrrol-3-yl)-5-fluoro-3-methyl-2-(trifluoromethyl)-1H-indole-7-carboxamide (237); 4-(1-(but-2-ynoyl)-2,5-dihydro-1H-pyrrol-3-yl)-5-fluoro-2,3-dimethyl-1H-indole-7-carboxamide (238); (S)-5-fluoro-2,3-dimethyl-4-(3-propiolamidopiperidin-1-yl)-1H-indole-7-carboxamide (242); (R)-4-(3-(but-2-ynamido)piperidin-1-yl)-5-fluoro-2,3-dimethyl-1H-indole-7-carboxamide (243); 4-(6-acryloyl-3,6-diazabicyclo[3.2.0]heptan-3-yl)-5-fluoro-2,3-dimethyl-1H-indole-7-carboxamide (244); 4-(6-(but-2-ynoyl)-3,6-diazabicyclo[3.2.0]heptan-3-yl)-5-fluoro-2,3-dimethyl-1H-indole-7-carboxamide (245); 4-(7-acryloyl-2,7-diazaspiro[4.4]nonan-2-yl)-5-fluoro-2,3-dimethyl-1H-indole-7-carboxamide (246); 4-(7-(but-2-ynoyl)-2,7-diazaspiro[4.4]nonan-2-yl)-5-fluoro-2,3-dimethyl-1H-indole-7-carboxamide (247); 5-fluoro-2,3-dimethyl-4-(2-vinylpyridin-3-yl)-1H-indole-7-carboxamide (248); 5-fluoro-3-methyl-2-(trifluoromethyl)-4-((6-vinylpyridin-3-yl)methyl)-1H-indole-7-carboxamide (249); 4-(1-acryloylpyrrolidin-3-yl)-5-fluoro-3-methyl-2-(trifluoromethyl)-1H-indole-7-carboxamide (250); 4-(1-acryloylpyrrolidin-2-yl)-5-fluoro-2,3-dimethyl-1H-indole-7-carboxamide (251); 4-(1-acryloylpyrrolidin-3-yl)-5-fluoro-2,3-dimethyl-1H-indole-7-carboxamide (252); 5-fluoro-2,3-dimethyl-4-(3-vinyl-5,6-dihydroisoquinolin-8-yl)-1H-indole-7-carboxamide (253); 4-(1-(but-2-ynoyl)-2,5-dihydro-1H-pyrrol-3-yl)-5-fluoro-3-methyl-2-(trifluoromethyl)-1H-indole-7-carboxamide (254); 4-(1-acryloyloctahydro-6H-pyrrolo[3,4-b]pyridin-6-yl)-5-fluoro-3-methyl-2-(trifluoromethyl)-1H-indole-7-carboxamide (255); 4-(1-(but-2-ynoyl)octahydro-6H-pyrrolo[3,4-b]pyridin-6-yl)-5-fluoro-3-methyl-2-(trifluoromethyl)-1H-indole-7-carboxamide (256); 4-((1-acryloylpiperidin-4-ylidene)methyl)-5-fluoro-2,3-dimethyl-1H-indole-7-carboxamide (257); 4-((1-acryloylpiperidin-4-yl)methyl)-5-fluoro-2,3-dimethyl-1H-indole-7-carboxamide (258); 4-((1-acryloylpyrrolidin-3-yl)methyl)-5-fluoro-2,3-dimethyl-1H-indole-7-carboxamide (259); 4-((1-(but-2-ynoyl)piperidin-4-yl)methyl)-5-fluoro-2,3-dimethyl-1H-indole-7-carboxamide (260); 4-((1-(but-2-ynoyl)piperidin-4-ylidene)methyl)-5-fluoro-2,3-dimethyl-1H-indole-7-carboxamide (261); 4-((1-(but-2-ynoyl)pyrrolidin-3-yl)methyl)-5-fluoro-2,3-dimethyl-1H-indole-7-carboxamide (262); or 5-fluoro-4-(3-fluoro-2-vinylpyridin-4-yl)-2,3-dimethyl-1H-indole-7-carboxamide (263).

One embodiment provides a compound of Formula (I) or a salt thereof, wherein $R_3$ is Cl and said compound is 5-chloro-2,3-dimethyl-4-(3-(N-methylvinylsulfonamido)phenyl)-1H-indole-7-carboxamide (27); 4-(2-acryloyl-1,2,3,4-tetrahydroisoquinolin-5-yl)-5-chloro-2,3-dimethyl-1H-indole-7-carboxamide, racemate (239); 4-(2-acryloyl-1,2,3,4-tetrahydroisoquinolin-5-yl)-5-chloro-2,3-dimethyl-1H-indole-7-carboxamide, atropisomer A (240); 4-(2-acryloyl-1,2,3,4-tetrahydroisoquinolin-5-yl)-5-chloro-2,3-dimethyl-1H-indole-7-carboxamide, atropisomer B (264); or 4-(2-(but-2-ynoyl)-1,2,3,4-tetrahydroisoquinolin-5-yl)-5-chloro-2,3-dimethyl-1H-indole-7-carboxamide (265).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$alkyl" denotes straight and branched chain alkyl groups with one to four carbon atoms.

The term "hydroxyalkyl" refers to both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl. "$C_{1-4}$ hydroxyalkyl" is intended to include $C_1$, $C_2$, $C_3$, and $C_4$ alkyl groups substituted with one or more hydroxyl groups.

As used herein, "alkylene" refers to a bivalent alkyl radical having the general formula —$(CH_2)_n$—, where n is 1 to 10. Non-limiting examples include methylene, dimethylene, trimethylene, tetramethylene, pentamethylene, and hexamethylene. For example, "$C_{1-6}$ alkylene" denotes straight and branched chain alkylene groups with one to six carbon atoms. Further, for example, "C0-4 alkylene" denotes a bond and straight and branched chain alkylene groups with one to four carbon atoms.

The term "cyano" refers to the group —CN.

The term "cycloalkyl", as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "cycloalkenyl", as used herein, refers to a cyclic hydrocarbons ring having 1 double bond. For example, "$C_{5-6}$ cycloalkenyl" denotes cyclopentenyl and cyclohexenyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

Certain compounds of Formula (I) may exist in a free form (with no ionization) or can form salts which are also within the scope of this invention. Unless otherwise indicated, reference to an inventive compound is understood to include reference to the free form and to salts thereof. The term "salt(s)" denotes acidic salts formed with inorganic and/or organic acids. Pharmaceutically acceptable (i.e., nontoxic, physiologically acceptable) salts are preferred, such as, for example, salts in which the anion does not contribute significantly to the toxicity or biological activity of the salt. However, other salts may be useful, e.g., in isolation or purification steps which may be employed during preparation, and thus, are contemplated within the scope of the invention. Salts of the compounds of the Formula (I) may be formed, for example, by reacting a compound of the Formula (I) with an amount of acid such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example, when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) Wermuth, C. G. et al., *The Practice of Medicinal Chemistry*, Chapter 31, Academic Press (1996);
b) Bundgaard, H. ed., *Design of Prodrugs*, Elsevier (1985);
c) Bundgaard, H., Chapter 5, "Design and Application of Prodrugs", *A Textbook of Drug Design and Development*, pp. 113-191, Krogsgaard-Larsen, P. et al., eds., Harwood Academic Publishers (1991); and
d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to Btk, or effective to treat or prevent autoimmune and/or inflammatory and/or proliferative disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended.

The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example, heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil such as, for example, *arachis* oil, olive oil, sesame oil and coconut oil; or in mineral oil such as, for example, liquid paraffin. An oily suspension can also contain at least one thickening agent such as, for example, beeswax, hard paraffin and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), co-solvent solubilization (i.e., propylene glycol) or micellar solubilization (i.e., Tween 80).

The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Utility

The compounds of the invention modulate kinase activity, including the modulation of Btk. Other types of kinase activity that may be modulated by the compounds of the instant invention include, but are not limited to, the Tec family of kinases, such as BMX, Btk, ITK, TXK and Tec, and mutants thereof.

Accordingly, compounds of Formula (I) have utility in treating conditions associated with the modulation of kinase activity, and particularly the selective inhibition of Btk activity. Such conditions include B-cell mediated diseases in which cytokine levels are modulated as a consequence of intracellular signaling.

As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

In view of their activity as selective inhibitors of Btk, compounds of Formula (I) are useful in treating cytokine-associated conditions including, but not limited to, inflammatory diseases such as Crohn's and ulcerative colitis, asthma, graft versus host disease and chronic obstructive pulmonary disease; autoimmune diseases such as Graves' disease, rheumatoid arthritis, systemic lupus erythematosis and psoriasis; destructive bone disorders such as bone resorption disease, osteoarthritis, osteoporosis and multiple myeloma-related bone disorder; proliferative disorders such as acute myelogenous leukemia and chronic myelogenous leukemia; angiogenic disorders such as solid tumors, ocular neovascularization, and infantile haemangiomas; infectious diseases such as sepsis, septic shock, and shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, HIV infection, AIDS and CMV retinitis.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, Sjögren's syndrome, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, Kawasaki disease, chronic inflammatory demyelinating polyneuropathy (CIDP), dermatomyositis, uveitis, anti-factor-VIII disease, ankylosing spondylitis, myasthenia gravis, Goodpasture's disease, antiphospholipid syndrome, ANCA-associated vasculitis, dermatomyositis/polymyositis, cerebral malaria, chronic pulmonary inflammatory disease, silicosis, pulmonary sarcoidosis, bone resorption disease, allograft rejections, fever and myalgias due to infection, cachexia secondary to infection, myeloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris.

Preferred methods of treatment are those wherein the condition is selected from Crohn's and ulcerative colitis, allograft rejection, rheumatoid arthritis, psoriasis, ankylosing spondylitis, psoriatic arthritis, pemphigus vulgaris and multiple sclerosis. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the Btk inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional Btk-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "Btk-associated condition" or "Btk-associated disease or disorder" are used herein, each is intended to encompass all of the conditions identified above as if repeated at length, as well as any other condition that is affected by Btk kinase activity.

"Therapeutically effective amount" is intended to include an amount of a compound of the present invention that is effective when administered alone or in combination to inhibit Btk.

One embodiment provides methods for treating such Btk kinase-associated conditions, comprising administering to a subject in need thereof at least one compound of Formula (I). A therapeutically-effective amount for treating such conditions may be administered. The methods of the present embodiment may be employed to treat Btk kinase-associated conditions such as treatment of allergic disorders and/or autoimmune and/or inflammatory diseases including, but not limited to, SLE, rheumatoid arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

The methods of treating Btk kinase-associated conditions may comprise administering at least one compound of Formula (I) alone or in combination with each other and/or other suitable therapeutic agents useful in treating such conditions. Therapeutically-effective amounts of at least one compound of Formula (I) and other suitable therapeutic agents for treating such conditions may be administered. Accordingly, "therapeutically effective amount" is also intended to include an amount of the combination of compounds claimed that is effective to treat Btk kinase-associated conditions. The combination of compounds is preferably a synergistic combination. Synergy, as described, for example, by Chou et al., Adv. Enzyme Regul., 22:27-55 (1984), occurs when the effect (in this case, inhibition of Btk) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-Btk effect, or some other beneficial effect of the combination compared with the individual components.

Exemplary of such other therapeutic agents include corticosteroids, rolipram, calphostin, cytokine-suppressive anti-inflammatory drugs (CSAIDs), 4-substituted imidazo[1,2-a] quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating Btk kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Another embodiment provides the compounds of Formula (I) for use in therapy. In the present embodiment, the use in therapy may include the administration of a therapeutically-effective amount of a compound of Formula (I).

The present invention also provides the use of the compounds of Formula (I) for the manufacture of a medicament for the treatment or prophylaxis of an allergic disorder and/or autoimmune and/or inflammatory disease. In the present embodiment, the use for the manufacture of a medicament may include the administration of a therapeutically-effective amount of a compound of Formula (I) for the treatment of prophylaxis of an allergic disorder and/or autoimmune and/or inflammatory disease.

The present invention also provides the use of the compounds of Formula (I) for the manufacture of a medicament for treatment of cancer. The present embodiment may include the use for the manufacture of a medicament includes the administration of a therapeutically-effective amount of a compound of Formula (I) for the treatment of prophylaxis of an allergic disorder and/or autoimmune and/or inflammatory disease.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; buccally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of Btk enzyme levels.

Examples of compounds of Formula (I) as specified in the "Examples" section below, have been tested in one or more of the assays described below.

In one embodiment, the compounds of Formula (I) inhibit Btk enzymes with $IC_{50}$ values of 10 nM or less, for example, from 0.001 to 10 nM, as measured by the human recombinant Btk enzyme assay. Preferably, the compounds of Formula (I) inhibit Btk enzymes with $IC_{50}$ values of 2 nM and less, for example, from 0.001 to 2 nM. Other preferred compounds inhibit Btk enzymes with $IC_{50}$ values of 1.0 nM and less, for example, from 0.001 to 1.0 nM.

In one embodiment, the compounds of Formula (I) have useful potency in the inhibition of intracellular calcium flux in Ramos RA1 B cells stimulated with anti-human IgM, with $IC_{50}$ values of 250 nM or less, for example, from 0.1 to 250 nM. More preferably, the compounds of Formula (I) have potency in the inhibition of intracellular calcium flux in Ramos RA1 B cells stimulated with anti-human IgM with $IC_{50}$ values of 160 nM or less, for example, from 0.1 to 160 nM; and with $IC_{50}$ values of 100 nM or less, for example, from 0.1 to 100 nM.

In one embodiment, the compounds of Formula (I) inhibit Btk enzymes with $IC_{50}$ values of 2 nM or less, for example, from 0.001 to 2 nM, as measured by the Human Recombinant Btk enzyme assay, and inhibit the intracellular calcium flux in Ramos RA1 B cells stimulated with anti-human IgM, with $IC_{50}$ values of 500 nM or less, for example, from 0.1 to 500 nM.

In one embodiment, the compounds of Formula (I) inhibit Btk enzymes with $IC_{50}$ values of 2 nM or less, for example, from 0.001 to 2 nM, as measured by the Human Recombinant Btk enzyme assay, and inhibit the intracellular calcium flux in Ramos RA1 B cells stimulated with anti-human IgM, with $IC_{50}$ values of 150 nM or less, for example, from 0.1 to 150 nM.

In one embodiment, the compounds of Formula (I) inhibit Btk enzymes with $IC_{50}$ values of 2 nM or less, for example, from 0.001 to 2 nM, as measured by the Human Recombinant Btk enzyme assay, and inhibit the intracellular calcium flux in Ramos RA1 B cells stimulated with anti-human IgM, with $IC_{50}$ values of 60 nM or less, for example, from 0.1 to 60 nM.

In one embodiment, the compounds of Formula (I) inhibit Btk enzymes with $IC_{50}$ values of 1 nM and less, for example, from 0.001 to 1 nM, as measured by the Human Recombinant Btk enzyme assay, and inhibit the intracellular calcium flux in Ramos RA1 B cells stimulated with anti-human IgM, with $IC_{50}$ values of 500 nM or less, for example, from 0.1 to 500 nM.

In one embodiment, the compounds of Formula (I) inhibit Btk enzymes with $IC_{50}$ values of 1 nM and less, for example, from 0.001 to 1 nM, as measured by the Human Recombinant Btk enzyme assay, and inhibit the intracellular calcium flux in Ramos RA1 B cells stimulated with anti-human IgM, with $IC_{50}$ values of 150 nM or less, for example, from 0.1 to 150 nM.

In one embodiment, the compounds of Formula (I) inhibit Btk enzymes with $IC_{50}$ values of 1 nM or less, for example, from 0.001 to 1 nM, as measured by the Human Recombinant Btk enzyme assay, and inhibit the intracellular calcium flux in Ramos RA1 B cells stimulated with anti-human IgM, with $IC_{50}$ values of 60 nM or less, for example, from 0.1 to 60 nM.

In one embodiment, the compounds of Formula (I) inhibit Btk enzymes with $IC_{50}$ values of 0.5 nM and less, for example, from 0.001 to 0.5 nM, as measured by the Human Recombinant Btk enzyme assay, and inhibit the intracellular calcium flux in Ramos RA1 B cells stimulated with anti-human IgM, with $IC_{50}$ values of 500 nM or less, for example, from 0.1 to 500 nM.

In one embodiment, the compounds of Formula (I) inhibit Btk enzymes with $IC_{50}$ values of 0.5 nM and less, for example, from 0.001 to 0.5 nM, as measured by the Human Recombinant Btk enzyme assay, and inhibit the intracellular calcium flux in Ramos RA1 B cells stimulated with anti-human IgM, with $IC_{50}$ values of 150 nM or less, for example, from 0.1 to 150 nM.

In one embodiment, the compounds of Formula (I) inhibit Btk enzymes with $IC_{50}$ values of 0.5 nM or less, for example, from 0.001 to 0.5 nM, as measured by the Human Recombinant Btk enzyme assay, and inhibit the intracellular calcium flux in Ramos RA1 B cells stimulated with anti-human IgM, with $IC_{50}$ values of 60 nM or less, for example, from 0.1 to 60 nM.

Methods of Preparation

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will be recognized by one skilled in the art of organic synthesis that some functional groups present in intermediate compounds, or in compounds of Formula (I), may be unstable to, or otherwise unsuited for, some of the reaction conditions used to prepare them or to convert them to other intermediates or to compounds of Formula (I). In these cases, the functional groups may be protected by conversion to alternative functional groups which are more stable to or suitable for the reaction conditions to be employed. These protected functional group can then be converted back to the original functional group at a later stage of the synthesis. Examples are the protection of a carboxylic acid as a carboxylate ester, the protection of a primary or secondary amine as a tert-butyloxycarbonyl (Boc) derivative or benzyloxycarbonyl (Cbz) derivative, or the protection of an indole nitrogen as a 2-trimethylsilylethoxymethyl (SEM) derivative. The use of protecting groups is well known in the literature; an authoritative account describing the many alternatives to the trained practitioner is Wuts, P. et al., *Greene's Protective Groups in Organic Synthesis*, Fourth Edition, Wiley-Interscience (2006).

Compound 3, representing certain compounds of Formula (I), can be prepared using methods shown in Scheme 1.

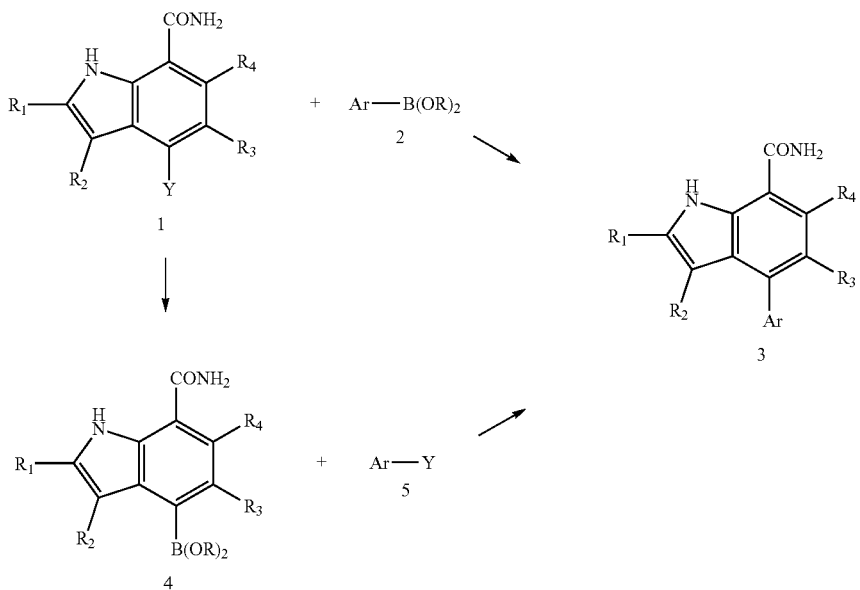

A substituted indolecarboxamide compound 1, where Y is an appropriate group such as Br, Cl, or trifluoromethanesulfonyloxy, can be reacted with a boronic acid or boronic acid ester compound 2, where Ar represents one of the groups A of Formula (I) in which the point of attachment to the indole moiety is located on a benzene or pyridine ring of A, to provide a compound 3. This reaction may be performed by using a suitable base such as potassium carbonate, cesium carbonate or tripotassium phosphate, and a suitable catalyst such as tetrakis(triphenylphosphine)palladium, 1,1'-bis(diphenylphosphino)ferrocene palladium(II) chloride, or 1,1'-bis(di-tert-butylphosphino)ferrocene palladium(II) chloride, in a suitable solvent such as 1,4-dioxane, N,N-dimethylformamide or tetrahydrofuran, optionally with one or more suitable co-solvents such as water or ethanol. Such coupling reactions are commonly known as Suzuki-Miyaura coupling reactions, and are well known in the chemical literature (see, for example, Heravi, M. et al., *Tetrahedron*, 68:9145 (2012), and references cited therein).

Alternatively, a substituted indolecarboxamide compound 1 can be converted to the corresponding boronic acid or boronic acid ester compound 4 using methods well known in the chemical literature (see, for example, Ishiyama, T. et al., *Tetrahedron*, 57:9813 (2001), and references cited therein). Examples of such methods are the reaction of a compound 1 with a reagent such as 4,4,4',4',5,5,5',5'-octamethyl-2,2'-bi(1,3,2-dioxaborolane) or 5,5,5',5'-tetramethyl-2,2'-bi(1,3,2-dioxaborinane) in the presence of a base such as potassium acetate and a suitable catalyst such as 1,1'-bis(diphenylphosphino) ferrocene palladium(II) chloride in a suitable solvent to provide a boronic acid ester compound 4. Alternatively, reaction of compound 1 where Y is Br with an organometallic reagent such as butyllithium or isopropylmagnesium chloride, followed by treatment with a boric acid ester such as trimethyl borate or tri-isopropyl borate, then followed by hydrolysis of the resulting boronic acid ester, can provide a boronic acid compound 4 (R=H). Reaction of a compound 4 with a suitable compound 5, wherein Ar represents one of the groups A of Formula (I) in which the point of attachment to the indole moiety is located on a benzene or pyridine ring of A, and Y is an appropriate group such as Br, Cl, or trifluoromethanesulfonyloxy, using the Suzuki-Miyaura coupling reaction as described above, can also provide a compound 3.

A compound 2 can be prepared from a compound 5 using the same method described for the preparation of a compound 4 from a compound 1.

Certain compounds of Formula (I), represented by 7, can be prepared using methods illustrated in Scheme 2.

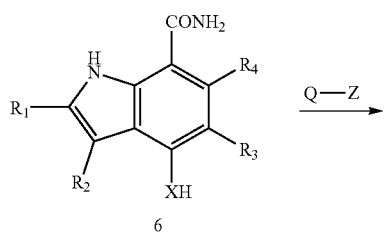

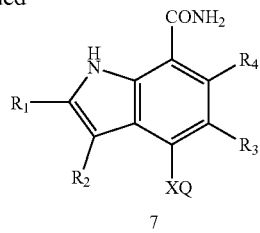

7

These methods involve reacting a compound 6 bearing a primary or secondary amine (that is, where XH represents a group A of Formula (I) where $Q_1$ is replaced by $NHR_7$ or $C(R_{10})_2NHR_7$, or where $Q_2$ is replaced by H) with an appropriate reagent Q-Z, where Q represents $Q_2$, an optionally substituted quinazoline-4-yl, or 4,6-dichloro-1,3,5-triazin-2-yl, or a precursor to such a group, and Z represents a leaving group such as Cl or OH, to provide a compound 7, where XQ represents one of the groups A of Formula (I) resulting from such a reaction. Such reactions of amines are well known in the literature.

One example of such a reaction is acylation of the amine with a carboxylic acid chloride or a carboxylic acid anhydride, usually performed in a suitable solvent such as tetrahydrofuran, ethyl acetate, acetonitrile, or dichloromethane, usually in the presence of a base such as triethylamine, diisopropylethylamine, pyridine, or an aqueous solution of an inorganic base such as sodium hydroxide or potassium carbonate. Alternatively, a solvent such as pyridine can be used, in which case the solvent can also serve as a base.

Another example of a reaction shown in Scheme 2 is acylation of the amine of a compound 6 with a carboxylic acid using any of a number of amide coupling reagents well known in the literature, for example, (benzotriazol-1-yloxy)tris(dimethylamino) phosphonium hexafluorophosphate (also known as BOP or Castro's reagent), O-(7-azabenzotriazol-1-yl)-N,N,N',N'-tetramethyluronium hexafluorophosphate (also known as HATU), or a reagent such as N,N'-dicyclohexylcarbodiimide (also known as DCC) or 1-ethyl-3-(3-dimethylaminopropyl)carbodiimide hydrochloride (also known as EDC) in the presence of a co-reagent such as 1-hydroxybenzotriazole (also known as HOBT) or 1-hydroxy-7-azabenzotriazole (also known as HOAT). Such reactions are usually performed in a suitable solvent such as ethyl acetate, dichloromethane, tetrahydrofuran, N,N-dimethylformamide or N-methylpyrrolidine-2-one, in the presence of a suitable base such as triethylamine or diisopropylethylamine.

Another example of a reaction shown in Scheme 2, which can be used to prepare a compound 7 where Q is $SO_2CH=CHR_{10}$, is treatment of the amine of a compound 6 with an appropriate 2-chloroethanesulfonyl chloride, in a suitable solvent such as dichloromethane or tetrahydrofuran, in the presence of a base such as triethylamine or diisopropylethylamine. In this case, an intermediate 2-chloroethanesulfonamide can be formed, which in the presence of base can undergo loss of HCl to provide the desired ethenesulfonamide.

Another example of a reaction shown in Scheme 2, which can be used to prepare a compound 7 where Q is 4,6-dichloro-1,3,5-triazin-2-yl or an optionally substituted quinazolin-4-yl, is the reaction of the amine of a compound 6 with cyanuric chloride or an optionally substituted 4-chloroquinazoline, respectively, in a suitable solvent such as tetrahydrofuran, in the presence of a suitable base such as potassium carbonate.

Another example of a reaction shown in Scheme 2, which can be used to prepare a compound 7 where Q is CN, is the reaction of the amine of a compound 6 with cyanogen bromide in a suitable solvent, such as N,N-dimethylformamide, in the presence of a suitable base, such as cesium carbonate.

Certain compounds of Formula (I) can be prepared from certain other compounds of Formula (I) using methods shown in Scheme 3.

Scheme 3

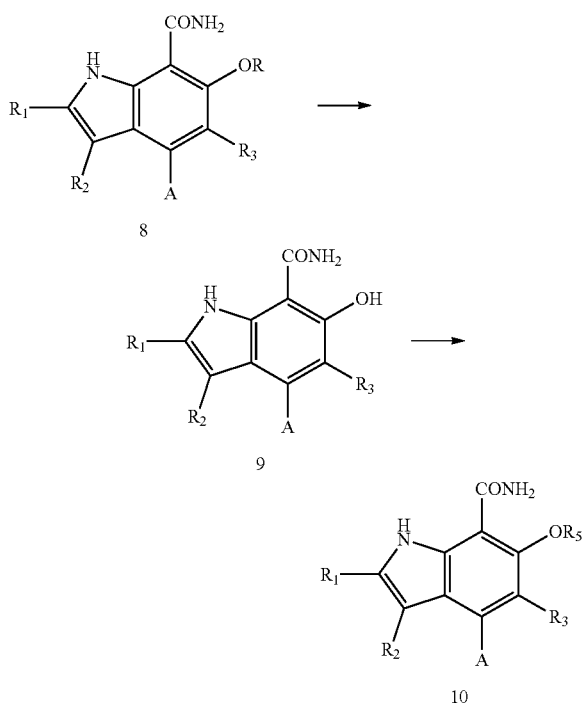

A compound 8 where R represents an optionally substituted benzyl group (which is an example of a compound of Formula (I)) can be converted to the corresponding hydroxy compound 9 (also an example of a compound of Formula (I)) using methods well-known in the literature, for example, by treatment with hydrogen in the presence of an appropriate catalyst such as palladium on charcoal in a suitable solvent such as ethanol, or (when R is p-methoxybenzyl) by treatment with a strong acid such as trifluoroacetic acid in an appropriate solvent. A compound 9 can be further converted into another compound of Formula (I), represented by 10, by treatment with an alkylating agent such as an optionally substituted alkyl bromide, alkyl chloride, alkyl iodide or alkyl sulfonate ester, in a suitable solvent and in the presence of a suitable base such as potassium carbonate.

Certain intermediate compounds 6 of Scheme 2 can be prepared using methods analogous to those shown in Scheme 1, as shown in Scheme 4.

Scheme 4

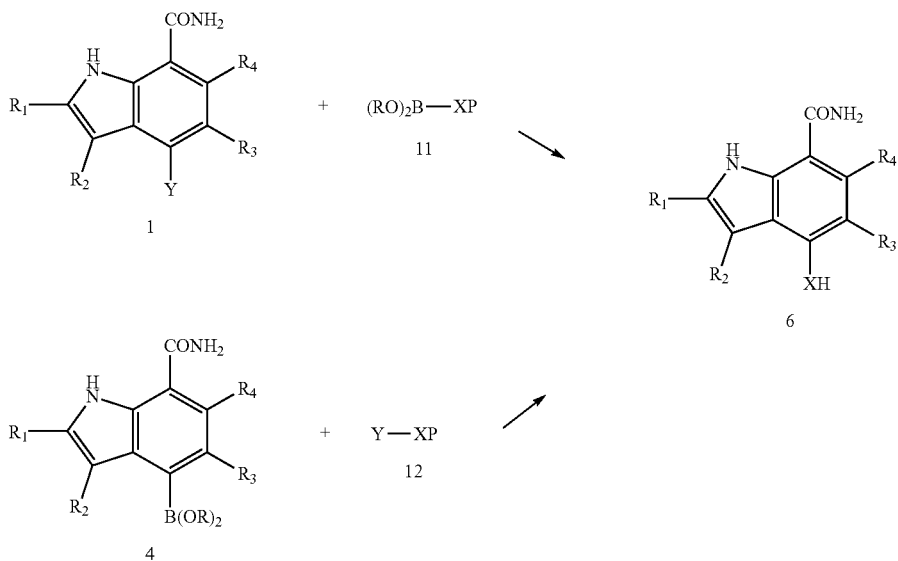

Reaction of a compound 1 with a boronic acid ester or boronic acid compound 11 (where XP is analogous to XH in Scheme 2; P can be either H or a suitable amine protecting group such as, for example, tert-butyloxycarbonyl (Boc) or benzyloxycarbonyl (Cbz), which are well known in the literature as protecting groups for amines), using the Suzuki-Miyaura coupling as described above (Scheme 1), can provide the corresponding compound 6 after removal of the protecting group P if necessary. If P in compound 11 represents H, compound 6 can be obtained directly.

By analogy to the methods illustrated in Scheme 1, an alternative method to prepare compound 6 of Scheme 2 is also shown in Scheme 4. Reaction of a boronic acid ester or boronic acid compound 4 of Scheme 1 with a compound 12, where Y is a suitable leaving group such as Br, Cl or trifluorosulfonyloxy, using the Suzuki-Miyaura coupling as described above, can also provide a compound 6. As described above, P can either be H, or a suitable protecting group in which case deprotection can provide the compound 6.

Also, a compound 11 can be prepared from a compound 12 using the same method described for the preparation of a compound 4 from a compound 1 (Scheme 1).

Compounds 15, which are examples of compounds 6 of Scheme 2, can be prepared using methods shown in Scheme 5.

Scheme 5

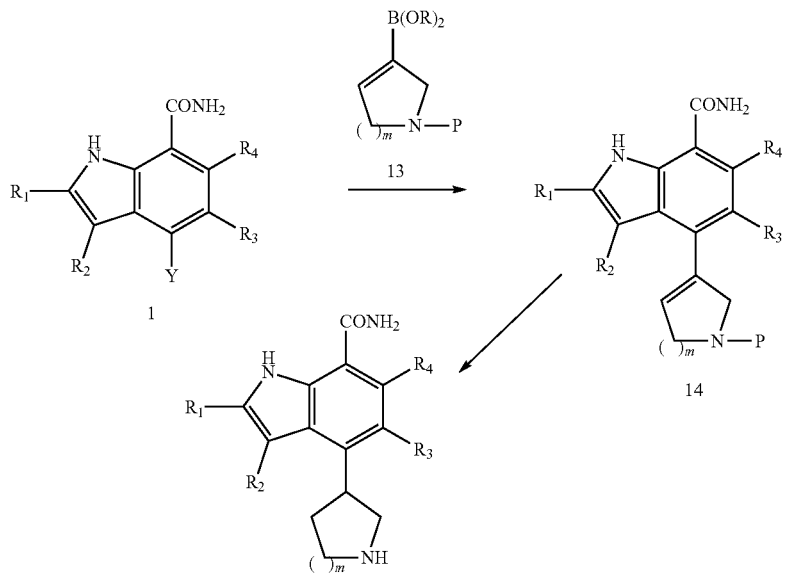

Reaction of a compound 1 with a vinylic boronic acid ester or boronic acid compound 13, where P is a suitable amine protecting group such as Boc or Cbz and m is 1 or 2, using the Suzuki-Miyaura reaction as described above (see Scheme 1) can provide a compound 14. The double bond of the dihydropyrrole (m=1) or tetrahydropiperidine (m=2) ring of 14 can be reduced using methods well known in the literature, for example, by treatment with hydrogen in the presence of a suitable catalyst such as palladium adsorbed on charcoal, in a suitable solvent such as methanol or ethanol, followed by removal of the protecting group using methods well known in the literature, to provide a compound 15. (If P represents a Cbz group, removal of the protecting group can be achieved in the same reaction as reduction of the double bond.) Alternatively, the order of the steps for the conversion of a compound 14 to a compound 15 can be reversed: a protecting group P can be removed using a suitable method, followed by hydrogenation of the double bond as described.

Compounds 19, representing certain compounds 6 of Scheme 2, can be prepared as shown in Scheme 6.

Scheme 6

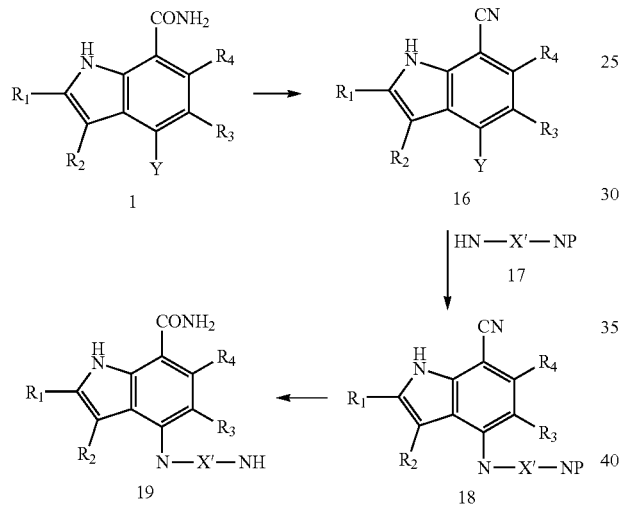

Reaction of a compound 1 with a dehydrating agent such as phosphorus oxychloride, using methods well-known in the literature, can provide a compound 16. Treatment of a compound 16 with a suitable mono-protected diamine such as an aminopyrrolidine, an aminopiperidine, a piperazine, an octahydropyrrolopyrrole or an octahydropyrrolopyridine (represented by HN—X'—NP, 17, where can P represent a suitable protecting group such as Cbz or Boc) can provide the corresponding compound 18. The conversion of a compound 16 to a compound 18 can be achieved using a suitable palladium catalyst such as, for example, tris(dibenzylideneacetone) dipalladium, a ligand such as, for example, 2,2'-bis(diphenylphosphino)-1,1'-binaphthalene (also known as BINAP) or 4,5-bis(diphenylphosphino)-9,9-dimethylxanthene (also known as Xantphos), and a base such as cesium carbonate or sodium tert-butoxide, in a suitable solvent such as 1,4-dioxane, toluene, N,N-dimethylacetamide or N-methylpyrrolidin-2-one. This reaction, commonly referred to as the Buchwald coupling, is well known in the literature (see, for example, Surry, D. et al., *Angew. Chem.*, 47:6338 (2008), and references cited therein). The nitrile moiety of a compound 18 can be hydrolyzed to the corresponding amide by treatment under suitable conditions, for example, by heating with concentrated aqueous sulfuric acid, to provide a compound 19, which is an example of a compound 6 of Scheme 2. A protecting group P, if present in a compound 18, can be removed during this reaction, or alternatively can be removed before or after the nitrile hydrolysis step using methods well-known in the chemical literature.

It will be noted that in some cases a compound 18 or 19 can possess a chiral center, for example, when 17 represents a protected 3-aminopyrrolidine, 3-aminopiperidine, octahydropyrrolopyridine, or non-symmetrical octahydropyrrolopyrrole. In these cases, a compound 18 or 19 can be prepared in racemic form by using a racemic compound 17 in the Buchwald coupling step. Alternatively, a compound 18 or 19 which possesses a chiral center can be prepared in enantiomerically pure or enantiomerically enriched form by using an enantiomerically pure or enantiomerically enriched compound 17 during the Buchwald coupling step. Alternatively, in cases where a chiral center is present, an enantiomerically pure or enantiomerically enriched compound 18 or 19 may be prepared from a racemic compound 18 or 19, respectively, using optical resolution methods well known in the literature, for example, by selective crystallization of a diastereomeric salt formed with an enantiomerically pure or enantiomerically enriched acid, or by chromatography on a chiral stationary phase.

Compound 19, representing certain compounds 6 of Scheme 2, can also be prepared as shown in Scheme 7.

Scheme 7

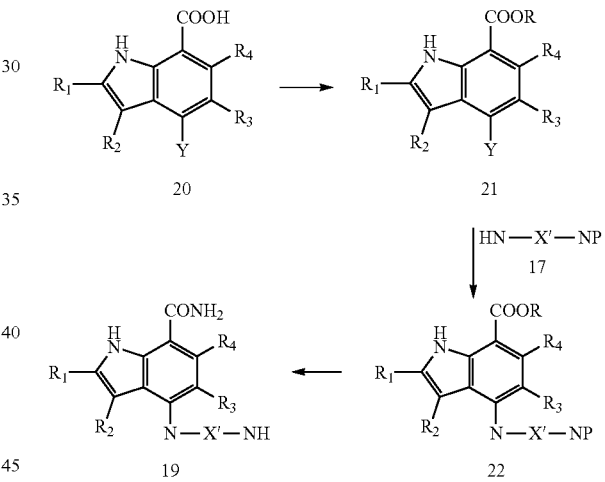

Conversion of a carboxylic acid 20 to an ester 21, such as a methyl ester ($R=CH_3$) or ethyl ester ($R=C_2H_5$), can be achieved using well-known methods, such as treatment with an acid catalyst such as sulfuric acid in a suitable alcoholic solvent such as methanol or ethanol. Using the Buchwald coupling procedure described for Scheme 6, a compound 21 can be converted into a compound 22. The carboxylic acid ester of a compound 22 can be converted to the corresponding amide, providing a compound 19 (with removal of the protecting group P if appropriate), using well known methods, such as hydrolysis of the ester using a suitable base such as aqueous lithium hydroxide or sodium hydroxide, optionally in a suitable co-solvent such as methanol, ethanol or tetrahydrofuran. The resulting carboxylic acid 22 ($R=H$) can then be converted into the amide 19 using methods well known in the literature, for example, by conversion of the carboxylic acid to the corresponding acid chloride by treatment with oxalyl chloride or thionyl chloride, followed by treatment with ammonia; or by treatment of the carboxylic acid with ammonia or ammonium chloride in the presence of a coupling reagent such as dicyclohexylcarbodiimide, or N-(3-dimethylaminopropyl)-N'-ethylcarbodiimide hydrochloride in the presence of 1-hydroxybenzotriazole or 1-hydroxy-7-azabenzotriazole.

Certain compounds 23 (which are examples of compounds 6 of Scheme 2) can be prepared by a method shown in Scheme 8.

Scheme 8

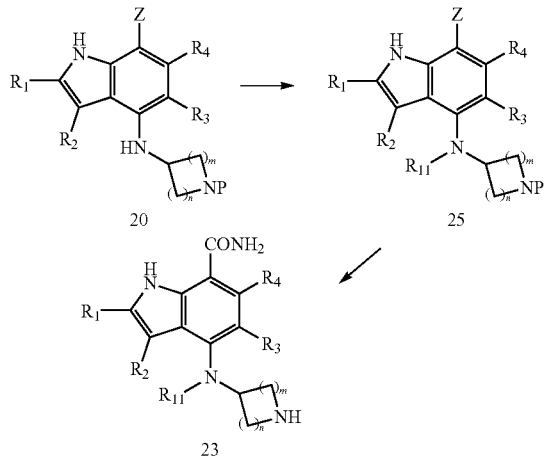

A compound 24 (where Z represents CN, which is an example of a compound 18 of Scheme 6; or where Z represents a carboxylic acid ester, which is an example of a compound 22 of Scheme 7; and m and n are chosen to form an appropriate piperidine or pyrrolidine ring) can be converted into the corresponding compound 25 using methods known in the literature, such as alkylation with an appropriate alkyl halide, or by treatment with an appropriate aldehyde or ketone followed by reduction of the intermediate iminium compound using a suitable reducing agent such as sodium cyanoborohydride or sodium triacetoxyborohydride. The resulting compound 25 can then be converted to the corresponding compound 23 using appropriate methods: for example, if Z is CN, using the method described for the conversion of a compound 18 to a compound 19 (Scheme 6); or if Z is a carboxylic acid ester, using the method described for the conversion of a compound 22 to a compound 19 (Scheme 7).

Compounds 26, which are examples of compounds of Formula (I), can be prepared by a method shown in Scheme 9. A compound 27 (which can be prepared by installing a suitable protecting group such as trimethylsilylethoxymethyl on a compound 16 of Scheme 6) can be reacted with a suitable organozinc compound such as 28, in the presence of a catalyst such as tetrakis(triphenylphosphine)palladium, to provide a compound 29. Such a palladium-catalyzed coupling of organozinc compounds, commonly known as the Negishi coupling, is well known in the chemical literature (see, for example, Negishi, E. et al., *Metal-Catalyzed Cross-Coupling Reactions*, Second Edition, p. 815, de Meijere, A. et al., eds., Wiley-VCH (2004)). Removal of the protecting group of a compound 29 and reaction with an appropriate organostannane such as $R_9Sn(CH_2CH_2CH_2CH_3)_3$ in the presence of a catalyst such as tetrakis (triphenylphosphine)palladium, can provide a compound 30. Such a palladium-catalyzed coupling of organotin compounds, commonly known as the Stille coupling, is well known in the chemical literature (see, for example, Stille, J., *Angew. Chem., Int. Ed. Engl.*, 25:508 (1986)). Conversion of the nitrile of a compound 30 to the carboxamide by hydrolysis, using methods described in Scheme 6 or related methods, can provide a compound 26. In cases where $R_8$ is not H, $R_8$ can be present in the organozinc reagent 28. Alternatively, a compound 29 where $R_8$ is H can be converted to the corresponding compound 29 where $R_8$ is alkyl using methods well-known in the literature, for example, by treatment with a suitable base such as potassium bis(trimethylsilyl)amide, followed by treatment with a suitable alkylating agent such as an iodoalkane.

Scheme 9

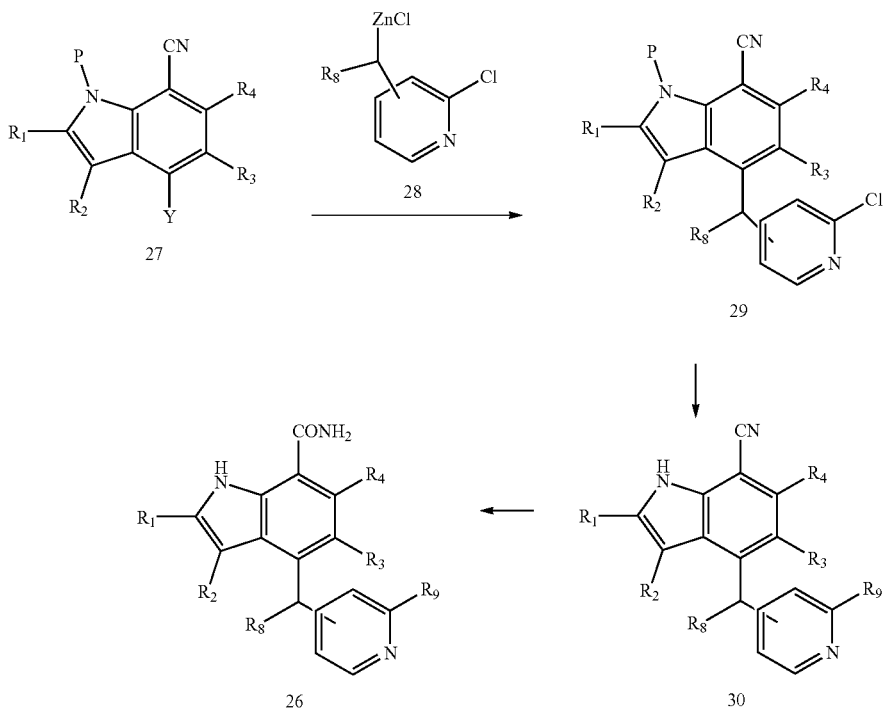

Compounds 1 (see Scheme 1) used in the preparation of compounds of Formula (I), and compounds 20 which can be used in the preparation of compounds 19 (see Scheme 7), can be prepared using procedures shown in Scheme 10.

Scheme 10

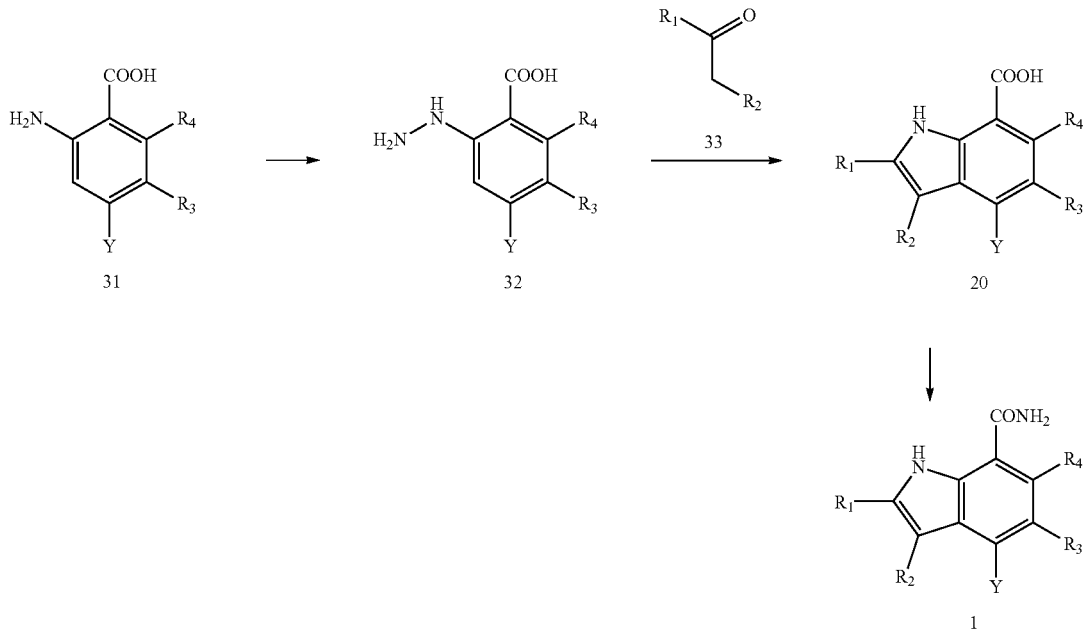

A substituted 2-aminobenzoic acid 31 (known in the literature, or prepared using procedures known in the literature) can be converted to the corresponding 2-hydrazinylbenzoic acid 32 as the hydrochloric acid salt using methods well known in the literature, for example, by conversion to the corresponding diazonium salt by treatment with sodium nitrite in aqueous hydrochloric acid, followed by reduction with tin(II) chloride. Reaction of a compound 32 with a suitable ketone 33 such as 2-butanone or acetone, in a suitable solvent with an appropriate catalyst, for example, ethanol with hydrochloric acid, toluene with p-toluenesulfonic acid or trifluoroacetic acid, or acetic acid (in which case the solvent also can serve as the catalyst), can provide the corresponding substituted indole 20. This reaction is commonly known as the Fischer indole synthesis, and is well known in the chemical literature (see, for example, Hughes, D., Org. Prep. Proc. Int., 25:607 (1993)). Alternatively, the Fischer indole synthesis can be carried out in two consecutive steps: a hydrazine 32 can react with the appropriate ketone or aldehyde 33 under suitable conditions (such as in an appropriate solvent such as ethanol or toluene, optionally with a suitable catalyst such as p-toluenesulfonic acid) to form an intermediate hydrazone, which can be isolated and then reacted further under suitable conditions (for example, ethanol with hydrochloric acid, acetic acid with zinc chloride, or toluene with trifluoroacetic acid) to provide a compound 20. The carboxylic acid of a compound 20 can be converted to the carboxamide of a compound 1 using methods described for the conversion of a compound 22 (R=H) to a compound 19 in Scheme 7.

An alternative method for preparing a compound 1 is shown in Scheme 11.

Scheme 11

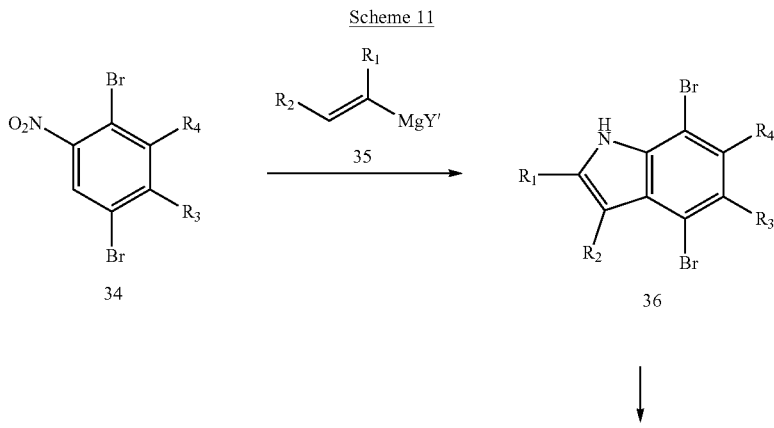

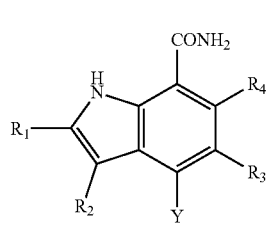

1

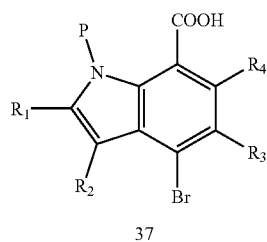

37

A dibromonitrobenzene 34 can be treated with an appropriate vinylic organomagnesium reagent 35 (Y'=Br or Cl) to provide a substituted indole 36. This method, commonly called the Bartoli indole synthesis, is well known in the chemical literature (see, for example, Bartoli, G. et al., *Tetrahedron Lett.*, 30:2129 (1989), and Dobson, D. et al., *Synlett*, 79 (1992)). A compound 36 can be converted into the corresponding compound 37 (P=H, a compound 20 of Schemes 7 and 9) by treatment with a suitable organolithium reagent such as n-butyllithium in a suitable solvent such as tetrahydrofuran, followed by treatment with carbon dioxide, then with an aqueous acid to neutralize the intermediate carboxylate salt. Optionally, the indole nitrogen of a compound 36 can be protected using methods well known in the literature, for example, by alkylation with 2-(trimethylsilyl)ethoxymethyl chloride to provide the corresponding 2-trimethylsilylethoxymethyl (SEM) derivative, followed by conversion to the corresponding carboxylic acid 37 (P=SEM) as described. The carboxylic acid of a compound 37 can then be converted to the carboxamide of a compound 1, using methods described for this transformation in Scheme 7. If the carboxamide so obtained is derived from a compound 37 where P is a protecting group, deprotection using suitable methods known in the literature can then provide a compound 1.

As shown in Scheme 12, a compound 38 can be converted to a compound 39, which is an example of a compound 2 of Scheme 1. Analogously, a compound 40 can be converted to a compound 41, which is an example of a compound 5 of Scheme 1.

Scheme 12

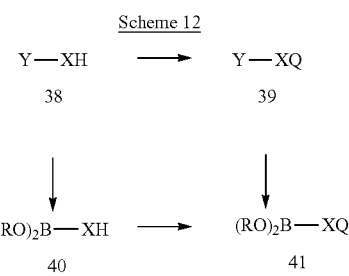

In Scheme 12, Y represents a suitable group such as Br, Cl or trifluoromethanesulfonyloxy; $(RO)_2B$ represents a boronic acid or boronic acid ester; and XH represents a group A of Formula (I) attached to the indole moiety of Formula (I) via a bond to a benzene or pyridine ring of A but where $Q_1$ (if present) is replaced by $NHR_7$ or $C(R_{10})_2NHR_7$ or $Q_2$ (if present) is replaced by H; and Q represents a group $Q_2$, $C(O)(C_{1-4}$ alkyl substituted with $R_6)$, $C(O)(C_{3-6}$ cycloalkyl substituted with $R_6)$, dichlorotriazinyl or quinazolin-4-yl substituted with $R_6$. Conversion of a compound 38 to a compound 39, and conversion of a compound 40 to a compound 41, can be accomplished using the same methods described for the analogous transformations of a compound 6 to a compound 7 in Scheme 2. Also, conversion of a compound 38 to a compound 40, and conversion of a compound 39 to a compound 41, can be accomplished using the methods described for the transformation of a compound 1 to a compound 4 in Scheme 1.

Scheme 13 shows the preparation of compounds 42 and 43 (which are examples of compounds 5 of Scheme 1) and of compounds 44 and 45 (which are examples of compounds 2 of Scheme 1).

Scheme 13

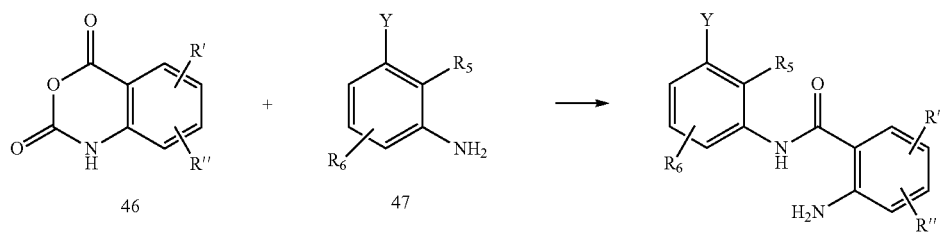

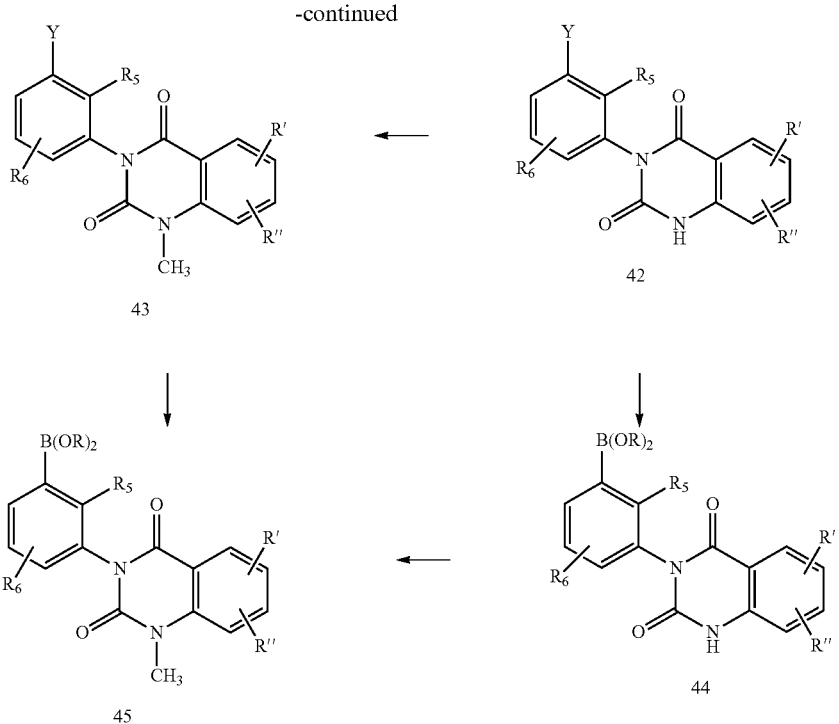

An isatoic anhydride 46 (where R' and R" represent optional substituents selected from F, Cl, CH₃, CN and OCH₃) can react with a substituted aniline 47 to produce an amide 48. Such reactions can be carried out under a variety of conditions, for example, by heating in a suitable solvent, or by heating in the presence of a reagent such as trimethylaluminum. A compound 48 can be converted into a substituted quinazolinedione 42, for example, by treatment in a suitable solvent with phosgene or bis(trichloromethyl) carbonate (triphosgene). Optionally, a compound 42 can be converted to the corresponding compound 44 using methods described for the conversion of a compound 1 to a compound 4 in Scheme 1. Alternatively, a compound 42 can optionally be converted into a compound 43 using methods known well known in the chemical literature, for example, by treatment with an alkylating agent such as iodomethane in the presence of a suitable base such as cesium carbonate. A compound 43 can then be converted into the corresponding compound 45 using the same methods described above. A compound 44 can also be optionally converted into the corresponding compound 45 by methods similar to those described for the conversion of a compound 42 into a compound 43.

If R₅ of a compound 42, 43, 44 or 45 is other than hydrogen, a compound 42, 43, 44 or 45 displays chirality, called atropisomerism, due to hindered rotation about the single bond connecting the substituted phenyl ring to the quinazolinedione moiety, and exists as two enantiomers. These enantiomeric atropisomers can be isolated as separate compounds which are stable to interconversion under normal storage conditions. If desired, a compound 42, 43, 44 or 45 can be resolved into separate enantiomeric atropisomers, for example, by chromatography on a chiral stationary phase. A separated enantiomeric atropisomer of a compound 42 or a compound 43 can then optionally be converted into a stable enantiomeric atropisomer of a compound 44 or a compound 45, respectively, as described above.

An alternative synthesis of a compound 48 of Scheme 13 is shown in Scheme 14. A substituted 2-nitrobenzoic acid 49 can be converted to a compound 50 using well-known amide bond forming reactions, for example, by conversion of a compound 49 to the corresponding carboxylic acid chloride and reaction with a substituted aniline 47, or by direct reaction of a compound 49 and a compound 47 in the presence of a suitable coupling reagent such O-(7-azabenzotriazol-1-yl)-1,1,3,3-tetramethyluronium hexafluorophosphate (HATU), or a mixture of 1-[3-(dimethylamino)propyl]-3-ethyl-carbodiimide hydrochloride (EDC) and 1-hydroxybenzotriazole hydrate (HOBT), using methods well known in the literature. The nitro group of a compound 50 can then be reduced, using one of a wide variety of methods known in the literature, to give a compound 48.

Scheme 14

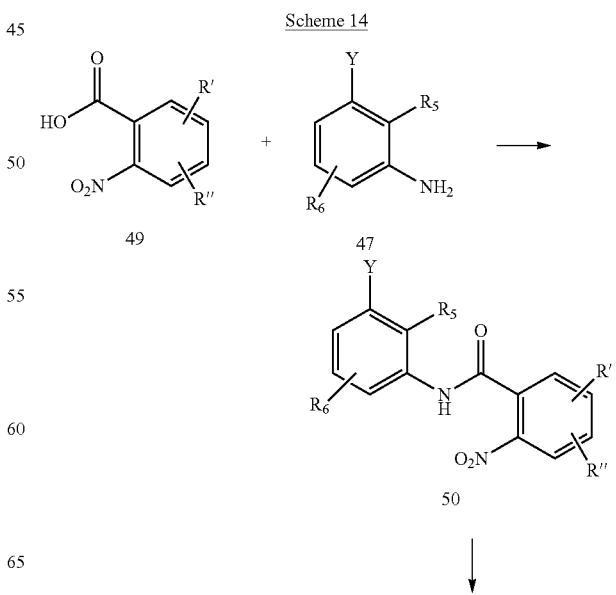

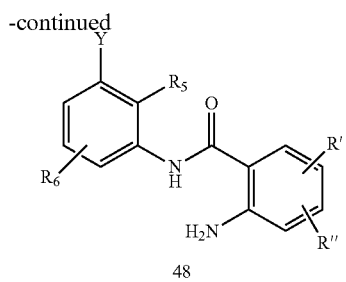

48

Other examples of compounds 2 and 5 of Scheme 1, and of compounds 11 and 12 of Scheme 4, are known in the literature, or can be prepared using methods known in the literature. For example, U.S. Pat. No. 8,084,620 describes the preparation of a number of such compounds useful in the preparation of compounds of Formula (I).

Certain compounds of Formula (I) may exhibit hindered rotation about the bond joining the group A to the indole ring. In some cases, the hindered rotation may be such that two isomers about this bond, known as atropisomers, can be isolated as separate compounds which are stable to interconversion under common storage and handling conditions. Cases where this hindered rotation may be observed are cases where $R_3$ is not hydrogen and where A is a substituted benzene or pyridine ring bearing a substituent $R_5$ which is also not hydrogen, or where $R_3$ is not hydrogen and where A is, for example, a substituted 1,2,3,4-tetrahydroisoquinolin-5-yl, a substituted 1,2,3,4-tetrahydroisoquinolin-8-yl, a substituted 1a,2,3,7b-tetrahydro-1H-cyclopropa[c]quinolin-7-yl, a substituted isoindolin-4-yl, a substituted 3,4-dihydro-2H-benzo[b][1,4]oxazin-8-yl, a substituted 3,4-dihydro-2H-benzo[b][1,4]thiazin-8-yl, a substituted indolin-4-yl, or a substituted 2,3,4,5-tetrahydrobenzo[b][1,4]oxazepin-9-yl group. In these cases, the compounds of Formula (I) may be prepared in racemic or scalemic form, and the two atropisomers may be separated using methods known in the literature, for example, by chromatography on a chiral stationary phase.

Likewise, a compound 6 of Schemes 2 and 4 may also exhibit hindered rotation about the bond joining the group XH to the indole ring, and can be isolated as separate compounds which are stable to interconversion under common storage and handling conditions. Cases where this hindered rotation may be observed are cases where $R_3$ is not hydrogen and where XH is a substituted benzene or pyridine ring bearing a substituent $R_5$ which is also not hydrogen, or where $R_3$ is not hydrogen and where XH is, for example, an optionally substituted 1,2,3,4-tetrahydroisoquinolin-5-yl, an optionally substituted 1,2,3,4-tetrahydroisoquinolin-8-yl, an optionally substituted 1a,2,3,7b-tetrahydro-1H-cyclopropa[c]quinolin-7-yl, an optionally substituted isoindolin-4-yl, an optionally substituted 3,4-dihydro-2H-benzo[b][1,4]oxazin-8-yl, an optionally substituted 3,4-dihydro-2H-benzo[b][1,4]thiazin-8-yl, an optionally substituted indolin-4-yl, or an optionally substituted 2,3,4,5-tetrahydrobenzo[b][1,4]oxazepin-9-yl group. In these cases, the compound 6 can be prepared in racemic or scalemic form as shown in Scheme 4, and the two atropisomers of 6 may be separated using methods known in the literature, for example, by chromatography on a chiral stationary phase. A separated enantiomeric atropisomer can then be converted into a single enantiomer of a compound 7, which represents certain compounds of Formula (I), as shown in Scheme 2.

In some cases, when the conversion of an intermediate compound into another intermediate compound or a compound of Formula (I) requires more than one synthetic reaction, the order of the individual steps can be changed. One example is shown in Scheme 12. Conversion of a compound 38 to a compound 41 can be done by (1) conversion of the amine of the compound 38 to the substituted amine of a compound 39, followed by (2) conversion of the group Y of the compound 39 to the boronic acid or boronic acid ester of the compound 41. Alternatively, the same conversion of a compound 38 to a compound 41 can be done by (1) conversion of the group Y of the compound 38 to the boronic acid or boronic acid ester of a compound 40, followed by (2) conversion of the amine of the compound 40 to the substituted amine of the compound 41. Such cases will be recognized by one skilled in the art of organic synthesis.

EXAMPLES

Compounds of the current invention, and intermediates used in the preparation of compounds of the current invention, can be prepared using procedures shown in the following Examples and related procedures. The methods and conditions used in these Examples, and the actual compounds prepared in these Examples, are not meant to be limiting, but are meant to demonstrate how the compounds of the current invention can be prepared. Starting materials and reagents used in these Examples, when not prepared by a procedure described herein, are generally either commercially available, or are reported in the chemical literature, or may be prepared by using procedures described in the chemical literature. The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In the examples given, the phrase "dried and concentrated" generally refers to removal of most residual water from a solution in an organic solvent using either anhydrous sodium sulfate or magnesium sulfate, followed by filtration and removal of the solvent from the filtrate (generally under reduced pressure and at a temperature suitable to the stability of the material being prepared). Column chromatography was generally performed using the flash chromatography technique (Still, W. et al., *J. Org. Chem.*, 43:2923 (1978)), or with pre-packed silica gel cartridges using an Isco medium pressure chromatography apparatus (Teledyne Corporation), eluting with the solvent or solvent mixture indicated. Preparative high pressure liquid chromatography (HPLC) was performed using a reverse-phase column (Waters SunFire Cis, Waters XBridge $C_{18}$, PHENOMENEX® Axia Cis, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Supercritical fluid chromatography (SFC), a form of normal phase HPLC using a mobile phase containing super- or subcritical fluid $CO_2$ and polar organic modifiers such as alcohols, was used to separate chiral compounds (White, C. et al., *J. Chromatography A*, 1074:175 (2005)). Chiral SFC separation of enantiomers or diastereomers was performed using conditions described for the individual cases. Mass spectral data were obtained by liquid chromatography-mass spectrometry using electrospray ionization. Chemical names were determined using CHEMDRAW® Ultra, version 9.0.5 (CambridgeSoft). The following abbreviations are used:

AcCN acetonitrile
BINAP 2,2'-bis(diphenylphosphino)-1,1'-binaphthyl
BOP benzotriazol-1-yloxy)tris(dimethylamino)phosphonium hexafluorophosphate
DCM dichloromethane
DDQ 2,3-dichloro-5,6-dicyano-1,4-benzoquinone
DIEA diisopropylethylamine
DMF N,N-dimethylformamide
DMSO dimethyl sulfoxide
dppf 1,1'-bis(diphenylphosphino)ferrocene
EDC 1-[3-(dimethylamino)propyl]-3-ethyl-carbodiimide hydrochloride
EtOAc ethyl acetate
h hour(s)
HATU O-(7-azabenzotriazol-1-yl)-1,1,3,3-tetramethyluronium hexafluorophosphate
HOBT 1-hydroxybenzotriazole hydrate
MeCN acetonitrile
MeOH methanol
min minute(s)
NBS N-bromosuccinimide
$PdCl_2$(dppf) 1,1'-bis(diphenylphosphino)ferrocene]dichloropalladium(II)
$Pd_2$(dba)$_3$ tris-(dibenzylideneacetone)dipalladium
Pd(PPh$_3$)$_4$ tetrakis(triphenylphosphine)palladium
TFA trifluoroacetic acid
THF tetrahydrofuran
HPLC high pressure liquid chromatography
g gram(s)
mL milliliter(s)
μL microliter(s)
mmol millimole(s)

Intermediate 1

4-Bromo-2,3-dimethyl-1H-indole-7-carboxamide

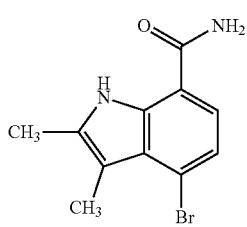

Intermediate 1A:
4-Bromo-2,3-dimethyl-1H-indole-7-carboxylic acid

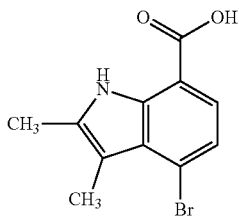

A suspension of 4-bromo-2-hydrazinylbenzoic acid hydrochloride [prepared according to U.S. Pat. No. 8,084,620, Intermediate 46-1, Step 1] (5.87 g, 21.9 mmol) in acetic acid (73 mL) at 75° C. was treated with 2-butanone (9.8 mL, 110 mmol). The mixture was heated on an oil bath at 110° C. After 18 h, the mixture was concentrated under vacuum to provide a dark brown solid. The residue was suspended in EtOAc and the insoluble material was collected by filtration, washed with EtOAc and air dried. The filtrates were concentrated and the residue was again suspended in EtOAc. Additional solid was collected by filtration, washed with EtOAc and air dried. The two solids were combined to provide 4-bromo-2,3-dimethyl-1H-indole-7-carboxylic acid as a brown solid (4.63 g, 79% yield). LCMS (M+H)$^+$ m/z 268, 270. $^1$H NMR (400 MHz, DMSO-d$_6$) δ 13.29-12.97 (m, 1H), 10.87 (br. s., 1H), 7.48 (d, J=7.9 Hz, 1H), 7.20 (d, J=8.1 Hz, 2H), 2.40 (s, 3H), 2.36 (s, 3H).

Intermediate 1

A mixture of 4-bromo-2,3-dimethyl-1H-indole-7-carboxylic acid (4.63 g, 17.3 mmol), EDC (4.97 g, 25.9 mmol) and HOBT (3.44 g, 22.5 mmol) in THF (276 mL) and DCM (69 mL) was stirred at room temperature for 1 h, then treated with 28% aqueous ammonium hydroxide (5.38 mL, 138 mmol). The resulting suspension was stirred at room temperature for 4 days. The mixture was concentrated and the residue was partitioned between water and EtOAc. The layers were separated and the aqueous phase was extracted again with EtOAc. The combined organic layers were washed with brine, dried and concentrated to provide 4-bromo-2,3-dimethyl-1H-indole-7-carboxamide as a yellow solid (3.34 g, 72% yield). Mass spectrum m/z 267, 269 (M+H)$^+$. $^1$H NMR (400 MHz, DMSO-d$_6$) δ 10.92 (s, 1H), 8.01 (br. s., 1H), 7.48-7.31 (m, 2H), 7.14 (d, J=7.9 Hz, 1H), 2.39 (d, J=0.4 Hz, 3H), 2.34 (s, 3H).

Intermediate 2

4-Bromo-5-fluoro-2,3-dimethyl-1H-indole-7-carboxamide

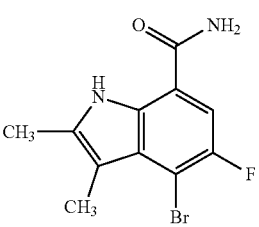

Intermediate 2A: 4-Bromo-2,5-difluorobenzoic acid

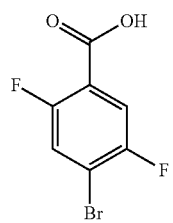

(I-2A)

A solution of 1,4-dibromo-2,5-difluorobenzene (640 mg, 2.35 mmol) in dry diethyl ether (10 mL) cooled in a dry ice-acetone bath was treated dropwise with 2.5 M n-butyllithium in hexanes (1.04 mL, 2.59 mmol). The resulting solution was stirred at −78° C. for 30 min, then was treated with a piece of dry ice. The cooling bath was removed after 5 min and the mixture was stirred for another 30 min while warming to room temperature. The mixture was diluted with EtOAc and water. The organic phase was separated and washed twice with saturated aqueous NaHCO$_3$. The combined aqueous phases were acidified with 1 M aqueous HCl, extracted twice with DCM, and the combined organic phases were dried and concentrated to give 4-bromo-2,5-difluorobenzoic acid as a white solid (297 mg, 53% yield).

Intermediate 2B: 4-Bromo-5-fluoro-2-hydrazinylbenzoic acid hydrochloride

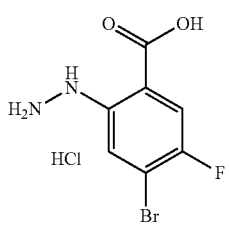

(I-2B)

A mixture of 4-bromo-2,5-difluorobenzoic acid (2.50 g, 10.6 mmol) and hydrazine (3.81 mL, 121 mmol) in N-methyl-2-pyrrolidinone (2 mL) was heated at 95° C. for 4 h. The cooled mixture was poured into vigorously stirred 6 M aqueous HCl (400 mL) which was cooled in an NaCl-ice bath. The resulting precipitate was collected by filtration, washed with 6 M aqueous HCl (200 mL) and dried under vacuum to give 4-bromo-5-fluoro-2-hydrazinylbenzoic acid hydrochloride as a yellow solid (1.88 g, 71% purity, 44% yield), used without further purification.

Alternative Synthesis of 4-Bromo-5-fluoro-2-hydrazinylbenzoic acid hydrochloride A suspension of 2-amino-4-bromo-5-fluorobenzoic acid (10.0 g, 42.7 mmol) in a mixture of 37% aqueous HCl (42.7 mL) and water (14.3 mL), cooled with an NaCl-ice bath, was treated dropwise with a solution of sodium nitrite (3.24 g, 47.0 mmol) in water (15.7 mL). When addition was complete, the mixture was stirred for 30 min more. A solution of tin(II) chloride dihydrate (28.9 g, 128 mmol) in 37% aqueous HCl (27.5 mL) was added dropwise. The cooling bath was removed and the mixture was stirred at room temperature for 45 min. The thick suspension was filtered and the collected precipitate was washed thoroughly with water and dried overnight under reduced pressure. The collected solid was triturated with MeOH with sonication, and the precipitate was collected by filtration, washed with MeOH and dried. The filtrate was concentrated, and the residue was triturated with DCM. The resulting precipitate was collected by filtration and dried, and the two batches of precipitate were combined to give 4-bromo-5-fluoro-2-hydrazinylbenzoic acid hydrochloride as a white solid (5.37 g, 44% yield). Mass spectrum m/z 249, 251 (M+H)$^+$.

Intermediate 2C: 4-Bromo-5-fluoro-2,3-dimethyl-1H-indole-7-carboxylic acid

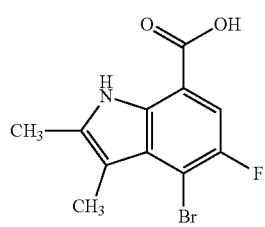

(I-2C)

A stirred suspension of 4-bromo-5-fluoro-2-hydrazinylbenzoic acid hydrochloride (1.00 g, 3.50 mmol) in acetic acid (11.7 mL) was treated with 2-butanone (1.26 mL, 14.0 mmol) at room temperature. The mixture was heated at 75° C. for 30 min, forming a brown solution, then was further heated at 110° C. After 16 h the mixture was concentrated, and the residue was suspended in EtOAc. The precipitate was collected by filtration, washed with EtOAc and air dried. The filtrates were concentrated and the residue was suspended in EtOAc, forming additional precipitate which was collected by filtration, washed with EtOAc and air dried. The two collected precipitates were combined to provide 4-bromo-5-fluoro-2,3-dimethyl-1H-indole-7-carboxylic acid as a brown solid (0.515 g, 51% yield). Mass spectrum m/z 286, 288 (M+H)$^+$. $^1$H NMR (400 MHz, DMSO-d$_6$) δ 13.84-12.75 (m, 1H), 10.96 (s, 1H), 7.45 (d, J=9.7 Hz, 1H), 2.40 (s, 3H), 2.37 (s, 3H).

Intermediate 2

Following the procedure used in the final step of the preparation of Intermediate 1, 4-bromo-5-fluoro-2,3-dimethyl-1H-indole-7-carboxylic acid was converted into 4-bromo-5-fluoro-2,3-dimethyl-1H-indole-7-carboxamide in 75% yield. Mass spectrum m/z 285, 287 (M+H)$^+$. $^1$H NMR (400 MHz, DMSO-d$_6$) δ 10.98 (s, 1H), 8.08 (br. s., 1H), 7.62-7.44 (m, 2H), 2.39 (s, 3H), 2.35 (s, 3H).

Intermediate 3

4-Bromo-5-chloro-2,3-dimethyl-1H-indole-7-carboxamide

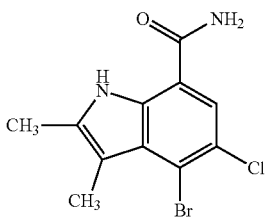
(I-3)

Intermediate 3A: 4-Bromo-5-chloro-2-hydrazinylbenzoic acid hydrochloride

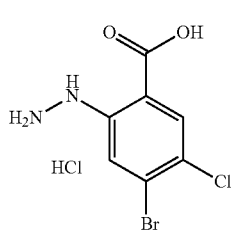
(I-3A)

Following the alternative procedure used for of the preparation of 4-bromo-5-fluoro-2-hydrazinylbenzoic acid HCl salt [Intermediate 2B], 2-amino-4-bromo-5-chlorobenzoic acid was converted into 4-bromo-5-chloro-2-hydrazinylbenzoic acid hydrochloride in 39% yield. Mass spectrum m/z 265, 267, 269 (M+H)$^+$. $^1$H NMR (400 MHz, DMSO-d$_6$) δ 8.82 (b, 1H), 7.86 (s, 1H), 7.58 (s, 1H).

Intermediate 3B: 4-Bromo-2-(2-(butan-2-ylidene)hydrazinyl)-5-chlorobenzoic acid

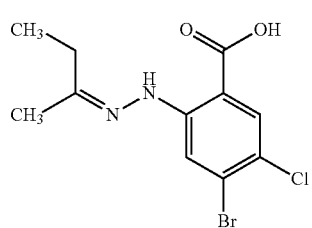
(I-3B)

A stirred suspension of 4-bromo-5-chloro-2-hydrazinylbenzoic acid hydrochloride (1.50 g, 4.97 mmol) in acetic acid (16.6 mL) was treated at room temperature with 2-butanone (1.34 mL, 14.9 mmol). The mixture was heated on an oil bath to 75° C. for 30 min, then was heated at 110° C. After 16 h the mixture was concentrated under vacuum and the residue was suspended in EtOAc. The precipitate was collected by filtration, washed with EtOAc and air dried to provide 4-bromo-2-(2-(butan-2-ylidene)hydrazinyl)-5-chlorobenzoic acid as a yellow solid (0.574 g, 36% yield). Mass spectrum m/z 319, 321, 323 (M+H)$^+$. $^1$H NMR (400 MHz, DMSO-d$_6$) δ 13.59 (br. s., 1H), 10.66 (s, 1H), 7.89 (s, 1H), 7.82 (s, 1H), 2.33 (q, J=7.5 Hz, 2H), 1.89 (s, 3H), 1.09 (t, J=7.4 Hz, 3H).

Intermediate 3C: 4-Bromo-5-chloro-2,3-dimethyl-1H-indole-7-carboxylic acid

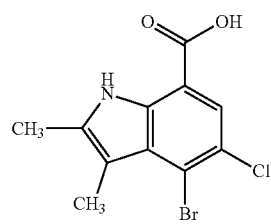
(I-3C)

A mixture of 4-bromo-2-(2-(butan-2-ylidene)hydrazinyl)-5-chlorobenzoic acid (0.574 g, 1.80 mmol) and TFA (1.11 mL, 14.4 mmol) in toluene (4.6 mL) was heated at 90° C. After 21 h, the mixture was concentrated under vacuum and the residue was suspended in EtOAc. The precipitate was collected by filtration, washed with EtOAc and air dried to provide 4-bromo-5-chloro-2,3-dimethyl-1H-indole-7-carboxylic acid as a dark-colored solid (0.373 g, 69% yield). Mass spectrum m/z 302, 304, 306 (M+H)$^+$. $^1$H NMR (400 MHz, DMSO-d$_6$) δ 13.40 (br. s., 1H), 11.06 (s, 1H), 7.67 (s, 1H), 2.40 (s, 3H), 2.37 (s, 3H).

Intermediate 3

Following the procedure used in the final step of the preparation of Intermediate 1, 4-bromo-5-chloro-2,3-dimethyl-1H-indole-7-carboxylic acid was converted into 4-bromo-5-chloro-2,3-dimethyl-1H-indole-7-carboxamide in 82% yield. Mass spectrum m/z 301, 303, 305 (M+H)$^+$. $^1$H NMR (400 MHz, DMSO-d$_6$) δ 11.08 (s, 1H), 8.13 (br. s., 1H), 7.76 (s, 1H), 7.51 (br. s., 1H), 2.40 (s, 3H), 2.36 (s, 3H).

Intermediate 4

4-Bromo-3-methyl-1H-indole-7-carboxamide

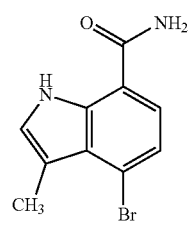
(I-4)

Intermediate 4A: 4,7-Dibromo-3-methyl-1H-indole

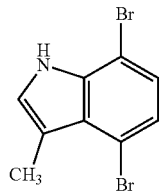

(I-4A)

A solution of 1,4-dibromo-2-nitrobenzene (4.60 g, 16.4 mmol) in THF (66 mL) cooled at −78° C. was treated over 10 min with 0.5 M (E)-prop-1-enylmagnesium bromide in THF (98.2 mL, 49.1 mmol). The resulting mixture was stirred at −78° C. for 2 h, then at room temperature for 2 h. The mixture was treated with saturated aqueous $NH_4Cl$ (100 mL), then with water and 1 M aqueous HCl (to pH about 1-2), then was extracted with EtOAc. The organic phase was washed with brine, dried and concentrated. The residue was subjected to column chromatography on silica gel (120 g), eluting with EtOAc-hexanes (gradient from 5-25%), to provide 4,7-dibromo-3-methyl-1H-indole (1.75 g, 37% yield). $^1$H NMR (400 MHz, $CDCl_3$) δ 8.16 (1H, br. s.), 7.16 (2H, s), 7.09 (1H, s), 2.57 (3H, d, J=1.1 Hz).

Intermediate 4B: 4,7-Dibromo-3-methyl-1-((2-(trimethylsilyl)ethoxy)methyl)-1H-indole

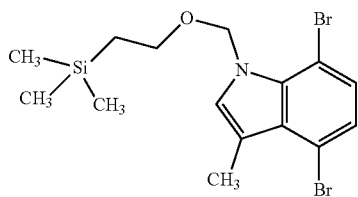

(I-4B)

A suspension of sodium hydride (60% in mineral oil, 0.254 g, 6.36 mmol) in THF (18.4 mL), cooled at 0° C., was treated portionwise with a solution of 4,7-dibromo-3-methyl-1H-indole (1.75 g, 6.06 mmol) in THF (1.8 mL), then with 2-(trimethylsilyl) ethoxymethyl chloride (1.19 mL, 6.06 mmol). The mixture became a light yellow solution which was stirred at room temperature for 3 h. The mixture was then treated with water and extracted with EtOAc. The organic phase was washed with brine, dried and concentrated. The residue was subjected to column chromatography on silica gel (80 g), eluting with EtOAc-hexanes (gradient from 0-5%), to provide 4,7-dibromo-3-methyl-1-((2-(trimethylsilyl)ethoxy)methyl)-1H-indole as a light yellow oil (2.4 g, 95% yield). Mass spectrum m/z 417, 419, 421 (M+H)+. $^1$H NMR (400 MHz, $CDCl_3$) δ 7.21-7.16 (m, 1H), 7.14-7.09 (m, 1H), 6.99 (d, J=0.9 Hz, 1H), 5.79 (s, 2H), 3.50 (dd, J=8.6, 7.7 Hz, 2H), 2.53 (d, J=0.9 Hz, 3H), 0.92-0.86 (m, 2H), −0.04 (s, 9H).

Intermediate 4C: 4-Bromo-3-methyl-1-((2-(trimethylsilyl)ethoxy)methyl)-1H-indole-7-carboxylic acid

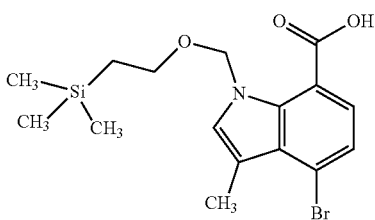

(I-4C)

A solution of 4,7-dibromo-3-methyl-1-((2-(trimethylsilyl)ethoxy)methyl)-1H-indole (2.30 g, 5.49 mmol) in THF (27.4 mL) at −78° C. was treated with 2.5 M n-butyllithium in hexanes (2.33 mL, 5.82 mmol). The mixture was stirred at −78° C. for 10 min, then was bubbled with carbon dioxide for 15 min. The mixture was then warmed to room temperature, stirred for 4 h, and treated with water. The pH was adjusted to 2-3 with 1 M aqueous HCl and the mixture was extracted with EtOAc. The organic phase was washed with brine, dried and concentrated to provide crude 4-bromo-3-methyl-1-((2-(trimethylsilyl)ethoxy)methyl)-1H-indole-7-carboxylic acid as a brown oil (2.0 g, 95% yield), used without further purification.

Intermediate 4D: 4-Bromo-3-methyl-1-((2-(trimethylsilyl)ethoxy)methyl)-1H-indole-7-carboxamide

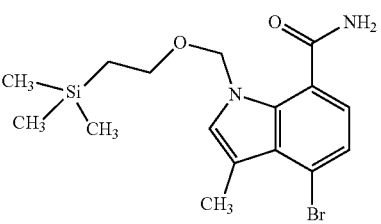

(I-4D)

Following the procedure used in the final step of the preparation of Intermediate 1, 4-bromo-3-methyl-1-((2-(trimethylsilyl)ethoxy)methyl)-1H-indole-7-carboxylic acid was converted into 4-bromo-3-methyl-1-((2-(trimethylsilyl)ethoxy)methyl)-1H-indole-7-carboxamide in 36% yield. Mass spectrum m/z 405, 407 (M+Na)+. $^1$H NMR (400 MHz, DMSO-$d_6$) δ 7.91 (s, 1H), 7.47 (s, 1H), 7.37 (d, J=0.9 Hz, 1H), 7.26 (d, J=7.7 Hz, 1H), 7.11 (d, J=7.9 Hz, 1H), 5.57 (s, 2H), 3.25 (dd, J=8.7, 7.6 Hz, 2H), 2.47 (d, J=0.9 Hz, 3H), 0.77-0.71 (m, 2H), −0.09 (s, 9H).

Intermediate 4

A solution of 4-bromo-3-methyl-1-((2-(trimethylsilyl)ethoxy)methyl)-1H-indole-7-carboxamide (0.72 g, 1.88 mmol), 1.0 M tetra-n-butylammonium fluoride in THF (5.63 mL, 5.63 mmol) and ethylenediamine (0.761 mL, 11.3 mmol) in DMF (9.4 mL) was heated at 45° C. for 4 days. Additional tetra-n-butylammonium fluoride (2 mL) was added and the mixture was heated at 50° C. After 5 days, additional ethylenediamine (4.0 mL) was added and the mixture was heated at 70° C. for 5 h. The mixture was cooled to room temperature, treated with water and 1 M aqueous HCl and extracted with EtOAc. The organic phase was washed sequentially with saturated aqueous NaHCO$_3$ and brine, dried and concentrated. The residue was subjected to column chromatography on silica gel (24 g), eluting with EtOAc-hexanes (gradient from 30-60%), to provide 4-bromo-3-methyl-1H-indole-7-carboxamide as an off-white solid (0.35 g, 74% yield). Mass spectrum m/z 253, 255 (M+H)$^+$. $^1$H NMR (400 MHz, CDCl$_3$) δ 10.24 (br. s., 1H), 7.32-7.29 (m, 3H), 7.22-7.18 (m, 1H), 7.15 (d, J=1.1 Hz, 1H), 2.60 (d, J=1.1 Hz, 3H).

Intermediate 5

4-Bromo-2-methyl-1H-indole-7-carboxamide

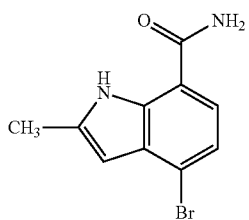

(I-5)

4-Bromo-2-methyl-1H-indole-7-carboxamide was prepared following the procedures used to prepare Intermediate 4 but substituting prop-1-en-2-ylmagnesium chloride for (E)-prop-1-enylmagnesium chloride. $^1$H NMR (400 MHz, DMSO-d$_6$) δ 11.18 (br. s., 1H), 8.04 (br. s., 1H), 7.49 (d, J=8.1 Hz, 1H), 7.40 (br. s., 1H), 7.20 (d, J=8.1 Hz, 1H), 6.16 (dd, J=2.2, 0.9 Hz, 1H), 2.44 (d, J=0.4 Hz, 3H).

Intermediate 6

4-Bromo-1H-indole-7-carboxamide

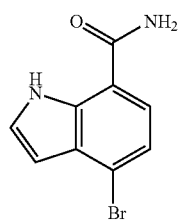

(I-6)

Intermediate 6A: 4,7-Dibromo-1H-indole

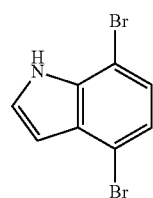

(I-6A)

Following the procedure used in the preparation of Intermediate 4A but substituting vinylmagnesium bromide for (E)-prop-1-enylmagnesium bromide, 1,4-dibromo-2-nitrobenzene was converted into 4,7-dibromo-1H-indole as a brown oil in 47% yield. $^1$H NMR (400 MHz, DMSO-d$_6$) δ 11.73 (br. s., 1H), 7.54 (t, J=2.9 Hz, 1H), 7.30-7.24 (m, 1H), 7.22-7.16 (m, 1H), 6.53 (dd, J=3.1, 2.0 Hz, 1H).

Intermediate 6B: 4-Bromo-1H-indole-7-carboxylic acid

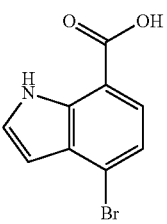

(I-6B)

Following the procedure used in the preparation of Intermediate 4C, 4,7-dibromo-1H-indole was converted into 4-bromo-1H-indole-7-carboxylic acid in 82% yield. Mass spectrum m/z 238, 240 (M–H)$^+$. $^1$H NMR (400 MHz, DMSO-d$_6$) δ 13.22 (br. s., 1H), 11.41 (br. s., 1H), 7.66 (d, J=8.1 Hz, 1H), 7.49-7.47 (m, 1H), 7.35 (d, J=7.9 Hz, 1H), 6.52 (dd, J=3.1, 2.2 Hz, 1H).

Intermediate 6

Following the procedure used in the final step of the preparation of Intermediate 1, 4-bromo-1H-indole-7-carboxylic acid was converted into 4-bromo-1H-indole-7-carboxamide in 71% yield. Mass spectrum m/z 239, 241 (M+H)$^+$. $^1$H NMR (400 MHz, DMSO-d$_6$) δ 11.44 (br. s., 1H), 8.11 (br. s., 1H), 7.62 (d, J=7.9 Hz, 1H), 7.49-7.41 (m, 2H), 7.30 (d, J=7.9 Hz, 1H), 6.45 (dd, J=3.1, 2.0 Hz, 1H).

Intermediate 7

4-Bromo-1-((2-(trimethylsilyl)ethoxy)methyl)-1H-indole-7-carboxamide

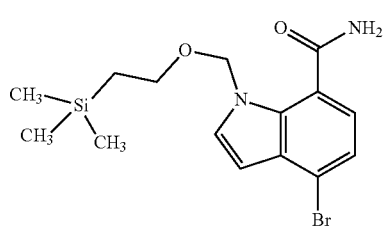

(I-7)

Following the procedures used in steps B through D of the preparation of Intermediate 4, 4,7-dibromo-1H-indole (Intermediate 6A) was converted into 4-bromo-1-((2-(trimethylsilyl)ethoxy)-methyl)-1H-indole-7-carboxamide as a solid. Mass spectrum m/z 369, 371 (M+H)$^+$, 391, 393 (M+Na)$^+$. $^1$H NMR (400 MHz, DMSO-d$_6$) δ 7.95 (s, 1H), 7.64 (d, J=3.3 Hz, 1H), 7.50 (s, 1H), 7.33 (d, J=7.7 Hz, 1H), 7.20 (d, J=7.9 Hz, 1H), 6.53 (d, J=3.3 Hz, 1H), 5.68 (s, 2H), 3.30 (s, 2H), 3.29-3.24 (m, 2H), 0.82-0.69 (m, 2H), −0.09 (s, 9H).

Intermediate 8

4-Bromo-6-((4-methoxybenzyl)oxy)-2,3-dimethyl-1H-indole-7-carboxamide

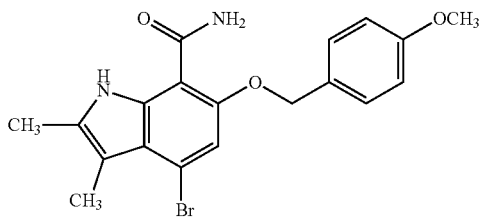

(I-8)

Intermediate 8A: 2,5-Dibromo-1-fluoro-3-nitrobenzene

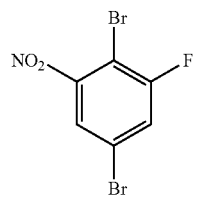

(I-8A)

A mixture of copper(II) bromide (0.713 g, 3.19 mmol) and tert-butyl nitrite (0.556 mL, 4.68 mmol) in acetonitrile (5.67 mL) was heated at 60° C. for 10 min, then was treated dropwise with a solution of 4-bromo-2-fluoro-6-nitroaniline (0.500 g, 2.13 mmol) in acetonitrile (8.51 mL). The mixture was stirred at 60° C. for 30 min, then was cooled to room temperature, treated with 1 M aqueous HCl and extracted with EtOAc. The organic phase was washed sequentially with saturated aqueous NaHCO$_3$ and brine, dried and concentrated. The residue was purified by column chromatography on silica gel (40 g), eluting with EtOAc-hexanes (5%), to provide 2,5-dibromo-1-fluoro-3-nitrobenzene as an off-white solid (0.534 g, 84% yield). $^1$H NMR (400 MHz, DMSO-d$_6$) δ 8.25 (t, J=2.0 Hz, 1H), 8.15 (dd, J=8.4, 2.2 Hz, 1H).

Intermediate 8B: 2,5-Dibromo-1-((4-methoxybenzyl)oxy)-3-nitrobenzene

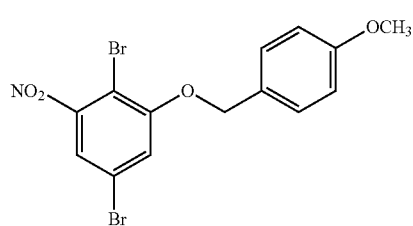

(I-8B)

A suspension of sodium hydride (60% in mineral oil, 0.637 g, 15.9 mmol) in THF (76 mL) was treated with (4-methoxyphenyl)methanol (1.89 g, 13.7 mmol) and stirred at room temperature for 30 min. The mixture was treated with 2,5-dibromo-1-fluoro-3-nitrobenzene (3.40 g, 11.4 mmol) and stirred at room temperature for 4 h. Water and saturated aqueous NH$_4$Cl were added and the mixture was extracted with EtOAc. The organic phase was washed with brine, dried and concentrated. The residue was crystallized from EtOAc-hexanes to provide a yellow solid (0.879 g). The filtrate from collection of the solid was concentrated and subjected to column chromatography on silica gel (80 g), eluting with EtOAc-hexanes (step gradient from 5-20%) to provide, after crystallization from EtOAc-hexanes, additional yellow solid (0.536 g). The filtrate was combined with additional impure material recovered from the chromatography column effluent, and crystallization was repeated three times, yielding additional yellow solids. All solids were combined to provide 2,5-dibromo-1-((4-methoxybenzyl)oxy)-3-nitrobenzene (2.28 g, 48%). $^1$H NMR (400 MHz, DMSO-d$_6$) δ 7.88 (d, J=2.0 Hz, 1H), 7.74 (d, J=2.2 Hz, 1H), 7.42 (d, J=8.6 Hz, 2H), 6.99 (d, J=8.8 Hz, 2H), 5.26 (s, 2H), 3.78 (s, 3H).

Intermediate 8C: 4,7-Dibromo-6-((4-methoxybenzyl)oxy)-2,3-dimethyl-1H-indole

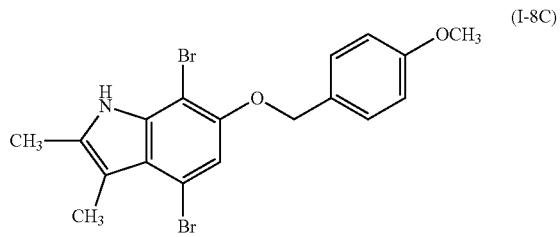 [SMILES: COc1ccc(COc2cc(Br)c3c(C)c(C)[nH]c3c2Br)cc1]

(I-8C)

Following the procedure used to prepare Intermediate 4A, but substituting (E)-but-2-en-2-ylmagnesium bromide for (E)-prop-1-enylmagnesium bromide, 2,5-dibromo-1-((4-methoxybenzyl)oxy)-3-nitrobenzene was converted into 4,7-dibromo-6-((4-methoxybenzyl)oxy)-2,3-dimethyl-1H-indole in 44% yield. Mass spectrum m/z 438, 440, 442 (M−H)$^+$.

Intermediate 8

Following the procedures used to convert Intermediate 4B to Intermediate 4D, 4,7-dibromo-6-((4-methoxybenzyl)oxy)-2,3-dimethyl-1H-indole was converted into 4-bromo-6-((4-methoxybenzyl)oxy)-2,3-dimethyl-1H-indole-7-carboxamide. Mass spectrum m/z 403, 405 (M−H)$^+$. $^1$H NMR (400 MHz, DMSO-d$_6$) δ 10.92 (s, 1H), 7.71 (br. s., 1H), 7.59 (br. s., 1H), 7.45 (d, J=8.6 Hz, 2H), 7.14 (s, 1H), 6.97 (d, J=8.6 Hz, 2H), 5.22 (s, 2H), 3.77 (s, 3H), 2.35 (s, 3H), 2.30 (s, 3H).

Intermediate 9

2,3-Dimethyl-4-(4,4,5,5-tetramethyl-1,3,2-dioxaborolan-2-yl)-1H-indole-7-carboxamide

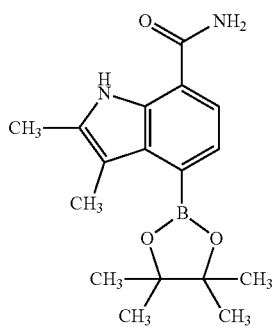
(I-9)

A mixture of 4-bromo-2,3-dimethyl-1H-indole-7-carboxamide [Intermediate 1](0.79 g, 2.96 mmol), 4,4,4',4',5,5,5',5'-octamethyl-2,2'-bi(1,3,2-dioxaborolane) (0.751 g, 2.96 mmol), potassium acetate (0.581 g, 5.91 mmol), and PdCl$_2$ (dppf) DCM adduct (0.121 g, 0.148 mmol) in 1,4-dioxane (9.9 mL) was bubbled with nitrogen for 2-3 min, then was heated at reflux under nitrogen. After 16 h, the mixture was cooled to room temperature, filtered through CELITE®, and the solids were washed with a mixture of THF and EtOAc. The combined filtrates were concentrated and the residue was subjected to column chromatography on silica gel (24 g), eluting with EtOAc-hexanes (gradient from 20-40%), to provide 2,3-dimethyl-4-(4,4,5,5-tetramethyl-1,3,2-dioxaborolan-2-yl)-1H-indole-7-carboxamide as a yellow glassy solid (0.798 g, 69% yield). Mass spectrum m/z 315 (M+H)$^+$. $^1$H NMR (400 MHz, CDCl$_3$) δ 10.01 (br. s., 1H), 7.48 (d, J=7.5 Hz, 1H), 7.27 (d, J=7.7 Hz, 1H), 5.88 (br. s., 2H), 2.43 (s, 3H), 2.39 (d, J=0.4 Hz, 3H), 1.44 (s, 12H).

Intermediate 10

2-Methyl-4-(4,4,5,5-tetramethyl-1,3,2-dioxaborolan-2-yl)-1H-indole-7-carboxamide

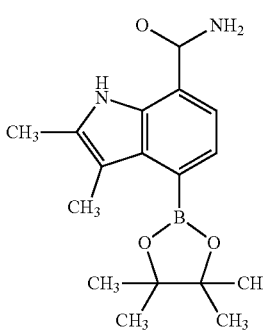
(I-10)

Following the procedure used in the preparation of Intermediate 9, 4-bromo-2-methyl-1H-indole-7-carboxamide [Intermediate 5] was converted into 2-methyl-4-(4,4,5,5-tetramethyl-1,3,2-dioxaborolan-2-yl)-1H-indole-7-carboxamide in 68% yield. Mass spectrum m/z 301 (M+H)$^+$. $^1$H NMR (400 MHz, DMSO-d$_6$) δ 10.82 (br. s., 1H), 8.03 (br. s., 1H), 7.53 (d, J=7.7 Hz, 1H), 7.37 (br. s., 1H), 7.33 (d, J=7.5 Hz, 1H), 6.50 (dd, J=2.2, 0.9 Hz, 1H), 2.44 (d, J=0.7 Hz, 3H), 1.33 (s, 12H).

Intermediate 11

4-Bromo-2,3-dimethyl-1H-indole-7-carbonitrile

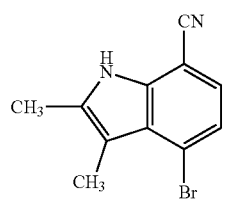
(I-11)

A suspension of 4-bromo-2,3-dimethyl-1H-indole-7-carboxamide [Intermediate 1](5.65 g, 21.2 mmol) in THF (151 mL) was treated slowly with phosphorus oxychloride (13.8 mL, 148 mmol). The resulting mixture was stirred at room temperature for 23 h, then was concentrated. The residue was suspended in EtOAc and the precipitate was collected by filtration, washed sequentially with water, saturated aqueous NaHCO$_3$ and again with water, and air dried. The organic filtrate was concentrated, and the residue was suspended in water. The resulting precipitate was collected by filtration, washed sequentially with water, saturated aqueous NaHCO$_3$ and again with water, and air dried. The two precipitates together provided 4-bromo-2,3-dimethyl-1H-indole-7-carbonitrile as a yellow solid (4.68 g, 89% yield). Mass spectrum m/z 249, 251 (M+H)$^+$. $^1$H NMR (400 MHz, DMSO-d$_6$) δ 11.89 (br. s., 1H), 7.35 (d, J=7.9 Hz, 1H), 7.26 (d, J=7.9 Hz, 1H), 2.39 (s, 3H), 2.34 (s, 3H).

Intermediate 12

4-Bromo-5-fluoro-2,3-dimethyl-1H-indole-7-carbonitrile

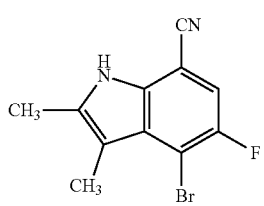
(I-12)

Following the procedure used to prepare Intermediate 11, 4-bromo-5-fluoro-2,3-dimethyl-1H-indole-7-carboxamide [Intermediate 2] was converted into 4-bromo-5-fluoro-2,3-dimethyl-1H-indole-7-carbonitrile in 56% yield. Mass spectrum m/z 267, 269 (M+H)$^+$.

Intermediate 13

(S)-4-(3-Aminopiperidin-1-yl)-2,3-dimethyl-1H-indole-7-carboxamide

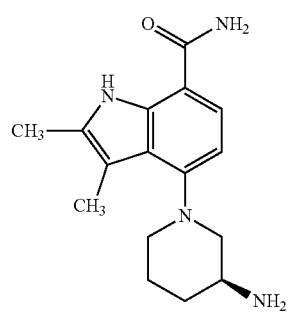
(I-13)

Intermediate 13A: (S)-Benzyl (1-(7-cyano-2,3-dimethyl-1H-indol-4-yl)piperidin-3-yl) carbamate

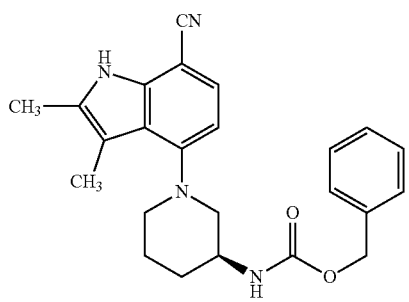
(I-13A)

A mixture of 4-bromo-2,3-dimethyl-1H-indole-7-carbonitrile [Intermediate 11](2.50 g, 10.0 mmol), (S)-benzyl piperidin-3-ylcarbamate (2.47 g, 10.5 mmol), 2,2'-bis(diphenylphosphino)-1,1'-binaphthalene (0.312 g, 0.502 mmol), tris(dibenzylideneacetone)dipalladium (0.460 g, 0.502 mmol) and $Cs_2CO_3$ (4.58 g, 14.1 mmol) in 1,4-dioxane (143 mL) was bubbled with nitrogen, then heated at 100° C. After 16 h, the mixture was cooled to room temperature, diluted with THF, filtered through CELITE®, and the solids were washed with THF. The combined filtrates were concentrated and the residue was subjected to chromatography on silica gel (80 g), eluting with EtOAc-hexanes (gradient from 15-30%), to provide (S)-benzyl (1-(7-cyano-2,3-dimethyl-1H-indol-4-yl)piperidin-3-yl)carbamate as a light yellow solid (2.13 g, 53% yield). Mass spectrum m/z 403 (M+H)$^+$. $^1$H NMR (400 MHz, DMSO-d$_6$) δ 11.43 (s, 1H), 7.40-7.26 (m, 7H), 6.62 (d, J=8.1 Hz, 1H), 5.08-4.94 (m, 2H), 3.79-3.65 (m, 1H), 3.41 (d, J=10.1 Hz, 1H), 3.20 (d, J=11.0 Hz, 1H), 2.60 (t, J=10.7 Hz, 1H), 2.43-2.16 (m, 7H), 1.92 (d, J=9.5 Hz, 1H), 1.86-1.78 (m, 1H), 1.71 (d, J=11.2 Hz, 1H), 1.40-1.26 (m, 1H).

Intermediate 13

A suspension of (S)-benzyl (1-(7-cyano-2,3-dimethyl-1H-indol-4-yl)piperidin-3-yl)carbamate (1.69 g, 3.44 mmol) in 80% aqueous $H_2SO_4$ (11.3 mL, 172 mmol) was heated at 60° C. After 2.5 h the mixture was cooled to room temperature, then poured onto ice. The pH of the mixture was adjusted to about 9-10 with concentrated aqueous KOH. The resulting mixture was extracted with 3:1 chloroform-isopropanol. The organic phase was dried and concentrated to provide (S)-4-(3-aminopiperidin-1-yl)-2,3-dimethyl-1H-indole-7-carboxamide as a brown solid (1.66 g, 50% purity, 99% yield) which was used without further purification. Mass spectrum m/z 287 (M+H)$^+$.

Intermediate 14

(R)-4-(3-Aminopiperidin-1-yl)-2,3-dimethyl-1H-indole-7-carboxamide

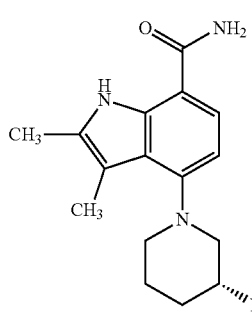
(I-14)

Following the procedures used to prepare Intermediate 13 but substituting (R)-benzyl piperidin-3-ylcarbamate for (S)-benzyl piperidin-3-ylcarbamate, 4-bromo-2,3-dimethyl-1H-indole-7-carbonitrile [Intermediate 11] was converted into (R)-4-(3-aminopiperidin-1-yl)-2,3-dimethyl-1H-indole-7-carboxamide. Mass spectrum m/z 287 (M+H)$^+$.

Intermediate 15

(RS)-4-(3-Aminopiperidin-1-yl)-2,3-dimethyl-1H-indole-7-carboxamide

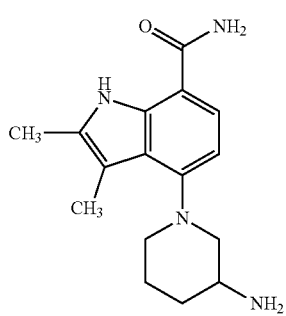
(I-15)

Following the procedures used to prepare Intermediate 13 but substituting (RS)-benzyl piperidin-3-ylcarbamate for (S)-benzyl piperidin-3-ylcarbamate, 4-bromo-2,3-dimethyl-1H-indole-7-carbonitrile [Intermediate 11] was converted into (RS)-4-(3-aminopiperidin-1-yl)-2,3-dimethyl-1H-indole-7-carboxamide. Mass spectrum m/z 287 (M+H)$^+$.

Intermediate 16

(S)-4-(3-Aminopiperidin-1-yl)-5-fluoro-2,3-dimethyl-1H-indole-7-carboxamide

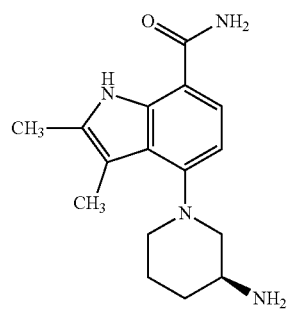

(I-16)

Following the procedures used to prepare Intermediate 13, 4-bromo-5-fluoro-2,3-dimethyl-1H-indole-7-carbonitrile [Intermediate 12] was converted into (S)-4-(3-aminopiperidin-1-yl)-5-fluoro-2,3-dimethyl-1H-indole-7-carboxamide. Mass spectrum m/z 305 (M+H)$^+$.

Intermediate 17

2,3-Dimethyl-4-(piperidin-4-ylamino)-1H-indole-7-carboxamide

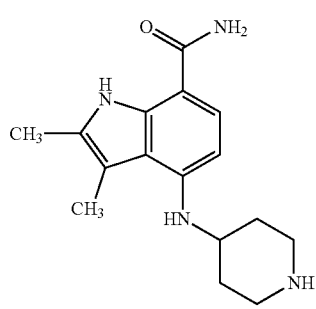

(I-17)

Following the procedures used to prepare Intermediate 13 but substituting benzyl 4-aminopiperidine-1-carboxylate for (S)-benzyl piperidin-3-ylcarbamate, 4-bromo-2,3-dimethyl-1H-indole-7-carbonitrile [Intermediate 11] was converted into 2,3-dimethyl-4-(piperidin-4-ylamino)-1H-indole-7-carboxamide. Mass spectrum m/z 287 (M+H)$^+$. $^1$H NMR (400 MHz, DMSO-d$_6$) δ 10.40 (s, 1H), 7.40 (d, J=8.1 Hz, 1H), 7.21-6.95 (m, 2H), 6.08 (d, J=8.4 Hz, 1H), 4.87 (d, J=7.9 Hz, 1H), 3.89-3.76 (m, 1H), 3.46 (br. s., 1H), 3.00-2.85 (m, 2H), 2.67-2.54 (m, 2H), 2.37 (s, 3H), 2.26 (s, 3H), 1.94 (d, J=9.5 Hz, 2H), 1.36 (d, J=9.0 Hz, 2H).

Intermediate 18

5-Fluoro-2,3-dimethyl-4-(piperidin-4-ylamino)-1H-indole-7-carboxamide

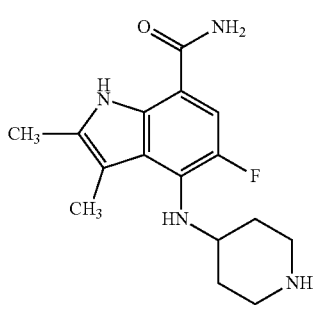

(I-18)

Following the procedures used to prepare Intermediate 13 but substituting benzyl 4-aminopiperidine-1-carboxylate for (S)-benzyl piperidin-3-ylcarbamate, 4-bromo-5-fluoro-2,3-dimethyl-1H-indole-7-carbonitrile [Intermediate 12] was converted into 5-fluoro-2,3-dimethyl-4-(piperidin-4-ylamino)-1H-indole-7-carboxamide. Mass spectrum m/z 305 (M+H)$^+$.

Intermediate 19

(RS)-2,3-Dimethyl-4-(pyrrolidin-3-ylamino)-1H-indole-7-carboxamide

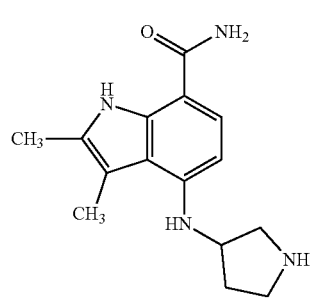

(I-19)

Following the procedures used to prepare Intermediate 13 but substituting (RS)-benzyl 3-aminopyrrolidine-1-carboxylate for (S)-benzyl piperidin-3-ylcarbamate, 4-bromo-2,3-dimethyl-1H-indole-7-carbonitrile [Intermediate 11] was converted into (RS)-2,3-dimethyl-4-(pyrrolidin-3-ylamino)-1H-indole-7-carboxamide. Mass spectrum m/z 273 (M+H)$^+$. $^1$H NMR (500 MHz, DMSO-d$_6$) δ 10.41 (s, 1H), 7.77-7.49 (m, 1H), 7.42 (d, J=7.9 Hz, 1H), 6.85 (br. s., 1H), 6.05 (d, J=8.5 Hz, 1H), 5.12 (d, J=6.1 Hz, 1H), 4.00 (br. s., 1H), 3.11 (dd, J=11.0, 6.1 Hz, 1H), 3.02-2.96 (m, 1H), 2.86-2.81 (m, 1H), 2.78 (dd, J=11.9, 3.4 Hz, 1H), 2.36 (s, 3H), 2.26 (s, 3H), 2.17-2.09 (m, 1H), 1.67 (d, J=5.5 Hz, 1H).

Intermediate 20

(RS)-5-Fluoro-2,3-dimethyl-4-(pyrrolidin-3-ylamino)-1H-indole-7-carboxamide

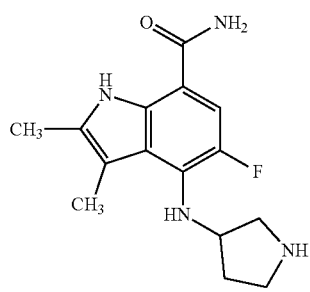
(I-20)

Following the procedures used to prepare Intermediate 13 but substituting (RS)-benzyl 3-aminopyrrolidine-1-carboxylate for (S)-benzyl piperidin-3-ylcarbamate, 4-bromo-5-fluoro-2,3-dimethyl-1H-indole-7-carbonitrile [Intermediate 12] was converted into (RS)-5-fluoro-2,3-dimethyl-4-(pyrrolidin-3-ylamino)-1H-indole-7-carboxamide. Mass spectrum m/z 291 (M+H)$^+$.

Intermediate 21

(S)-5-Fluoro-2,3-dimethyl-4-(pyrrolidin-3-ylamino)-1H-indole-7-carboxamide

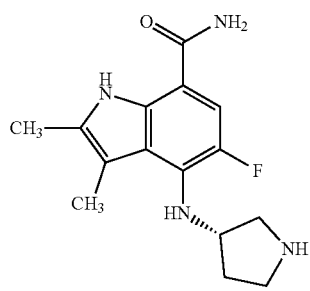
(I-21)

Intermediate 21A: (S)-Benzyl 3-((7-cyano-5-fluoro-2,3-dimethyl-1H-indol-4-yl)amino) pyrrolidine-1-carboxylate

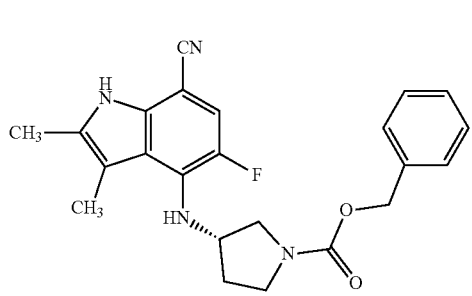
(I-21A)

Following the procedure used to prepare Intermediate 13A but substituting (S)-benzyl 3-aminopyrrolidine-1-carboxylate for (S)-benzyl piperidin-3-ylcarbamate, 4-bromo-5-fluoro-2,3-dimethyl-1H-indole-7-carbonitrile [Intermediate 12] was converted into (S)-benzyl 3-((7-cyano-5-fluoro-2,3-dimethyl-1H-indol-4-yl)amino)pyrrolidine-1-carboxylate in 39% yield. Mass spectrum m/z 407 (M+H)$^+$.

Intermediate 21

Following the procedure used to prepare Intermediate 13 from Intermediate 13A, (S)-benzyl 3-((7-cyano-5-fluoro-2,3-dimethyl-1H-indol-4-yl)amino)pyrrolidine-1-carboxylate was converted into (S)-5-fluoro-2,3-dimethyl-4-(pyrrolidin-3-ylamino)-1H-indole-7-carboxamide in 77% yield. Mass spectrum m/z 291 (M+H)$^+$.

Intermediate 22

(RS)-4-(3-Aminopyrrolidin-1-yl)-2,3-dimethyl-1H-indole-7-carboxamide

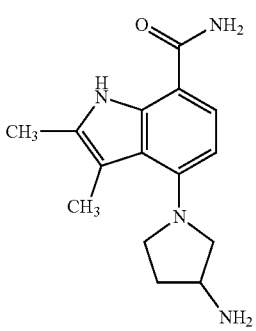
(I-22)

Following the procedures used to prepare Intermediate 13 but substituting (RS)-benzyl pyrrolidin-3-ylcarbamate for (S)-benzyl piperidin-3-ylcarbamate, 4-bromo-2,3-dimethyl-1H-indole-7-carbonitrile [Intermediate 11] was converted into (RS)-4-(3-aminopyrrolidin-1-yl)-2,3-dimethyl-1H-indole-7-carboxamide. Mass spectrum m/z 273 (M+H)$^+$. $^1$H NMR (400 MHz, DMSO-d$_6$) δ 10.60 (s, 1H), 7.73 (dd, J=8.7, 5.6 Hz, 1H), 7.44 (d, J=8.1 Hz, 1H), 6.96 (br. s., 3H), 6.44 (d, J=8.1 Hz, 1H), 3.56-3.46 (m, 1H), 3.26-3.08 (m, 3H), 2.82 (dd, J=9.5, 5.3 Hz, 1H), 2.33 (s, 3H), 2.30 (s, 3H), 2.19-2.11 (m, 1H), 1.61-1.50 (m, 1H).

Intermediate 23

(R)-4-(3-Aminopyrrolidin-1-yl)-2,3-dimethyl-1H-indole-7-carboxamide

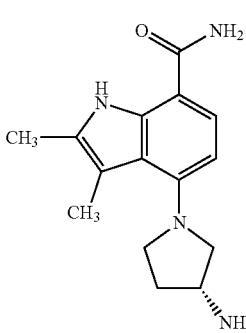
(I-23)

Following the procedures used to prepare Intermediate 13 but substituting (R)-benzyl pyrrolidin-3-ylcarbamate for (S)-benzyl piperidin-3-ylcarbamate, 4-bromo-2,3-dimethyl-1H-indole-7-carbonitrile [Intermediate 11] was converted into (R)-4-(3-aminopyrrolidin-1-yl)-2,3-dimethyl-1H-indole-7-carboxamide. Mass spectrum m/z 273 (M+H)$^+$.

Intermediate 24

(S)-4-(3-Aminopyrrolidin-1-yl)-5-fluoro-2,3-dimethyl-1H-indole-7-carboxamide

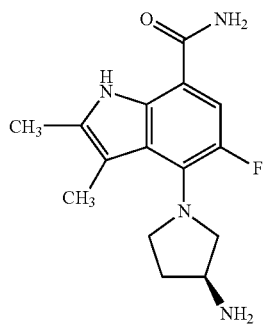

(I-24)

Following the procedures used to prepare Intermediate 13 but substituting (S)-benzyl pyrrolidin-3-ylcarbamate for (S)-benzyl piperidin-3-ylcarbamate, 4-bromo-5-fluoro-2,3-dimethyl-1H-indole-7-carbonitrile [Intermediate 12] was converted into (S)-4-(3-aminopyrrolidin-1-yl)-5-fluoro-2,3-dimethyl-1H-indole-7-carboxamide. Mass spectrum m/z 291 (M+H)$^+$.

Intermediate 25

(RS)-2,3-Dimethyl-4-(piperidin-3-ylamino)-1H-indole-7-carboxamide

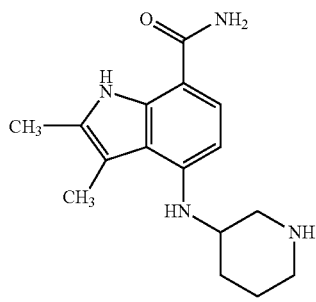

(I-25)

Following the procedures used to prepare Intermediate 13 but substituting (RS)-benzyl 3-aminopiperidine-1-carboxylate for (S)-benzyl piperidin-3-ylcarbamate, 4-bromo-2,3-dimethyl-1H-indole-7-carbonitrile [Intermediate 11] was converted into (RS)-2,3-dimethyl-4-(piperidin-3-ylamino)-1H-indole-7-carboxamide. Mass spectrum m/z 287 (M+H)$^+$. $^1$H NMR (500 MHz, DMSO-d$_6$) δ 10.40 (s, 1H), 7.94 (s, 1H), 7.56 (br. s., 1H), 7.41 (d, J=7.9 Hz, 1H), 6.81 (br. s., 1H), 6.08 (d, J=8.5 Hz, 1H), 5.40-5.23 (m, 1H), 3.77-3.56 (m, 2H), 3.06 (d, J=12.2 Hz, 1H), 2.78 (br. s., 1H), 2.70-2.61 (m, 2H), 2.38 (s, 3H), 2.26 (s, 3H), 1.86-1.78 (m, 1H), 1.69-1.60 (m, 2H), 1.52-1.41 (m, 1H).

Intermediate 26

(S)-2,3-Dimethyl-4-(pyrrolidin-3-ylamino)-1H-indole-7-carboxamide

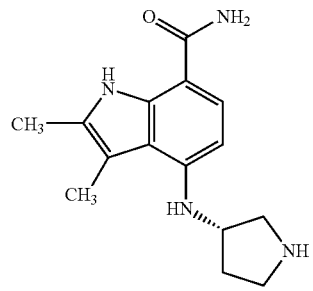

(I-26)

Intermediate 26A: (S)-tert-Butyl 3-((7-cyano-2,3-dimethyl-1H-indol-4-yl)amino) pyrrolidine-1-carboxylate

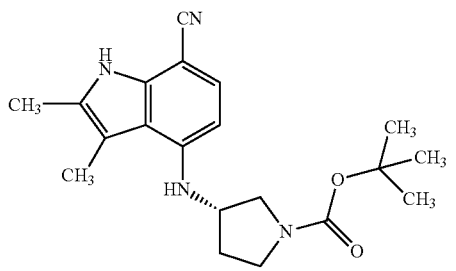

(I-26A)

A mixture of 4-bromo-2,3-dimethyl-1H-indole-7-carbonitrile [Intermediate 11] (0.400 g, 1.61 mmol), (S)-tert-butyl 3-aminopyrrolidine-1-carboxylate (0.336 g, 1.80 mmol) and 1,4-dioxane (15 mL) was bubbled with nitrogen for 5 min 2,2'-bis(diphenylphosphino)-1,1'-binaphthalene (0.050 g, 0.080 mmol), tris(dibenzylideneacetone)dipalladium (0.074 g, 0.080 mmol) and Cs$_2$CO$_3$ (0.732 g, 2.25 mmol) were added, and the mixture was sealed under a nitrogen atmosphere and heated at 100° C. After 19 h, the mixture was cooled to room temperature. Water (50 mL) and EtOAc (50 mL) were added, and the mixture was extracted with EtOAc (3×50 mL). The combined organic extracts were washed with brine, dried and concentrated. The residue was subjected to column chromatography on silica gel, eluting with EtOAc-hexanes, to provide (S)-tert-butyl 3-((7-cyano-2,3-dimethyl-1H-indol-4-yl)amino) pyrrolidine-1-carboxylate as a pale yellow solid (0.47 g, 79% yield). Mass spectrum m/z 355 (M+H)$^+$. $^1$H NMR (400 MHz, DMSO-d$_6$) δ 11.16 (s, 1H), 7.24 (d, J=8.1 Hz, 1H), 6.23 (d, J=8.4 Hz, 1H), 5.36 (br. s., 1H), 4.25-4.08 (m, 1H), 3.69-3.57 (m, 1H), 3.48-3.37 (m, 1H), 3.38-3.31 (m, 1H), 3.27-3.16 (m, 1H), 2.34 (s, 3H), 2.24 (s, 3H), 2.22-2.13 (m, 1H), 1.97-1.86 (m, 1H), 1.49-1.31 (m, 9H).

Intermediate 26B: (S)-2,3-Dimethyl-4-(pyrrolidin-3-ylamino)-1H-indole-7-carbonitrile TFA Salt

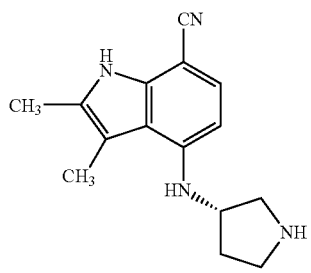

(I-26B)

A mixture of (S)-tert-butyl 3-((7-cyano-2,3-dimethyl-1H-indol-4-yl)amino) pyrrolidine-1-carboxylate (0.470 g, 1.33 mmol) and DCM (5 mL) was cooled to 0° C., treated with TFA (5 mL) and stirred for 1 h. The mixture was concentrated to provide crude (S)-2,3-dimethyl-4-(pyrrolidin-3-ylamino)-1H-indole-7-carbonitrile TFA salt, used without further purification. Mass spectrum m/z 255 (M+H)$^+$. $^1$H NMR (400 MHz, DMSO-d$_6$) δ 11.23 (s, 1H), 8.93-8.72 (m, 1H), 7.27 (d, J=8.1 Hz, 1H), 6.21 (d, J=8.6 Hz, 1H), 5.48 (br. s., 1H), 4.27 (br. s., 1H), 3.54-3.44 (m, 1H), 3.42-3.33 (m, 1H), 3.31-3.17 (m, 2H), 2.38 (s, 3H), 2.36-2.28 (m, 1H), 2.26 (s, 3H), 2.09-2.00 (m, 1H).

Intermediate 26

A mixture of (S)-2,3-dimethyl-4-(pyrrolidin-3-ylamino)-1H-indole-7-carbonitrile TFA salt (488 mg, 1.33 mmol) and 80% aqueous H$_2$SO$_4$ (3 mL) was heated at 60° C. After 2 h, the mixture was cooled to room temperature, then was slowly added to 10 M aqueous NaOH at 0° C. The aqueous supernatant was removed from the resulting sticky brown solid by decantation. Water was added to the solid and the mixture was extracted with EtOAc (4×50 mL). The combined organic extracts were washed with brine, dried and concentrated to provide (S)-2,3-dimethyl-4-(pyrrolidin-3-ylamino)-1H-indole-7-carboxamide as an orange solid (270 mg, 75% yield). Mass spectrum m/z 273 (M+H)$^+$. $^1$H NMR (400 MHz, DMSO-d$_6$) δ 10.40 (s, 1H), 7.59 (br. s., 1H), 7.42 (d, J=8.4 Hz, 1H), 6.85 (br. s., 1H), 6.05 (d, J=8.4 Hz, 1H), 5.07 (d, J=6.8 Hz, 1H), 3.99-3.89 (m, 1H), 3.30 (br. s., 1H), 3.04 (dd, J=11.1, 6.1 Hz, 1H), 2.98-2.88 (m, 1H), 2.82-2.67 (m, 2H), 2.36 (s, 3H), 2.26 (s, 3H), 2.10 (td, J=13.4, 7.5 Hz, 1H), 1.68-1.53 (m, 1H).

Intermediate 27

(R)-2,3-Dimethyl-4-(pyrrolidin-3-ylamino)-1H-indole-7-carboxamide

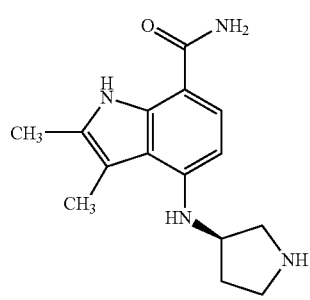

(I-27)

Following the procedures used to prepared Intermediate 26 but substituting (R)-tert-butyl 3-aminopyrrolidine-1-carboxylate for (S)-tert-butyl 3-aminopyrrolidine-1-carboxylate, 4-bromo-2,3-dimethyl-1H-indole-7-carbonitrile [Intermediate 11] was converted into (R)-2,3-dimethyl-4-(pyrrolidin-3-ylamino)-1H-indole-7-carboxamide. Mass spectrum and $^1$H NMR were the same as those for Intermediate 26.

Intermediate 28

(S)-2,3-Dimethyl-4-(methyl(pyrrolidin-3-yl)amino)-1H-indole-7-carboxamide

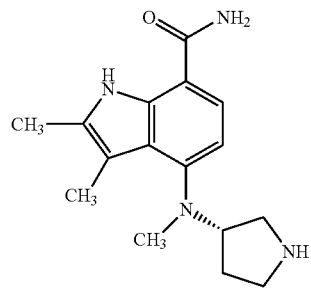

(I-28)

Following the procedures used to prepare Intermediate 26 but substituting (S)-tert-butyl 3-(methylamino)pyrrolidine-1-carboxylate for (S)-tert-butyl 3-aminopyrrolidine-1-carboxylate, 4-bromo-2,3-dimethyl-1H-indole-7-carbonitrile [Intermediate 11] was converted into (S)-2,3-dimethyl-4-(methyl(pyrrolidin-3-yl)amino)-1H-indole-7-carboxamide. Mass spectrum m/z 287 (M+H)$^+$.

Intermediate 29

(RS-cis)-5-Fluoro-4-(hexahydro-1H-pyrrolo[3,4-b]pyridin-6(2H)-yl)-2,3-dimethyl-1H-indole-7-carboxamide

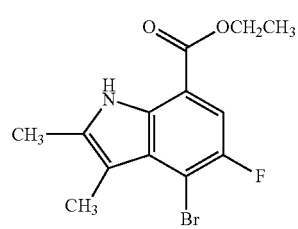

(I-29)

Intermediate 29A: Ethyl 4-bromo-5-fluoro-2,3-dimethyl-1H-indole-7-carboxylate (I-29A)

A mixture of 4-bromo-5-fluoro-2,3-dimethyl-1H-indole-7-carboxylic acid [Intermediate 2C] (2.00 g, 6.99 mmol) and concentrated H₂SO₄ (0.373 mL, 6.99 mmol) in ethanol (30 mL) was stirred at reflux for 6 days. The mixture was cooled to room temperature and concentrated. The residue was partitioned between EtOAc and water, and the organic layer was dried and concentrated. The residue was purified by column chromatography on silica gel, eluting with EtOAc-hexanes (gradient from 0-100%) to provide ethyl 4-bromo-5-fluoro-2,3-dimethyl-1H-indole-7-carboxylate as an off-white solid (1.67 g, 72% yield). Mass spectrum m/z 314, 316 (M+H)⁺. ¹H NMR (400 MHz, CDCl₃) δ 9.57 (br. s., 1H), 7.54 (d, J=9.4 Hz, 1H), 4.45 (q, J=7.2 Hz, 2H), 2.49 (d, J=0.5 Hz, 3H), 2.40 (s, 3H), 1.46 (t, J=7.2 Hz, 3H).

Intermediate 29B: (RS-cis)-tert-Butyl 6-(7-(ethoxycarbonyl)-5-fluoro-2,3-dimethyl-1H-indol-4-yl)octahydro-1H-pyrrolo[3,4-b]pyridine-1-carboxylate

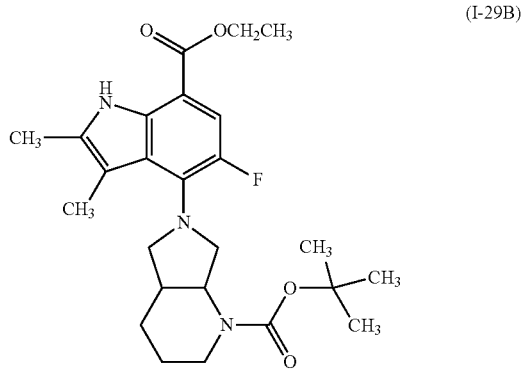 [SMILES: CCOC(=O)c1cc(F)c(N2CC3CCCN(C(=O)OC(C)(C)C)C3C2)c2c(C)c(C)[nH]c12]

(I-29B)

Following the procedure used to prepare Intermediate 13A but substituting (RS-cis)-tert-butyl octahydro-1H-pyrrolo[3,4-b]pyridine-1-carboxylate for (S)-benzyl piperidine-3-ylcarbamate, ethyl 4-bromo-5-fluoro-2,3-dimethyl-1H-indole-7-carboxylate was converted into (RS-cis)-tert-butyl 6-(7-(ethoxycarbonyl)-5-fluoro-2,3-dimethyl-1H-indol-4-yl)octahydro-1H-pyrrolo[3,4-b]pyridine-1-carboxylate as a light yellow glassy solid in 61% yield. Mass spectrum m/z 460 (M+H)⁺.

Intermediate 29C: (RS-cis)-4-(1-(tert-Butoxycarbonyl)hexahydro-1H-pyrrolo[3,4-b]pyridin-6(2H)-yl)-5-fluoro-2,3-dimethyl-1H-indole-7-carboxylic acid

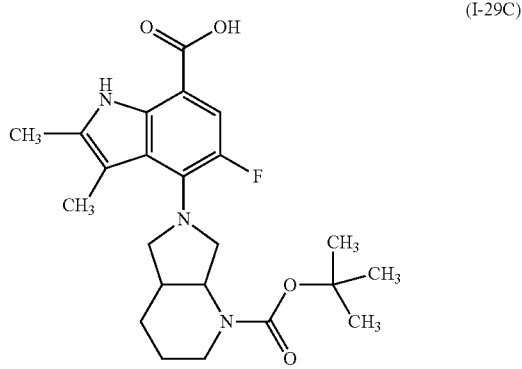 [SMILES: Cc1[nH]c2c(C(=O)O)cc(F)c(N3CC4CCCN(C(=O)OC(C)(C)C)C4C3)c2c1C]

(I-29C)

A mixture of (RS-cis)-tert-butyl 6-(7-(ethoxycarbonyl)-5-fluoro-2,3-dimethyl-1H-indol-4-yl)octahydro-1H-pyrrolo[3,4-b]pyridine-1-carboxylate (91 mg, 0.198 mmol) and 1 M aqueous NaOH (1.98 mL, 1.98 mmol) in THF (1 mL) and MeOH (1 mL) was stirred at room temperature overnight. The mixture was treated with 1 M aqueous HCl (to pH about 6) and extracted twice with EtOAc. The combined organic phases were dried and concentrated to provide (RS-cis)-4-(1-(tert-butoxycarbonyl)hexahydro-1H-pyrrolo[3,4-b]pyridin-6(2H)-yl)-5-fluoro-2,3-dimethyl-1H-indole-7-carboxylic acid as a yellow glassy solid (73 mg, 85% yield), used without further purification. Mass spectrum m/z 432 (M+H)⁺.

Intermediate 29D: (RS-cis)-tert-Butyl 6-(7-carbamoyl-5-fluoro-2,3-dimethyl-1H-indol-4-yl)octahydro-1H-pyrrolo[3,4-b]pyridine-1-carboxylate

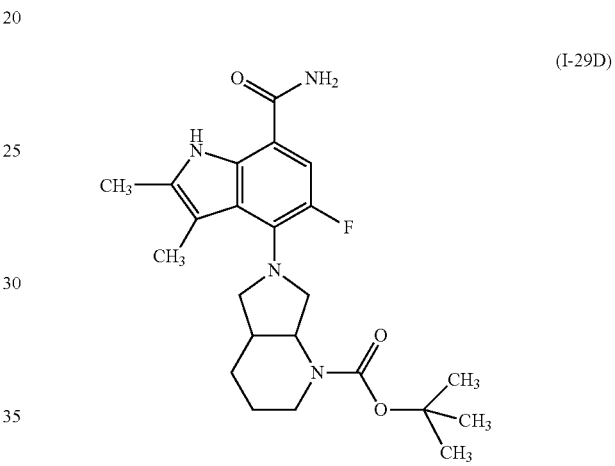

(I-29D)

A solution of (RS-cis)-4-(1-(tert-butoxycarbonyl)hexahydro-1H-pyrrolo[3,4-b]pyridin-6(2H)-yl)-5-fluoro-2,3-dimethyl-1H-indole-7-carboxylic acid (73 mg, 0.169 mmol), NH₄Cl (45.2 mg, 0.846 mmol) and HATU (70.8 mg, 0.186 mmol) in DMF (1 mL) was treated with triethylamine (0.118 mL, 0.846 mmol) and stirred at room temperature for 2 h. The mixture was diluted with DCM, washed with water, dried and concentrated. The residue was purified by column chromatography on silica gel, eluting with EtOAc-hexanes (gradient from 0-100%), to provide (RS-cis)-tert-butyl 6-(7-carbamoyl-5-fluoro-2,3-dimethyl-1H-indol-4-yl)octahydro-1H-pyrrolo[3,4-b]pyridine-1-carboxylate as a yellow gum (74.2 mg, 92% yield). Mass spectrum m/z 431 (M+H)⁺.

Intermediate 29

A solution of (RS-cis)-tert-butyl 6-(7-carbamoyl-5-fluoro-2,3-dimethyl-1H-indol-4-yl)octahydro-1H-pyrrolo[3,4-b]pyridine-1-carboxylate (70 mg, 0.163 mmol) and TFA (0.5 mL, 6.49 mmol) in DCM (1.5 mL) was stirred at room temperature for 30 min. The mixture was concentrated, and the residue was partitioned between DCM and saturated aqueous NaHCO₃. The organic phase was dried and concentrated to provide (RS-cis)-5-fluoro-4-(hexahydro-1H-pyrrolo[3,4-b]pyridin-6(2H)-yl)-2,3-dimethyl-1H-indole-7-carboxamide as a yellow glassy solid (53 mg, 99% yield), used without further purification. Mass spectrum m/z 331 (M+H)⁺.

Alternative Synthesis of Intermediate 29:

Following the procedures used to prepare Intermediate 26 but substituting (RS-cis)-tert-butyl octahydro-1H-pyrrolo[3,4-b]pyridine-1-carboxylate for (S)-tert-butyl 3-aminopyrrolidine-1-carboxylate, 4-bromo-5-fluoro-2,3-dimethyl-1H-indole-7-carbonitrile [Intermediate 12] was converted into (RS-cis)-5-fluoro-4-(hexahydro-1H-pyrrolo[3,4-b]pyridin-6(2H)-yl)-2,3-dimethyl-1H-indole-7-carboxamide.

Intermediate 30

(RS-cis)-5-Fluoro-4-(hexahydropyrrolo[3,4-b]pyrrol-1(2H)-yl)-2,3-dimethyl-1H-indole-7-carboxamide

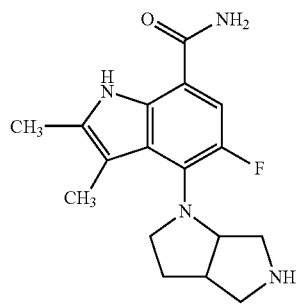

(I-30)

Following the procedures used to prepare Intermediate 26 but substituting (RS-cis)-tert-butyl hexahydropyrrolo[3,4-b]pyrrole-5(1H)-carboxylate for (S)-tert-butyl 3-aminopyrrolidine-1-carboxylate, 4-bromo-5-fluoro-2,3-dimethyl-1H-indole-7-carbonitrile [Intermediate 12] was converted into (RS-cis)-5-fluoro-4-(hexahydropyrrolo[3,4-b]pyrrol-1(2H)-yl)-2,3-dimethyl-1H-indole-7-carboxamide. Mass spectrum m/z 317 (M+H)$^+$.

Intermediate 31

(RS-cis)-5-Fluoro-4-(hexahydropyrrolo[3,4-b]pyrrol-5(1H)-yl)-2,3-dimethyl-H-indole-7-carboxamide

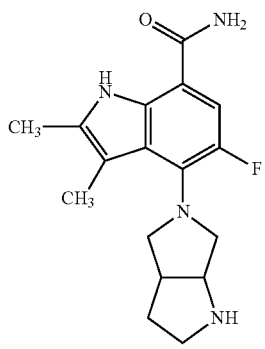

(I-31)

Following the procedures used to prepare Intermediate 26 but substituting (RS-cis)-tert-butyl hexahydropyrrolo[3,4-b]pyrrole-1(2H)-carboxylate for (S)-tert-butyl 3-aminopyrrolidine-1-carboxylate, 4-bromo-5-fluoro-2,3-dimethyl-1H-indole-7-carbonitrile [Intermediate 12] was converted into (RS-cis)-5-fluoro-4-(hexahydropyrrolo[3,4-b]pyrrol-5(1H)-yl)-2,3-dimethyl-1H-indole-7-carboxamide. Mass spectrum m/z 317 (M+H)$^+$.

Intermediate 32 cis-5-Fluoro-4-(hexahydropyrrolo[3,4-c]pyrrol-2(1H)-yl)-2,3-dimethyl-1H-indole-7-carboxamide

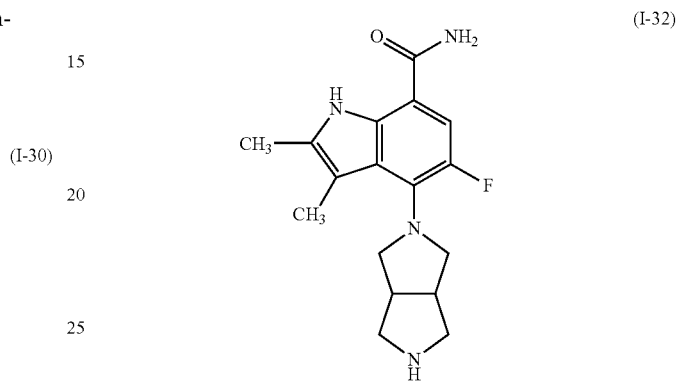

(I-32)

Following the procedures used to prepare Intermediate 26 but substituting cis-tert-butyl hexahydropyrrolo[3,4-c]pyrrole-2(1H)-carboxylate for (S)-tert-butyl 3-aminopyrrolidine-1-carboxylate, 4-bromo-5-fluoro-2,3-dimethyl-1H-indole-7-carbonitrile [Intermediate 12] was converted into cis-5-fluoro-4-(hexahydropyrrolo[3,4-c]pyrrol-2(1H)-yl)-2,3-dimethyl-1H-indole-7-carboxamide. Mass spectrum m/z 317 (M+H)$^+$.

Intermediate 33

(S)-4-(3-(Ethylamino)piperidin-1-yl)-5-fluoro-2,3-dimethyl-1H-indole-7-carboxamide

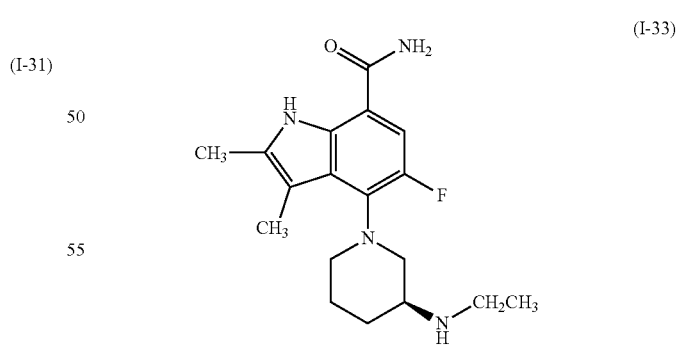

(I-33)

Following the procedures used to prepare Intermediate 26 but substituting (S)-tert-butyl ethyl(piperidin-3-yl)carbamate for (S)-tert-butyl 3-aminopyrrolidine-1-carboxylate, 4-bromo-5-fluoro-2,3-dimethyl-1H-indole-7-carbonitrile [Intermediate 12] was converted into (S)-4-(3-(ethylamino)piperidin-1-yl)-5-fluoro-2,3-dimethyl-1H-indole-7-carboxamide.

Intermediate 34

2,3-Dimethyl-4-(piperazin-1-yl)-1H-indole-7-carboxamide

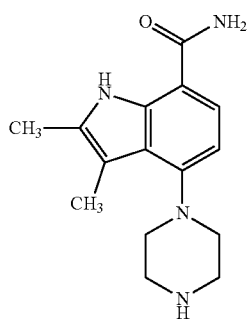

(I-34)

Intermediate 34A: 2,3-Dimethyl-4-(piperazin-1-yl)-1H-indole-7-carbonitrile

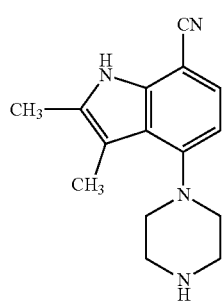

(I-34A)

A mixture of 4-bromo-2,3-dimethyl-1H-indole-7-carbonitrile [Intermediate 11] (100 mg, 0.401 mmol), piperazine (69.2 mg, 0.803 mmol), tris(dibenzylideneacetone) dipalladium (18.4 mg, 0.020 mmol), 2,2'-bis(diphenylphosphino)-1,1'-binaphthalene (12.5 mg, 0.020 mmol) and $Cs_2CO_3$ (183 mg, 0.562 mmol) in 1,4-dioxane (4 mL) in a sealed reaction vessel was subjected to three evacuate-fill cycles with nitrogen. The mixture was heated at 100° C. for 16 h, then was cooled to room temperature, filtered and the collected precipitate was washed with EtOAc. The filtrate was concentrated and the residue was subjected to column chromatography on silica gel (12 g), eluting with MeOH-DCM (gradient from 0-30%), to provide 2,3-dimethyl-4-(piperazin-1-yl)-1H-indole-7-carbonitrile as a light brown solid (56 mg, 55% yield). Mass spectrum m/z 255 (M+H)$^+$.

Intermediate 34

A mixture of 2,3-dimethyl-4-(piperazin-1-yl)-1H-indole-7-carbonitrile (56 mg, 0.220 mmol) and 80% aqueous $H_2SO_4$ (2 mL) was heated at 60° C. for 3 h. The mixture was poured onto ice and the pH of the resulting mixture was adjusted to about 10 with solid KOH. The mixture was then extracted three times with a mixture of 3:1 DCM-isopropanol. The combined organic phases were washed with water, dried and concentrated to provide 2,3-dimethyl-4-(piperazin-1-yl)-1H-indole-7-carboxamide as a yellow solid (35 mg, 58% yield). Mass spectrum m/z 273 (M+H)$^+$.

Intermediate 35

(RS)-2,3-Dimethyl-4-(3-(methylamino)piperidin-1-yl)-1H-indole-7-carboxamide

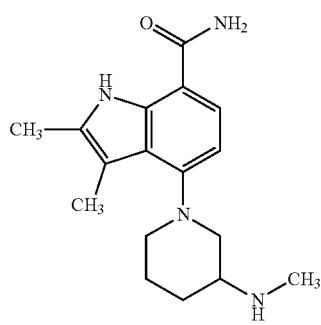

(I-35)

Intermediate 35A: (RS)-tert-Butyl 3-(((benzyloxy)carbonyl)(methyl)amino)piperidine-1-carboxylate

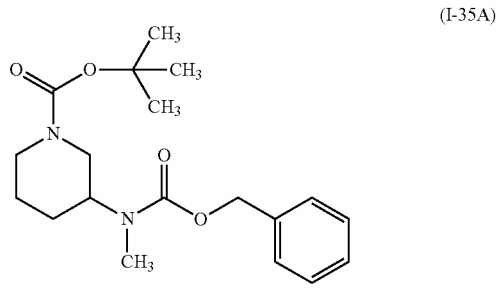 [SMILES: CN(C(=O)OCc1ccccc1)C1CCCN(C(=O)OC(C)(C)C)C1]

(I-35A)

A solution of (RS)-tert-butyl 3-(methylamino)piperidine-1-carboxylate (1.60 g, 7.47 mmol) and DIEA (1.57 mL, 8.96 mmol) in DCM (29.9 mL) was cooled to 0° C. and slowly treated with benzyl chloroformate (1.08 mL, 7.54 mmol). The resulting mixture was stirred at room temperature for 1 h, then was concentrated. The residue was subjected to column chromatography on silica gel to provide (RS)-tert-butyl 3-(((benzyloxy)carbonyl)(methyl)amino)piperidine-1-carboxylate as a colorless oil (2.56 g, 98% yield). Mass spectrum m/z 371 (M+Na)$^+$. $^1$H NMR (400 MHz, CDCl$_3$) δ 7.40-7.29 (m, 5H), 5.16 (s, 2H), 4.21-3.81 (m, 3H), 2.87 (s, 3H), 2.76 (t, J=10.9 Hz, 1H), 2.56 (t, J=11.9 Hz, 1H), 1.85 (d, J=12.3 Hz, 1H), 1.78-1.70 (m, 1H), 1.66-1.60 (m, 1H), 1.45 (br. s., 10H).

Intermediate 35B: (RS)-Benzyl methyl(piperidin-3-yl)carbamate

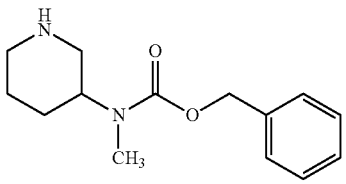

(I-35B)

A solution of (RS)-tert-butyl 3-(((benzyloxy)carbonyl)(methyl)amino)piperidine-1-carboxylate (2.56 g, 7.34 mmol) in DCM (14.7 mL) was cooled to 0° C. and treated slowly with TFA (2.80 mL, 36.7 mmol). The resulting mixture was stirred at room temperature for 16 h, then was concentrated. The residue was partitioned between 1 M aqueous NaOH and EtOAc. The organic phase was washed with brine, dried and concentrated to provide (RS)-benzyl methyl(piperidin-3-yl)carbamate as a light yellow oil (1.71 g, 94% yield). Mass spectrum m/z 249 (M+H)$^+$.

Intermediate 35

Following the procedures used to prepare Intermediate 13 but substituting (RS)-benzyl methyl(piperidin-3-yl)carbamate for (S)-benzyl piperidin-3-ylcarbamate, 4-bromo-2,3-dimethyl-1H-indole-7-carbonitrile [Intermediate 11] was converted into (RS)-2,3-dimethyl-4-(3-(methylamino)piperidin-1-yl)-1H-indole-7-carboxamide. Mass spectrum m/z 301 (M+H)$^+$. $^1$H NMR (500 MHz, DMSO-d$_6$) δ 10.60 (s, 1H), 7.81 (br. s., 1H), 7.47 (d, J=8.1 Hz, 1H), 7.10 (br. s., 1H), 6.53 (d, J=8.4 Hz, 1H), 2.70 (br. s., 1H), 2.59 (br. s., 1H), 2.37-2.29 (m, 10H), 1.97 (d, J=10.4 Hz, 1H), 1.89 (s, 3H), 1.81-1.65 (m, 2H), 1.13 (br. s., 1H).

Intermediate 36

(S)-5-Fluoro-2,3-dimethyl-4-(3-(methylamino)piperidin-1-yl)-1H-indole-7-carboxamide

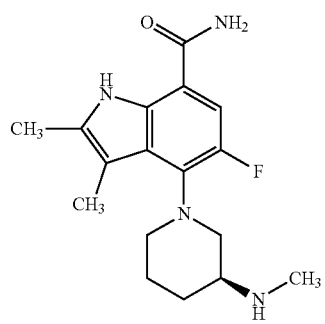

(I-36)

Following the procedures used to prepare Intermediate 13 but substituting (S)-tert-butyl methyl(piperidin-3-yl)carbamate for (S)-benzyl piperidin-3-ylcarbamate, 4-bromo-5-fluoro-2,3-dimethyl-1H-indole-7-carbonitrile [Intermediate 12] was converted into (S)-5-fluoro-2,3-dimethyl-4-(3-(methylamino)piperidin-1-yl)-1H-indole-7-carboxamide. Mass spectrum m/z 319 (M+H)$^+$.

Intermediate 37

(S)-5-Fluoro-2,3-dimethyl-4-(methyl(pyrrolidin-3-yl)amino)-1H-indole-7-carboxamide

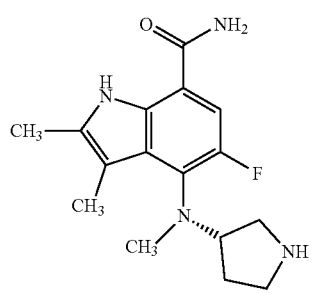

(I-37)

Intermediate 37A: (S)-Benzyl 3-((7-cyano-5-fluoro-2,3-dimethyl-1H-indol-4-yl)(methyl) amino)-pyrrolidine-1-carboxylate

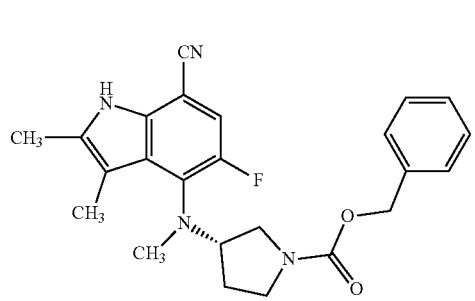

(I-37A)

A mixture of (S)-benzyl 3-((7-cyano-5-fluoro-2,3-dimethyl-1H-indol-4-yl)amino) pyrrolidine-1-carboxylate [Intermediate 21A] (0.114 g, 0.280 mmol), paraformaldehyde (0.025 g, 0.841 mmol), acetic acid (0.048 mL, 0.841 mmol), and sodium cyanoborohydride (0.035 g, 0.561 mmol) in MeOH (2.5 mL) was stirred at room temperature overnight. The mixture was then heated at 50° C. for about 24 h, then was stirred at room temperature overnight. The mixture was diluted with EtOAc and washed sequentially with water and brine. The organic layer was collected, and the aqueous layers were sequentially extracted twice with EtOAc. The combined organic layers were dried and concentrated. The residue was subjected to column chromatography on silica gel, eluting with EtOAc-hexane (5%, 13% and 20%, sequentially), to give (S)-benzyl 3-((7-cyano-5-fluoro-2,3-dimethyl-1H-indol-4-yl)(methyl)amino)pyrrolidine-1-carboxylate as a colorless viscous oil (0.049 g, 42% yield). Mass spectrum m/z 421 (M+H)$^+$.

Intermediate 37

Following the procedure used in the last step of the preparation of Intermediate 13, (S)-benzyl 3-((7-cyano-5-fluoro-2,3-dimethyl-1H-indol-4-yl)(methyl)amino) pyrrolidine-1-carboxylate was converted into (S)-5-fluoro-2,3-dimethyl-4-(methyl (pyrrolidin-3-yl)amino)-1H-indole-7-carboxamide in 94% yield. Mass spectrum m/z 305 (M+H)$^+$.

Intermediate 38

(RS)-2,3-Dimethyl-4-(piperidin-3-yl)-1H-indole-7-carboxamide, TFA Salt

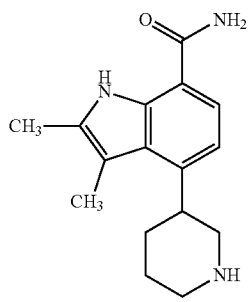

(I-38)

Intermediate 38A: tert-Butyl 3-(7-carbamoyl-2,3-dimethyl-1H-indol-4-yl)-5,6-dihydropyridine-1(2H)-carboxylate

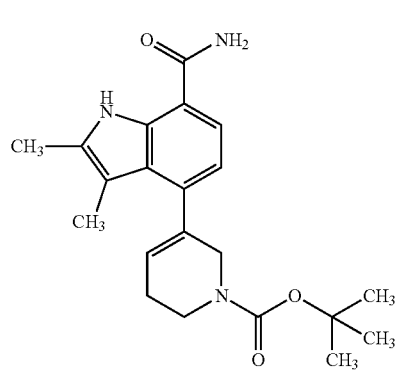

(I-38A)

A mixture of 4-bromo-2,3-dimethyl-1H-indole-7-carboxamide [Intermediate 1] (175 mg, 0.655 mmol), tert-butyl 3-(4,4,5,5-tetramethyl-1,3,2-dioxaborolan-2-yl)-5,6-dihydropyridine-1(2H)-carboxylate (203 mg, 0.655 mmol), 1,4-dioxane (5 mL) and water (1 mL) was bubbled with nitrogen for 5 min and treated with PdCl$_2$(dppf) DCM adduct (32.1 mg, 0.039 mmol) and Cs$_2$CO$_3$ (640 mg, 1.97 mmol). The mixture was sealed under an atmosphere of nitrogen and heated at 90° C. After 15 h the mixture was cooled to room temperature and diluted with EtOAc (15 mL) and water (15 mL). The layers were separated and the aqueous layer was extracted three times with EtOAc. The combined organic extracts were dried and concentrated. The residue was subjected to column chromatography on silica gel, eluting with EtOAc-hexanes, to provide tert-butyl 3-(7-carbamoyl-2,3-dimethyl-1H-indol-4-yl)-5,6-dihydropyridine-1(2H)-carboxylate as a yellow solid (174 mg, 69% yield). Mass spectrum m/z 370 (M+H)$^+$. $^1$H NMR (400 MHz, DMSO-d$_6$) δ 10.69 (s, 1H), 7.91 (br. s., 1H), 7.50 (d, J=7.7 Hz, 1H), 7.23 (br. s., 1H), 6.75 (d, J=7.5 Hz, 1H), 6.62 (br. s., 1H), 3.62-3.56 (m, 2H), 2.40-2.29 (m, 5H), 2.13 (s, 3H), 1.97-1.87 (m, 2H), 1.55-1.31 (m, 9H).

Intermediate 38B: tert-Butyl (RS)-3-(7-carbamoyl-2,3-dimethyl-1H-indol-4-yl)piperidine-1-carboxylate

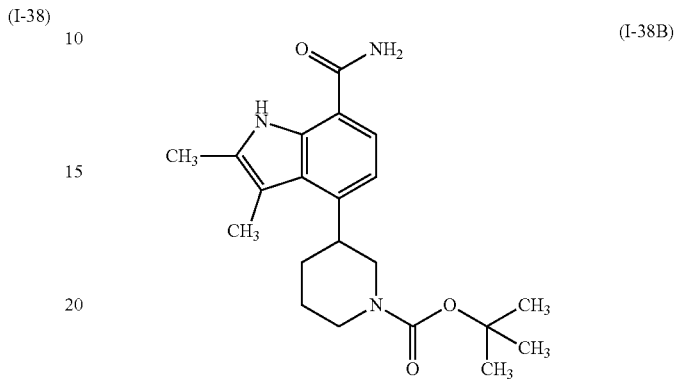

(I-38B)

A mixture of tert-butyl 3-(7-carbamoyl-2,3-dimethyl-1H-indol-4-yl)-5,6-dihydropyridine-1(2H)-carboxylate (94 mg, 0.254 mmol), DMF (1 mL) and MeOH (5 mL) was treated with palladium on carbon (94 mg) and stirred at room temperature under an atmosphere of hydrogen. After 20 h, additional palladium on carbon (94 mg) was added and stirring under an atmosphere of hydrogen was continued for a total of three days. The mixture was filtered and the filtrate was concentrated. The residue was dissolved in EtOAc, washed with water, and the aqueous layer was extracted three times with EtOAc. The organic extracts were combined, washed sequentially with brine and 10% aqueous LiCl, dried and concentrated to provide (RS)-tert-butyl 3-(7-carbamoyl-2,3-dimethyl-1H-indol-4-yl)piperidine-1-carboxylate as a yellow solid (72.5 mg, 73% yield). Mass spectrum m/z 372 (M+H)$^+$. $^1$H NMR (400 MHz, DMSO-d$_6$) δ 10.66 (s, 1H), 7.91 (br. s., 1H), 7.51 (d, J=7.9 Hz, 1H), 7.22 (br. s., 1H), 6.87 (d, J=7.9 Hz, 1H), 4.15-4.06 (m, 1H), 3.50-3.38 (m, 1H), 2.93-2.73 (m, 2H), 2.60 (s, 6H), 1.96-1.88 (m, 1H), 1.86-1.67 (m, 2H), 1.61-1.47 (m, 1H), 1.40 (s, 9H), 1.28-1.21 (m, 1H).

Intermediate 38

A solution of (RS)-tert-butyl 3-(7-carbamoyl-2,3-dimethyl-1H-indol-4-yl) piperidine-1-carboxylate (74 mg, 0.179 mmol) in DCM (2 mL) was cooled to 0° C. and treated slowly with TFA (2 mL). The mixture was stirred at room temperature for 2 h, then was concentrated to provide (RS)-2,3-dimethyl-4-(piperidin-3-yl)-1H-indole-7-carboxamide TFA salt as a yellow solid (76 mg, quantitative yield). Mass spectrum m/z 272 (M+H)$^+$. $^1$H NMR (400 MHz, DMSO-d$_6$) δ 10.72 (s, 1H), 7.93 (br. s., 1H), 7.54 (d, J=7.9 Hz, 1H), 7.27 (br. s., 1H), 6.89 (d, J=7.9 Hz, 1H), 3.86-3.75 (m, 1H), 3.35 (d, J=11.9 Hz, 2H), 3.27-3.13 (m, 1H), 3.03-2.84 (m, 1H), 2.41-2.32 (m, 6H), 1.93 (d, J=11.9 Hz, 1H), 1.88-1.70 (m, 2H), 1.30-1.22 (m, 1H), 0.95 (d, J=7.0 Hz, 1H).

Intermediate 39

(RS)-3-Methyl-4-(piperidin-3-yl)-1H-indole-7-carboxamide

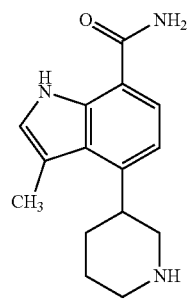
(I-39)

Intermediate 39A: tert-Butyl 3-(7-carbamoyl-3-methyl-1H-indol-4-yl)-5,6-dihydropyridine-1(2H)-carboxylate

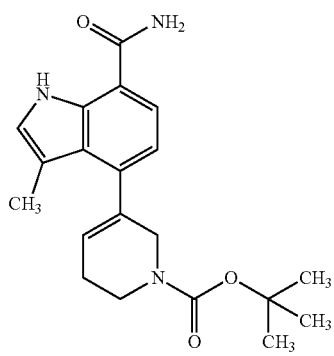
(I-39A)

Following the procedure used to prepare Intermediate 38A, 4-bromo-3-dimethyl-1H-indole-7-carboxamide [Intermediate 4] was converted into tert-butyl 3-(7-carbamoyl-3-methyl-1H-indol-4-yl)-5,6-dihydropyridine-1(2H)-carboxylate in 53% yield. Mass spectrum m/z 356 (M+H)$^+$. $^1$H NMR (400 MHz, MeOH-d$_4$) δ 7.42-7.27 (m, 1H), 7.16-7.03 (m, 1H), 6.97-6.73 (m, 2H), 3.75-3.59 (m, 2H), 2.43 (br. s., 2H), 2.30 (s, 3H), 2.02 (br. s., 2H), 1.54-1.37 (m, 9H).

Intermediate 39B: 3-Methyl-4-(1,2,5,6-tetrahydropyridin-3-yl)-1H-indole-7-carboxamide

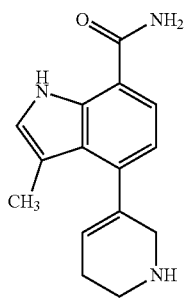
(I-39B)

Following the procedure used to prepare Intermediate 38 from Intermediate 38B, followed by neutralization of the resulting TFA salt, tert-butyl 3-(7-carbamoyl-3-methyl-1H-indol-4-yl)-5,6-dihydropyridine-1(2H)-carboxylate was converted into 3-methyl-4-(1,2,5,6-tetrahydropyridin-3-yl)-1H-indole-7-carboxamide in 93% yield. Mass spectrum m/z 256 (M+H)$^+$.

Intermediate 39

A solution of 3-methyl-4-(1,2,5,6-tetrahydropyridin-3-yl)-1H-indole-7-carboxamide (20 mg, 0.078 mmol) in MeOH (3 mL) was treated with palladium on charcoal (8.3 mg) and stirred under a hydrogen atmosphere for 12 h at room temperature. The mixture was filtered through CELITE® and the filtrate was concentrated to provide (RS)-3-methyl-4-(piperidin-3-yl)-1H-indole-7-carboxamide as a white solid (20 mg, 99% yield). Mass spectrum m/z 258 (M+H)$^+$.

Intermediate 40

(RS)-2,3-Dimethyl-4-(pyrrolidin-3-yl)-1H-indole-7-carboxamide

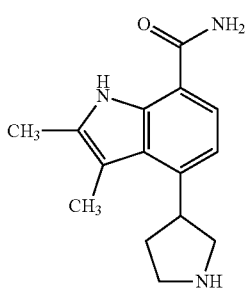
(I-40)

Following the procedures used to prepare Intermediate 38 but substituting tert-butyl 3-(4,4,5,5-tetramethyl-1,3,2-dioxaborolan-2-yl)-2,5-dihydro-1H-pyrrole-1-carboxylate for tert-butyl 3-(4,4,5,5-tetramethyl-1,3,2-dioxaborolan-2-yl)-5,6-dihydropyridine-1(2H)-carboxylate, 4-bromo-2,3-dimethyl-1H-indole-7-carboxamide [Intermediate 1] was converted into (RS)-2,3-dimethyl-4-(pyrrolidin-3-yl)-1H-indole-7-carboxamide. Mass spectrum m/z 258 (M+H)$^+$. $^1$H NMR (400 MHz, DMSO-d$_6$) δ 10.76 (s, 1H), 8.92 (br. s., 1H), 7.96 (s, 1H), 7.58 (d, J=7.9 Hz, 1H), 7.29 (br. s., 1H), 6.99 (d, J=7.9 Hz, 1H), 4.35-4.17 (m, 1H), 3.69-3.57 (m, 1H), 3.48-3.39 (m, 1H), 3.38-3.30 (m, 1H), 3.27-3.17 (m, 1H), 2.37 (s, 6H), 2.36-2.29 (m, 1H), 2.15-2.03 (m, 1H).

Intermediate 41

4-(3-Amino-2-methylphenyl)-2,3-dimethyl-1H-indole-7-carboxamide

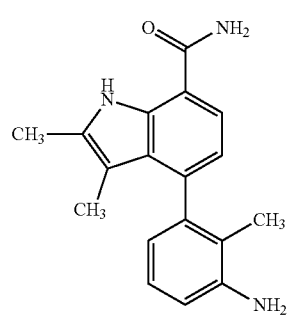
(I-41)

A mixture of 4-bromo-2,3-dimethyl-1H-indole-7-carboxamide [Intermediate 1](0.25 g, 0.936 mmol), 2-methyl-3-(4,4,5,5-tetramethyl-1,3,2-dioxaborolan-2-yl)aniline [prepared according to the procedure of U.S. Pat. No. 8,084,620, Intermediate 50-1](0.229 g, 0.983 mmol), and tetrakis(triphenylphosphine)palladium (0.054 g, 0.047 mmol) in toluene (10.8 mL) and ethanol (3.6 mL) was bubbled with argon for about 2 to 3 min. The mixture was treated with 2 M aqueous $Na_2CO_3$ (1.17 mL, 2.34 mmol), bubbled again with argon, and the reaction vessel was sealed under argon and heated at 90° C. After 16 h the mixture was cooled to room temperature and partitioned between water and EtOAc. The organic phase was concentrated and the residue was subjected to column chromatography on silica gel (24 g), eluting with EtOAc-hexanes (gradient from 50-70%), to provide 4-(3-amino-2-methylphenyl)-2,3-dimethyl-1H-indole-7-carboxamide as a light yellow solid (0.142 g, 52% yield). Mass spectrum m/z 294 $(M+H)^+$.

Intermediate 42

(RS)-5-Fluoro-2,3-dimethyl-4-(1,2,3,4-tetrahydroisoquinolin-5-yl)-1H-indole-7-carboxamide

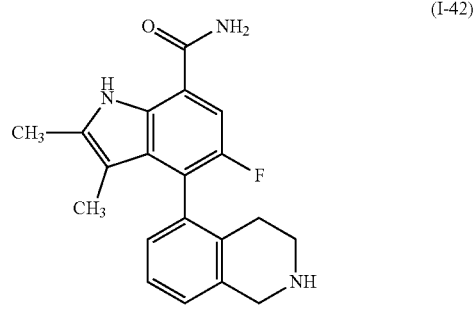 [SMILES: Cc1[nH]c2c(C(N)=O)cc(F)c(-c3cccc4c3CCNC4)c2c1C]

(I-42)

Intermediate 42A: tert-Butyl (RS)-5-(7-carbamoyl-5-fluoro-2,3-dimethyl-1H-indol-4-yl)-3,4-dihydroisoquinoline-2(1H)-carboxylate

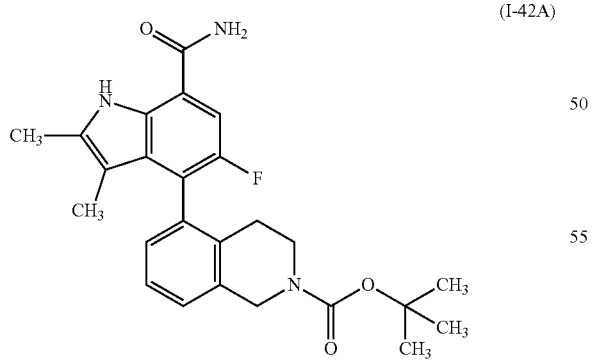

(I-42A)

A mixture of 4-bromo-5-fluoro-2,3-dimethyl-1H-indole-7-carboxamide [Intermediate 2] (0.200 g, 0.701 mmol), tert-butyl 5-(4,4,5,5-tetramethyl-1,3,2-dioxaborolan-2-yl)-3,4-dihydroisoquinoline-2(1H)-carboxylate (0.302 g, 0.842 mmol), 2 M aqueous $K_3PO_4$ (1.05 mL, 2.10 mmol) and THF (4 mL) was subjected to 3 evacuate-fill cycles with nitrogen. $PdCl_2$(dppf) DCM adduct (0.023 g, 0.035 mmol) was added, and the mixture was subjected to 2 more evacuate-fill cycles with nitrogen. The mixture was stirred at room temperature overnight, then was diluted with EtOAc, washed sequentially with water and brine, dried and concentrated. The residue was subjected to column chromatography on silica gel, eluting with EtOAc-hexanes, to provide tert-butyl (RS)-5-(7-carbamoyl-5-fluoro-2,3-dimethyl-1H-indol-4-yl)-3,4-dihydroisoquinoline-2(1H)-carboxylate as an off-white solid (0.307 g, quantitative yield). Mass spectrum m/z 438 $(M+H)^+$.

Intermediate 42

A mixture of tert-butyl (RS)-5-(7-carbamoyl-5-fluoro-2,3-dimethyl-1H-indol-4-yl)-3,4-dihydroisoquinoline-2(1H)-carboxylate (0.312 g, 0.713 mmol) and TFA (5 mL) was stirred at room temperature for 30 min. The mixture was concentrated under reduced pressure, and the residue was diluted with EtOAc, washed sequentially with 1.5 M aqueous $Na_2HPO_4$ and brine, dried and concentrated to provide (RS)-5-fluoro-2,3-dimethyl-4-(1,2,3,4-tetrahydroisoquinolin-5-yl)-1H-indole-7-carboxamide as an orange solid (0.241 g, quantitative yield). Mass spectrum m/z 338 $(M+H)^+$.

Intermediate 43

5-Fluoro-2,3-dimethyl-4-(1,2,3,4-tetrahydroquinolin-6-yl)-1H-indole-7-carboxamide TFA Salt

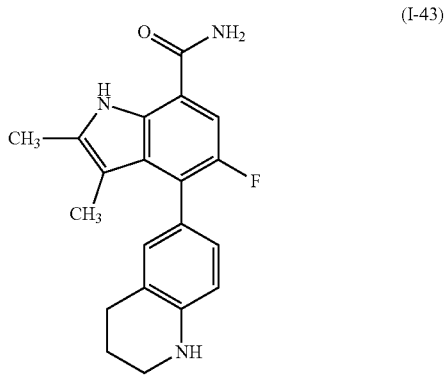 [SMILES: Cc1[nH]c2c(C(N)=O)cc(F)c(-c3ccc4c(c3)CCCN4)c2c1C]

(I-43)

Intermediate 43A: tert-Butyl 6-(4,4,5,5-tetramethyl-1,3,2-dioxaborolan-2-yl)-3,4-dihydroquinoline-1(2H)-carboxylate

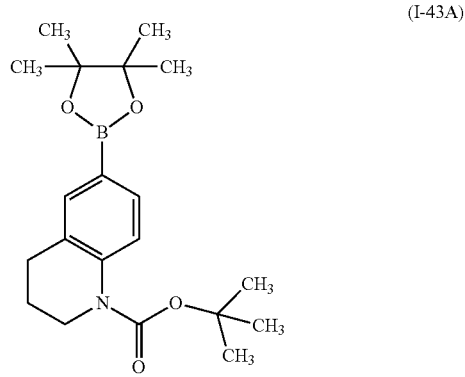 [SMILES: CC(C)(C)OC(=O)N1CCCc2cc(B3OC(C)(C)C(C)(C)O3)ccc21]

(I-43A)

Following the procedure used to prepare Intermediate 9, tert-butyl 6-bromo-3,4-dihydroquinoline-1(2H)-carboxylate was converted into tert-butyl 6-(4,4,5,5-tetramethyl-1,3,2-dioxaborolan-2-yl)-3,4-dihydroquinoline-1(2H)-carboxylate as a white solid in 82% yield. Mass spectrum m/z 360 (M+H)+, 304 (M+H—$C_4H_8$)+. $^1$H NMR (400 MHz, $CDCl_3$) δ 7.71-7.66 (m, 1H), 7.62-7.57 (m, 1H), 7.56 (s, 1H), 3.77-3.68 (m, 2H), 2.79 (t, J=6.6 Hz, 2H), 1.93 (dt, J=12.5, 6.4 Hz, 2H), 1.54 (s, 9H), 1.36 (s, 12H).

Intermediate 43

Following the procedures used to prepare Intermediate 42 but omitting the treatment with aqueous $Na_2HPO_4$ in the last step, tert-butyl 6-(4,4,5,5-tetramethyl-1,3,2-dioxaborolan-2-yl)-3,4-dihydroquinoline-1(2H)-carboxylate was converted into 5-fluoro-2,3-dimethyl-4-(1,2,3,4-tetrahydroquinolin-6-yl)-1H-indole-7-carboxamide TFA salt. Mass spectrum m/z 338 (M+H)+.

Intermediate 44

5-Fluoro-2,3-dimethyl-4-(1,2,3,4-tetrahydroisoquinolin-7-yl)-1H-indole-7-carboxamide TFA Salt

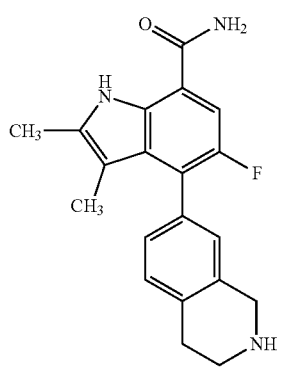

(I-44)

Following the procedures used to prepare Intermediate 43, tert-butyl 7-bromo-3,4-dihydroisoquinoline-2(1H)-carboxylate was converted into 5-fluoro-2,3-dimethyl-4-(1,2,3,4-tetrahydroisoquinolin-7-yl)-1H-indole-7-carboxamide, TFA salt. Mass spectrum m/z 338 (M+H)+.

Intermediate 45

5-Fluoro-4-(isoindolin-4-yl)-2,3-dimethyl-1H-indole-7-carboxamide TFA Salt

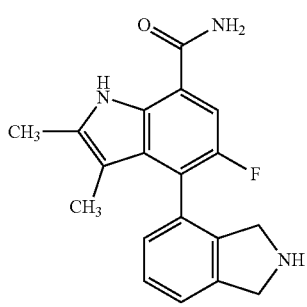

(I-45)

Following the procedures used to prepare Intermediate 43, tert-butyl 4-bromoisoindoline-2-carboxylate was converted into 5-fluoro-4-(isoindolin-4-yl)-2,3-dimethyl-1H-indole-7-carboxamide, TFA salt. Mass spectrum m/z 324 (M+H)+.

Intermediate 46

5-Fluoro-2,3-dimethyl-4-(1,2,3,4-tetrahydroquinolin-7-yl)-1H-indole-7-carboxamide TFA Salt

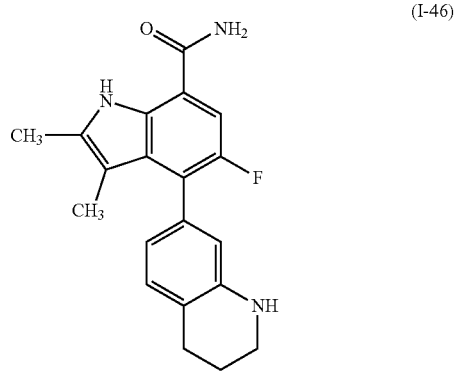 [SMILES: Cc1[nH]c2c(C(N)=O)cc(F)c(-c3ccc4c(c3)NCCC4)c2c1C]

(I-46)

Following the procedures used to prepare Intermediate 43, tert-butyl 7-bromo-3,4-dihydroquinoline-1(2H)-carboxylate was converted into 5-fluoro-2,3-dimethyl-4-(1,2,3,4-tetrahydroquinolin-7-yl)-1H-indole-7-carboxamide, TFA salt. Mass spectrum m/z 338 (M+H)+.

Intermediate 47

5-Fluoro-4-(isoindolin-5-yl)-2,3-dimethyl-1H-indole-7-carboxamide TFA Salt

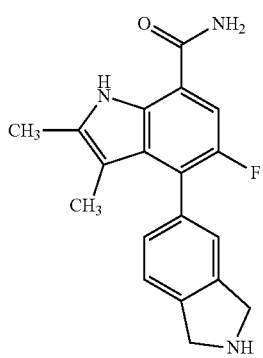

(I-47)

Following the procedures used to prepare Intermediate 43, tert-butyl 5-bromo-isoindoline-2-carboxylate was converted into 5-fluoro-4-(isoindolin-5-yl)-2,3-dimethyl-1H-indole-7-carboxamide, TFA salt. Mass spectrum m/z 324 (M+H)+.

Intermediate 48

(RS-cis)-5-Fluoro-2,3-dimethyl-4-(1a,2,3,7b-tetra-hydro-1H-cyclopropa[c]quinolin-7-yl)-1H-indole-7-carboxamide TFA Salt

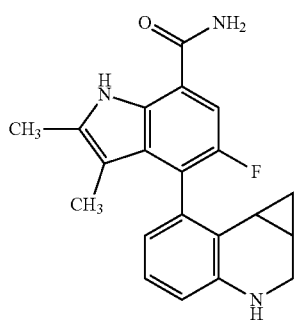

(I-48)

Intermediate 48A: (RS-cis)-tert-Butyl 7-bromo-1a,2-dihydro-1H-cyclopropa[c]quinoline-3(7bH)-carboxylate

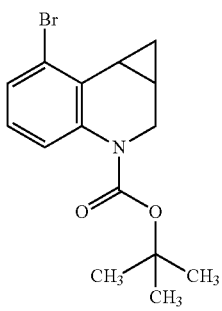

(I-48A)

A solution of (RS-cis)-7-bromo-1a,2,3,7b-tetrahydro-1H-cyclopropa[c]quinoline [prepared according to procedures described in Example 9 of PCT Publication No. WO 2012/149236] (700 mg, 3.12 mmol) and di-tert-butyl dicarbonate (1.08 mL, 4.69 mmol) in 1,4-dioxane (5.0 mL) was stirred at 80° C. for 18. The cooled mixture was diluted with saturated aqueous NaHCO₃ (15 mL) and extracted with EtOAc (20 mL). The organic layer was dried and concentrated, and the residue was subjected to column chromatography on silica gel, eluting with EtOAc-hexanes (gradient from 0-50%), to provide (RS-cis)-tert-butyl 7-bromo-11a,2-dihydro-1H-cyclopropa[c]quinoline-3(7bH)-carboxylate as a light brown gum (963 mg, 67% yield). Mass spectrum m/z 324, 326 (M+H—C₄H₈)⁺. ¹H NMR (400 MHz, CDCl₃) δ 7.33 (dd, J=8.0, 1.2 Hz, 1H), 7.25 (d, J=7.9 Hz, 1H), 6.95 (t, J=8.0 Hz, 1H), 4.51 (dd, J=13.0, 1.3 Hz, 1H), 2.94 (d, J=12.1 Hz, 1H), 2.44 (td, J=8.6, 4.5 Hz, 1H), 1.88 (dtq, J=8.0, 5.8, 1.9 Hz, 1H), 1.47 (s, 9H), 1.11 (td, J=8.3, 5.3 Hz, 1H), 0.74 (q, J=4.9 Hz, 1H).

Intermediate 48

Following the procedures used to prepare Intermediate 43, (RS-cis)-tert-butyl 7-bromo-1a,2-dihydro-1H-cyclopropa[c]quinoline-3(7bH)-carboxylate was converted into (RS-cis)-5-fluoro-2,3-dimethyl-4-(1a,2,3,7b-tetrahydro-1H-cyclopropa[c]quinolin-7-yl)-1H-indole-7-carboxamide, TFA salt. Mass spectrum m/z 350 (M+H)⁺.

Intermediate 49

4-(3,4-Dihydro-2H-benzo[b][1,4]oxazin-8-yl)-5-fluoro-2,3-dimethyl-1H-indole-7-carboxamide TFA Salt

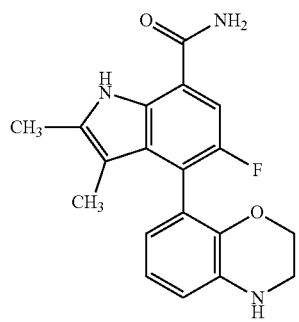

(I-49)

Following the procedures used to prepare Intermediate 48, 8-bromo-3,4-dihydro-2H-benzo[b][1,4]oxazine [prepared according to procedures described in Example 10 of PCT Publication No. WO 2012/149236] was converted into 4-(3,4-dihydro-2H-benzo[b][1,4]oxazin-8-yl)-5-fluoro-2,3-dimethyl-1H-indole-7-carboxamide, TFA salt. Mass spectrum m/z 340 (M+H)⁺. ¹H NMR (400 MHz, DMSO-d₆) δ 10.66 (s, 1H), 8.01 (br. s., 1H), 7.45 (d, J=10.8 Hz, 1H), 7.40 (br. s., 1H), 6.77-6.68 (m, 1H), 6.63 (dd, J=7.9, 1.7 Hz, 1H), 6.37 (dd, J=7.5, 1.6 Hz, 1H), 4.08-3.92 (m, 2H), 3.31-3.22 (m, 2H), 2.29 (s, 3H), 1.62 (s, 3H).

Intermediate 50

(RS)-5-Fluoro-4-(4-fluoro-1,2,3,4-tetrahydroisoquinolin-5-yl)-2,3-dimethyl-1H-indole-7-carboxamide TFA Salt

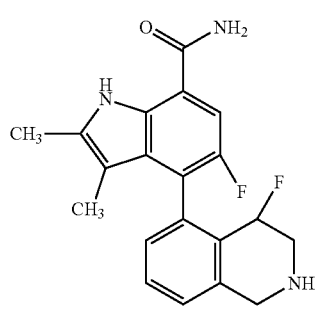

(I-50)

Intermediate 50A: tert-Butyl 5-bromo-4-oxo-3,4-dihydroisoquinoline-2(1H)-carboxylate

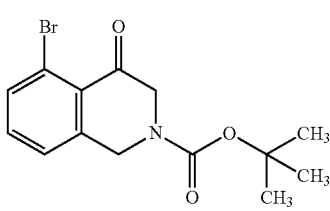

(I-50A)

A mixture of 5-bromo-2,3-dihydroisoquinolin-4(1H)-one hydrochloride (1.05 g, 4.00 mmol), di-tert-butyl dicarboxylate (1.02 mL, 4.40 mmol) and triethylamine (1.67 mL, 12.0 mmol) in MeOH (20 mL) was stirred at room temperature for 90 min. The mixture was concentrated and the residue was subjected to column chromatography on silica gel, eluting with EtOAc-hexanes (gradient from 0-30%), to provide tert-butyl 5-bromo-4-oxo-3,4-dihydroisoquinoline-2(1H)-carboxylate as a gum (640 mg, 47% yield). Mass spectrum m/z 270, 272 (M+H—$C_4H_8$)$^+$. $^1$H NMR (400 MHz, CDCl$_3$) δ 7.67 (dt, J=7.9, 0.6 Hz, 1H), 7.40-7.32 (m, 1H), 7.31-7.26 (m, 1H), 4.75 (s, 2H), 4.37 (s, 2H), 1.50 (s, 9H).

Intermediate 50B: (RS)-tert-Butyl 5-bromo-4-hydroxy-3,4-dihydroisoquinoline-2(1H)-carboxylate

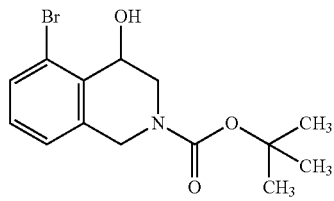

(I-50B)

A solution of tert-butyl 5-bromo-4-oxo-3,4-dihydroisoquinoline-2(1H)-carboxylate (150 mg, 0.460 mmol) in THF (3.0 mL) and MeOH (3.0 mL) was treated with sodium borohydride (17.4 mg, 0.460 mmol). The mixture was stirred at room temperature for 60 min and concentrated. The residue was subjected to column chromatography on silica gel, eluting with EtOAc-hexanes (gradient from 0-100%) to provide (RS)-tert-butyl 5-bromo-4-hydroxy-3,4-dihydroisoquinoline-2(1H)-carboxylate as a white glassy solid (137 mg, 86% yield). Mass spectrum m/z 254, 256 (M+H—($H_2O+C_4H_8$))$^+$. $^1$H NMR (400 MHz, CDCl$_3$) δ 7.50 (dd, J=8.3, 0.6 Hz, 1H), 7.21-7.15 (m, 1H), 7.14-7.09 (m, 1H), 5.02 (br. s., 2H), 4.48 (d, J=10.8 Hz, 1H), 4.26 (d, J=17.2 Hz, 1H), 3.19 (d, J=12.3 Hz, 1H), 2.36 (br. s., 1H), 1.52 (s, 9H).

Intermediate 50C: (RS)-tert-Butyl 5-bromo-4-fluoro-3,4-dihydroisoquinoline-2(1H)-carboxylate

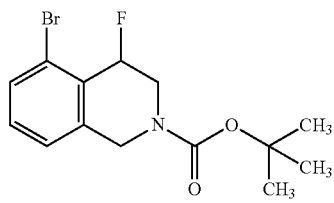

(I-50C)

A solution of (RS)-tert-butyl 5-bromo-4-hydroxy-3,4-dihydroisoquinoline-2(1H)-carboxylate (137 mg, 0.417 mmol) in DCM (5.0 mL) at −78° C. was treated dropwise with diethylaminosulfur trifluoride [DAST] (0.331 mL, 2.51 mmol) and the mixture was stirred at −78° C. for 10 min. The mixture was treated with saturated aqueous NaHCO$_3$ (5.0 mL). The DCM layer was separated, dried and concentrated. The residue was subjected to column chromatography on silica gel, eluting with EtOAc-hexanes (gradient from 0-100%), to provide (RS)-tert-butyl 5-bromo-4-fluoro-3,4-dihydroisoquinoline-2(1H)-carboxylate as a colorless gum (100 mg, 69% yield). Mass spectrum m/z 254, 256 (M+H—(HF+$C_4H_8$))$^+$. $^1$H NMR (400 MHz, CDCl$_3$) δ 7.55 (d, J=7.9 Hz, 1H), 7.25 (td, J=7.8, 2.1 Hz, 1H), 7.20-7.13 (m, 1H), 5.95-5.64 (m, 1H), 5.25-4.91 (m, 1H), 4.69 (br. s., 1H), 4.26 (br. s., 1H), 3.43-3.03 (m, 1H), 1.52 (s, 9H).

Intermediate 50

Following the procedures used to prepare Intermediate 43, (RS)-tert-butyl 5-bromo-4-hydroxy-3,4-dihydroisoquinoline-2(1H)-carboxylate was converted into (RS)-5-fluoro-4-(4-fluoro-1,2,3,4-tetrahydroisoquinolin-5-yl)-2,3-dimethyl-1H-indole-7-carboxamide, TFA salt. Mass spectrum m/z 356 (M+H)$^+$.

Intermediate 51

N-(3-Bromobenzyl)acrylamide

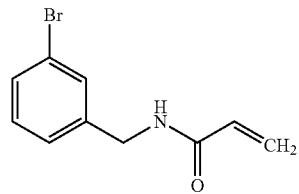

(I-51)

A solution of (3-bromophenyl)methanamine (0.500 g, 2.69 mmol) in DCM (13.4 mL) at 0° C. was treated with DIEA (0.939 mL, 5.37 mmol), then was treated dropwise with acryloyl chloride (0.240 mL, 2.96 mmol). The mixture was stirred at room temperature for 3 h, then was concentrated. The residue was subjected to column chromatography on silica gel (24 g), eluting with EtOAc-hexanes (gradient from 30-45%), to provide N-(3-bromobenzyl)acrylamide as a white solid (0.476 g, 74% yield). Mass spectrum m/z 240, 242 (M+H)$^+$. $^1$H NMR (400 MHz, CDCl$_3$) δ 7.47-7.40 (m, 2H), 7.25-7.19 (m, 2H), 6.35 (dd, J=16.9, 1.3 Hz, 1H), 6.17-6.09 (m, 1H), 5.84 (br. s., 1H), 5.71 (dd, J=10.2, 1.4 Hz, 1H), 4.52 (d, J=5.9 Hz, 2H).

Intermediate 52

1-(6-Bromoindolin-1-yl)prop-2-en-1-one

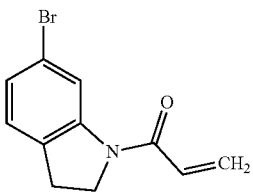

(I-52)

Following the procedure used to prepare Intermediate 51, 6-bromoindoline [prepared according to the procedure of PCT Publication No. WO 2010/093949, Example 82, Step 1] was converted into 1-(6-bromoindolin-1-yl)prop-2-en-1-one in 94% yield. Mass spectrum m/z 252, 254 (M+H)⁺. ¹H NMR (400 MHz, DMSO-d₆) δ 8.31 (br. s., 1H), 7.21-7.19 (m, 2H), 6.79-6.66 (m, 1H), 6.31 (dd, J=16.7, 2.2 Hz, 1H), 5.84 (dd, J=10.3, 2.2 Hz, 1H), 4.23 (t, J=8.6 Hz, 2H), 3.12 (t, J=8.5 Hz, 2H).

Intermediate 53

N-(4-Bromopyridin-2-yl)acrylamide

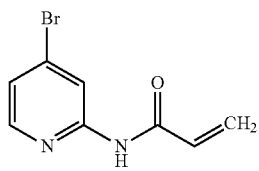

(I-53)

Following the procedure used to prepare Intermediate 51, 4-bromo-2-aminopyridine was converted into N-(4-bromopyridin-2-yl)acrylamide in 50% yield after purification by preparative reverse-phase HPLC. Mass spectrum m/z 227, 229 (M+H)⁺.

Intermediate 54

6-Bromo-1-(vinylsulfonyl)indoline

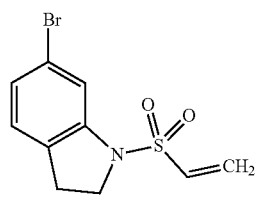

(I-54)

A solution of 6-bromoindoline [prepared according to the procedure of PCT Publication No. WO 2010/093949, Example 82, Step 1] (0.290 g, 0.732 mmol) in DCM (3.7 mL) was cooled to 0° C. and treated with DIEA (0.205 mL, 1.17 mmol), then was treated dropwise with 2-chloroethanesulfonyl chloride (0.092 mL, 0.879 mmol). The mixture was stirred at room temperature for 18 h. The mixture was concentrated and the residue was subjected to chromatography on silica gel (12 g), eluting with EtOAc-hexanes (gradient from 5-20%), to provide 6-bromo-1-(vinylsulfonyl)indoline as a white solid (0.148 g, 70% yield). Mass spectrum m/z 288, 290 (M+H)+. ¹H NMR (400 MHz, DMSO-d₆) δ 7.32 (d, J=1.1 Hz, 1H), 7.25-7.17 (m, 2H), 6.94 (dd, J=16.3, 9.9 Hz, 1H), 6.32-6.18 (m, 2H), 3.94 (t, J=8.5 Hz, 2H), 3.06 (t, J=8.5 Hz, 2H).

Intermediate 55

N-(3-Bromophenyl)ethenesulfonamide

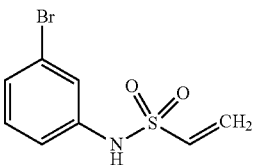

(I-55)

Following the procedure used to prepare Intermediate 54, 3-bromoaniline was converted into N-(3-bromophenyl)ethenesulfonamide in 17% yield. ¹H NMR (400 MHz, CDCl₃) δ 7.35-7.29 (m, 2H), 7.20 (t, J=7.9 Hz, 1H), 7.13-7.09 (m, 1H), 6.57 (dd, J=16.4, 9.8 Hz, 1H), 6.37-6.31 (m, 2H), 6.02 (d, J=9.9 Hz, 1H).

Intermediate 56

N-(3-Bromobenzyl)ethenesulfonamide

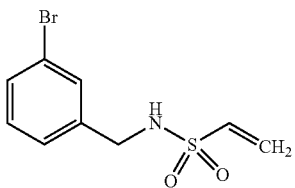

(I-56)

Following the procedure used to prepare Intermediate 54, (3-bromophenyl) methanamine was converted into N-(3-bromobenzyl)ethenesulfonamide in 41% yield. Mass spectrum m/z 298, 300 (M+Na)⁺. ¹H NMR (400 MHz, CDCl₃) δ 7.50-7.43 (m, 2H), 7.29-7.21 (m, 2H), 6.51 (dd, J=16.5, 9.9 Hz, 1H), 6.28 (d, J=16.5 Hz, 1H), 5.96 (d, J=9.9 Hz, 1H), 4.64 (br. s., 1H), 4.20 (d, J=6.2 Hz, 2H).

Intermediate 57

N-(2-(3-Bromophenyl)propan-2-yl)ethenesulfonamide

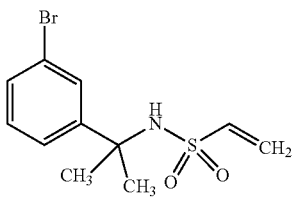

(I-57)

Following the procedure used to prepare Intermediate 54, 2-(3-bromophenyl) propan-2-amine was converted into N-(2-(3-bromophenyl)propan-2-yl)ethenesulfonamide in 74% yield. Mass spectrum m/z 326, 328 (M+Na)⁺. ¹H NMR (400 MHz, CDCl₃) δ 7.60 (t, J=1.9 Hz, 1H), 7.42 (dddd, J=7.9, 4.9, 1.9, 1.0 Hz, 2H), 7.26-7.21 (m, 1H), 6.37 (dd, J=16.5, 9.7 Hz, 1H), 6.04 (d, J=16.5 Hz, 1H), 5.72 (d, J=9.7 Hz, 1H), 4.64 (s, 1H), 1.73 (s, 6H).

Intermediate 58

1-(3-Bromophenyl)-3-methylenepyrrolidin-2-one

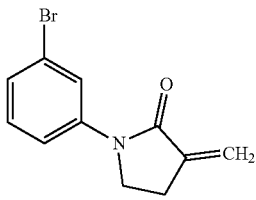
(I-58)

Intermediate 58A:
1-(3-Bromophenyl)pyrrolidin-2-one

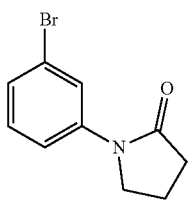
(I-58A)

A mixture of dihydrofuran-2(3H)-one (1.51 mL, 19.7 mmol), 3-bromoaniline (1.79 mL, 16.5 mmol), and concentrated aqueous HCl (0.70 mL) was heated at 160° C. After 16 h the mixture was cooled to room temperature. Additional dihydrofuran-2(3H)-one (0.5 mL) was added and heating was resumed at 160° C. After a total of 36 h the mixture was cooled to room temperature and partitioned between water and EtOAc. The organic phase was washed with brine and concentrated. The residue was subjected to column chromatography on silica gel (40 g), eluting with EtOAc-hexanes (gradient from 40-50%), to provide 1-(3-bromophenyl)pyrrolidin-2-one as a solid (4.16 g, quantitative yield). Mass spectrum m/z 240, 242 (M+H)$^+$. $^1$H NMR (400 MHz, CDCl$_3$) δ 7.80 (t, J=2.0 Hz, 1H), 7.65-7.60 (m, 1H), 7.30-7.27 (m, 1H), 7.26-7.20 (m, 1H), 3.85 (t, J=7.0 Hz, 2H), 2.63 (t, J=8.0 Hz, 2H), 2.23-2.10 (m, 2H).

Intermediate 58B: Ethyl 2-(1-(3-bromophenyl)-2-oxopyrrolidin-3-yl)-2-oxoacetate

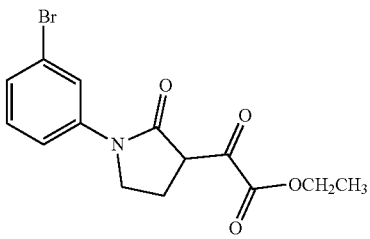
(I-58B)

A stirred mixture of sodium hydride (60% in mineral oil, 1.84 g, 46.0 mmol) in THF (43.8 mL) was treated slowly with a solution of 1-(3-bromophenyl)pyrrolidin-2-one (4.15 g, 16.4 mmol) and diethyl oxalate (4.45 mL, 32.8 mmol) in THF (21.9 mL). The mixture was heated at reflux for 6 h, then cooled to room temperature and stirred for 16 h. Acetic acid (1.03 mL, 18.1 mmol) was added dropwise and the mixture was stirred at room temperature for 1 h, then was partitioned between EtOAc and water. The pH of the aqueous layer was adjusted to 2-3 with 1 M aqueous HCl and the layers were separated. The organic phase was washed with brine, dried and concentrated. The residue was subjected to column chromatography on silica gel (80 g), eluting with EtOAc-hexanes (gradient from 20-30%), to provide a sticky white solid. This was suspended in EtOAc and the precipitate was collected by filtration to provide ethyl 2-(1-(3-bromophenyl)-2-oxopyrrolidin-3-yl)-2-oxoacetate as a white solid (1.71 g, 31% yield). Mass spectrum m/z 340, 342 (M+H)$^+$. $^1$H NMR (400 MHz, DMSO-d$_6$) δ 11.75 (s, 1H), 8.08-8.05 (m, 1H), 7.67 (dt, J=7.0, 2.2 Hz, 1H), 7.44-7.39 (m, 2H), 4.27 (q, J=7.2 Hz, 2H), 3.97 (t, J=7.0 Hz, 2H), 3.07 (t, J=6.9 Hz, 2H), 1.29 (t, J=7.2 Hz, 3H).

Intermediate 58

A suspension of ethyl 2-(1-(3-bromophenyl)-2-oxopyrrolidin-3-yl)-2-oxoacetate (1.71 g, 5.03 mmol) and diethylamine (1.57 mL, 15.1 mmol) in water (10.1 mL) at 0° C. was treated slowly with a 36.5% aqueous formaldehyde (1.52 mL, 20.1 mmol). The mixture was stirred at room temperature for 21 h, forming a sticky solid. The supernatant was removed by decantation, and the residue was subjected to column chromatography on silica gel (24 g), eluting with EtOAc-hexanes (gradient from 20-30%), to provide 1-(3-bromophenyl)-3-methylenepyrrolidin-2-one as a white solid (0.497 g, 39% yield). Mass spectrum m/z 252, 254 (M+H)$^+$. $^1$H NMR (400 MHz, CDCl$_3$) δ 7.92 (t, J=1.9 Hz, 1H), 7.76-7.71 (m, 1H), 7.33-7.29 (m, 1H), 7.28-7.23 (m, 1H), 6.19-6.15 (m, 1H), 5.50-5.46 (m, 1H), 3.88-3.81 (m, 2H), 2.92 (tt, J=6.9, 2.6 Hz, 2H).

Intermediate 59

Mixture of 3-Methylene-1-(3-(4,4,5,5-tetramethyl-1,3,2-dioxaborolan-2-yl)phenyl) pyrrolidin-2-one, and 3-Methyl-1-(3-(4,4,5,5-tetramethyl-1,3,2-dioxaborolan-2-yl) phenyl)-1H-pyrrol-2(5H)-one

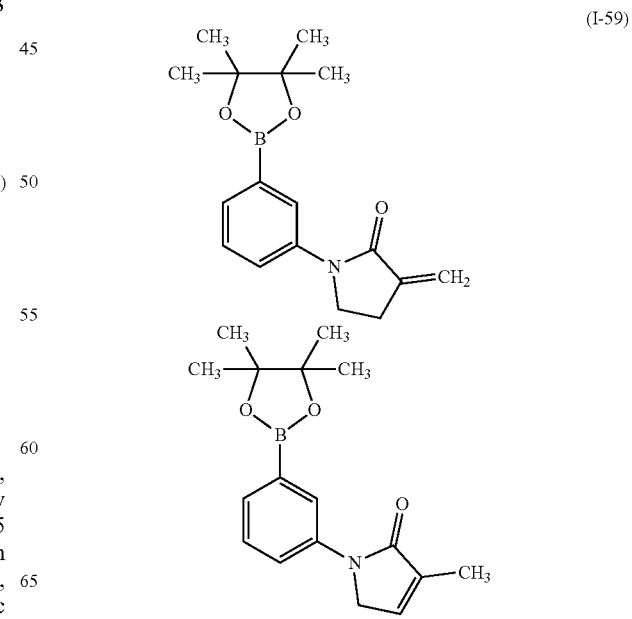
(I-59)

A mixture of 1-(3-bromophenyl)-3-methylenepyrrolidin-2-one [Intermediate 58](0.22 g, 0.873 mmol), 4,4,4',4',5,5,5',5'-octamethyl-2,2'-bi(1,3,2-dioxaborolane) (0.233 g, 0.916 mmol), potassium acetate (0.171 g, 1.745 mmol), and PdCl$_2$(dppf) DCM adduct (0.036 g, 0.044 mmol) in 1,4-dioxane (2.18 mL) was bubbled with nitrogen for about 2-3 min, then was heated at 90° C. under a nitrogen atmosphere. After 2 h, the mixture was cooled to room temperature and filtered through CELITE®. The solids were washed with EtOAc, MeOH and acetone, and the combined filtrates were concentrated. The residue was purified by column chromatography on silica gel (12 g), eluting with EtOAc-hexanes (gradient from 20-30%), to provide a mixture of 3-methylene-1-(3-(4,4,5,5-tetramethyl-1,3,2-dioxaborolan-2-yl)phenyl)pyrrolidin-2-one and 3-methyl-1-(3-(4,4,5,5-tetramethyl-1,3,2-dioxaborolan-2-yl)phenyl)-1H-pyrrol-2(5H)-one as a colorless oil. Mass spectrum m/z 300 (M+H)$^+$.

Intermediate 60

1-(3-Bromo-2-methylphenyl)-3-methylenepyrrolidin-2-one

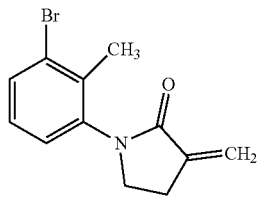

(I-60)

Following the procedures used to prepare Intermediate 58, 3-bromo-2-methylaniline was converted into 1-(3-bromo-2-methylphenyl)-3-methylenepyrrolidin-2-one. Mass spectrum m/z 266, 268 (M+H)+. $^1$H NMR (400 MHz, CDCl$_3$) δ 7.56 (dd, J=7.6, 1.7 Hz, 1H), 7.19-7.08 (m, 2H), 6.17-6.10 (m, 1H), 5.51-5.43 (m, 1H), 3.76-3.68 (m, 2H), 2.98 (tt, J=6.8, 2.6 Hz, 2H), 2.30 (s, 3H).

Intermediate 61

N-(2-Methyl-3-(4,4,5,5-tetramethyl-1,3,2-dioxaborolan-2-yl)phenyl)methacrylamide

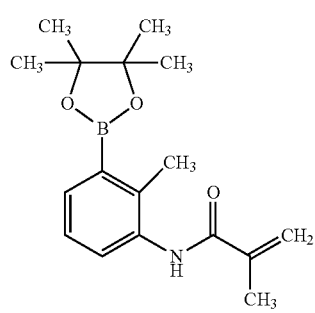

(I-61)

A solution of 2-methyl-3-(4,4,5,5-tetramethyl-1,3,2-dioxaborolan-2-yl)aniline [prepared according to U.S. Pat. No. 8,084,620, Intermediate 50-1] (0.200 g, 0.858 mmol), EDC (0.296 g, 1.54 mmol), HOBT (0.236 g, 1.54 mmol), methacrylic acid (0.073 mL, 0.867 mmol), and DIEA (0.420 mL, 2.40 mmol) in THF (7.2 mL) and DCM (7.2 mL) was stirred at room temperature for 4 days. The mixture was concentrated and subjected to column chromatography on silica gel (24 g), eluting with EtOAc-hexanes (gradient from 10-30%), to provide N-(2-methyl-3-(4,4,5,5-tetramethyl-1,3,2-dioxaborolan-2-yl)phenyl)methacrylamide as an off-white solid (0.164 g, 64% yield). Mass spectrum m/z 302 (M+H)$^+$. $^1$H NMR (400 MHz, DMSO-d$_6$) δ 9.34 (s, 1H), 7.50 (dd, J=7.4, 1.4 Hz, 1H), 7.34-7.29 (m, 1H), 7.20-7.14 (m, 1H), 5.84 (s, 1H), 5.50-5.47 (m, 1H), 2.32 (s, 3H), 1.96 (s, 3H), 1.31 (s, 12H).

Intermediate 62

N-(2-Methyl-3-(4,4,5,5-tetramethyl-1,3,2-dioxaborolan-2-yl)phenyl)cyclohex-1-enecarboxamide

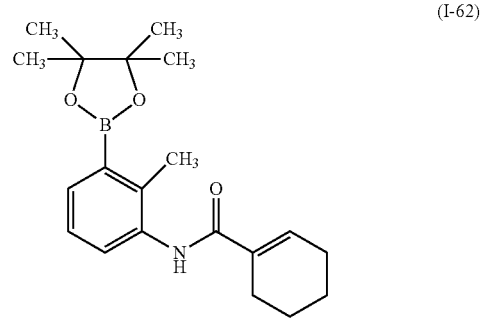 [SMILES: Cc1c(NC(=O)C2=CCCCC2)cccc1B1OC(C)(C)C(C)(C)O1]

(I-62)

Following the procedure used to prepare Intermediate 61 but substituting cyclohex-1-enecarboxylic acid for methacrylic acid, 2-methyl-3-(4,4,5,5-tetramethyl-1,3,2-dioxaborolan-2-yl)aniline [prepared according to U.S. Pat. No. 8,084,620, Intermediate 50-1] was converted into N-(2-methyl-3-(4,4,5,5-tetramethyl-1,3,2-dioxaborolan-2-yl)phenyl)cyclohex-1-enecarboxamide in 55% yield. Mass spectrum m/z 342 (M+H)$^+$. $^1$H NMR (400 MHz, DMSO-d$_6$) δ 9.10 (s, 1H), 7.48 (dd, J=7.5, 1.3 Hz, 1H), 7.31 (dd, J=7.8, 1.2 Hz, 1H), 7.15 (t, J=7.6 Hz, 1H), 6.73-6.68 (m, 1H), 2.31 (s, 3H), 2.29-2.23 (m, 2H), 2.18 (dd, J=5.9, 2.2 Hz, 2H), 1.68-1.54 (m, 4H), 1.30 (s, 12H).

Intermediate 63

2-Cyano-N-(2-methyl-3-(4,4,5,5-tetramethyl-1-1,3,2-dioxaborolan-2-yl)phenyl)acetamide

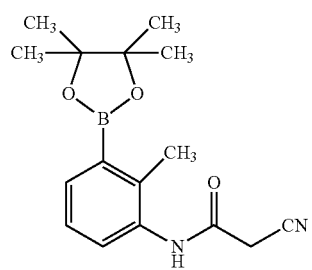

(I-63)

Following the procedure used to prepare Intermediate 61 but substituting 2-cyanoacetic acid for methacrylic acid, 2-methyl-3-(4,4,5,5-tetramethyl-1,3,2-dioxaborolan-2-yl)aniline [prepared according to U.S. Pat. No. 8,084,620, Intermediate 50-1] was converted into 2-cyano-N-(2-methyl-3-(4,4,5,5-tetramethyl-1,3,2-dioxaborolan-2-yl)phenyl)acetamide in 89% yield. Mass spectrum m/z 301 (M+H)$^+$. $^1$H NMR (400 MHz, DMSO-d$_6$) δ 9.68 (s, 1H), 7.52-7.47 (m, 1H), 7.43-7.38 (m, 1H), 7.18 (t, J=7.6 Hz, 1H), 3.91 (s, 2H), 2.34 (s, 3H), 1.30 (s, 12H).

Intermediate 64

1-Cyano-N-(2-methyl-3-(4,4,5,5-tetramethyl-1,3,2-dioxaborolan-2-yl)phenyl)cyclopropanecarboxamide

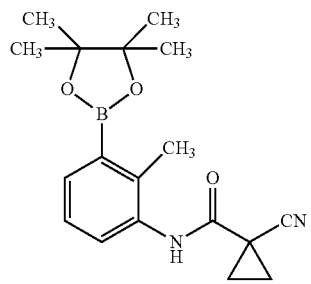
(I-64)

Following the procedure used to prepare Intermediate 61 but substituting 1-cyanocyclopropanecarboxylic acid for methacrylic acid, 2-methyl-3-(4,4,5,5-tetramethyl-1,3,2-dioxaborolan-2-yl)aniline [prepared according to U.S. Pat. No. 8,084,620, Intermediate 50-1] was converted into 1-cyano-N-(2-methyl-3-(4,4,5,5-tetramethyl-1,3,2-dioxaborolan-2-yl)phenyl)cyclopropanecarboxamide in 60% yield. Mass spectrum m/z 327 (M+H)$^+$. $^1$H NMR (400 MHz, DMSO-$d_6$) δ 9.65 (s, 1H), 7.54 (dd, J=7.5, 1.3 Hz, 1H), 7.30 (dd, J=7.9, 1.3 Hz, 1H), 7.22-7.15 (m, 1H), 2.31 (s, 3H), 1.72-1.66 (m, 2H), 1.66-1.60 (m, 2H), 1.31 (s, 12H).

Intermediate 65

N-(3-(4,4,5,5-Tetramethyl-1,3,2-dioxaborolan-2-yl)phenyl)acrylamide

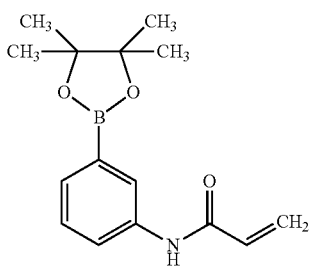
(I-65)

Intermediate 65A: 3-(4,4,5,5-Tetramethyl-1,3,2-dioxaborolan-2-yl)aniline

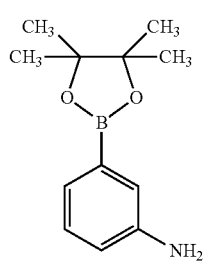
(I-65A)

A mixture of 3-bromoaniline (1.00 g, 5.81 mmol), 4,4,4',4',5,5,5',5'-octamethyl-2,2'-bi(1,3,2-dioxaborolane) (1.55 g, 6.10 mmol) and potassium acetate (1.14 g, 11.6 mmol) in 1,4-dioxane (14.5 mL) was bubbled with nitrogen for 10 min. The mixture was treated with PdCl$_2$(dppf) DCM adduct (0.114 g, 0.140 mmol) and bubbled with nitrogen for 5 min more. The mixture was heated to reflux for 2.75 h, then cooled to room temperature and filtered through CELITE®. The solids were washed with EtOAc and THF. The combined filtrates were concentrated and the residue was subjected to column chromatography on silica gel (40 g), eluting with EtOAc-hexanes (gradient from 10-25%), to provide 3-(4,4,5,5-tetramethyl-1,3,2-dioxaborolan-2-yl)aniline as an off-white solid (1.27 g, quantitative yield). Mass spectrum m/z 220 (M+H)$^+$. $^1$H NMR (400 MHz, CDCl$_3$) δ 7.24-7.13 (m, 3H), 6.82-6.77 (m, 1H), 3.64 (br. s., 2H), 1.35 (s, 12H).

Intermediate 65

A solution of 3-(4,4,5,5-tetramethyl-1,3,2-dioxaborolan-2-yl)aniline (0.300 g, 1.37 mmol) and DIEA (0.311 mL, 1.78 mmol) in DCM (9.1 mL) was cooled in an ice-bath and treated with acryloyl chloride (0.117 mL, 1.44 mmol). The mixture was stirred at room temperature for 40 min, then was concentrated and the residue was subjected to column chromatography on silica gel (24 g), eluting with EtOAc-hexanes (gradient from 15-40%), to provide N-(3-(4,4,5,5-tetramethyl-1,3,2-dioxaborolan-2-yl)phenyl) acrylamide as a white solid (0.292 g, 78% yield). Mass spectrum m/z 270 (M+H)$^+$.

Intermediate 66

N-(2-Methyl-3-(4,4,5,5-tetramethyl-1,3,2-dioxaborolan-2-yl)phenyl)acrylamide

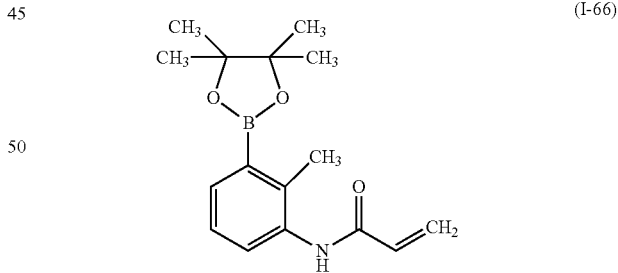
(I-66)

Following the procedure used to prepare Intermediate 65, 2-methyl-3-(4,4,5,5-tetramethyl-1,3,2-dioxaborolan-2-yl)aniline [prepared according to U.S. Pat. No. 8,084,620, Intermediate 50-1] was converted into N-(2-methyl-3-(4,4,5,5-tetramethyl-1,3,2-dioxaborolan-2-yl)phenyl)acrylamide in 80% yield. Mass spectrum m/z 288 (M+H)$^+$. $^1$H NMR (400 MHz, CDCl$_3$) δ 8.01 (br. s., 1H), 7.64 (d, J=5.9 Hz, 1H), 7.23 (t, J=7.7 Hz, 1H), 7.07 (br. s., 1H), 6.48-6.40 (m, 1H), 6.32 (br. s., 1H), 5.78 (d, J=9.5 Hz, 1H), 2.49 (s, 3H), 1.36 (s, 12H).

Intermediate 67

(E)-N-(2-Methyl-3-(4,4,5,5-tetramethyl-1,3,2-dioxaborolan-2-yl)phenyl)but-2-enamide

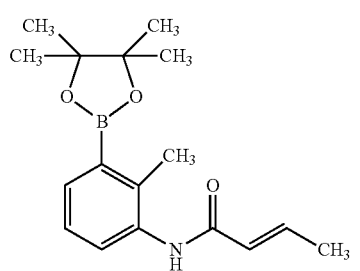

(I-67)

Following the procedure used to prepare Intermediate 65 but substituting (E)-but-2-enoyl chloride for acryloyl chloride, 2-methyl-3-(4,4,5,5-tetramethyl-1,3,2-dioxaborolan-2-yl)aniline [prepared according to U.S. Pat. No. 8,084,620, Intermediate 50-1] was converted into (E)-N-(2-methyl-3-(4,4,5,5-tetramethyl-1,3,2-dioxaborolan-2-yl)phenyl)but-2-enamide in 85% yield. Mass spectrum m/z 302 (M+H)$^+$. $^1$H NMR (400 MHz, DMSO-d$_6$) δ 9.28 (s, 1H), 7.46 (d, J=7.5 Hz, 2H), 7.15 (t, J=7.7 Hz, 1H), 6.83-6.66 (m, 1H), 6.21 (d, J=14.7 Hz, 1H), 2.34 (s, 3H), 1.86 (dd, J=6.9, 1.2 Hz, 3H), 1.30 (s, 12H).

Intermediate 68

3-Methyl-N-(2-methyl-3-(4,4,5,5-tetramethyl-1,3,2-dioxaborolan-2-yl)phenyl)but-2-enamide

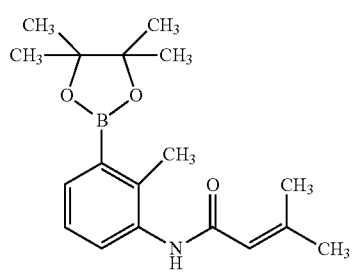

(I-68)

Following the procedure used to prepare Intermediate 65 but substituting 3-methylbut-2-enoyl chloride for acryloyl chloride, 2-methyl-3-(4,4,5,5-tetramethyl-1,3,2-dioxaborolan-2-yl)aniline [prepared according to U.S. Pat. No. 8,084,620, Intermediate 50-1] was converted into 3-methyl-N-(2-methyl-3-(4,4,5,5-tetramethyl-1,3,2-dioxaborolan-2-yl) phenyl)but-2-enamide in 85% yield. Mass spectrum m/z 316 (M+H)$^+$. $^1$H NMR (400 MHz, DMSO-d$_6$) δ 9.14 (s, 1H), 7.44 (d, J=7.3 Hz, 2H), 7.14 (t, J=7.6 Hz, 1H), 5.95 (br. s., 1H), 2.33 (s, 3H), 2.12 (d, J=1.1 Hz, 3H), 1.86 (s, 3H), 1.30 (s, 12H).

Intermediate 69

N-(2-Methyl-3-(4,4,5,5-tetramethyl-1,3,2-dioxaborolan-2-yl)phenyl) cyclopropanecarboxamide

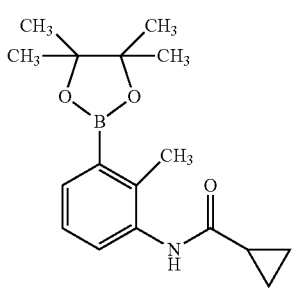

(I-69)

Following the procedure used to prepare Intermediate 65 but substituting cyclopropanecarbonyl chloride for acryloyl chloride, 2-methyl-3-(4,4,5,5-tetramethyl-1,3,2-dioxaborolan-2-yl)aniline [prepared according to U.S. Pat. No. 8,084,620, Intermediate 50-1] was converted into N-(2-methyl-3-(4,4,5,5-tetramethyl-1,3,2-dioxaborolan-2-yl)phenyl) cyclopropanecarboxamide in 71% yield. Mass spectrum m/z 302 (M+H)$^+$. $^1$H NMR (400 MHz, DMSO-d$_6$) δ 9.50 (br. s., 1H), 7.43 (dd, J=10.0, 7.8 Hz, 2H), 7.13 (t, J=7.6 Hz, 1H), 2.35 (s, 3H), 1.87 (d, J=6.6 Hz, 1H), 1.30 (s, 12H), 0.79-0.74 (m, 4H).

Intermediate 70

N-(2-Methyl-3-(4,4,5,5-tetramethyl-1,3,2-dioxaborolan-2-yl)phenyl)propionamide

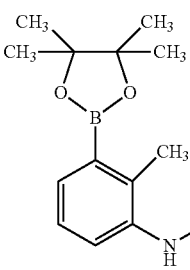

(I-70)

Following the procedure used to prepare Intermediate 65 but substituting propionic anhydride for acryloyl chloride, 2-methyl-3-(4,4,5,5-tetramethyl-1,3,2-dioxaborolan-2-yl) aniline [prepared according to U.S. Pat. No. 8,084,620, Intermediate 50-1] was converted into N-(2-methyl-3-(4,4,5,5-tetramethyl-1,3,2-dioxaborolan-2-yl) phenyl)propionamide in 88% yield. Mass spectrum m/z 290 (M+H)$^+$. $^1$H NMR (400 MHz, DMSO-d$_6$) δ 9.21 (s, 1H), 7.52-7.34 (m, 2H), 7.14 (t, J=7.6 Hz, 1H), 2.37-2.30 (m, 5H), 1.30 (s, 12H), 1.10 (t, J=7.6 Hz, 3H).

Intermediate 71

(E)-4-(Dimethylamino)-N-(2-methyl-3-(4,4,5,5-tetramethyl-1,3,2-dioxaborolan-2-yl) phenyl)but-2-enamide

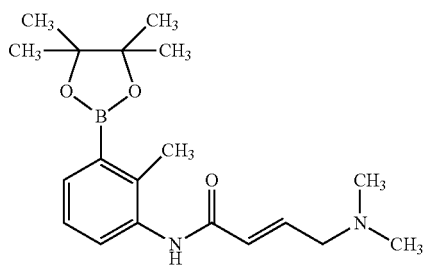

(I-71)

A mixture of (E)-4-(dimethylamino)but-2-enoic acid hydrochloride (0.300 g, 1.81 mmol) and a catalytic amount of DMF (7 µL, 0.091 mmol) in THF (22.6 mL) was cooled to 0° C. Oxalyl chloride (0.153 mL, 1.81 mmol) was added dropwise and the mixture was warmed to room temperature and stirred for 2 h, then was heated at 50° C. for 30 min. The solution was cooled at 0° C., treated sequentially with DIEA (0.633 mL, 3.62 mmol) and 2-methyl-3-(4,4,5,5-tetramethyl-1,3,2-dioxaborolan-2-yl)aniline [prepared according to the procedure of U.S. Pat. No. 8,084,620, Intermediate 50-1] (0.380 g, 1.63 mmol), and the resulting mixture was stirred at room temperature. After 30 min, the mixture was partitioned between saturated aqueous NaHCO$_3$ and EtOAc. The organic phase was washed with brine, dried and concentrated. The residue was subjected to column chromatography on silica gel (24 g), eluting with EtOAc containing increasing amounts of 2 M NH$_3$ in MeOH (sequentially 0%, 5% and 10%), to provide (E)-4-(dimethylamino)-N-(2-methyl-3-(4,4,5,5-tetramethyl-1,3,2-dioxaborolan-2-yl)phenyl) but-2-enamide as a brown syrup (88 mg, 14% yield). Mass spectrum m/z 345 (M+H)$^+$. $^1$H NMR (400 MHz, DMSO-d$_6$) δ 9.37 (s, 1H), 7.53-7.42 (m, 2H), 7.15 (t, J=7.6 Hz, 1H), 6.70 (dt, J=15.4, 5.9 Hz, 1H), 6.35 (d, J=15.2 Hz, 1H), 3.05 (d, J=5.3 Hz, 2H), 2.34 (s, 3H), 2.17 (s, 6H), 1.30 (s, 12H).

Intermediate 72

N-Methyl-N-(2-methyl-3-(4,4,5,5-tetramethyl-1,3,2-dioxaborolan-2-yl)phenyl)acrylamide

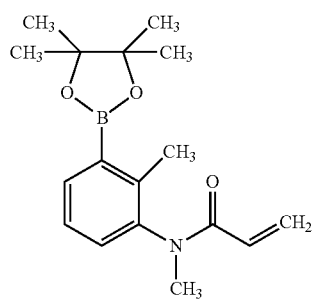

(I-72)

Intermediate 72A: N,2-Dimethyl-3-(4,4,5,5-tetramethyl-1,3,2-dioxaborolan-2-yl)aniline

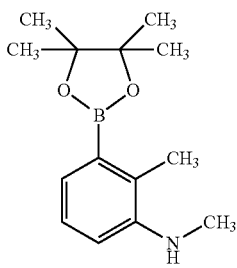

(I-72A)

A mixture of 3-bromo-N,2-dimethylaniline (1.90 g, 9.50 mmol), 4,4,4',4',5,5,5',5'-octamethyl-2,2'-bi(1,3,2-dioxaborolane) (2.53 g, 9.97 mmol) and potassium acetate (1.86 g, 19.0 mmol) in 1,4-dioxane (23.7 mL) was bubbled with nitrogen for 10 min. The mixture was treated with PdCl$_2$(dppf) DCM adduct (0.194 g, 0.237 mmol) and the mixture was bubbled with nitrogen for another 5 min, then was heated at reflux. After 2.75 h, the mixture was cooled to room temperature, filtered through CELITE®, and the solids were washed with EtOAc. The combined filtrates were concentrated and the residue was subjected to column chromatography on silica gel (40 g), eluting with EtOAc-hexanes (gradient from 5-15%), to provide N,2-dimethyl-3-(4,4,5,5-tetramethyl-1,3,2-dioxaborolan-2-yl)aniline as an off-white waxy solid (2.26 g, 96% yield). Mass spectrum m/z 249 (M+H)$^+$. $^1$H NMR (400 MHz, CDCl$_3$) δ 7.21-7.12 (m, 2H), 6.72 (dd, J=6.5, 2.8 Hz, 1H), 3.63 (br. s., 1H), 2.90 (s, 3H), 2.36 (s, 3H), 1.35 (s, 12H).

Intermediate 72

Following the procedure used to prepare Intermediate 51, N,2-dimethyl-3-(4,4,5,5-tetramethyl-1,3,2-dioxaborolan-2-yl)aniline was converted into N-methyl-N-(2-methyl-3-(4,4,5,5-tetramethyl-1,3,2-dioxaborolan-2-yl)phenyl)acrylamide as a white solid in 98% yield. Mass spectrum m/z 302 (M+H)$^+$. $^1$H NMR (400 MHz, CDCl$_3$) δ 7.77 (dd, J=7.3, 1.3 Hz, 1H), 7.25-7.16 (m, 2H), 6.37 (dd, J=16.8, 2.1 Hz, 1H), 5.90 (dd, J=16.9, 10.3 Hz, 1H), 5.47 (dd, J=10.3, 2.2 Hz, 1H), 3.25 (s, 3H), 2.38 (s, 3H), 1.37 (s, 12H).

Intermediate 73

N-Methyl-N-(3-(4,4,5,5-tetramethyl-1,3,2-dioxaborolan-2-yl)phenyl)acrylamide

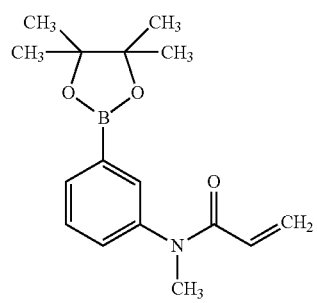

(I-73)

Intermediate 73A: N-Methyl-3-(4,4,5,5-tetramethyl-1,3,2-dioxaborolan-2-yl)aniline

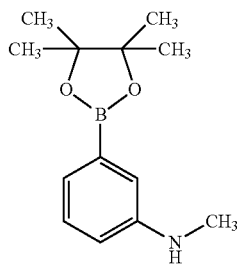
(I-73A)

Following the procedure used in the preparation of Intermediate 72A, 3-bromo-N-methylaniline was converted into N-methyl-3-(4,4,5,5-tetramethyl-1,3,2-dioxaborolan-2-yl)aniline in quantitative yield. Mass spectrum m/z 234 (M+H)$^+$. $^1$H NMR (400 MHz, CDCl$_3$) δ 7.25-7.15 (m, 2H), 7.07 (d, J=2.4 Hz, 1H), 6.73 (ddd, J=7.7, 2.6, 1.3 Hz, 1H), 4.02-3.43 (b, 1H), 2.87 (s, 3H), 1.35 (s, 12H).

Intermediate 73

Following the procedure used in the preparation of Intermediate 72, N-methyl-3-(4,4,5,5-tetramethyl-1,3,2-dioxaborolan-2-yl)aniline was converted into N-methyl-N-(3-(4,4,5,5-tetramethyl-1,3,2-dioxaborolan-2-yl)phenyl)acrylamide in 88% yield. Mass spectrum m/z 288 (M+H)$^+$. $^1$H NMR (400 MHz, CDCl$_3$) δ 7.77 (d, J=7.3 Hz, 1H), 7.62 (d, J=1.5 Hz, 1H), 7.42 (t, J=7.7 Hz, 1H), 7.26-7.23 (m, 1H), 6.37 (dd, J=16.7, 2.0 Hz, 1H), 6.06 (dd, J=16.7, 10.6 Hz, 1H), 5.51 (dd, J=10.3, 2.0 Hz, 1H), 3.36 (s, 3H), 1.36 (s, 12H).

Intermediate 74

N-(2-Fluoro-3-(4,4,5,5-tetramethyl-1,3,2-dioxaborolan-2-yl)phenyl)-N-methylacrylamide

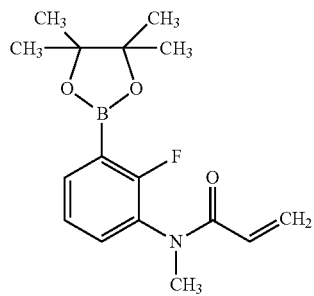
(I-74)

Intermediate 74A: 2 N-(3-Bromo-2-methylphenyl)formamide

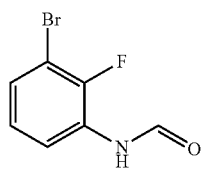
(I-74A)

A solution of 3-bromo-2-fluoroaniline (1.00 g, 5.26 mmol) in formic acid (1.99 mL, 52.6 mmol) was heated at 90° C. for 16 h. The mixture was cooled to room temperature and partitioned between EtOAc and water. The organic phase was washed sequentially with saturated aqueous NaHCO$_3$ and brine, dried and concentrated to provide N-(3-bromo-2-fluorophenyl)formamide as a beige solid (1.02 g, 89% yield). Mass spectrum m/z 218, 220 (M+H)$^+$. $^1$H NMR (400 MHz, CDCl$_3$) δ 8.50 (s, 1H), 8.40-8.17 (m, 1H), 7.53-7.41 (m, 1H), 7.31 (ddd, J=8.0, 6.6, 1.4 Hz, 1H), 7.05 (td, J=8.2, 1.4 Hz, 1H).

Intermediate 74B: 3-Bromo-2-fluoro-N-methylaniline

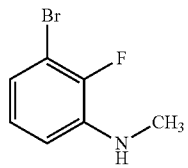
(I-74B)

A solution of N-(3-bromo-2-fluorophenyl)formamide (1.00 g, 4.59 mmol) in THF (15 mL) was cooled to 0° C., treated dropwise with borane-methyl sulfide complex (6.88 mL, 13.8 mmol) and heated at 70° C. for 2 h. The mixture was cooled to room temperature and treated with MeOH, stirred at room temperature for 30 min, then was treated slowly with 1 M aqueous HCl. The mixture was heated to 70° C. for 1 h, then was cooled to room temperature, treated with 1 M aqueous NaOH and extracted with EtOAc. The organic extract was washed with brine, dried and concentrated. The residue was subjected to column chromatography on silica gel, eluting with EtOAc-hexanes, to provide 3-bromo-2-fluoro-N-methylaniline as a colorless oil (0.800 g, 85% yield). Mass spectrum m/z 204, 206 (M+H)$^+$. $^1$H NMR (400 MHz, CDCl$_3$) δ 6.92-6.86 (m, 1H), 6.84-6.78 (m, 1H), 6.63-6.56 (m, 1H), 4.03 (br. s., 1H), 2.88 (d, J=4.6 Hz, 3H).

Intermediate 74C: 2-Fluoro-N-methyl-3-(4,4,5,5-tetramethyl-1,3,2-dioxaborolan-2-yl) aniline

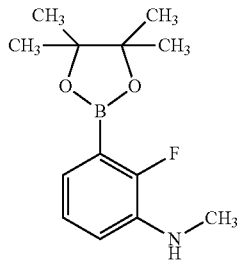
(I-74C)

Following the procedure used in the preparation of Intermediate 72A, 3-bromo-2-fluoro-N-methylaniline was converted into 2-fluoro-N-methyl-3-(4,4,5,5-tetramethyl-1,3,2-dioxaborolan-2-yl)aniline in 71% yield. Mass spectrum m/z 252 (M+H)$^+$. $^1$H NMR (400 MHz, CDCl$_3$) δ 7.02 (d, J=7.3 Hz, 2H), 6.85-6.73 (m, 1H), 4.07-3.85 (m, 1H), 2.86 (s, 3H), 1.38-1.32 (m, 12H).

Intermediate 74

Following the procedure used in the preparation of Intermediate 72, 2-fluoro-N-methyl-3-(4,4,5,5-tetramethyl-1,3,2-dioxaborolan-2-yl)aniline was converted into N-(2-fluoro-3-(4,4,5,5-tetramethyl-1,3,2-dioxaborolan-2-yl)phenyl)-N-methylacrylamide in 56% yield. $^1$H NMR (400 MHz, CDCl$_3$) δ 7.74 (s, 1H), 7.33-7.27 (m, 1H), 7.22-7.06 (m, 1H), 6.37 (d, J=16.7 Hz, 1H), 6.16-5.87 (m, 1H), 5.52 (d, J=10.1 Hz, 1H), 3.30 (s, 3H), 1.38 (s, 12H).

Intermediate 75

N-Methyl-N-(2-methyl-3-(4,4,5,5-tetramethyl-1,3,2-dioxaborolan-2-yl)phenyl) ethenesulfonamide

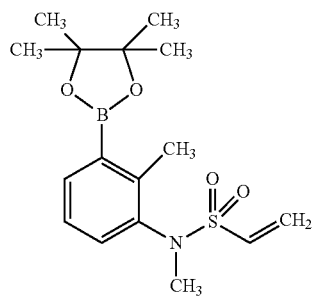

(I-75)

A solution of N,2-dimethyl-3-(4,4,5,5-tetramethyl-1,3,2-dioxaborolan-2-yl)aniline [Intermediate 72A] (0.500 g, 2.02 mmol) in DCM (10.1 mL), cooled to 0° C., was treated with DIEA (0.530 mL, 3.03 mmol), then 2-chloroethanesulfonyl chloride (0.254 mL, 2.43 mmol) was added dropwise. The mixture was stirred at room temperature for 3 h, then was concentrated. The residue was subjected to column chromatography on silica gel (24 g), eluting with EtOAc-hexanes (gradient from 10-20%), to provide N-methyl-N-(2-methyl-3-(4,4,5,5-tetramethyl-1,3,2-dioxaborolan-2-yl)phenyl)ethenesulfonamide as a white waxy solid (0.432 g, 63% yield). Mass spectrum m/z 338 (M+H)$^+$. $^1$H NMR (400 MHz, CDCl$_3$) δ 7.75 (dd, J=7.3, 1.3 Hz, 1H), 7.27-7.23 (m, 1H), 7.21-7.15 (m, 1H), 6.62 (dd, J=16.5, 9.9 Hz, 1H), 6.23 (d, J=16.7 Hz, 1H), 6.02 (d, J=9.9 Hz, 1H), 3.15 (s, 3H), 2.61 (s, 3H), 1.35 (s, 12H).

Intermediate 76

N-Methyl-N-(3-(4,4,5,5-tetramethyl-1,3,2-dioxaborolan-2-yl)phenyl)ethenesulfonamide

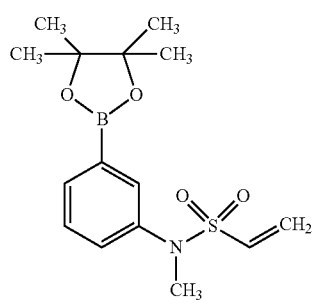

(I-76)

Following the procedure used to prepare Intermediate 75, N-methyl-3-(4,4,5,5-tetramethyl-1,3,2-dioxaborolan-2-yl)aniline [Intermediate 73A] was converted into N-methyl-N-(3-(4,4,5,5-tetramethyl-1,3,2-dioxaborolan-2-yl)phenyl)ethenesulfonamide in 61% yield. Mass spectrum m/z 324 (M+H)$^+$. $^1$H NMR (400 MHz, DMSO-d$_6$) δ 7.62-7.54 (m, 2H), 7.51-7.37 (m, 2H), 6.86 (dd, J=16.4, 10.0 Hz, 1H), 6.14 (d, J=10.1 Hz, 1H), 6.02 (d, J=16.5 Hz, 1H), 3.18 (s, 3H), 1.30 (s, 12H).

Intermediate 77

N-(2-Methyl-3-(4,4,5,5-tetramethyl-1,3,2-dioxaborolan-2-yl)phenyl)ethenesulfonamide

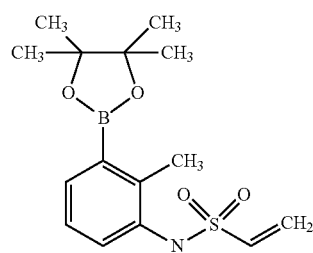

(I-77)

Following the procedure used to prepare Intermediate 75, 2-methyl-3-(4,4,5,5-tetramethyl-1,3,2-dioxaborolan-2-yl)aniline [prepared according to the procedure of U.S. Pat. No. 8,084,620, Intermediate 46-1, Step 1] was converted into N-(2-methyl-3-(4,4,5,5-tetramethyl-1,3,2-dioxaborolan-2-yl)phenyl)ethenesulfonamide in 49% yield. Mass spectrum m/z 324 (M+H)$^+$. $^1$H NMR (400 MHz, DMSO-d$_6$) δ 9.24 (s, 1H), 7.52-7.47 (m, 1H), 7.27 (d, J=6.6 Hz, 1H), 7.19-7.13 (m, 1H), 6.83 (dd, J=16.5, 9.9 Hz, 1H), 5.99-5.89 (m, 2H), 2.44 (s, 3H), 1.30 (s, 12H).

Intermediate 78

N-(3-(4,4,5,5-Tetramethyl-1,3,2-dioxaborolan-2-yl)phenyl)ethenesulfonamide

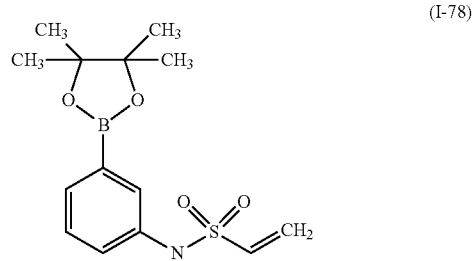

(I-78)

Following the procedure used to prepare Intermediate 75, 3-(4,4,5,5-tetramethyl-1,3,2-dioxaborolan-2-yl)aniline [Intermediate 65A] was converted into N-(3-(4,4,5,5-tetramethyl-1,3,2-dioxaborolan-2-yl)phenyl)ethenesulfonamide in 40% yield. Mass spectrum m/z 310 (M+H)$^+$. $^1$H NMR (400 MHz, CDCl$_3$) δ 7.63 (d, J=7.0 Hz, 1H), 7.47 (d, J=2.2 Hz, 1H), 7.44-7.40 (m, 1H), 7.40-7.34 (m, 1H), 6.57 (dd, J=16.5, 9.9 Hz, 1H), 6.34-6.26 (m, 2H), 5.97 (d, J=9.9 Hz, 1H), 1.36 (s, 12H).

Intermediate 79

4,4,5,5-Tetramethyl-2-(3-(vinylsulfonyl)phenyl)-1,3,2-dioxaborolane

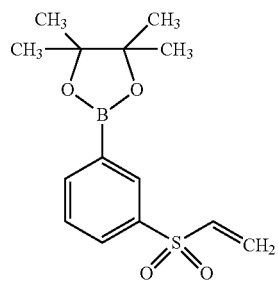
(I-79)

Intermediate 79A:
(3-Bromophenyl)(2-chloroethyl)sulfane

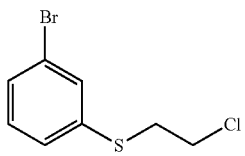
(I-79A)

A mixture of 3-bromobenzenethiol (1.09 mL, 10.6 mmol), 1-bromo-2-chloroethane (1.76 mL, 21.2 mmol) and $K_2CO_3$ (1.46 g, 10.6 mmol) in DMF (10.6 mL) was heated at 60° C. for 5 h. The mixture was cooled to room temperature and stirred overnight. After 16 h, the mixture was partitioned between water and ether. The organic phase was washed with brine, dried and concentrated to provide (3-bromophenyl)(2-chloroethyl)sulfane as a colorless oil (2.63 g, 99% yield), used without further purification. $^1$H NMR (400 MHz, $CDCl_3$) δ 7.53 (t, J=1.8 Hz, 1H), 7.38 (ddd, J=8.0, 1.8, 1.0 Hz, 1H), 7.31 (ddd, J=7.8, 1.8, 1.0 Hz, 1H), 7.22-7.15 (m, 1H), 3.65-3.60 (m, 2H), 3.27-3.22 (m, 2H).

Intermediate 79B:
1-Bromo-3-((2-chloroethyl)sulfonyl)benzene

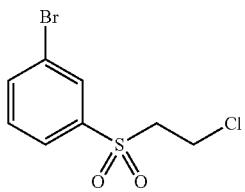
(I-79B)

A solution of (3-bromophenyl)(2-chloroethyl)sulfane (2.63 g, 10.5 mmol) in DCM (10.5 mL) was cooled to 0° C. and treated portionwise with a solution of m-chloroperoxybenzoic acid (6.01 g, 26.1 mmol) in DCM (40 mL). The resulting suspension was stirred at 0° C. for 4 h. The mixture was diluted with DCM, treated with saturated aqueous $NaHCO_3$ and sodium thiosulfate. The organic phase was separated, washed with brine, dried and concentrated. The residue was subjected to column chromatography on silica gel (40 g), eluting with EtOAc-hexanes (gradient from 5-30%), to provide 1-bromo-3-((2-chloroethyl)sulfonyl)benzene as a white solid (2.93 g, 99% yield). Mass spectrum m/z 283, 285 (M+H)$^+$. $^1$H NMR (400 MHz, $CDCl_3$) δ 8.08 (t, J=1.9 Hz, 1H), 7.86 (dddd, J=14.5, 7.9, 1.8, 1.1 Hz, 2H), 7.49 (t, J=7.9 Hz, 1H), 3.81-3.76 (m, 2H), 3.59-3.52 (m, 2H).

Intermediate 79

A mixture of 1-bromo-3-((2-chloroethyl)sulfonyl)benzene (0.500 g, 1.76 mmol), 4,4,4',4',5,5,5',5'-octamethyl-2,2'-bi(1,3,2-dioxaborolane) (0.470 g, 1.85 mmol), potassium acetate (0.346 g, 3.53 mmol) and $PdCl_2$(dppf) DCM adduct (0.036 g, 0.044 mmol) in 1,4-dioxane (4.41 mL) was bubbled with nitrogen for about 2-3 min, then was heated at reflux. After 2.5 h, the mixture was cooled to room temperature and filtered through CELITE®. The solids were washed with EtOAc, and the combined filtrates were concentrated. The residue was subjected to column chromatography on silica gel (24 g), eluting with EtOAc-hexanes (gradient from 10-25%), to provide 4,4,5,5-tetramethyl-2-(3-(vinylsulfonyl)phenyl)-1,3,2-dioxaborolane as a light yellow waxy solid (0.196 g, 80% purity, 30% yield), used without further purification. Mass spectrum m/z 295 (M+H)$^+$. $^1$H NMR (400 MHz, $CDCl_3$) δ 8.33 (s, 1H), 8.09-8.02 (m, 1H), 8.01-7.95 (m, 1H), 7.60-7.51 (m, 1H), 6.73-6.63 (m, 1H), 6.48 (d, J=16.5 Hz, 1H), 6.04 (d, J=9.7 Hz, 1H), 1.36 (s, 12H).

Intermediate 80

N-(Cyanomethyl)-2-methyl-3-(4,4,5,5-tetramethyl-1,3,2-dioxaborolan-2-yl)benzamide

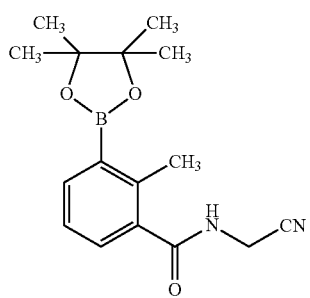
(I-80)

Intermediate 80A:
3-Bromo-N-(cyanomethyl)-2-methylbenzamide

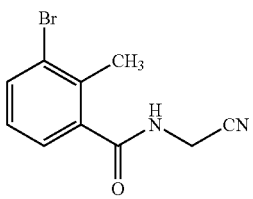
(I-80A)

A solution of 3-bromo-2-methylbenzoic acid (0.500 g, 2.33 mmol), EDC (0.669 g, 3.49 mmol), HOBT (0.534 g, 3.49 mmol), and DIEA (1.22 mL, 6.98 mmol) in THF (14.5 mL) and DCM (14.5 mL) was stirred at room temperature for 30 min, then was treated with 2-aminoacetonitrile hydrochloride (0.237 g, 2.56 mmol). The mixture was stirred at room temperature for 5 h, then was partitioned between saturated aqueous NaHCO$_3$ and EtOAc. The organic phase was dried and concentrated, and the residue was purified by column chromatography on silica gel (24 g), eluting with EtOAc-hexanes (gradient from 20-40%) to provide 3-bromo-N-(cyanomethyl)-2-methylbenzamide as a white solid (0.554 g, 94% yield). Mass spectrum m/z 253, 255 (M+H)$^+$. $^1$H NMR (400 MHz, CDCl$_3$) δ 7.67 (dd, J=8.0, 1.0 Hz, 1H), 7.30 (dd, J=7.7, 0.9 Hz, 1H), 7.14-7.08 (m, 1H), 6.14 (br. s., 1H), 4.38 (d, J=5.9 Hz, 2H), 2.48 (s, 3H).

Intermediate 80

Following the procedure used to prepare Intermediate 65A, 3-bromo-N-(cyanomethyl)-2-methylbenzamide was converted into N-(cyanomethyl)-2-methyl-3-(4,4,5,5-tetramethyl-1,3,2-dioxaborolan-2-yl)benzamide as a yellow solid in 91% yield. Mass spectrum m/z 301 (M+H)$^+$. $^1$H NMR (400 MHz, DMSO-d$_6$) δ 8.96 (t, J=5.6 Hz, 1H), 7.69 (dd, J=7.5, 1.5 Hz, 1H), 7.37 (dd, J=7.6, 1.4 Hz, 1H), 7.30-7.18 (m, 1H), 4.28 (d, J=5.5 Hz, 2H), 2.45 (s, 3H), 1.31 (s, 12H).

Intermediate 81

8-Fluoro-1-methyl-3-(2-methyl-3-(4,4,5,5-tetramethyl-1,3,2-dioxaborolan-2-yl)phenyl)quinazoline-2,4(1H,3H)-dione

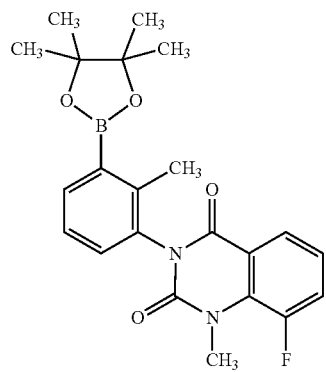
(I-81)

Intermediate 81A: 2-Amino-N-(3-bromo-2-methylphenyl)-3-fluorobenzamide

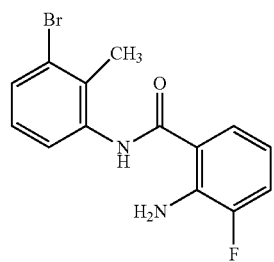
(I-81A)

A solution of 8-fluoro-1H-benzo[d][1,3]oxazine-2,4-dione (2.00 g, 11.0 mmol) and 3-bromo-2-methylaniline (4.11 g, 22.1 mmol) in 1,4-dioxane (20 mL) in a sealed reaction vessel was heated at 110° C. for 4 days. The mixture was cooled to room temperature and treated with 10% aqueous K$_2$CO$_3$ and stirred for 30 min. The mixture was extracted three times with DCM, and the combined organic phases were washed with water, dried and concentrated. The residue was triturated with ether, and the precipitate was collected by filtration to give a gray solid (2.50 g). The filtrate was concentrated and the residue was again triturated with ether to give a gray solid (230 mg). The two solids were combined to provide 2-amino-N-(3-bromo-2-methylphenyl)-3-fluorobenzamide as a gray solid (2.73 g, 78% yield). Mass spectrum m/z 323, 325 (M+H)$^+$. $^1$H NMR (400 MHz, CDCl$_3$) δ 7.69 (d, J=7.9 Hz, 1H), 7.65 (br. s., 1H), 7.50-7.46 (m, 1H), 7.32 (d, J=8.1 Hz, 1H), 7.19-7.11 (m, 2H), 6.73-6.64 (m, 1H), 5.69 (br. s., 2H), 2.44 (s, 3H).

Alternative Synthesis of 2-Amino-N-(3-bromo-2-methylphenyl)-3-fluorobenzamide

A suspension of 8-fluoro-1H-benzo[d][1,3]oxazine-2,4-dione (3.00 g, 16.6 mmol) in xylenes (50 mL) was treated with 3-bromo-2-methylaniline (3.08 g, 16.6 mmol) and heated to reflux. After 6 h the mixture was allowed to cool to room temperature overnight. The resulting suspension was diluted with hexanes and the precipitate was collected by filtration, rinsed with hexanes and air-dried to provide 2-amino-N-(3-bromo-2-methylphenyl)-3-fluorobenzamide as a white solid (4.50 g, 84% yield).

Intermediate 81B: 3-(3-Bromo-2-methylphenyl)-8-fluoroquinazoline-2,4(1H,3H)-dione

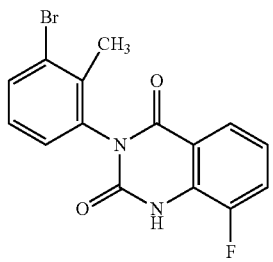
(I-81B)

A solution of 2-amino-N-(3-bromo-2-methylphenyl)-3-fluorobenzamide (5.70 g, 17.6 mmol) in THF (100 mL) was treated with bis(trichloromethyl) carbonate [triphosgene] (6.28 g, 21.2 mmol) at room temperature and stirred for 15 min. The mixture was diluted with EtOAc, carefully treated with saturated aqueous NaHCO$_3$ and stirred at room temperature until gas evolution stopped. The organic phase was separated and washed sequentially with saturated aqueous NaHCO$_3$, water and brine, and was dried and concentrated. The residue was triturated with ether to provide 3-(3-bromo-2-methylphenyl)-8-fluoroquinazoline-2,4(1H,3H)-dione as an off-white solid (6.00 g, 97% yield). Mass spectrum m/z 349, 351 (M+H)+. $^1$H NMR (400 MHz, CDCl$_3$) δ 8.59 (d, J=17.6 Hz, 1H), 7.99 (d, J=8.1 Hz, 1H), 7.70 (dd, J=7.8, 1.2 Hz, 1H), 7.54-7.43 (m, 1H), 7.28-7.21 (m, 2H), 7.21-7.17 (m, 1H), 2.28 (s, 3H).

Intermediate 81C: 3-(3-Bromo-2-methylphenyl)-8-fluoro-1-methylquinazoline-2,4(1H,3H)-dione

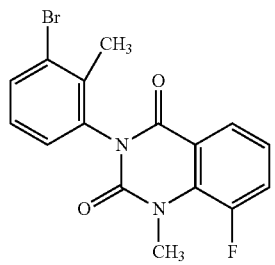

(I-81C)

A solution of 3-(3-bromo-2-methylphenyl)-8-fluoroquinazoline-2,4(1H,3H)-dione (4.80 g, 13.8 mmol) in DMF (25 mL) was treated with $Cs_2CO_3$ (13.4 g, 41.2 mmol). The suspension was stirred at room temperature and treated quickly dropwise with iodomethane (4.30 mL, 68.7 mmol) and stirred rapidly at room temperature for 1 h. The mixture was diluted with EtOAc and water (200 mL). The organic phase was separated and washed sequentially with water and brine, then was dried and concentrated to provide 3-(3-bromo-2-methylphenyl)-8-fluoro-1-methylquinazoline-2,4(1H,3H)-dione as a tan glassy solid (4.80 g, 96% yield). Mass spectrum m/z 363, 365 $(M+H)^+$.

Intermediate 81

A mixture of 3-(3-bromo-2-methylphenyl)-8-fluoro-1-methylquinazoline-2,4(1H,3H)-dione (4.80 g, 13.2 mmol), 4,4,4',4',5,5,5',5'-octamethyl-2,2'-bi(1,3,2-dioxaborolane) (4.36 g, 17.2 mmol), potassium acetate (3.89 g, 39.6 mmol) and $PdCl_2$(dppf) DCM adduct (0.540 g, 0.661 mmol) in 1,4-dioxane (65 mL) was heated to reflux for 2 h. After cooling to room temperature, the mixture was filtered through CELITE® and the solids were rinsed with EtOAc. The filtrate was diluted with EtOAc, washed with water, and dried and concentrated. The residue was subjected to column chromatography on silica gel (80 g), eluting with EtOAc-hexanes (gradient from 20-50%), to provide 8-fluoro-1-methyl-3-(2-methyl-3-(4,4,5,5-tetramethyl-1,3,2-dioxaborolan-2-yl)phenyl)quinazoline-2,4(1H,3H)-dione as a white solid (4.61 g, 85% yield). Mass spectrum m/z 411 $(M+H)^+$. $^1$H NMR (400 MHz, $CDCl_3$) δ 8.14-8.08 (m, 1H), 7.93 (dd, J=7.5, 1.3 Hz, 1H), 7.48 (ddd, J=14.0, 8.0, 1.5 Hz, 1H), 7.34 (t, J=7.6 Hz, 1H), 7.27-7.20 (m, 2H), 3.88 (d, J=7.9 Hz, 3H), 2.36 (s, 3H), 1.36 (s, 12H).

Intermediate 82

1-Methyl-3-(2-methyl-3-(4,4,5,5-tetramethyl-1,3,2-dioxaborolan-2-yl)phenyl) quinazoline-2,4(1H,3H)-dione

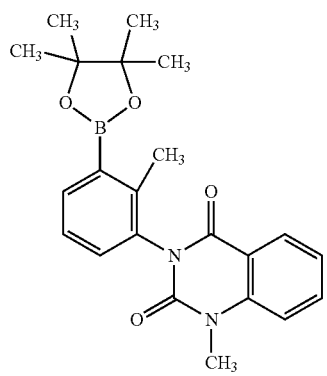

(I-82)

Intermediate 82A: 2-Amino-N-(3-bromo-2-methylphenyl)benzamide

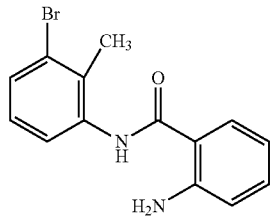

(I-82A)

A solution of 2-aminobenzoic acid (5.00 g, 36.5 mmol) and thionyl chloride (8.68 g, 72.9 mmol) in toluene (50 mL) was heated at reflux for 60 min. The mixture was concentrated and the residue was suspended in THF (50 mL), cooled in an ice-water bath and treated with 3-bromo-2-methylaniline (20.35 g, 109 mmol). The resulting suspension was heated at reflux for 2 h. The mixture was cooled to room temperature and treated with 10% aqueous $K_2CO_3$ (50 mL), stirred vigorously for 15 min, and extracted with EtOAc. The organic phase was dried and concentrated. The residue was purified by column chromatography on silica gel to give 2-amino-N-(3-bromo-2-methylphenyl) benzamide as a light yellow solid (4.70 g, 42% yield). Mass spectrum m/z 305, 307 $(M+H)^+$. $^1$H NMR (400 MHz, $CDCl_3$) δ 7.72 (d, J=7.9 Hz, 1H), 7.67 (br. s., 1H), 7.54 (dd, J=8.3, 1.2 Hz, 1H), 7.48 (dd, J=7.9, 0.9 Hz, 1H), 7.36-7.31 (m, 1H), 7.15 (t, J=8.0 Hz, 1H), 6.81-6.73 (m, 2H), 5.59 (br. s., 2H), 2.45 (s, 3H).

Alternative Synthesis of 2-Amino-N-(3-bromo-2-methylphenyl)benzamide

A suspension of 1H-benzo[d][1,3]oxazine-2,4-dione (5.00 g, 30.7 mmol) and 3-bromo-2-methylaniline (5.70 g, 30.7 mmol) in xylenes (50 mL) was heated at reflux for 8 h. The solvent was removed by distillation and the residue was purified by column chromatography on silica gel (120 g), eluting with EtOAc-hexanes (gradient from 0-50%), to give 2-amino-N-(3-bromo-2-methylphenyl)benzamide as an off-white solid (2.30 g, 24% yield).

Intermediate 82B: 3-(3-Bromo-2-methylphenyl)quinazoline-2,4(1H,3H)-dione

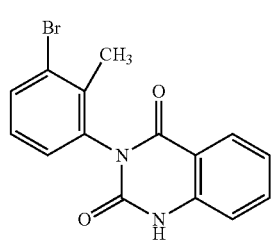

(I-82B)

A solution of 2-amino-N-(3-bromo-2-methylphenyl)benzamide (2.00 g, 6.55 mmol) in THF (50 mL) was treated with bis(trichloromethyl) carbonate [triphosgene](2.92 g, 9.83 mmol) and heated at reflux for 60 min. The mixture was cooled to room temperature and treated with saturated aqueous $NaHCO_3$, extracted with EtOAc, and the combined organic phases were washed twice with saturated $NaHCO_3$, then with water, dried and concentrated. The residue was triturated with DCM to give a white solid which was collected by filtration. The residue from concentration of the filtrate was triturated with DCM to give additional white solid which was collected by filtration. The two solids were combined to give 3-(3-bromo-2-methylphenyl)quinazoline-2,4(1H,3H)-dione as a white solid (2.10 g, 97% yield). Mass spectrum m/z 331, 333 (M+H)⁺. ¹H NMR (400 MHz, MeOH-d₄) δ 8.07 (dd, J=7.92, 1.32 Hz, 1H), 7.65-7.75 (m, 2H), 7.21-7.32 (m, 4H), 2.20 (s, 3H). ¹H NMR (400 MHz, CDCl₃) δ 9.38 (br. s., 1H), 8.19 (dd, J=7.9, 1.1 Hz, 1H), 7.76-7.69 (m, 1H), 7.69-7.60 (m, 1H), 7.35-7.17 (m, 3H), 7.04-6.97 (m, 1H), 2.28 (s, 3H).

Intermediate 82C: 3-(3-Bromo-2-methylphenyl)-1-methylquinazoline-2,4(1H,3H)-dione

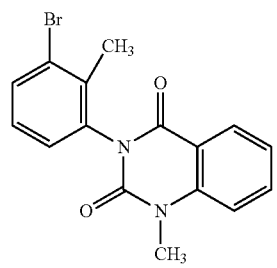

(I-82C)

A suspension of 3-(3-bromo-2-methylphenyl)quinazoline-2,4(1H,3H)-dione (23.02 g, 69.5 mmol) and Cs₂CO₃ (34.0 g, 104 mmol) in DMF (70 mL) cooled in an ice-water bath was treated portionwise with iodomethane (5.22 mL, 83 mmol). The mixture was warmed to room temperature and stirred for 30 min. The mixture was filtered and the filtrate was concentrated. The residue was partitioned between EtOAc and water, forming a precipitate which was collected by filtration. The collected solid was washed with water and dried overnight under vacuum to give a white solid. The organic phase of the filtrate was separated, washed three times with 10% aqueous LiCl, then was washed twice with water, dried and concentrated to give additional solid. The two solids were combined to give 3-(3-bromo-2-methylphenyl)-1-methylquinazoline-2,4(1H,3H)-dione as a white solid (15.56 g, 92% yield). Mass spectrum m/z 345, 347 (M+H)⁺.

Intermediate 82

A mixture of 3-(3-bromo-2-methylphenyl)-1-methylquinazoline-2,4(1H,3H)-dione (36.39 g, 105 mmol), 4,4,4',4',5,5,5',5'-octamethyl-2,2'-bi(1,3,2-dioxaborolane) (40.2 g, 158 mmol), PdCl₂(dppf) DCM adduct (4.30 g, 5.27 mmol) and potassium acetate (31.0 g, 316 mmol) in 1,4-dioxane (500 mL) and DMSO (50 mL) was heated at reflux for 24 h. Additional PdCl₂(dppf) DCM adduct (1.47 g) was added and the mixture was heated at reflux for 6 h more. The cooled mixture was filtered through CELITE® and the filtrate was concentrated. The residue was diluted with EtOAc, shaken with water, and both phases were filtered through CELITE® to remove a black precipitate. The organic phase of the filtrate was separated, washed sequentially with water and brine, dried and concentrated. The residue was purified by column chromatography on silica gel (2 330 g columns), eluting with EtOAc-hexanes (gradient from 20-100%). The residue from concentration of the product-containing effluent was triturated with EtOAc to give a solid which was collected by filtration. The filtrate was concentrated and crystallized from EtOAc to give additional solid. The mother liquor from this crystallization was concentrated and the residue was purified by column chromatography on silica gel (330 g), eluting with EtOAc-hexanes (gradient from 20-50%), to give additional solid. The three solids were combined to give 1-methyl-3-(2-methyl-3-(4,4,5,5-tetramethyl-1,3,2-dioxaborolan-2-yl)phenyl)quinazoline-2,4(1H,3H)-dione as a white solid (21.2 g, 51% yield). Mass spectrum m/z 393 (M+H)⁺. ¹H NMR (400 MHz, CDCl₃) δ 8.35 (d, J=7.9 Hz, 1H), 7.64 (ddd, J=8.5, 7.3, 1.5 Hz, 1H), 7.59 (dd, J=7.4, 1.4 Hz, 1H), 7.33-7.27 (m, 1H), 7.24-7.17 (m, 1H), 7.12 (d, J=8.1 Hz, 2H), 3.55 (s, 3H), 1.59 (s, 3H), 1.39 (s, 12H).

Intermediate 83

5-Fluoro-2,3-dimethyl-4-(4,4,5,5-tetramethyl-1,3,2-dioxaborolan-2-yl)-1H-indole-7-carboxamide

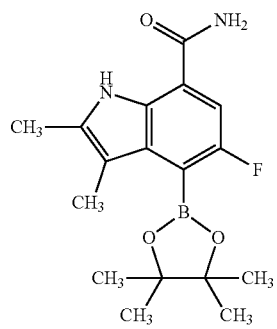

(I-83)

Following the procedure used to prepare Intermediate 9, 4-bromo-5-fluoro-2,3-dimethyl-1H-indole-7-carboxamide [Intermediate 2] was converted into 5-fluoro-2,3-dimethyl-4-(4,4,5,5-tetramethyl-1,3,2-dioxaborolan-2-yl)-1H-indole-7-carboxamide in 38% yield. Mass spectrum m/z 333 (M+H)⁺. ¹H NMR (400 MHz, MeOH-d₄) δ 7.27 (d, J=10.1 Hz, 1H), 2.39 (s, 3H), 2.24 (s, 3H), 1.44 (s, 12H).

Intermediate 84

(RS)-5-Fluoro-2,3-dimethyl-4-(2,3,4,5-tetrahydrobenzo[b][1,4]oxazepin-9-yl)-1H-indole-7-carboxamide TFA Salt

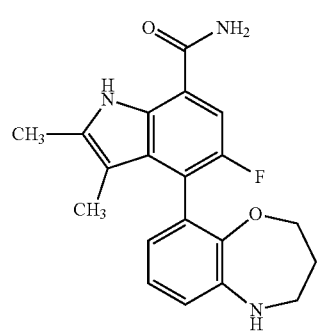

(I-84)

Following the procedures used to prepare Intermediate 48, 9-bromo-2,3,4,5-tetrahydrobenzo[b][1,4]oxazepine [prepared according to procedures described in Example 13 of PCT Publication No. WO 2012/149236] was converted into (RS)-5-fluoro-2,3-dimethyl-4-(2,3,4,5-tetrahydrobenzo[b][1,4]oxazepin-9-yl)-1H-indole-7-carboxamide. Mass spectrum m/z 354 (M+H)+.

Intermediate 85

(RS)-5-Fluoro-4-(7-fluoro-1,2,3,4-tetrahydroisoquinolin-5-yl)-2,3-dimethyl-1H-indole-7-carboxamide TFA Salt

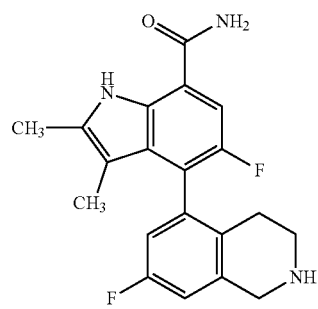

(I-85)

Intermediate 85A: Ethyl 2-bromo-4-fluorophenethylcarbamate

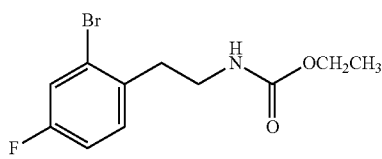

(I-85A)

A mixture of 3-(2-bromo-4-fluorophenyl)propanoic acid (2.00 g, 8.10 mmol), EtOH (0.945 mL, 16.2 mmol), TEA (3.38 mL, 24.3 mmol) and diphenylphosphoryl azide (2.45 g, 8.90 mmol) in anhydrous THF (20 mL) was heated at 80° C. for 18 h. The mixture was concentrated and the residue was subjected to column chromatography on silica gel, eluting with EtOAc-hexanes (gradient from 0-100%) to provide ethyl 2-bromo-4-fluorophenethylcarbamate as a colorless gum (2.03 g, 82% yield). Mass spectrum m/z 290, 292 (M+H)+. $^1$H NMR (400 MHz, CDCl$_3$) δ 7.31 (dd, J=8.3, 2.5 Hz, 1H), 7.24-7.16 (m, 1H), 6.99 (td, J=8.3, 2.6 Hz, 1H), 4.68 (br. s., 1H), 4.19-4.06 (m, 2H), 3.43 (q, J=6.6 Hz, 2H), 2.95 (t, J=6.9 Hz, 2H), 1.30-1.19 (m, 3H).

Intermediate 85B: Ethyl 5-bromo-7-fluoro-3,4-dihydroisoquinoline-2(1H)-carboxylate

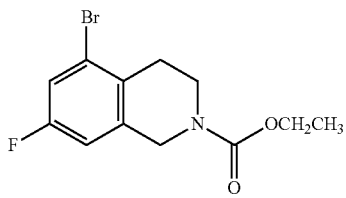

(I-85B)

A solution of ethyl 2-bromo-4-fluorophenethylcarbamate (1.30 g, 4.48 mmol) in acetic acid (9.00 mL, 157 mmol) and sulfuric acid (3.00 mL, 56.3 mmol) was stirred at 0° C. and treated with paraformaldehyde (0.148 g, 4.93 mmol). The mixture was stirred at room temperature for three days, then was diluted with water (50 mL) and was extracted with EtOAc. The organic layer was washed sequentially with saturated aqueous NaHCO$_3$ and 1 M aqueous M HCl, dried and concentrated. The residue was subjected to column chromatography on silica gel, eluting with EtOAc-hexanes (gradient from 0-30%) to provide ethyl 5-bromo-7-fluoro-3,4-dihydroisoquinoline-2(1H)-carboxylate as a white solid (334 mg, 23% yield). Mass spectrum m/z 302, 304 (M+H)+.

Intermediate 85C: 5-Bromo-7-fluoro-1,2,3,4-tetrahydroisoquinoline

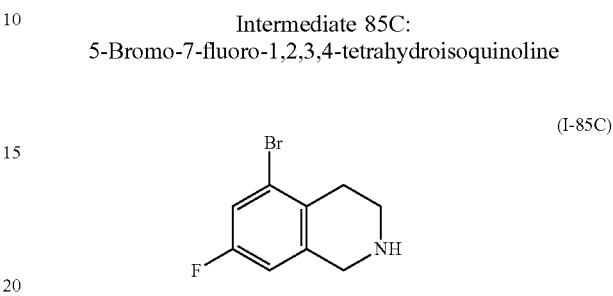

(I-85C)

A solution of ethyl 5-bromo-7-fluoro-3,4-dihydroisoquinoline-2(1H)-carboxylate (350 mg, 1.16 mmol) in ethylene glycol (7.0 mL) was treated with a solution of KOH (5.85 g, 104 mmol) in water (5.6 mL) and the mixture was stirred at 90° C. for 18 h. The mixture was cooled to room temperature, diluted with water (30 mL) and extracted with EtOAc (50 mL). The organic layer was dried and concentrated to provide 5-bromo-7-fluoro-1,2,3,4-tetrahydroisoquinoline, used without further purification. Mass spectrum m/z 230, 232 (M+H)+.

Intermediate 85

Following the procedures used to prepare Intermediate 48, 5-bromo-7-fluoro-1,2,3,4-tetrahydroisoquinoline was converted into (RS)-5-fluoro-4-(7-fluoro-1,2,3,4-tetrahydroisoquinolin-5-yl)-2,3-dimethyl-1H-indole-7-carboxamide, TFA salt. Mass spectrum m/z 356 (M+H)+.

Intermediate 86

5-Fluoro-2,3-dimethyl-4-(1,2,3,4-tetrahydroisoquinolin-6-yl)-1H-indole-7-carboxamide TFA Salt

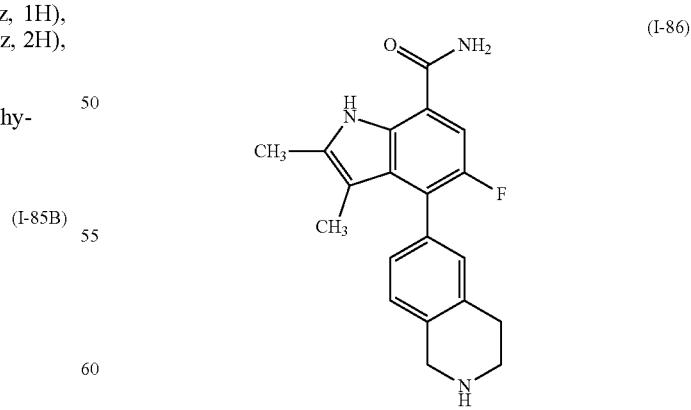

(I-86)

Following the procedures used to prepare Intermediate 48, 6-bromo-1,2,3,4-tetrahydroisoquinoline hydrochloride was converted into 5-fluoro-2,3-dimethyl-4-(1,2,3,4-tetrahydroisoquinolin-6-yl)-1H-indole-7-carboxamide, TFA salt. Mass spectrum m/z 338 (M+H)+. $^1$H NMR (400 MHz, MeOH-d$_4$) δ 7.42 (d, J=10.6 Hz, 1H), 7.37-7.27 (m, 3H), 4.48 (s, 2H), 3.59 (td, J=6.4, 2.3 Hz, 2H), 3.25-3.18 (m, 2H), 2.36 (s, 3H), 1.65 (s, 3H).

Intermediate 87

(RS)-5-Fluoro-4-(indolin-4-yl)-2,3-dimethyl-1H-indole-7-carboxamide TFA Salt

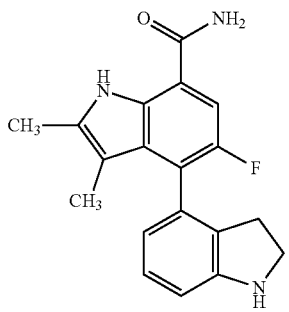
(I-87)

Following the procedures used to prepare Intermediate 48, 4-bromoindoline was converted into (RS)-5-fluoro-4-(indolin-4-yl)-2,3-dimethyl-1H-indole-7-carboxamide TFA salt. Mass spectrum m/z 324 (M+H)$^+$.

Intermediate 88

(RS)-4-(3,4-Dihydro-2H-benzo[b][1,4]thiazin-8-yl)-5-fluoro-2,3-dimethyl-1H-indole-7-carboxamide TFA Salt

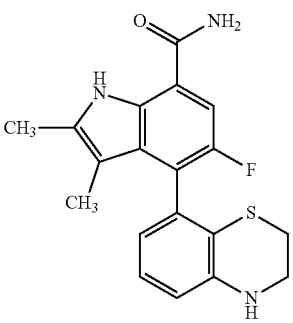
(I-88)

Following the procedures used to prepare Intermediate 48, 8-bromo-3,4-dihydro-2H-benzo[b][1,4]thiazine [prepared according to procedures described in Example 331 of PCT Publication No. WO 2012/149236] was converted into (RS)-4-(3,4-dihydro-2H-benzo[b][1,4]thiazin-8-yl)-5-fluoro-2,3-dimethyl-1H-indole-7-carboxamide TFA salt. Mass spectrum m/z 356 (M+H)+. $^1$H NMR (400 MHz, MeOH-d$_4$) δ 7.38 (d, J=10.4 Hz, 1H), 7.11-7.02 (m, 1H), 6.87 (dd, J=8.1, 1.3 Hz, 1H), 6.76 (dd, J=7.4, 1.2 Hz, 1H), 3.63 (dtd, J=8.1, 6.0, 1.9 Hz, 2H), 3.05 (dt, J=6.6, 4.0 Hz, 2H), 2.35 (s, 3H), 1.67 (s, 3H).

Intermediate 89

(S)-4-(3-(Cyclopropylamino)piperidin-1-yl)-5-fluoro-2,3-dimethyl-1H-indole-7-carboxamide

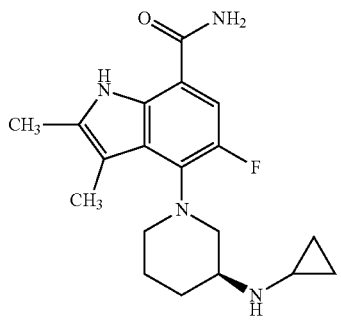
(I-89)

Intermediate 89A: (S)-tert-Butyl 3-(cyclopropylamino)piperidine-1-carboxylate

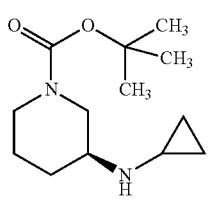
(I-89A)

A solution of (S)-tert-butyl 3-aminopiperidine-1-carboxylate (1.00 g, 4.99 mmol), (1-ethoxycyclopropoxy)trimethylsilane (0.870 g, 4.99 mmol) and acetic acid (2.86 mL, 49.9 mmol) in MeOH (15 mL) was treated with sodium cyanoborohydride (0.471 g, 7.49 mmol) and the mixture was stirred at 60° C. for 14 h. The mixture was cooled to room temperature, diluted with EtOAc, washed with saturated aqueous NaHCO$_3$, dried and concentrated. The residue was subjected to column chromatography on silica gel, eluting with EtOAc-hexanes (gradient from 0-100%) to provide (S)-tert-butyl 3-(cyclopropylamino)piperidine-1-carboxylate as a colorless oil (180 mg, 15% yield). Mass spectrum m/z 241 (M+H)+. $^1$H NMR (400 MHz, MeOH-d$_4$) δ 4.19-4.09 (m, 1H), 3.84 (d, J=12.8 Hz, 1H), 2.83 (ddd, J=13.5, 10.9, 3.1 Hz, 1H), 2.71-2.60 (m, 2H), 2.18 (tt, J=7.0, 3.6 Hz, 1H), 2.05-1.96 (m, 1H), 1.75-1.66 (m, 1H), 1.52-1.40 (m, 11H), 1.37-1.27 (m, 1H), 0.53-0.47 (m, 2H), 0.38-0.33 (m, 2H).

Intermediate 89B: (S)-tert-Butyl 3-(((benzyloxy)carbonyl)(cyclopropyl)amino)piperidine-1-carboxylate

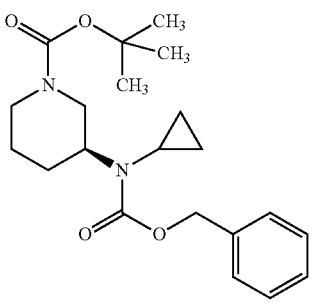
(I-89B)

A solution of (S)-tert-butyl 3-(cyclopropylamino)piperidine-1-carboxylate (180 mg, 0.749 mmol) and benzyl (2,5-dioxopyrrolidin-1-yl) carbonate (560 mg, 2.25 mmol) in THF (2 mL) was treated with TEA (313 μL, 2.25 mmol) and the mixture was stirred at room temperature for 14 h. The mixture was diluted with EtOAc, washed with saturated aqueous NaHCO₃, dried and concentrated. The residue was subjected to column chromatography on silica gel, eluting with EtOAc-hexanes (gradient from 0-100%), then was purified by followed by preparative reverse-phase HPLC to provide (S)-tert-butyl 3-(((benzyloxy)carbonyl)(cyclopropyl)amino)piperidine-1-carboxylate as a colorless viscous oil (200 mg, 71% yield). $^1$H NMR (400 MHz, MeOH-d₄) δ 7.44-7.26 (m, 5H), 5.12 (s, 2H), 4.00 (d, J=11.4 Hz, 2H), 3.62-3.45 (m, 1H), 3.10 (t, J=11.9 Hz, 1H), 2.72-2.50 (m, 2H), 2.10 (qd, J=12.5, 3.9 Hz, 1H), 1.89 (d, J=11.7 Hz, 1H), 1.74 (d, J=13.6 Hz, 1H), 1.55-1.38 (m, 10H), 0.90-0.77 (m, 2H), 0.74-0.61 (m, 2H).

Intermediate 89C: (S)-Benzyl cyclopropyl(piperidin-3-yl)carbamate

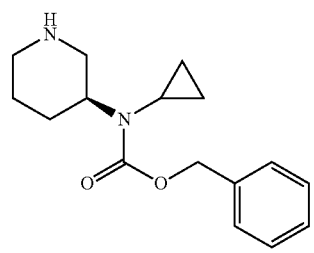

(I-89C)

A solution of (S)-tert-butyl 3-(((benzyloxy)carbonyl)(cyclopropyl)amino)-piperidine-1-carboxylate (200 mg, 0.534 mmol) in DCM (1 mL) was treated with TFA (0.50 mL, 6.49 mmol) and the mixture was allowed to stand at room temperature for 30 min. The solution was concentrated and the residue was dissolved in DCM, washed with saturated aqueous NaHCO₃, dried and concentrated to provide (S)-benzyl cyclopropyl(piperidin-3-yl)carbamate as a colorless oil (140 mg, 96% yield). Mass spectrum m/z 275 (M+H)⁺. $^1$H NMR (400 MHz, MeOH-d₄) δ 7.43-7.16 (m, 5H), 5.11 (s, 2H), 3.66 (dtd, J=11.7, 7.9, 4.0 Hz, 1H), 2.96-2.86 (m, 3H), 2.56-2.49 (m, 1H), 2.41 (td, J=12.7, 2.9 Hz, 1H), 2.10-1.98 (m, 1H), 1.87 (dd, J=12.3, 3.1 Hz, 1H), 1.81-1.72 (m, 1H), 1.60-1.46 (m, 1H), 0.83-0.76 (m, 2H), 0.70-0.62 (m, 2H).

Intermediate 89

Following the procedures used to prepare Intermediate 13, (S)-benzyl cyclopropyl(piperidin-3-yl)carbamate and 4-bromo-5-fluoro-2,3-dimethyl-1H-indole-7-carbonitrile [Intermediate 12] were converted into (S)-4-(3-(cyclopropylamino)piperidin-1-yl)-5-fluoro-2,3-dimethyl-1H-indole-7-carboxamide. Mass spectrum m/z 345 (M+H)⁺.

Intermediate 90

5-Fluoro-2,3-dimethyl-4-(piperazin-1-yl)-1H-indole-7-carboxamide

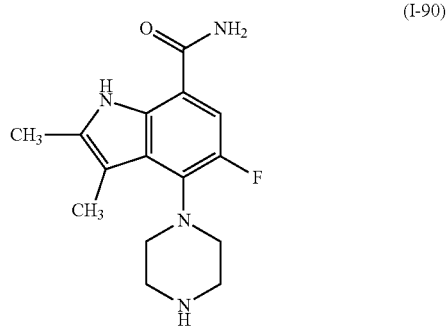 [SMILES: Cc1[nH]c2c(C(N)=O)cc(F)c(N3CCNCC3)c2c1C]

(I-90)

Intermediate 90A: tert-Butyl 4-(7-cyano-5-fluoro-2,3-dimethyl-1H-indol-4-yl)piperazine-1-carboxylate

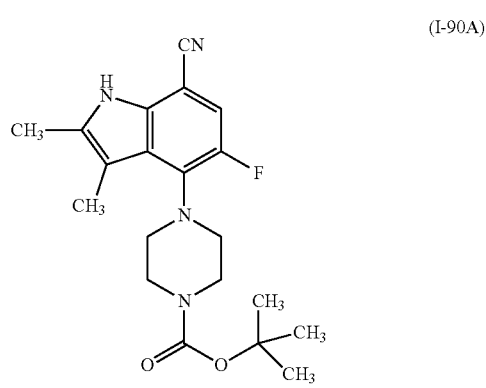 [SMILES: Cc1[nH]c2c(C#N)cc(F)c(N3CCN(C(=O)OC(C)(C)C)CC3)c2c1C]

(I-90A)

A mixture of 4-bromo-5-fluoro-2,3-dimethyl-1H-indole-7-carbonitrile [Intermediate 12] (0.200 g, 0.749 mmol), tert-butyl piperazine-1-carboxylate (0.146 g, 0.786 mmol), Cs₂CO₃ (0.488 g, 1.50 mmol), 2,2'-bis(diphenylphosphino)-1,1'-binaphthalene (0.023 g, 0.037 mmol), and tris(dibenzylideneacetone)dipalladium (0.034 g, 0.037 mmol) in 1,4-dioxane (5 mL) was bubbled with nitrogen and heated overnight at 95° C. The mixture was cooled to room temperature, filtered through CELITE® and concentrated. The residue was subjected to column chromatography on silica gel, eluting with EtOAc-hexanes (gradient from 0-100%), to provide tert-butyl 4-(7-cyano-5-fluoro-2,3-dimethyl-1H-indol-4-yl)piperazine-1-carboxylate as a yellow solid (0.194 g, 70% yield). Mass spectrum m/z 373 (M+H)⁺.

Intermediate 90

A mixture of tert-butyl 4-(7-cyano-5-fluoro-2,3-dimethyl-1H-indol-4-yl)piperazine-1-carboxylate (0.195 g, 0.524

Intermediate 91

4-Bromo-5-fluoro-3-methyl-2-(trifluoromethyl)-1H-indole-7-carboxamide

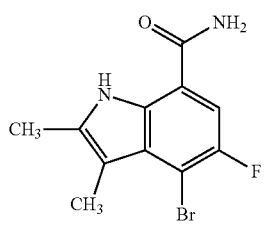
(I-91)

4-Bromo-5-fluoro-3-methyl-2-(trifluoromethyl)-1H-indole-7-carboxamide was prepared following the procedures used to prepare Intermediate 2, substituting 1,1,1-trifluoro-2-butanone for 2-butanone. Mass spectrum m/z 339, 341 (M+H)$^+$. $^1$H NMR (400 MHz, MeOH-d$_4$) δ 7.75 (d, J=9.7 Hz, 1H), 2.70 (q, J=1.7 Hz, 3H).

Intermediate 92

(RS)-5-Fluoro-3-methyl-4-(1,2,3,4-tetrahydroisoquinolin-5-yl)-2-(trifluoromethyl)-1H-indole-7-carboxamide TFA Salt

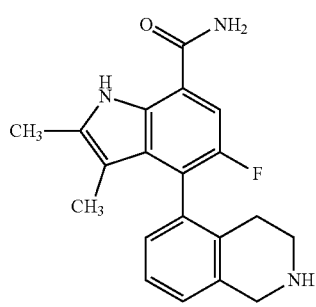
(I-92)

Following the procedures used to prepare Intermediate 42, 4-bromo-5-fluoro-3-methyl-2-(trifluoromethyl)-1H-indole-7-carboxamide [Intermediate 91] was converted into (RS)-5-fluoro-3-methyl-4-(1,2,3,4-tetrahydroisoquinolin-5-yl)-2-(trifluoromethyl)-1H-indole-7-carboxamide TFA salt. Mass spectrum m/z 392 (M+H)$^+$.

Intermediate 93

(RS)-5-Fluoro-2,3-dimethyl-4-(1,2,3,4-tetrahydroisoquinolin-8-yl)-1H-indole-7-carboxamide TFA Salt

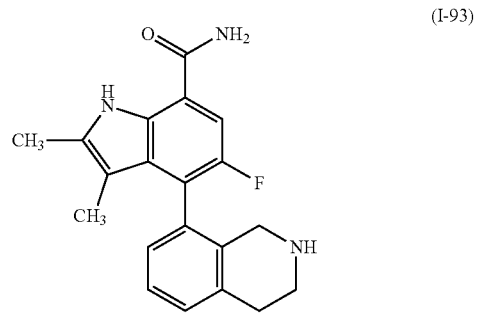 [SMILES: Cc1[nH]c2c(C(N)=O)cc(F)c(-c3cccc4c3CNCC4)c2c1C]
(I-93)

Following the procedures used to prepare Intermediate 48, 8-bromo-1,2,3,4-tetrahydroisoquinoline HCl salt was converted into (RS)-5-fluoro-2,3-dimethyl-4-(1,2,3,4-tetrahydroisoquinolin-8-yl)-1H-indole-7-carboxamide TFA salt. Mass spectrum m/z 338 (M+H)$^+$.

Intermediate 94

5-Fluoro-4-(indolin-6-yl)-2,3-dimethyl-1H-indole-7-carboxamide TFA Salt

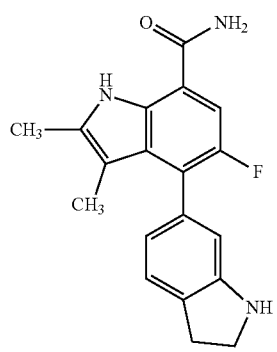
(I-94)

Following the procedures used to prepare Intermediate 48, 6-bromoindoline was converted into 5-fluoro-4-(indolin-6-yl)-2,3-dimethyl-1H-indole-7-carboxamide TFA salt. Mass spectrum m/z 324 (M+H)$^+$.

Intermediate 95

4-Bromo-6-fluoro-2,3-dimethyl-1H-indole-7-carboxamide

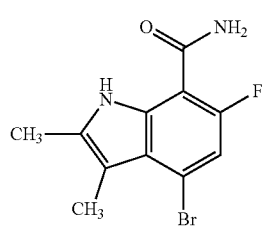
(I-95)

Following the procedures used to prepare Intermediate 2 from Intermediate 2A, 4-bromo-2,6-difluorobenzoic acid was converted into 4-bromo-6-fluoro-2,3-dimethyl-1H-indole-7-carboxamide. Mass spectrum m/z 285, 287 (M+H)+. $^1$H NMR (400 MHz, MeOH-d$_4$) δ 7.08 (d, J=12.0 Hz, 1H), 2.44 (d, J=0.5 Hz, 3H), 2.36 (s, 3H).

Intermediate 96

6-Fluoro-2,3-dimethyl-4-(1,2,3,4-tetrahydroisoquinolin-5-yl)-1H-indole-7-carboxamide TFA Salt

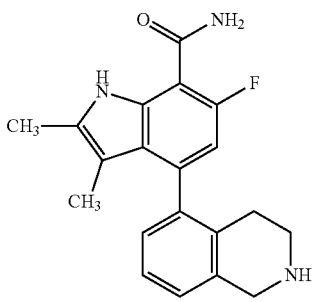
(I-96)

Following the procedures used to prepare Intermediate 42, 4-bromo-6-fluoro-2,3-dimethyl-1H-indole-7-carboxamide [Intermediate 95] was converted into 6-fluoro-2,3-dimethyl-4-(1,2,3,4-tetrahydroisoquinolin-5-yl)-1H-indole-7-carboxamide TFA salt. Mass spectrum m/z 338 (M+H)+. $^1$H NMR (400 MHz, MeOH-d$_4$) δ 7.45-7.38 (m, 1H), 7.37-7.31 (m, 1H), 7.29 (d, J=7.3 Hz, 1H), 6.64 (d, J=13.0 Hz, 1H), 4.48 (d, J=2.9 Hz, 2H), 3.48-3.39 (m, 2H), 2.82-2.60 (m, 2H), 2.33 (s, 3H), 1.57 (d, J=0.5 Hz, 3H).

Intermediate 97

4-Bromo-3-cyclopropyl-5-fluoro-2-methyl-1H-indole-7-carboxamide

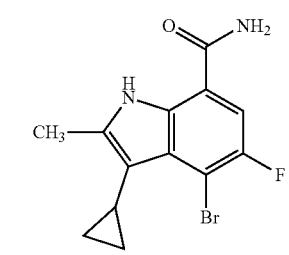
(I-97)

Following the procedures used to prepare Intermediate 2 from Intermediate 2B, 1-cyclopropylpropan-2-one was converted into 4-bromo-3-cyclopropyl-5-fluoro-2-methyl-1H-indole-7-carboxamide. Mass spectrum m/z 312, 314 (M+H)+. $^1$H NMR (400 MHz, MeOH-d$_4$) δ 7.49 (d, J=9.5 Hz, 1H), 2.49 (s, 3H), 1.93 (br. s., 1H), 1.04 (d, J=6.5 Hz, 2H), 0.68 (d, J=4.3 Hz, 2H).

Intermediate 98

(RS)-3-Cyclopropyl-5-fluoro-2-methyl-4-(1,2,3,4-tetrahydroisoquinolin-5-yl)-1H-indole-7-carboxamide TFA Salt

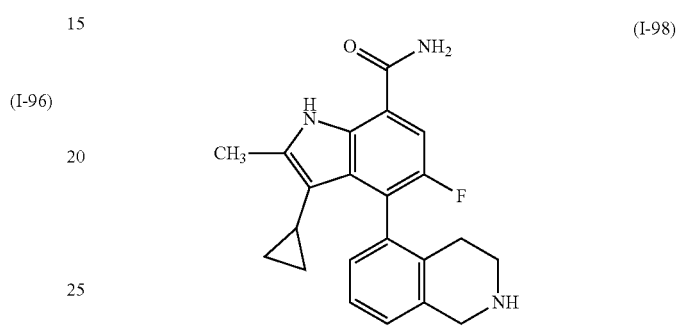
(I-98)

Following the procedures used to prepare Intermediate 42, 4-bromo-3-cyclopropyl-5-fluoro-2-methyl-1H-indole-7-carboxamide [Intermediate 97] was converted into (RS)-3-cyclopropyl-5-fluoro-2-methyl-4-(1,2,3,4-tetrahydroisoquinolin-5-yl)-1H-indole-7-carboxamide TFA salt. Mass spectrum m/z 364 (M+H)+.

Intermediate 99

4-Bromo-5-fluoro-3-(4-fluorophenyl)-2-methyl-1H-indole-7-carboxamide

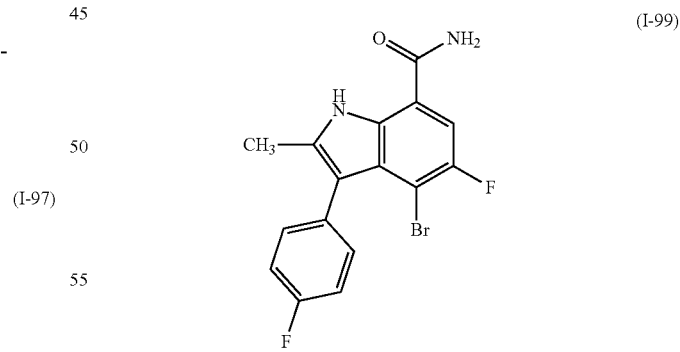
(I-99)

Following the procedures used to prepare Intermediate 2 from Intermediate 2B, 1-(4-fluorophenyl)propan-2-one was converted into 4-bromo-5-fluoro-3-(4-fluorophenyl)-2-methyl-1H-indole-7-carboxamide. Mass spectrum m/z 365, 367 (M+H)+. $^1$H NMR (400 MHz, MeOH-d$_4$) δ 7.51 (d, J=9.9 Hz, 1H), 7.38-7.30 (m, 2H), 7.18-7.09 (m, 2H), 2.31 (s, 3H).

Intermediate 100

(RS)-5-Fluoro-3-(4-fluorophenyl)-2-methyl-4-(1,2,3,4-tetrahydroisoquinolin-5-yl)-1H-indole-7-carboxamide TFA Salt

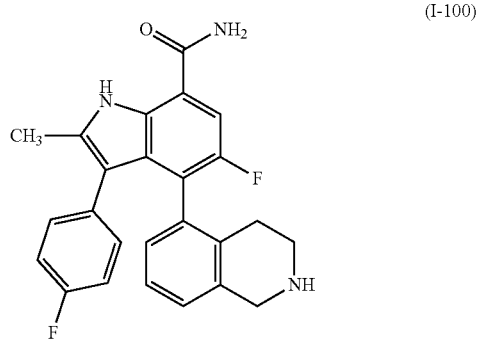 [SMILES: Cc1[nH]c2c(C(N)=O)cc(F)c(-c3cccc4c3CCNC4)c2c1-c1ccc(F)cc1]
(I-100)

Following the procedures used to prepare Intermediate 42, 4-bromo-5-fluoro-3-(4-fluorophenyl)-2-methyl-1H-indole-7-carboxamide [Intermediate 99] was converted into (RS)-5-fluoro-3-(4-fluorophenyl)-2-methyl-4-(1,2,3,4-tetrahydroisoquinolin-5-yl)-1H-indole-7-carboxamide TFA salt. Mass spectrum m/z 418 (M+H)$^+$.

Intermediate 101

4-Bromo-5-fluoro-2-(4-fluorophenyl)-3-methyl-1H-indole-7-carboxamide

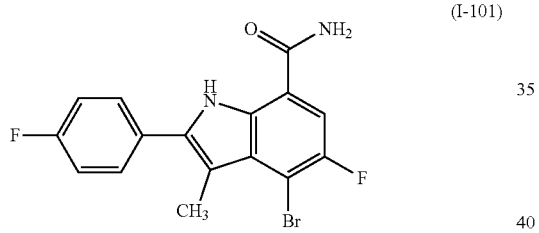
(I-101)

Following the procedures used to prepare Intermediate 2 from Intermediate 2B, 1-(4-fluorophenyl)propan-1-one was converted into 4-bromo-5-fluoro-2-(4-fluorophenyl)-3-methyl-1H-indole-7-carboxamide. Mass spectrum m/z 365, 367 (M+H)$^+$. $^1$H NMR (400 MHz, MeOH-d$_4$) δ 7.67-7.61 (m, 2H), 7.56 (d, J=9.9 Hz, 1H), 7.31-7.24 (m, 2H), 2.64 (s, 3H).

Intermediate 102

(RS)-5-Fluoro-2-(4-fluorophenyl)-3-methyl-4-(1,2,3,4-tetrahydroisoquinolin-5-yl)-1H-indole-7-carboxamide TFA Salt

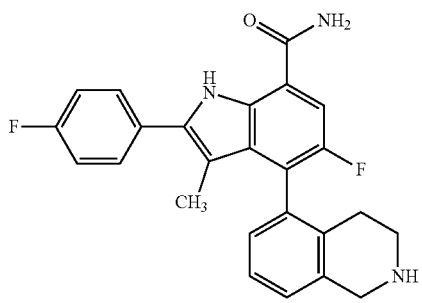
(I-102)

Following the procedures used to prepare Intermediate 42, 4-bromo-5-fluoro-2-(4-fluorophenyl)-3-methyl-1H-indole-7-carboxamide [Intermediate 101] was converted into (RS)-5-fluoro-2-(4-fluorophenyl)-3-methyl-4-(1,2,3,4-tetrahydroisoquinolin-5-yl)-1H-indole-7-carboxamide TFA salt. Mass spectrum m/z 418 (M+H)$^+$.

Intermediate 103

5-Fluoro-2,3-dimethyl-4-(1,2,5,6-tetrahydropyridin-3-yl)-1H-indole-7-carboxamide TFA Salt

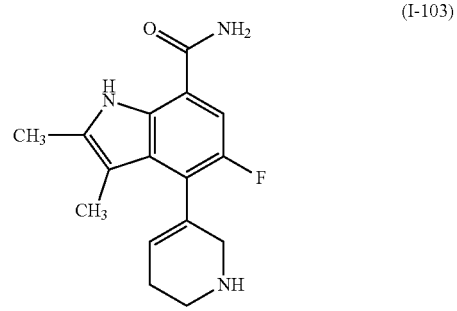 [SMILES: Cc1[nH]c2c(C(N)=O)cc(F)c(C3=CCCNC3)c2c1C]
(I-103)

Intermediate 103A: tert-Butyl 3-(7-carbamoyl-5-fluoro-2,3-dimethyl-1H-indol-4-yl)-5,6-dihydropyridine-1 (2H)-carboxylate

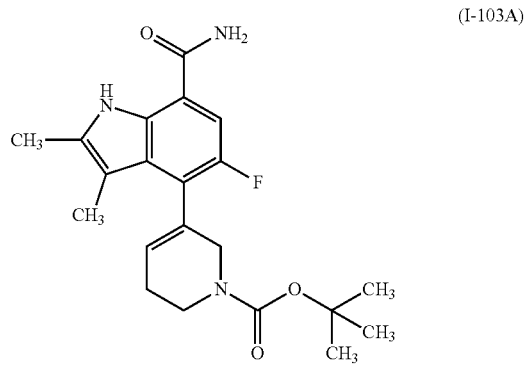 [SMILES: Cc1[nH]c2c(C(N)=O)cc(F)c(C3=CCCN(C(=O)OC(C)(C)C)C3)c2c1C]
(I-103A)

A mixture of 4-bromo-5-fluoro-2,3-dimethyl-1H-indole-7-carboxamide [Intermediate 2] (120 mg, 0.421 mmol), tert-butyl 3-(4,4,5,5-tetramethyl-1,3,2-dioxaborolan-2-yl)-5,6-dihydropyridine-1(2H)-carboxylate (130 mg, 0.421 mmol), K$_3$PO$_4$ (179 mg, 0.842 mmol) and 1,1'-bis(di-tert-butylphosphino)ferrocene palladium dichloride (13.7 mg, 0.021 mmol) in THF (2 mL) and water (0.2 mL) was purged with nitrogen and stirred at 60° C. overnight. The mixture was cooled to room temperature, filtered through CELITE® and concentrated. The residue was subjected to column chromatography on silica gel, eluting with EtOAc-hexanes (gradient from 0-50%), to provide tert-butyl 3-(7-carbamoyl-5-fluoro-2,3-dimethyl-1H-indol-4-yl)-5,6-dihydropyridine-1(2H)-carboxylate as a yellow gum (135 mg, 74% yield). Mass spectrum m/z 388 (M+H)$^+$.

Intermediate 103

A solution of tert-butyl 3-(7-carbamoyl-5-fluoro-2,3-dimethyl-1H-indol-4-yl)-5,6-dihydropyridine-1(2H)-carboxylate (69 mg, 0.178 mmol) and TFA (0.5 mL, 6.49 mmol) in DCM (1.5 mL) was stirred at room temperature for 30 min. The mixture was concentrated to provide 5-fluoro-2,3-dimethyl-4-(1,2,5,6-tetrahydropyridin-3-yl)-1H-indole-7-carboxamide TFA salt, as a light brown solid (70 mg, 88% yield). Mass spectrum m/z 288 (M+H)$^+$. $^1$H NMR (400 MHz, MeOH-d$_4$) δ 7.37 (d, J=11.1 Hz, 1H), 6.01 (tt, J=3.9, 1.9 Hz, 1H), 4.03-3.80 (m, 2H), 3.57-3.39 (m, 2H), 2.72-2.62 (m, 2H), 2.40-2.36 (m, 3H), 2.22 (s, 3H).

Intermediate 104

(RS)-5-Fluoro-2,3-dimethyl-4-(piperidin-3-yl)-1H-indole-7-carboxamide TFA salt

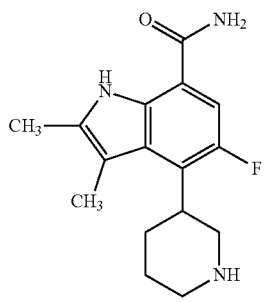

(I-104)

Following the procedures used to prepare Intermediate 38, 4-bromo-5-fluoro-2,3-dimethyl-1H-indole-7-carboxamide [Intermediate 2] was converted into (RS)-5-fluoro-2,3-dimethyl-4-(piperidin-3-yl)-1H-indole-7-carboxamide TFA salt. Mass spectrum m/z 290 (M+H)$^+$. $^1$H NMR (400 MHz, MeOH-d$_4$) δ 7.39-7.32 (m, 1H), 4.11-3.99 (m, 1H), 3.68-3.58 (m, 1H), 3.55-3.44 (m, 2H), 3.16-3.03 (m, 1H), 2.44 (s, 3H), 2.40 (s, 3H), 2.23-1.86 (m, 4H).

Intermediates 105 and 106

5-Fluoro-2,3-dimethyl-4-(1,2,3,4-tetrahydroisoquinolin-5-yl)-1H-indole-7-carboxamide (Single enantiomers)

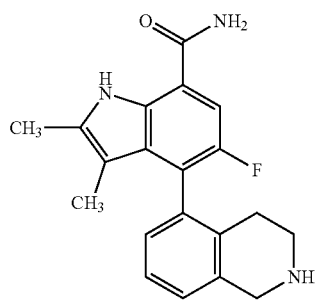

(I-105 and I-106)

Intermediates 105A and 106A: tert-Butyl 5-(7-carbamoyl-5-fluoro-2,3-dimethyl-1H-indol-4-yl)-3,4-dihydroisoquinoline-2(1H)-carboxylate (Single enantiomers)

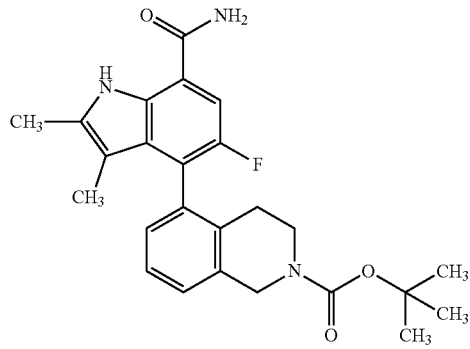

(I-105A and I-106A)

A sample of (RS)-tert-butyl 5-(7-carbamoyl-5-fluoro-2,3-dimethyl-1H-indol-4-yl)-3,4-dihydroisoquinoline-2(1H)-carboxylate [Intermediate 42A] (754 mg) was separated by chiral super-critical fluid chromatography (Column: AD-H (3×25 cm, 5 m); mobile phase: CO$_2$-MeOH (85:15) at 150 mL/min; sample preparation: 37.7 mg/mL in MeOH-DCM (1:1); injection: 1 mL).

The first peak eluting from the column provided one enantiomer of tert-butyl 5-(7-carbamoyl-5-fluoro-2,3-dimethyl-1H-indol-4-yl)-3,4-dihydroisoquinoline-2(1H)-carboxylate [Intermediate 105A] as a white solid (249 mg). Mass spectrum m/z 438 (M+H)$^+$.

The second peak eluting from the column provided the other enantiomer of tert-butyl 5-(7-carbamoyl-5-fluoro-2,3-dimethyl-1H-indol-4-yl)-3,4-dihydroisoquinoline-2(1H)-carboxylate [Intermediate 106A] as an off-white solid (232 mg). Analytical chiral super-critical fluid chromatography indicated contamination by 1.5% of the first enantiomer. The chiral super-critical fluid chromatographic separation was repeated to provide the second enantiomer [Intermediate 106A] as a white solid (203 mg). Mass spectrum m/z 438 (M+H)$^+$.

An alternative chiral super-critical fluid chromatographic separation of (RS)-tert-butyl 5-(7-carbamoyl-5-fluoro-2,3-dimethyl-1H-indol-4-yl)-3,4-dihydroisoquinoline-2(1H)-carboxylate [Intermediate 42A] (754 mg) used similar conditions but with a mobile phase consisting of CO$_2$-MeOH (75:25) containing 0.1% aqueous NH$_4$OH. The second peak eluting from the column provided Intermediate 106A as a white solid.

The absolute stereochemistries of Intermediates 105A and 106A have not been assigned.

Intermediate 105

A mixture of a single enantiomer of tert-butyl 5-(7-carbamoyl-5-fluoro-2,3-dimethyl-1H-indol-4-yl)-3,4-dihydroisoquinoline-2(1H)-carboxylate [Intermediate 105A] (0.249 g, 0.569 mmol) and TFA (3 mL) was stirred at room temperature for 45 min. The mixture was concentrated and the residue was dissolved in EtOAc, washed twice with 1.5 M aqueous Na$_2$HPO$_4$, then with brine. The aqueous layers were extracted with EtOAc, and the combined organic layers were dried and concentrated to provide a single enantiomer of 5-fluoro-2,3-dimethyl-4-(1,2,3,4-tetrahydroisoquinolin-5-yl)-1H-indole-7-carboxamide as a pale yellow solid (0.192 g, 100% yield). Mass spectrum m/z 338 (M+H)⁺. The absolute stereochemistry has not been assigned.

Intermediate 106

Following the procedure used to prepare Intermediate 105, a single enantiomer of tert-butyl 5-(7-carbamoyl-5-fluoro-2,3-dimethyl-1H-indol-4-yl)-3,4-dihydroisoquinoline-2(1H)-carboxylate [Intermediate 106A] (0.203 g, 0.464 mmol) was converted into a single enantiomer of 5-fluoro-2,3-dimethyl-4-(1,2,3,4-tetrahydroisoquinolin-5-yl)-1H-indole-7-carboxamide as a pale yellow solid (0.157 g, 96% yield). Mass spectrum m/z 338 (M+H)⁺. The absolute stereochemistry has not been assigned.

Intermediate 107

(RS)-5-Fluoro-2,3-dimethyl-4-(2,7-diazaspiro[4.4]nonan-2-yl)-1H-indole-7-carboxamide

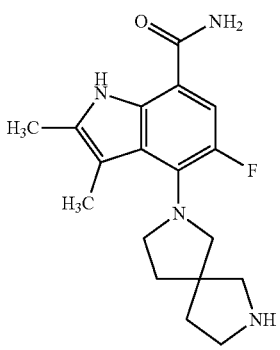

(I-107)

Following the procedures used to prepare Intermediate 26 but substituting with (RS)-tert-butyl 7-(7-cyano-5-fluoro-2,3-dimethyl-1H-indol-4-yl)-2,7-diazaspiro[4.4]nonane-2-carboxylate for (S)-tert-butyl 3-aminopyrrolidine-1-carboxylate, 4-bromo-5-fluoro-2,3-dimethyl-1H-indole-7-carbonitrile [Intermediate 12] was converted into (RS)-5-fluoro-2,3-dimethyl-4-(2,7-diazaspiro[4.4]nonan-2-yl)-1H-indole-7-carboxamide. Mass spectrum m/z 331 (M+H)⁺.

Intermediate 108

5-Fluoro-2,3-dimethyl-4-(1,4,5,6-tetrahydropyridin-3-yl)-1H-indole-7-carboxamide TFA Salt

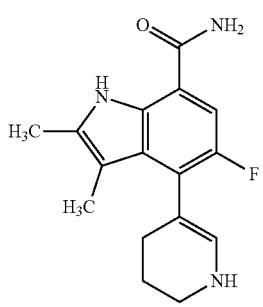

(I-108)

Following the procedures used to prepare Intermediate 26, tert-butyl 5-(7-carbamoyl-5-fluoro-2,3-dimethyl-1H-indol-4-yl)-3,4-dihydropyridine-1(2H)-carboxylate was converted into 5-fluoro-2,3-dimethyl-4-(1,4,5,6-tetrahydropyridin-3-yl)-1H-indole-7-carboxamide TFA salt. Mass spectrum m/z 288 (M+H)⁺.

Intermediate 109

Ethyl 4-bromo-5-fluoro-3-methyl-2-(trifluoromethyl)-1H-indole-7-carboxylate

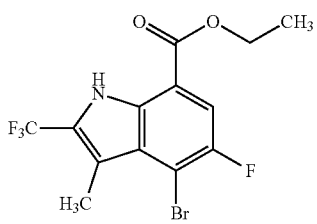

(I-109)

Intermediate 109A: 4-Bromo-5-fluoro-3-methyl-2-(trifluoromethyl)-1H-indole-7-carboxylic acid

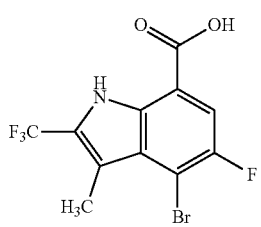

(I-109A)

A mixture of 4-bromo-5-fluoro-2-hydrazinylbenzoic acid, HCl (5.0 g, 17.51 mmol), and 1,1,1-trifluoro-2-butanone (6.62 g, 52.5 mmol) in TFA (8.0 mL) was stirred at reflux for 18 hr. The mixture was concentrated. The crude product was added to DCM and the precipitate was collected by filtration and dried under high vacuum. Yield was 4-bromo-5-fluoro-3-methyl-2-(trifluoromethyl)-1H-indole-7-carboxylic acid (3.86 g, 10.22 mmol, 58.3% yield) as white solid. ¹H NMR (400 MHz, methanol-d₄) δ 7.75 (d, J=9.3 Hz, 1H), 2.69 (q, J=1.7 Hz, 3H). LCMS: 1.07 min, M+H product not ionize.

Intermediate 109

A mixture of 4-bromo-5-fluoro-3-methyl-2-(trifluoromethyl)-1H-indole-7-carboxylic acid (3.86 g, 11.35 mmol) and sulfuric acid (0.605 mL, 11.35 mmol) in EtOH (80 mL) was stirred at reflux for three days. The mixture was concentrated. The mixture was diluted with EtOAc (65 mL) and was washed with aqueous 1.0 M HCl (65 mL) and a solution of aqueous saturated sodium bicarbonate (2×65 mL). The ethyl acetate layer was dried over sodium sulfate and concentrated. The crude product was subjected to ISCO flash chromatography (silica gel/hexane-EtOAc 100:0 to 0:100 gradient). Yield was ethyl 4-bromo-5-fluoro-3-methyl-2-(trifluoromethyl)-1H-indole-7-carboxylate (1.80 g, 4.65 mmol, 40.9% yield) as white solid. ¹H NMR (400

MHz, methanol-d$_4$) δ 7.81 (s, 1H), 4.49 (d, J=7.1 Hz, 2H), 2.76-2.65 (m, 3H), 1.46 (t, J=7.2 Hz, 3H). LCMS: 1.26 min, M+H product not ionize.

Example 1

4-(3-Acrylamido-2-methylphenyl)-3-methyl-1H-indole-7-carboxamide

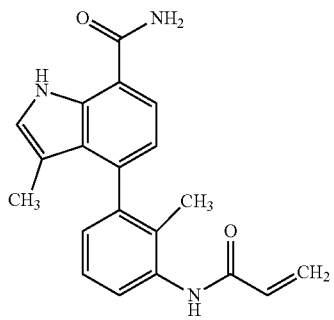

(1)

A mixture of 4-bromo-3-methyl-1H-indole-7-carboxamide [Intermediate 4](0.030 g, 0.119 mmol), N-(2-methyl-3-(4,4,5,5-tetramethyl-1,3,2-dioxaborolan-2-yl)phenyl)acrylamide [Intermediate 66] (30.4 mg, 0.130 mmol), and tetrakis(triphenylphosphine)palladium (6.85 mg, 5.93 μmol) in toluene (2.22 mL) and ethanol (741 μL) was bubbled with nitrogen for about 2-5 min. The mixture was treated with 2 M aqueous Na$_2$CO$_3$ (148 μL, 0.296 mmol), bubbled again with nitrogen, and the vessel was sealed and heated at 90° C. After 16 h, the mixture was cooled to room temperature and concentrated. The residue was dissolved in DMF-MeOH, filtered, and purified by preparative reverse-phase HPLC to provide 4-(3-acrylamido-2-methylphenyl)-3-methyl-1H-indole-7-carboxamide (21.9 mg, 61% yield). Mass spectrum m/z 438 (M+H)$^+$. $^1$H NMR (500 MHz, DMSO-d$_6$) δ 10.86 (s, 1H), 8.04 (br. s., 1H), 7.67 (d, J=7.4 Hz, 1H), 7.33 (br. s., 1H), 7.06 (s, 1H), 6.92 (t, J=7.7 Hz, 1H), 6.73-6.64 (m, 2H), 6.39 (d, J=6.4 Hz, 1H), 4.87 (s, 2H), 1.71 (s, 3H), 1.63 (d, J=1.0 Hz, 3H).

Example 2

2,3-Dimethyl-4-(3-(vinylsulfonyl)phenyl)-1H-indole-7-carboxamide

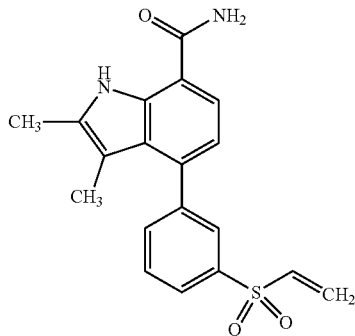

(2)

A mixture of 4-bromo-2,3-dimethyl-1H-indole-7-carboxamide [Intermediate 1](30.0 mg, 0.112 mmol), 4,4,5,5-tetramethyl-2-(3-(vinylsulfonyl)phenyl)-1,3,2-dioxaborolane [Intermediate 79] (43.4 mg, 0.118 mmol), and 1,1'-bis(di-tert-butylphosphino)ferrocene palladium dichloride (3.66 mg, 5.62 μmol) in THF (3 mL) was bubbled with nitrogen, treated with 2 M aqueous K$_3$PO$_4$ (0.168 mL, 0.336 mmol), bubbled again with nitrogen, and heated at 50° C. under nitrogen. After 16 h, the mixture was cooled to room temperature and concentrated. The residue was dissolved in DMF, filtered, and purified by preparative reverse-phase HPLC to provide 2,3-dimethyl-4-(3-(vinylsulfonyl)phenyl)-1H-indole-7-carboxamide (12.7 mg, 30% yield). Mass spectrum m/z 355 (M+H)$^+$. $^1$H NMR (500 MHz, DMSO-d$_6$) δ 10.92 (s, 1H), 8.07 (br. s., 1H), 7.93-7.89 (m, 1H), 7.80-7.72 (m, 3H), 7.63 (d, J=7.4 Hz, 1H), 7.40 (br. s., 1H), 7.21 (dd, J=16.3, 9.9 Hz, 1H), 6.87 (d, J=7.4 Hz, 1H), 6.38 (d, J=16.8 Hz, 1H), 6.23 (d, J=9.9 Hz, 1H), 2.35 (s, 3H), 1.63 (s, 3H).

Example 3

5-Fluoro-2,3-dimethyl-4-(3-(N-methylacrylamido)phenyl)-1H-indole-7-carboxamide

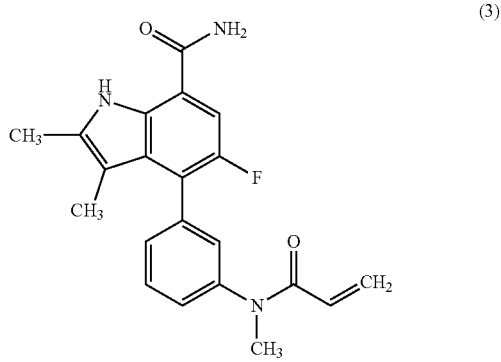 [SMILES: C=CC(=O)N(C)c1cccc(-c2c(F)cc(C(N)=O)c3[nH]c(C)c(C)c23)c1]

(3)

A mixture of 4-bromo-5-fluoro-2,3-dimethyl-1H-indole-7-carboxamide [Intermediate 2] (29.0 mg, 0.102 mmol), N-methyl-N-(3-(4,4,5,5-tetramethyl-1,3,2-dioxaborolan-2-yl)phenyl)acrylamide [Intermediate 73] (32.1 mg, 0.112 mmol), and Cs$_2$CO$_3$ (83.0 mg, 0.254 mmol) in 6:1 THF-water (3.39 mL) was bubbled with nitrogen, then was treated with PdCl$_2$(dppf) DCM adduct (4.15 mg, 5.09 μmol). The mixture was bubbled with nitrogen again, then heated at 50° C. under nitrogen. After 16 h, the mixture was cooled to room temperature and concentrated. The residue was dissolved in DMF, filtered, and purified by preparative reverse-phase HPLC to provide 5-fluoro-2,3-dimethyl-4-(3-(N-methylacrylamido)phenyl)-1H-indole-7-carboxamide (27 mg, 73% yield). Mass spectrum m/z 366 (M+H)$^+$. $^1$H NMR (500 MHz, DMSO-d$_6$) δ 10.86 (s, 1H), 8.09 (br. s., 1H), 7.57-7.52 (m, 2H), 7.49 (br. s., 1H), 7.38-7.33 (m, 2H), 7.29 (d, J=1.5 Hz, 1H), 6.22-6.06 (m, 2H), 5.63-5.55 (m, 1H), 3.29 (s, 3H), 2.31 (s, 3H), 1.58 (s, 3H).

Example 4

2,3-Dimethyl-4-(3-(vinylsulfonamido)phenyl)-1H-indole-7-carboxamide

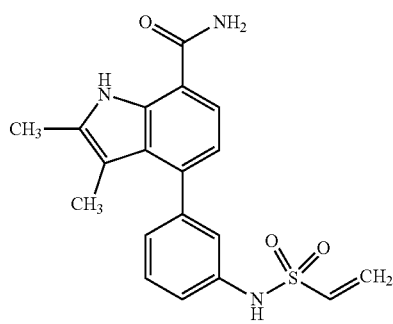

(4)

A mixture of 2,3-dimethyl-4-(4,4,5,5-tetramethyl-1,3,2-dioxaborolan-2-yl)-1H-indole-7-carboxamide [Intermediate 9] (35.0 mg, 0.0890 mmol), N-(3-bromophenyl) ethenesulfonamide [Intermediate 55] (25.7 mg, 0.0980 mmol) and $Cs_2CO_3$ (72.6 mg, 0.223 mmol) in 4:1 THF-water (2.97 mL) was bubbled with nitrogen, then was treated with $PdCl_2$ (dppf) DCM adduct (3.64 mg, 4.46 μmol). The mixture was bubbled again with nitrogen, then was heated at 50° C. under nitrogen. After 16 h, the mixture was cooled to room temperature and concentrated. The residue was dissolved in DMF, filtered, and purified by preparative reverse-phase HPLC to provide 2,3-dimethyl-4-(3-(vinylsulfonamido)phenyl)-1H-indole-7-carboxamide (12 mg, 36% yield). Mass spectrum m/z 370 (M+H)$^+$. $^1$H NMR (500 MHz, DMSO-$d_6$) δ 10.82 (s, 1H), 10.08 (s, 1H), 8.02 (br. s., 1H), 7.58 (d, J=7.9 Hz, 1H), 7.40-7.32 (m, 2H), 7.22-7.18 (m, 1H), 7.12 (s, 1H), 7.08 (d, J=7.4 Hz, 1H), 6.84-6.73 (m, 2H), 6.11-6.01 (m, 2H), 2.33 (s, 3H), 1.66 (s, 3H).

Additional Examples which were prepared by procedures described in Examples 1 through 4 or similar procedures, using the indicated starting materials, are shown in Table 1. (Starting materials prepared using literature procedures are indicated in footnotes to the Table.)

TABLE 1

| Example | Structure | Starting Materials | Mass Spectrum |
|---|---|---|---|
| 5 | 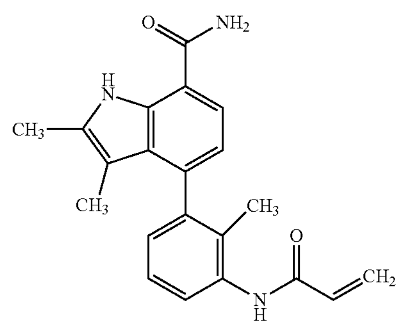 [SMILES: C=CC(=O)Nc1cccc(-c2ccc(C(N)=O)c3[nH]c(C)c(C)c23)c1C] | Intermediates 1 and 66 | m/z 348 (M + H)$^+$ |
| 6 | 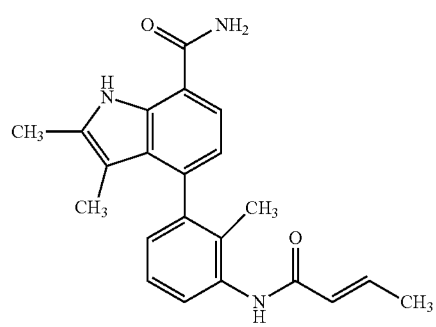 [SMILES: C/C=C/C(=O)Nc1cccc(-c2ccc(C(N)=O)c3[nH]c(C)c(C)c23)c1C] | Intermediates 1 and 67 | m/z 362 (M + H)$^+$ |
| 7 | 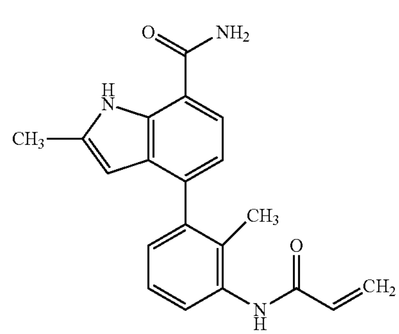 [SMILES: C=CC(=O)Nc1cccc(-c2ccc(C(N)=O)c3[nH]c(C)cc23)c1C] | Intermediates 5 and 66 | m/z 334 (M + H)$^+$ |

TABLE 1-continued
| Example | Structure | Starting Materials | Mass Spectrum |
|---|---|---|---|
| 8 | 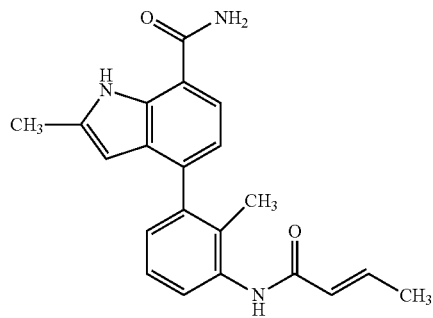 [SMILES: C/C=C/C(=O)Nc1cccc(-c2ccc(C(N)=O)c3[nH]c(C)cc23)c1C] | Intermediates 5 and 67 | m/z 348 (M + H)+ |
| 9 | 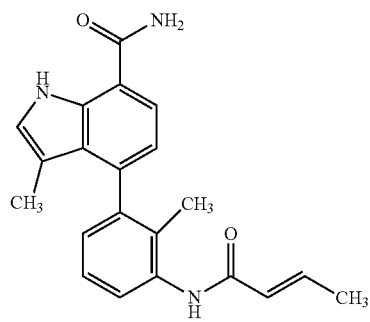 [SMILES: C/C=C/C(=O)Nc1cccc(-c2ccc(C(N)=O)c3[nH]cc(C)c23)c1C] | Intermediates 4 and 67 | m/z 348 (M + H)+ |
| 10 | 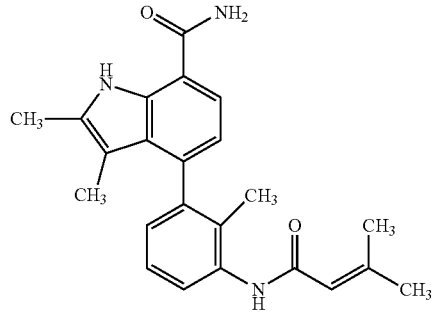 [SMILES: CC(C)=CC(=O)Nc1cccc(-c2ccc(C(N)=O)c3[nH]c(C)c(C)c23)c1C] | Intermediates 1 and 68 | m/z 376 (M + H)+ |
| 11 | 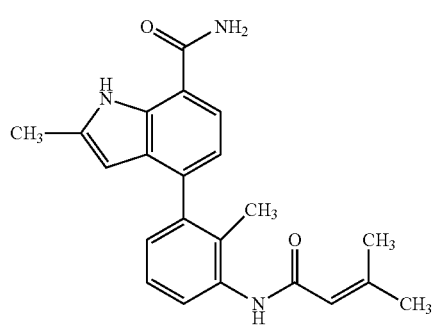 [SMILES: CC(C)=CC(=O)Nc1cccc(-c2ccc(C(N)=O)c3[nH]c(C)cc23)c1C] | Intermediates 5 and 68 | m/z 362 (M + H)+ |

TABLE 1-continued

| Example | Structure | Starting Materials | Mass Spectrum |
|---|---|---|---|
| 12 | 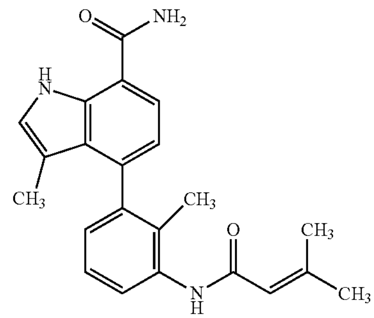 [SMILES: CC(C)=CC(=O)Nc1cccc(-c2ccc(C(N)=O)c3[nH]cc(C)c23)c1C] | Intermediates 4 and 68 | m/z 362 (M + H)+ |
| 13 | 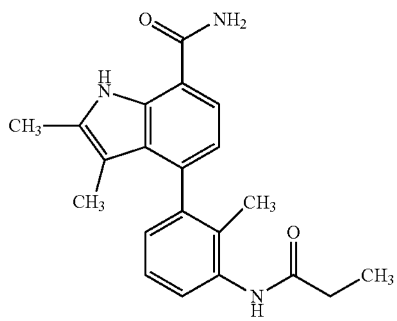 [SMILES: CCC(=O)Nc1cccc(-c2ccc(C(N)=O)c3[nH]c(C)c(C)c23)c1C] | Intermediates 1 and 70 | m/z 350 (M + H)+ |
| 14 | 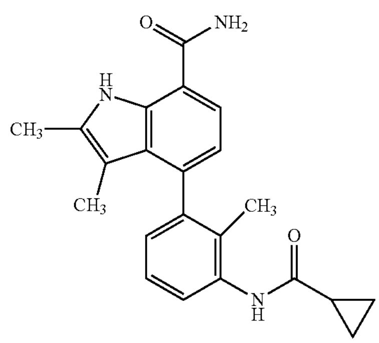 [SMILES: Cc1[nH]c2c(C(N)=O)ccc(-c3cccc(NC(=O)C4CC4)c3C)c2c1C] | Intermediates 1 and 69 | m/z 362 (M + H)+ |
| 15 | 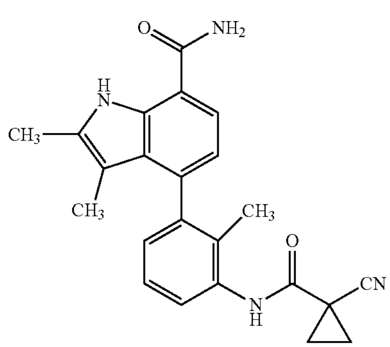 [SMILES: Cc1[nH]c2c(C(N)=O)ccc(-c3cccc(NC(=O)C4(C#N)CC4)c3C)c2c1C] | Intermediates 1 and 64 | m/z 387 (M + H)+ |

TABLE 1-continued

| Example | Structure | Starting Materials | Mass Spectrum |
|---|---|---|---|
| 16 | 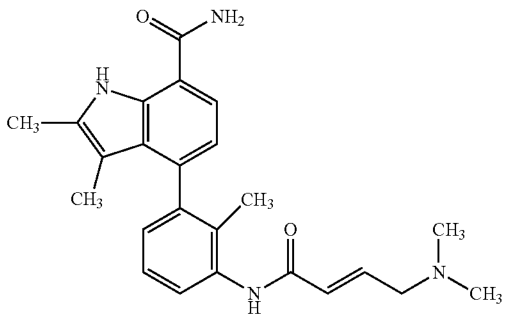 | Intermediates 1 and 71 | m/z 405 (M + H)+ |
| 17 | 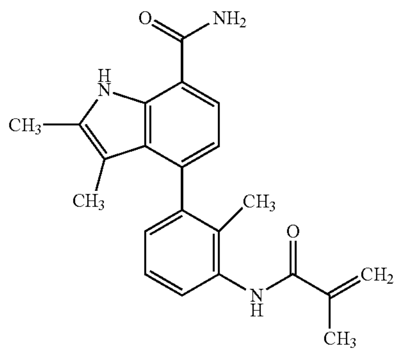 [SMILES: C=C(C)C(=O)Nc1cccc(-c2ccc(C(N)=O)c3[nH]c(C)c(C)c23)c1C] | Intermediates 1 and 61 | m/z 362 (M + H)+ |
| 18 | 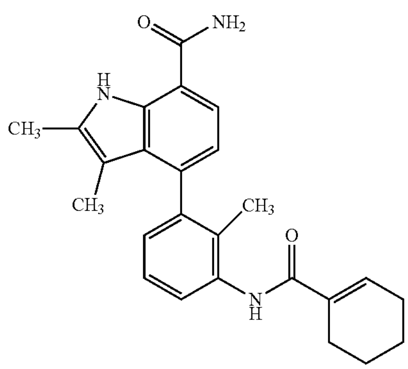 [SMILES: Cc1[nH]c2c(C(N)=O)ccc(-c3cccc(NC(=O)C4=CCCCC4)c3C)c2c1C] | Intermediates 1 and 62 | m/z 402 (M + H)+ |
| 19 | 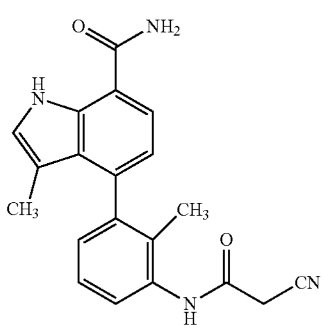 [SMILES: Cc1c(NC(=O)CC#N)cccc1-c1ccc(C(N)=O)c2[nH]cc(C)c12] | Intermediates 4 and 63 | m/z 347 (M + H)+ |

TABLE 1-continued

| Example | Structure | Starting Materials | Mass Spectrum |
|---|---|---|---|
| 20 | 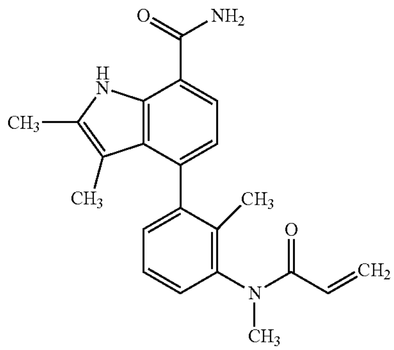 [SMILES: C=CC(=O)N(C)c1cccc(-c2ccc(C(N)=O)c3[nH]c(C)c(C)c23)c1C] | Intermediates 1 and 72 | m/z 362 (M + H)+ |
| 21 | 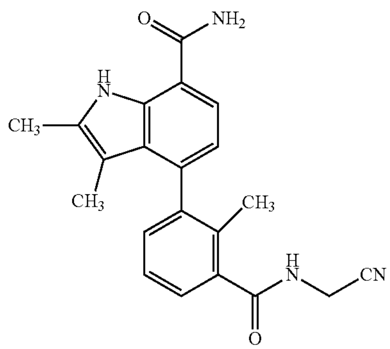 [SMILES: Cc1[nH]c2c(C(N)=O)ccc(-c3cccc(C(=O)NCC#N)c3C)c2c1C] | Intermediates 1 and 80 | m/z 361 (M + H)+ |
| 22 | 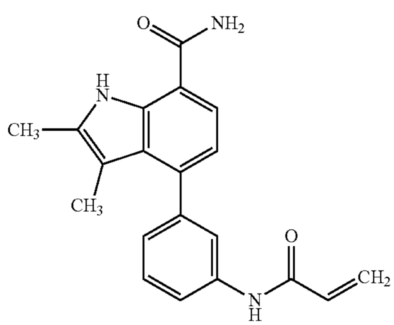 [SMILES: C=CC(=O)Nc1cccc(-c2ccc(C(N)=O)c3[nH]c(C)c(C)c23)c1] | Intermediates 1 and 65 | m/z 334 (M + H)+ |
| 23 | 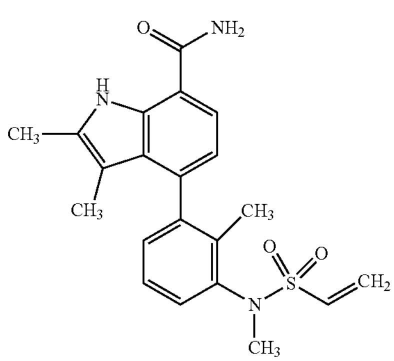 [SMILES: C=CS(=O)(=O)N(C)c1cccc(-c2ccc(C(N)=O)c3[nH]c(C)c(C)c23)c1C] | Intermediates 1 and 75 | m/z 398 (M + H)+ |

TABLE 1-continued

| Example | Structure | Starting Materials | Mass Spectrum |
|---------|-----------|--------------------|---------------|
| 24 | 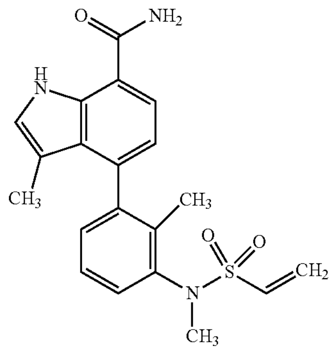 [SMILES: C=CS(=O)(=O)N(C)c1cccc(-c2ccc(C(N)=O)c3[nH]cc(C)c23)c1C] | Intermediates 4 and 75 | m/z 384 (M + H)+ |
| 25 | 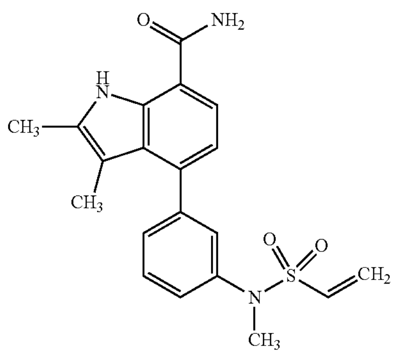 [SMILES: C=CS(=O)(=O)N(C)c1cccc(-c2ccc(C(N)=O)c3[nH]c(C)c(C)c23)c1] | Intermediates 1 and 76 | m/z 384 (M + H)+ |
| 26 | 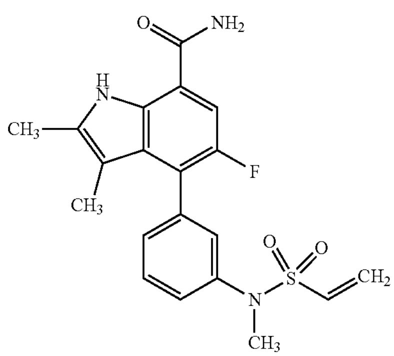 | Intermediates 2 and 76 | m/z 402 (M + H)+ |
| 27 | 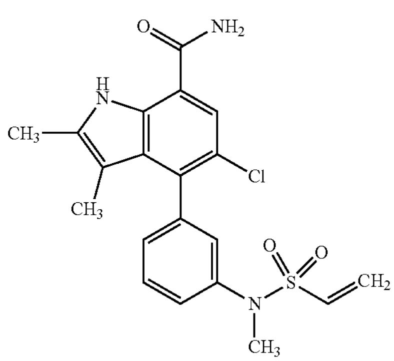 | Intermediates 3 and 76 | m/z 418, 420 (M + H)+ |

TABLE 1-continued
| Example | Structure | Starting Materials | Mass Spectrum |
|---|---|---|---|
| 28 | 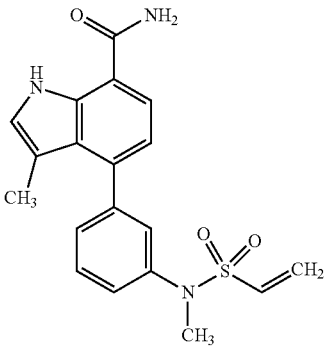 [SMILES: C=CS(=O)(=O)N(C)c1cccc(-c2ccc(C(N)=O)c3[nH]cc(C)c23)c1] | Intermediates 4 and 76 | m/z 370 (M + H)+ |
| 29 | 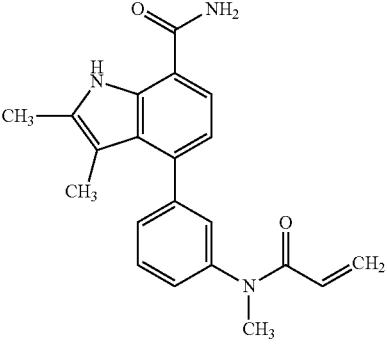 | Intermediates 1 and 73 | m/z 348 (M + H)+ |
| 30 | 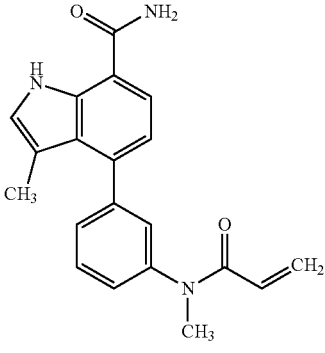 [SMILES: C=CC(=O)N(C)c1cccc(-c2ccc(C(N)=O)c3[nH]cc(C)c23)c1] | Intermediates 4 and 73 | m/z 334 (M + H)+ |
| 31 | 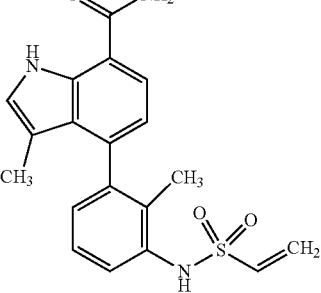 | Intermediates 4 and 77 | m/z 370 (M + H)+ |

TABLE 1-continued

| Example | Structure | Starting Materials | Mass Spectrum |
|---------|-----------|--------------------|----|
| 32 | 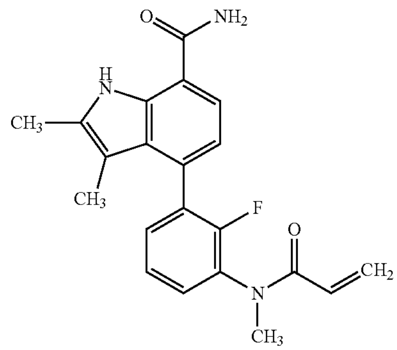 [SMILES: C=CC(=O)N(C)c1cccc(-c2ccc(C(N)=O)c3[nH]c(C)c(C)c23)c1F] | Intermediates 1 and 74 | m/z 366 (M + H)+ |
| 33 | 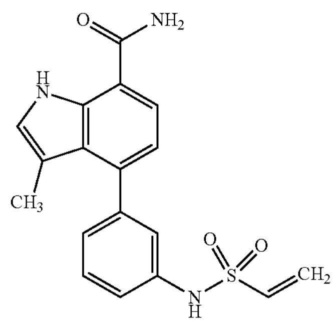 [SMILES: C=CS(=O)(=O)Nc1cccc(-c2ccc(C(N)=O)c3[nH]cc(C)c23)c1] | Intermediates 4 and 78 | m/z 356 (M + H)+ |
| 34 | 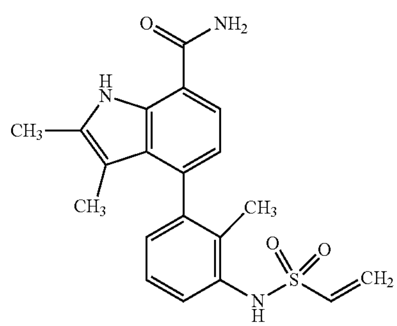 [SMILES: C=CS(=O)(=O)Nc1cccc(-c2ccc(C(N)=O)c3[nH]c(C)c(C)c23)c1C] | Intermediates 1 and 77 | m/z 384 (M + H)+ |
| 35 | 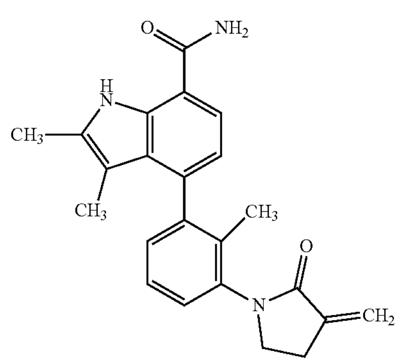 | Intermediates 9 and 60 | m/z 374 (M + H)+ |

TABLE 1-continued

| Example | Structure | Starting Materials | Mass Spectrum |
|---|---|---|---|
| 36 | (structure) | Intermediates 9 and 58 | m/z 360 (M + H)+ |
| 37 | (structure) | Intermediates 2 and 59 | m/z 378 (M + H)+ |
| 38 | (structure) | Intermediates 9 and 52 | m/z 360 (M + H)+ |
| 39 | (structure) | Intermediates 9 and 54 | m/z 396 (M + H)+ |

TABLE 1-continued

| Example | Structure | Starting Materials | Mass Spectrum |
|---|---|---|---|
| 40 | 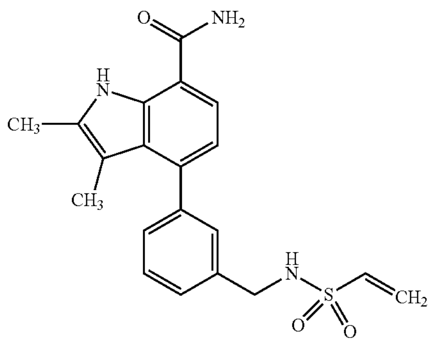 [SMILES: C=CS(=O)(=O)NCc1cccc(-c2ccc(C(N)=O)c3[nH]c(C)c(C)c23)c1] | Intermediates 9 and 56 | m/z 384 (M + H)+ |
| 41 | 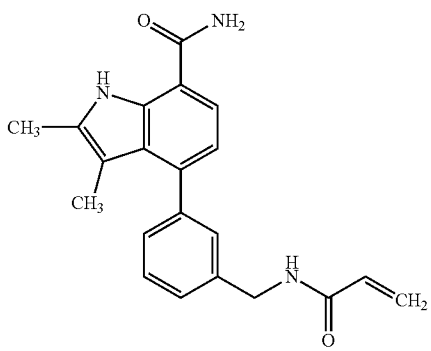 [SMILES: C=CC(=O)NCc1cccc(-c2ccc(C(N)=O)c3[nH]c(C)c(C)c23)c1] | Intermediates 9 and 51 | m/z 348 (M + H)+ |
| 42 | 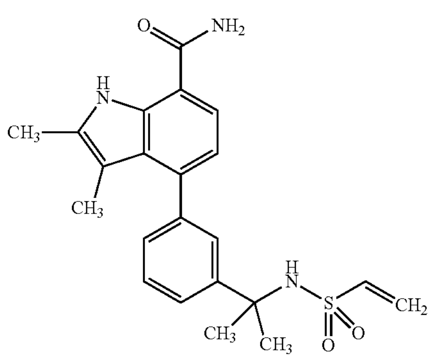 [SMILES: C=CS(=O)(=O)NC(C)(C)c1cccc(-c2ccc(C(N)=O)c3[nH]c(C)c(C)c23)c1] | Intermediates 9 and 57 | m/z 412 (M + H)+ |
| 43 | 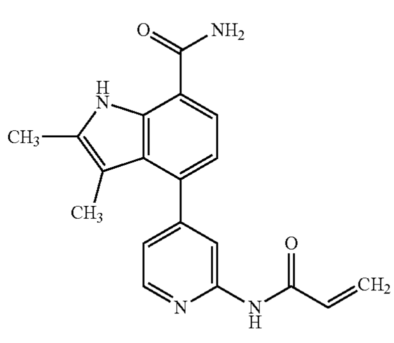 [SMILES: C=CC(=O)Nc1cc(-c2ccc(C(N)=O)c3[nH]c(C)c(C)c23)ccn1] | Intermediates 9 and 53 | m/z 335 (M + H)+ |

TABLE 1-continued

| Example | Structure | Starting Materials | Mass Spectrum |
|---|---|---|---|
| 44 | 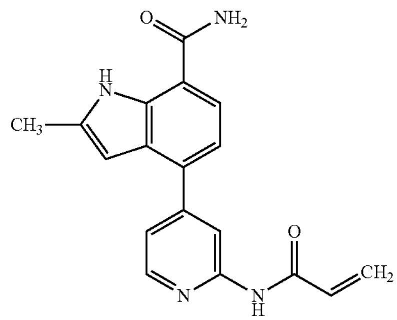 [SMILES: C=CC(=O)Nc1cc(-c2ccc(C(N)=O)c3[nH]c(C)cc23)ccn1] | Intermediates 10 and 53 | m/z 321 (M + H)+ |
| 45 | 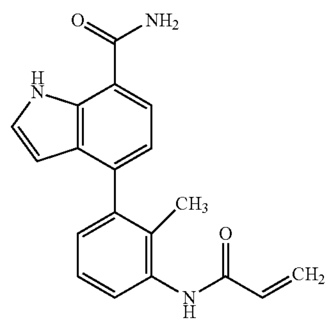 [SMILES: C=CC(=O)Nc1cccc(-c2ccc(C(N)=O)c3[nH]ccc23)c1C] | Intermediates 6 and 66 | m/z 320 (M + H)+ |
| 46 | 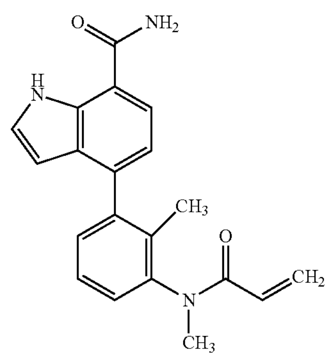 [SMILES: C=CC(=O)N(C)c1cccc(-c2ccc(C(N)=O)c3[nH]ccc23)c1C] | Intermediates 6 and 72 | m/z 334 (M + H)+ |
| 47 | 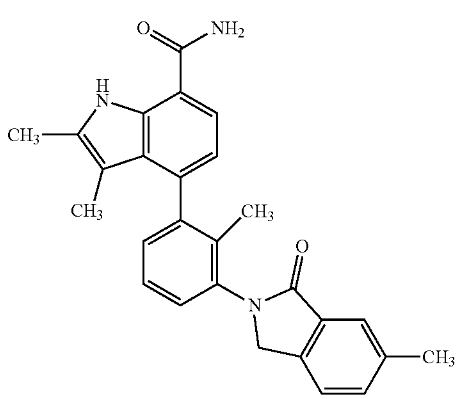 | Intermediates 1 and (a) | m/z 424 (M + H)+ |

TABLE 1-continued

| Example | Structure | Starting Materials | Mass Spectrum |
|---|---|---|---|
| 48 | 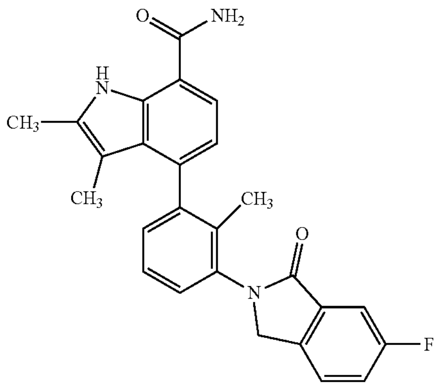 [SMILES: Cc1[nH]c2c(C(N)=O)ccc(-c3cccc(N4Cc5ccc(F)cc5C4=O)c3C)c2c1C] | Intermediates 1 and (b) | m/z 428 (M + H)+ |
| 49 | 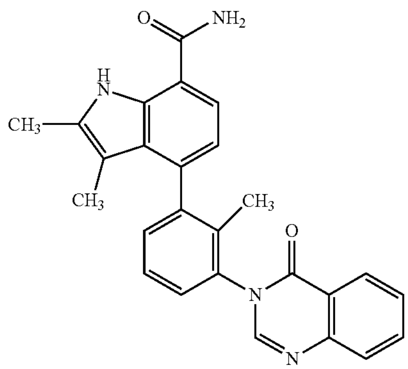 [SMILES: Cc1[nH]c2c(C(N)=O)ccc(-c3cccc(-n4cnc5ccccc5c4=O)c3C)c2c1C] | Intermediates 1 and (c) | m/z 423 (M + H)+ |
| 50 | 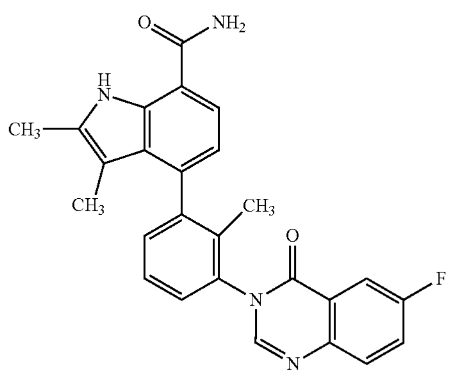 [SMILES: Cc1[nH]c2c(C(N)=O)ccc(-c3cccc(-n4cnc5ccc(F)cc5c4=O)c3C)c2c1C] | Intermediates 1 and (d) | m/z 441 (M + H)+ |
| 51 | 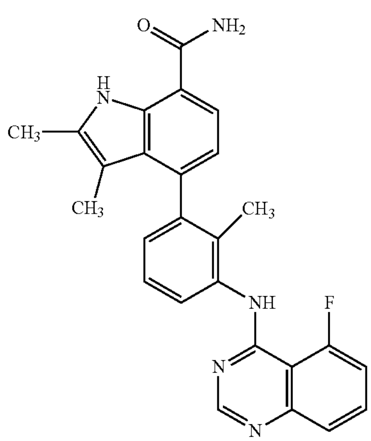 [SMILES: Cc1[nH]c2c(C(N)=O)ccc(-c3cccc(Nc4ncnc5cccc(F)c45)c3C)c2c1C] | Intermediates 1 and (e) | m/z 440 (M + H)+ |

TABLE 1-continued
| Example | Structure | Starting Materials | Mass Spectrum |
|---|---|---|---|
| 52 | 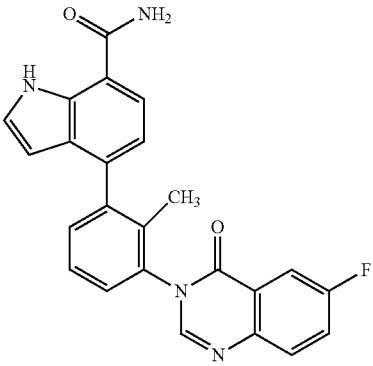 [SMILES: Cc1c(-c2ccc(C(N)=O)c3[nH]ccc23)cccc1-n1cnc2ccc(F)cc2c1=O] | Intermediates 6 and (d) | m/z 413 (M + H)+ |
| 53 | 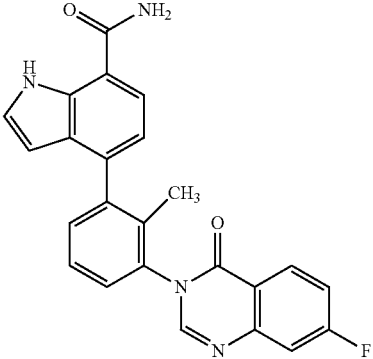 [SMILES: Cc1c(-c2ccc(C(N)=O)c3[nH]ccc23)cccc1-n1cnc2cc(F)ccc2c1=O] | Intermediates 6 and (f) | m/z 413 (M + H)+ |
| 54 | 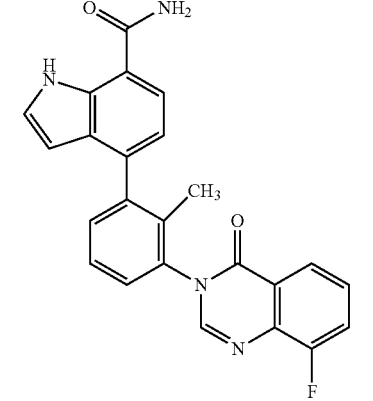 [SMILES: Cc1c(-c2ccc(C(N)=O)c3[nH]ccc23)cccc1-n1cnc2c(F)cccc2c1=O] | Intermediates 6 and (g) | m/z 413 (M + H)+ |
| 55 | 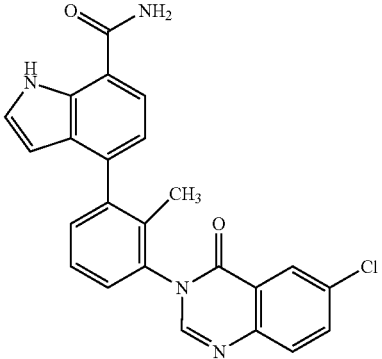 [SMILES: Cc1c(-c2ccc(C(N)=O)c3[nH]ccc23)cccc1-n1cnc2ccc(Cl)cc2c1=O] | Intermediates 6 and (h) | m/z 429, 431 (M + H)+ |

TABLE 1-continued

| Example | Structure | Starting Materials | Mass Spectrum |
|---|---|---|---|
| 56 | 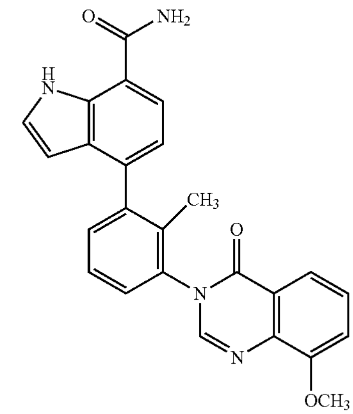 [SMILES: COc1cccc2c(=O)n(-c3cccc(-c4ccc(C(N)=O)c5[nH]ccc45)c3C)cnc12] | Intermediates 6 and (i) | m/z 425 (M + H)+ |
| 57 | 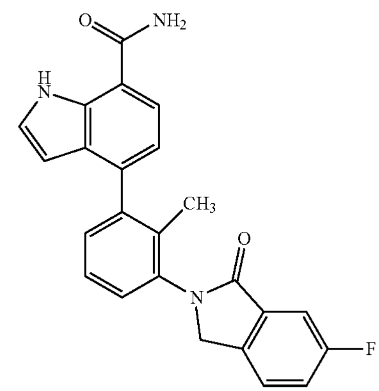 [SMILES: Cc1c(-c2ccc(C(N)=O)c3[nH]ccc23)cccc1N1Cc2ccc(F)cc2C1=O] | Intermediates 6 and (b) | m/z 400 (M + H)+ |
| 58 | 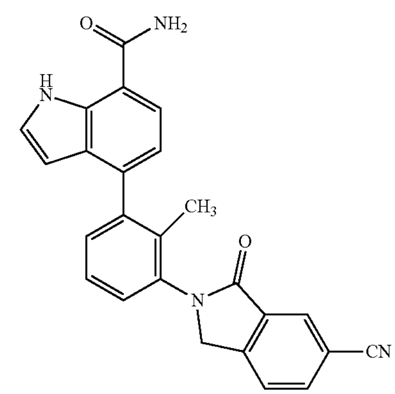 [SMILES: Cc1c(-c2ccc(C(N)=O)c3[nH]ccc23)cccc1N1Cc2ccc(C#N)cc2C1=O] | Intermediates 6 and (j) | m/z 407 (M + H)+ |
| 59 | 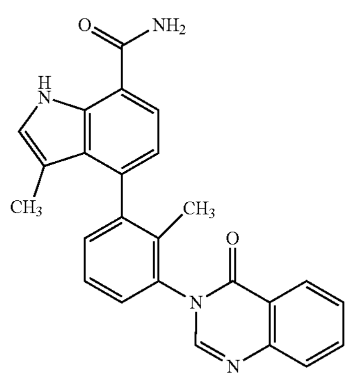 [SMILES: Cc1c(-c2ccc(C(N)=O)c3[nH]cc(C)c23)cccc1-n1cnc2ccccc2c1=O] | Intermediates 4 and (c) | m/z 409 (M + H)+ |

TABLE 1-continued

| Example | Structure | Starting Materials | Mass Spectrum |
|---|---|---|---|
| 60 | 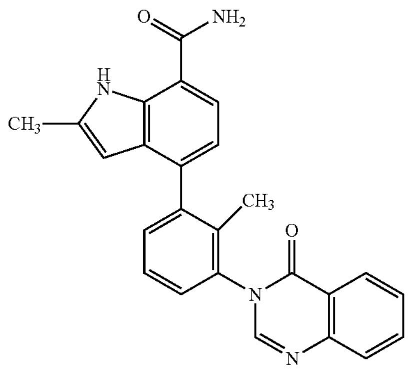 [SMILES: Cc1cc2c(-c3cccc(-n4cnc5ccccc5c4=O)c3C)ccc(C(N)=O)c2[nH]1] | Intermediates 5 and (c) | m/z 409 (M + H)+ |
| 61 | 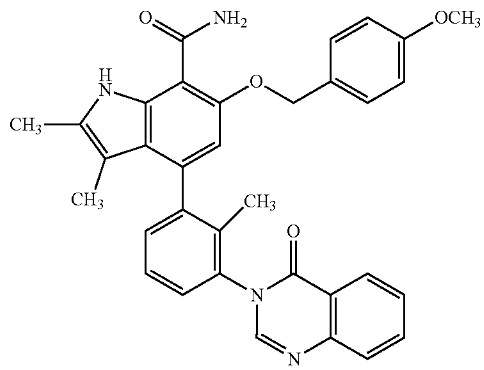 [SMILES: COc1ccc(COc2cc(-c3cccc(-n4cnc5ccccc5c4=O)c3C)c3c(C)c(C)[nH]c3c2C(N)=O)cc1] | Intermediates 8 and (c) | m/z 559 (M + H)+ |
| 62 | 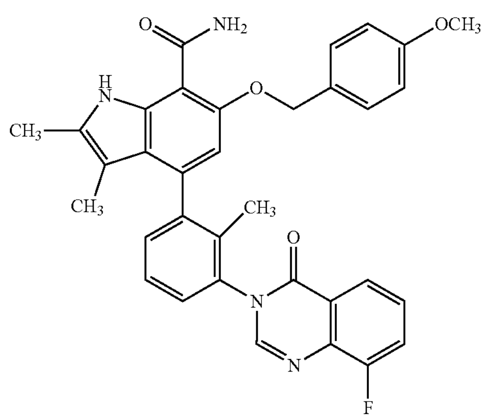 [SMILES: COc1ccc(COc2cc(-c3cccc(-n4cnc5c(F)cccc5c4=O)c3C)c3c(C)c(C)[nH]c3c2C(N)=O)cc1] | Intermediates 8 and (g) | m/z 577 (M + H)+ |
| 63 | 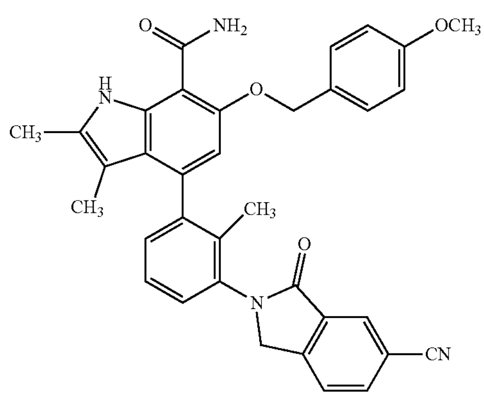 [SMILES: COc1ccc(COc2cc(-c3cccc(N4Cc5ccc(C#N)cc5C4=O)c3C)c3c(C)c(C)[nH]c3c2C(N)=O)cc1] | Intermediates 8 and (j) | m/z 571 (M + H)+ |

TABLE 1-continued

| Example | Structure | Starting Materials | Mass Spectrum |
|---|---|---|---|
| 64 | 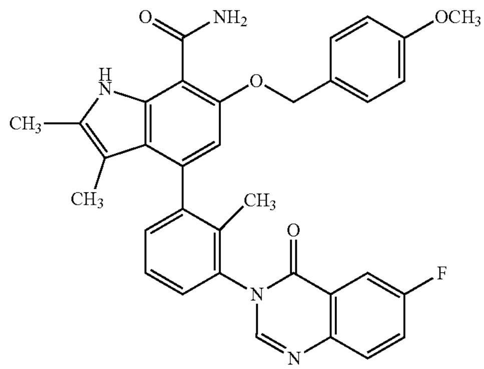 [SMILES: COc1ccc(COc2cc(-c3cccc(-n4cnc5ccc(F)cc5c4=O)c3C)c3c(C)c(C)[nH]c3c2C(N)=O)cc1] | Intermediates 8 and (d) | m/z 577 (M + H)+ |
| 65 | 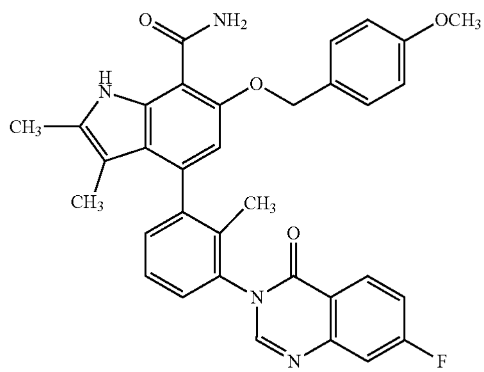 [SMILES: COc1ccc(COc2cc(-c3cccc(-n4cnc5cc(F)ccc5c4=O)c3C)c3c(C)c(C)[nH]c3c2C(N)=O)cc1] | Intermediates 8 and (f) | m/z 577 (M + H)+ |
| 66 | 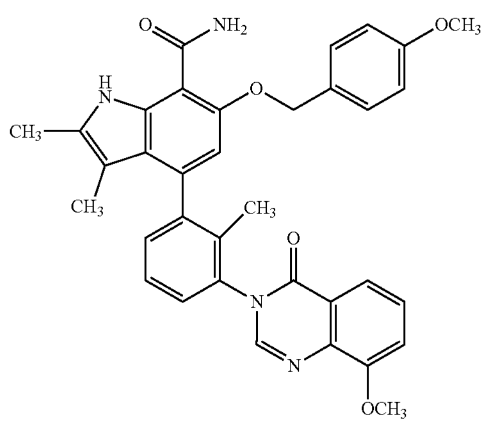 [SMILES: COc1ccc(COc2cc(-c3cccc(-n4cnc5c(OC)cccc5c4=O)c3C)c3c(C)c(C)[nH]c3c2C(N)=O)cc1] | Intermediates 8 and (i) | m/z 589 (M + H)+ |
| 67 | 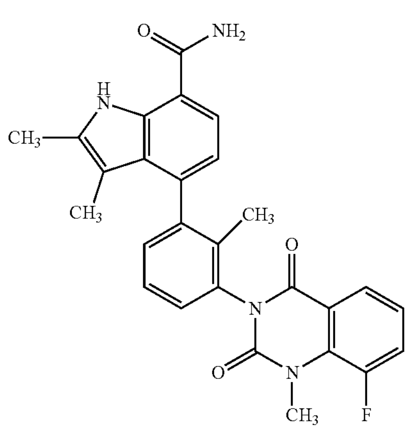 [SMILES: Cc1[nH]c2c(C(N)=O)ccc(-c3cccc(-n4c(=O)c5cccc(F)c5n(C)c4=O)c3C)c2c1C] | Intermediates 1 and 81 | m/z 471 (M + H)+ |

TABLE 1-continued

| Example | Structure | Starting Materials | Mass Spectrum |
|---|---|---|---|
| 68 | (structure shown) | Intermediates 1 and 82 | m/z 453 (M + H)+ |

(a) Intermediate 50-8,
(b) Intermediate 50-5,
(c) Intermediate 50-24,
(d) Intermediate 50-27,
(e) Intermediate 50-55,
(f) Intermediate 50-60,
(g) Intermediate 50-48, Intermediate 50-26,
(i) Intermediate 50-51, and
(j) Intermediate 50-9, each from U.S. Pat. No. 8,084,620.

Example 69

4-(2-Methyl-3-(4-oxoquinazolin-3(4H)-yl)phenyl)-1H-indole-7-carboxamide (69)

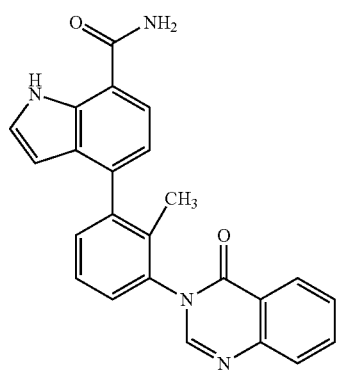

Example 69A: 4-(2-Methyl-3-(4-oxoquinazolin-3(4H)-yl)phenyl)-1-((2-(trimethylsilyl) ethoxy)-methyl)-1H-indole-7-carboxamide (69A)

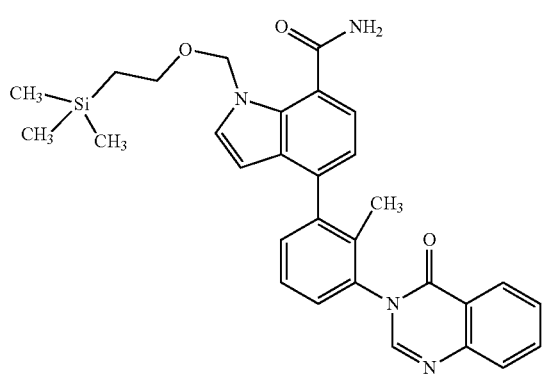

A solution of 4-bromo-1-((2-(trimethylsilyl)ethoxy)methyl)-1H-indole-7-carboxamide [Intermediate 7] (0.50 g, 1.35 mmol), 3-(2-methyl-3-(4,4,5,5-tetramethyl-1,3,2-dioxaborolan-2-yl)phenyl)quinazolin-4(3H)-one [prepared according to the procedures of U.S. Pat. No. 8,084,620, Intermediate 50-24] (0.515 g, 1.42 mmol), tetrakis(triphenylphosphine)palladium (0.078 g, 0.068 mmol), 2.0 M aqueous $Na_2CO_3$ (1.69 mL, 3.38 mmol), in 5:1 toluene-ethanol (16.9 mL) was heated under a nitrogen atmosphere at 90° C. for 16 h. The mixture was cooled to room temperature and partitioned between EtOAc and saturated aqueous $NaHCO_3$. The organic phase was washed with brine, dried and concentrated. The residue was combined with that from another identical reaction, and the material was purified by column chromatography on silica gel (40 g), eluting with EtOAc-hexanes, to provide 4-(2-methyl-3-(4-oxoquinazolin-3 (4H)-yl)phenyl)-1-((2-(trimethylsilyl) ethoxy)-methyl)-1H-indole-7-carboxamide as a glassy solid (1.40 g, 94% yield). Mass spectrum m/z 525 (M+H)+. $^1$H NMR (400 MHz, DMSO-$d_6$) δ 8.50 (1H, br. s.), 8.35 (1H, br. s.), 8.08 (1H, br. s.), 7.98-8.06 (1H, m), 7.90 (1H, d, J=7.9 Hz), 7.74 (1H, t, J=7.5 Hz), 7.52-7.70 (5H, m), 7.50 (1H, d, J=7.3 Hz), 7.17 (1H, d, J=7.5 Hz), 6.19-6.46 (1H, m), 5.83 (2H, d, J=7.3 Hz), 2.10 (1H, s), 1.96 (3H, s), 0.86 (2H, dd, J=9.4, 6.9 Hz), −0.04-0.03 (9H, m).

Example 69

A solution of 4-(2-methyl-3-(4-oxoquinazolin-3(4H)-yl)phenyl)-1-((2-(trimethylsilyl)ethoxy)methyl)-1H-indole-7-carboxamide (40 mg, 0.076 mmol), 1.0 M tetra-n-butylammonium fluoride in THF (229 µL, 0.229 mmol) and 1,2-diaminoethane (31 µL, 0.457 mmol) in DMF (762 µL) was heated at 60° C. After 17 h, more tetra-n-butylammonium fluoride solution (0.25 mL) was added and heating was continued for another day. The mixture was cooled to room temperature and treated with 1.0 M aqueous HCl and the mixture was stirred for 4 days. The mixture was concentrated and the residue was subjected to preparative reverse-phase HPLC to provide 4-(2-methyl-3-(4-oxoquinazolin-3 (4H)-yl)phenyl)-1H-indole-7-carboxamide (1.1 mg, 4% yield). Mass spectrum m/z 395 (M+H)$^+$. $^1$H NMR (500 MHz, MeOH-d$_4$) δ 8.38 (d, J=8.0 Hz, 1H), 8.24 (d, J=19.7 Hz, 1H), 7.95-7.87 (m, 1H), 7.82 (d, J=8.0 Hz, 1H), 7.72 (d, J=7.5 Hz, 1H), 7.68-7.62 (m, 1H), 7.52 (q, J=7.8 Hz, 2H), 7.43-7.36 (m, 2H), 7.09 (d, J=15.0 Hz, 1H), 6.41-6.24 (m, 1H), 1.99 (br. s., 3H).

Example 70

4-(3-(2-Cyano-2-(methylsulfonyl)vinyl)phenyl)-2,3-dimethyl-1H-indole-7-carboxamide

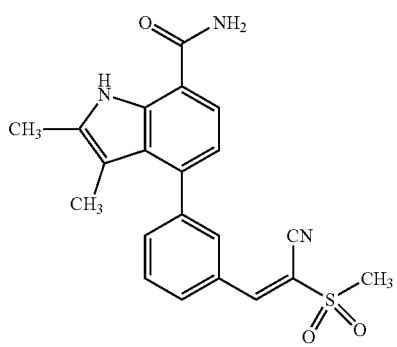

(70)

Example 70A: 4-(3-Formylphenyl)-2,3-dimethyl-1H-indole-7-carboxamide

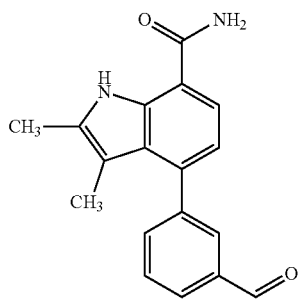

(70A)

A mixture of 4-bromo-2,3-dimethyl-1H-indole-7-carboxamide [Intermediate 1](50 mg, 0.187 mmol), (3-formylphenyl)boronic acid (33.7 mg, 0.225 mmol), 2.0 M aqueous K$_3$PO$_4$ (0.187 mL, 0.374 mmol) and 1,1'-bis(di-tert-butylphosphino)ferrocene palladium dichloride (6.1 mg, 9.36 μmol) in THF (2 mL) in a sealed tube was subjected to 3 evacuate-fill cycles with nitrogen. The mixture was stirred at room temperature for three days, then was concentrated. The residue was subjected to column chromatography on silica gel (12 g), eluting with EtOAc-hexanes (gradient from 0-100%), to provide 4-(3-formylphenyl)-2,3-dimethyl-1H-indole-7-carboxamide as an off-white solid (36 mg, 66% yield). $^1$H NMR (400 MHz, CDCl$_3$) δ 10.17 (br. s., 1H), 10.12 (s, 1H), 7.98-7.93 (m, 2H), 7.75-7.71 (m, 1H), 7.66-7.61 (m, 1H), 7.36 (d, J=7.7 Hz, 1H), 6.96 (d, J=7.7 Hz, 1H), 2.41 (s, 3H), 1.76 (s, 3H).

Example 70

A solution of 4-(3-formylphenyl)-2,3-dimethyl-1H-indole-7-carboxamide (26 mg, 0.089 mmol) and 2-(methylsulfonyl)acetonitrile (42.4 mg, 0.356 mmol) in ethanol (1 mL) was treated with 1,8-diazabicyclo[5.4.0]undec-7-ene (0.054 mL, 0.356 mmol). The mixture was stirred at room temperature for 2 h, then was combined with the reaction mixture from an identical reaction using 4-(3-formylphenyl)-2,3-dimethyl-1H-indole-7-carboxamide (7.7 mg, 0.026 mmol), 2-(methylsulfonyl)acetonitrile (12.6 mg, 0.105 mmol) and 1,8-diazabicyclo[5.4.0]undec-7-ene (0.016 mL, 0.105 mmol). The combined mixtures were diluted with EtOAc, washed once with 1 M aqueous HCl and twice with water, dried and concentrated. The residue was purified by column chromatography on silica gel (12 g), eluting with EtOAc-hexanes (gradient from 10-100%), to provide 4-(3-(2-cyano-2-(methylsulfonyl)vinyl)phenyl)-2,3-dimethyl-1H-indole-7-carboxamide as a yellow solid (24 mg, 91% yield). Mass spectrum m/z 394 (M+H)$^+$. $^1$H NMR (400 MHz, DMSO-d$_6$) δ 10.89 (s, 1H), 8.44 (s, 1H), 8.12-8.08 (m, 2H), 8.04 (br. s., 1H), 7.73-7.70 (m, 2H), 7.64 (d, J=7.7 Hz, 1H), 7.36 (br. s., 1H), 6.86 (d, J=7.7 Hz, 1H), 2.36 (s, 3H), 1.70 (s, 3H).

Example 71

6-Hydroxy-2,3-dimethyl-4-(2-methyl-3-(4-oxoquinazolin-3 (4H)-yl)phenyl)-1H-indole-7-carboxamide

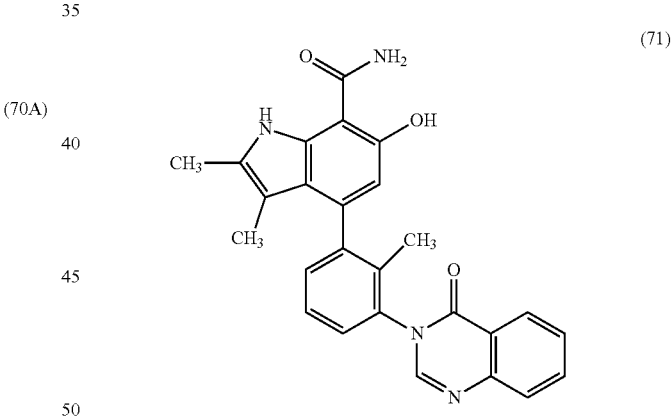

(71)

A solution of 6-(4-methoxybenzyloxy)-2,3-dimethyl-4-(2-methyl-3-(4-oxoquinazolin-3(4H)-yl)phenyl)-1H-indole-7-carboxamide [Example 61] (218 mg, 0.390 mmol) and thioanisole (369 μL, 3.12 mmol) in DCM (4.13 mL) was treated with TFA (2.07 mL) and the mixture was stirred at room temperature for 3.5 h. The mixture was concentrated and partitioned between EtOAc and 1 M aqueous NaOH combined with saturated aqueous NaHCO$_3$ (pH about 9). The organic phase was washed with brine, dried and concentrated. The residue was purified by column chromatography on silica gel (24 g), eluting with EtOAc-hexanes, to provide 6-hydroxy-2,3-dimethyl-4-(2-methyl-3-(4-oxoquinazolin-3(4H)-yl)phenyl)-1H-indole-7-carboxamide as a light yellow glassy solid (124 mg, 73% yield). Mass spectrum m/z 439 (M+H)$^+$.

Example 72

6-Ethoxy-2,3-dimethyl-4-(2-methyl-3-(4-oxoquinazolin-3 (4H)-yl)phenyl)-1H-indole-7-carboxamide

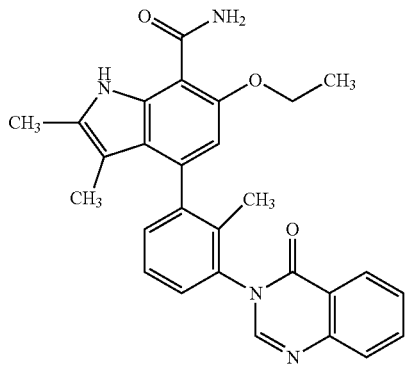

A mixture of 6-hydroxy-2,3-dimethyl-4-(2-methyl-3-(4-oxoquinazolin-3(4H)-yl) phenyl)-1H-indole-7-carboxamide [Example 71] (20 mg, 0.046 mmol), iodoethane (7 μL, 0.091 mmol), K$_2$CO$_3$ (37.8 mg, 0.274 mmol) and acetone (0.91 mL) was heated at 60° C. for 80 min. The mixture was cooled to room temperature and subjected to preparative reverse-phase HPLC to provide 6-ethoxy-2,3-dimethyl-4-(2-methyl-3-(4-oxoquinazolin-3(4H)-yl)phenyl)-1H-indole-7-carboxamide (12.7 mg, 59% yield). Mass spectrum m/z 467 (M+H)$^+$. $^1$H NMR (500 MHz, MeOH-d$_4$) δ 10.45 (2s, 1H), 8.41-8.32 (m, 1H), 8.22-8.12 (2s, 1H), 7.94-7.86 (m, 1H), 7.82 (t, J=7.4 Hz, 1H), 7.69-7.61 (m, 1H), 7.54-7.44 (m, 2H), 7.43-7.35 (m, 1H), 6.72-6.57 (2s, 1H), 4.35-4.23 (m, 2H), 2.33 (s, 3H), 1.89 (2s, 3H), 1.74-1.58 (2 s, 3H), 1.54 (t, J=6.9 Hz, 3H) (Mixture of rotamers).

Additional Examples which were prepared from Example 71 by the procedure described in Example 72 or similar procedures, using the indicated alkylating agent, are shown in Table 2.

TABLE 2

| Example | Structure | Alkylating Agent | Mass Spectrum |
|---|---|---|---|
| 73 | (structure) | iodomethane | m/z 453 (M + H)$^+$ |
| 74 | (structure) | chloromethyl-benzene | m/z 467 (M + H)$^+$ |

TABLE 2-continued

| Example | Structure | Alkylating Agent | Mass Spectrum |
|---|---|---|---|
| 75 | 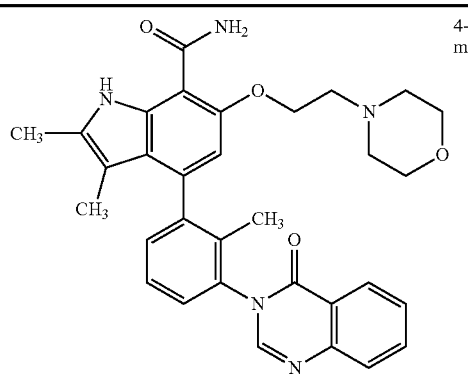 | 4-(2-chloroethyl)-morpholine HCl | m/z 552 (M + H)+ |
| 76 | 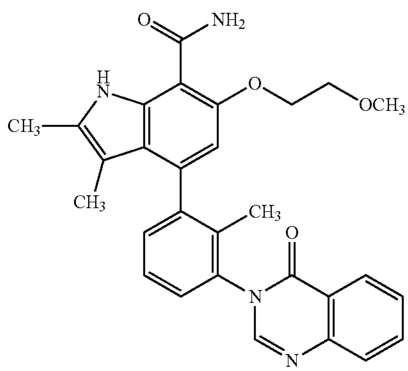 [SMILES: COCCOc1cc(-c2cccc(-n3cnc4ccccc4c3=O)c2C)c2c(C)c(C)[nH]c2c1C(N)=O] | 1-chloro-2-methoxyethane | m/z 497 (M + H)+ |

Example 77

4-(3-((4,6-Dichloro-1,3,5-triazin-2-yl)amino)-2-methylphenyl)-2,3-dimethyl-1H-indole-7-carboxamide

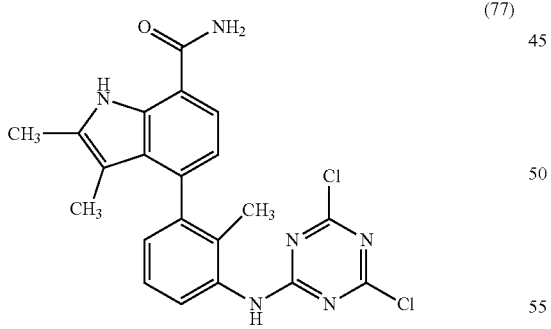

(77)

A suspension of cyanuric chloride (0.026 mL, 0.187 mmol) and $K_2CO_3$ (59.0 mg, 0.426 mmol) in THF (1 mL) was stirred on an ice-water bath and treated dropwise with a solution of 4-(3-amino-2-methylphenyl)-2,3-dimethyl-1H-indole-7-carboxamide [Intermediate 41] (50.0 mg, 0.170 mmol) in THF (1 mL). The mixture was stirred at room temperature for 2.25 h, then was filtered and concentrated. The residue was purified by column chromatography on silica gel (12 g), eluting with EtOAc-hexanes (gradient from 10-80%), to provide 4-(3-((4,6-dichloro-1,3,5-triazin-2-yl) amino)-2-methylphenyl)-2,3-dimethyl-1H-indole-7-carboxamide as an off-white solid (56.8 mg, 74% yield). Mass spectrum m/z 441, 443, 445 (M+H)+. $^1$H NMR (400 MHz, DMSO-$d_6$) δ 10.80 (s, 1H), 10.75 (s, 1H), 8.00 (br. s., 1H), 7.61 (d, J=7.7 Hz, 1H), 7.39-7.25 (m, 3H), 7.16 (dd, J=7.2, 1.7 Hz, 1H), 6.72 (d, J=7.5 Hz, 1H), 2.31 (s, 3H), 1.82 (s, 3H), 1.55 (s, 3H).

Example 78

(RS)-2,3-Dimethyl-4-(3-(N-methylacrylamido)piperidin-1-yl)-1H-indole-7-carboxamide

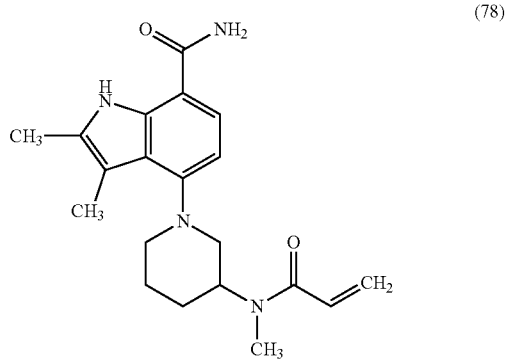 [SMILES: C=CC(=O)N(C)C1CCCN(c2ccc(C(N)=O)c3[nH]c(C)c(C)c23)C1]

(78)

A solution of (RS)-2,3-dimethyl-4-(3-(methylamino)piperidin-1-yl)-1H-indole-7-carboxamide [Intermediate 35]

(60.0 mg, 0.114 mmol) in 1:1 DCM-THF (2.08 mL) was cooled to 0° C. and treated with DIEA (33.8 μL, 0.194 mmol). Acryloyl chloride (13.0 μL, 0.159 mmol) was added slowly and the mixture was stirred at 0° C. After 1 h, the mixture was concentrated and the residue was subjected to column chromatography on silica gel (4 g), eluting with EtOAc-hexanes (gradient from 50-70%), to provide (RS)-2,3-dimethyl-4-(3-(N-methylacrylamido)piperidin-1-yl)-1H-indole-7-carboxamide as a solid (23 mg, 53% yield).

Mass spectrum m/z 355 (M+H)$^+$. $^1$H NMR (400 MHz, CDCl$_3$) δ 10.17-9.93 (m, 1H), 7.24 (br. s., 1H), 6.76-6.52 (m, 2H), 6.34 (d, J=16.7 Hz, 1H), 6.08-5.57 (m, 3H), 5.07-4.14 (m, 1H), 3.43 (br. s., 2H), 3.00 (d, J=6.8 Hz, 3H), 2.80-2.56 (m, 1H), 2.54-2.43 (m, 3H), 2.38 (s, 3H), 1.95 (br. s., 3H), 1.83-1.60 (m, 2H).

Additional Examples which were prepared by procedure described in Example 78 or similar procedures, using the indicated starting material, are shown in Table 3.

TABLE 3

| Example | Structure | Starting Material | Mass Spectrum |
|---|---|---|---|
| 79 | 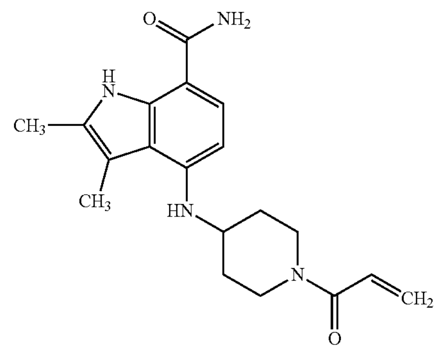 [SMILES: C=CC(=O)N1CCC(Nc2ccc(C(N)=O)c3[nH]c(C)c(C)c23)CC1] | Intermediate 17 | m/z 341 (M + H)$^+$ |
| 80 | 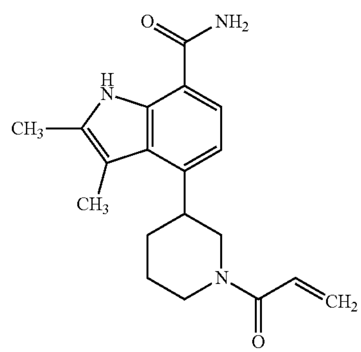 [SMILES: C=CC(=O)N1CCCC(c2ccc(C(N)=O)c3[nH]c(C)c(C)c23)C1] | Intermediate 38 | m/z 326 (M + H)$^+$ |
| 81 | 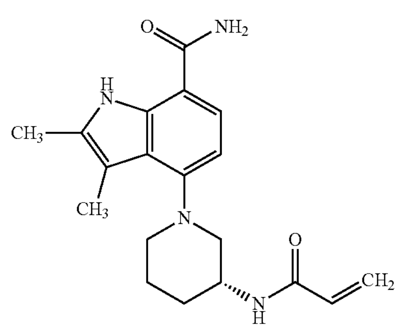 [SMILES: C=CC(=O)N[C@@H]1CCCN(c2ccc(C(N)=O)c3[nH]c(C)c(C)c23)C1] | Intermediate 14 | m/z 341 (M + H)$^+$ |

TABLE 3-continued

| Example | Structure | Starting Material | Mass Spectrum |
|---|---|---|---|
| 82 | 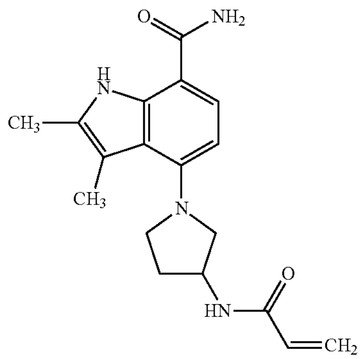 [SMILES: C=CC(=O)NC1CCN(c2ccc(C(N)=O)c3[nH]c(C)c(C)c23)C1] | Intermediate 22 | m/z 327 (M + H)+ |
| 83 | 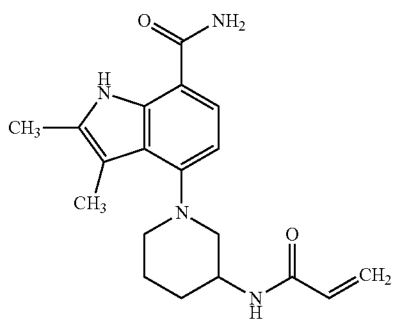 [SMILES: C=CC(=O)NC1CCCN(c2ccc(C(N)=O)c3[nH]c(C)c(C)c23)C1] | Intermediate 15 | m/z 341 (M + H)+ |
| 84 | 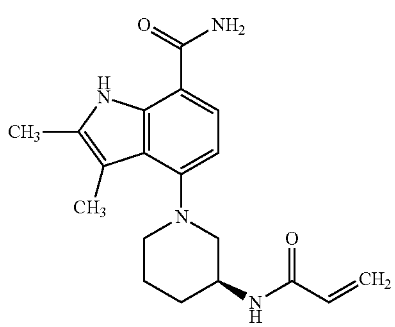 [SMILES: C=CC(=O)N[C@H]1CCCN(c2ccc(C(N)=O)c3[nH]c(C)c(C)c23)C1] | Intermediate 13 | m/z 341 (M + H)+ |
| 85 | 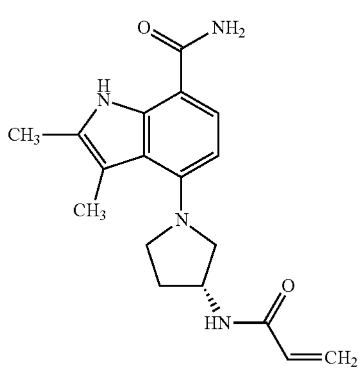 [SMILES: C=CC(=O)N[C@@H]1CCN(c2ccc(C(N)=O)c3[nH]c(C)c(C)c23)C1] | Intermediate 23 | m/z 327 (M + H)+ |

TABLE 3-continued

| Example | Structure | Starting Material | Mass Spectrum |
|---|---|---|---|
| 86 | 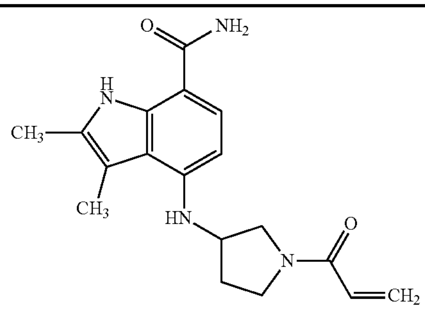 | Intermediate 19 | m/z 327 (M + H)+ |
| 87 | 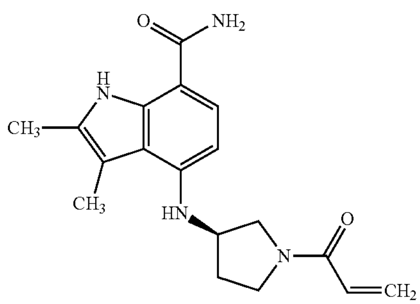 [SMILES: C=CC(=O)N1CC[C@@H](Nc2ccc(C(N)=O)c3[nH]c(C)c(C)c23)C1] | Intermediate 27 | m/z 327 (M + H)+ |
| 88 | 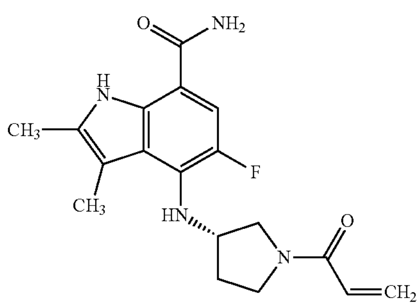 [SMILES: C=CC(=O)N1CC[C@H](Nc2c(F)cc(C(N)=O)c3[nH]c(C)c(C)c23)C1] | Intermediate 21 | m/z 345 (M + H)+ |
| 89 | 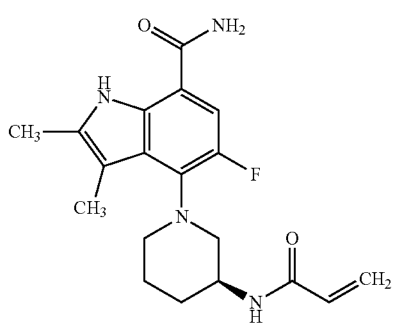 [SMILES: C=CC(=O)N[C@H]1CCCN(c2c(F)cc(C(N)=O)c3[nH]c(C)c(C)c23)C1] | Intermediate 16 | m/z 359 (M + H)+ |
| 90 | 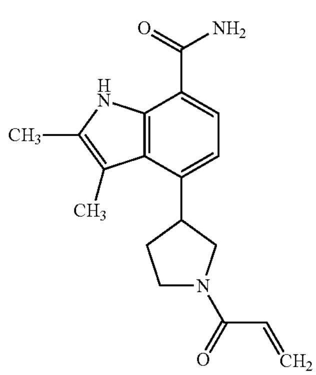 [SMILES: C=CC(=O)N1CCC(c2ccc(C(N)=O)c3[nH]c(C)c(C)c23)C1] | Intermediate 40 | m/z 312 (M + H)+ |

TABLE 3-continued

| Example | Structure | Starting Material | Mass Spectrum |
|---|---|---|---|
| 91 | (2,3-dimethyl-4-((1-acryloylpiperidin-3-yl)amino)-1H-indole-7-carboxamide) | Intermediate 25 | m/z 341 (M + H)+ |
| 92 | (2,3-dimethyl-4-((1-acryloylpiperidin-4-yl)amino)-5-fluoro-1H-indole-7-carboxamide) | Intermediate 18 | m/z 359 (M + H)+ |
| 93 | (2,3-dimethyl-4-((1-acryloylpiperidin-4-yl)amino)-1H-indole-7-carboxamide) | Intermediate 39 | m/z 312 (M + H)+ |
| 94 | (2,3-dimethyl-4-(((S)-1-acryloylpyrrolidin-3-yl)(methyl)amino)-1H-indole-7-carboxamide) | Intermediate 28 | m/z 341 (M + H)+ |

TABLE 3-continued

| Example | Structure | Starting Material | Mass Spectrum |
|---------|-----------|-------------------|---------------|
| 95 | 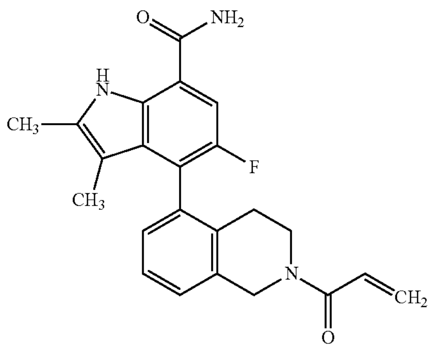 [SMILES: C=CC(=O)N1CCc2c(cccc2-c2c(F)cc(C(N)=O)c3[nH]c(C)c(C)c23)C1] | Intermediate 42 | m/z 392 (M + H)+ |
| 96 | 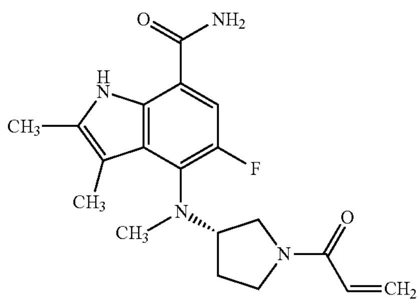 [SMILES: C=CC(=O)N1CC[C@H](N(C)c2c(F)cc(C(N)=O)c3[nH]c(C)c(C)c23)C1] | Intermediate 37 | m/z 359 (M + H)+ |
| 97 | 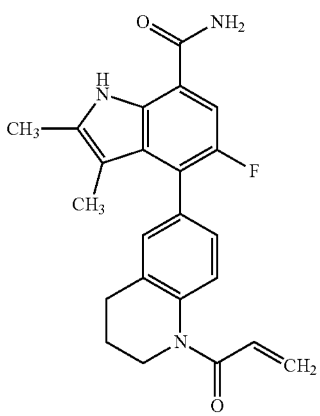 [SMILES: C=CC(=O)N1CCCc2cc(-c3c(F)cc(C(N)=O)c4[nH]c(C)c(C)c34)ccc21] | Intermediate 43 | m/z 392 (M + H)+ |
| 98 | 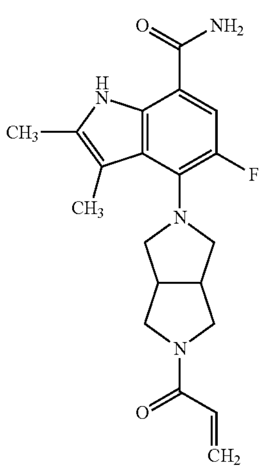 [SMILES: C=CC(=O)N1CC2CN(c3c(F)cc(C(N)=O)c4[nH]c(C)c(C)c34)CC2C1] | Intermediate 32 | m/z 371 (M + H)+ |

TABLE 3-continued

| Example | Structure | Starting Material | Mass Spectrum |
|---|---|---|---|
| 99 | 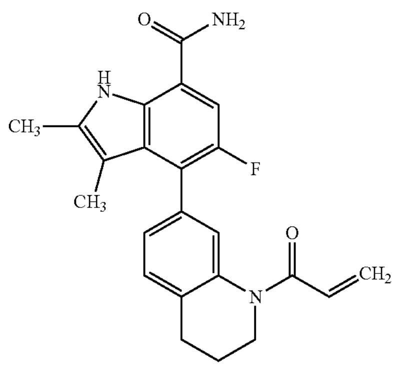 [SMILES: C=CC(=O)N1CCCc2ccc(-c3c(F)cc(C(N)=O)c4[nH]c(C)c(C)c34)cc21] | Intermediate 46 | m/z 392 (M + H)+ |
| 100 | 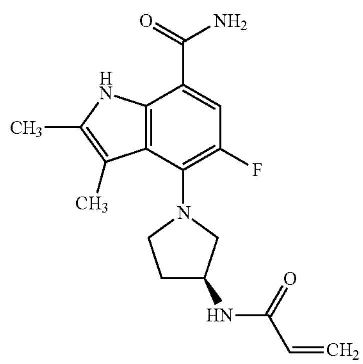 [SMILES: C=CC(=O)N[C@H]1CCN(c2c(F)cc(C(N)=O)c3[nH]c(C)c(C)c23)C1] | Intermediate 24 | m/z 345 (M + H)+ |
| 101 | 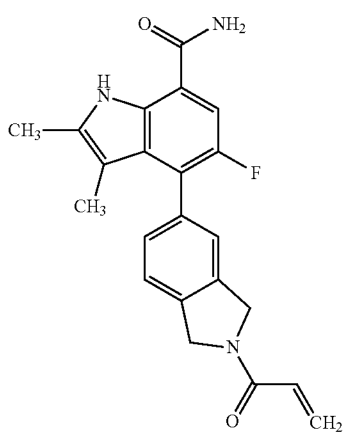 [SMILES: C=CC(=O)N1Cc2ccc(-c3c(F)cc(C(N)=O)c4[nH]c(C)c(C)c34)cc2C1] | Intermediate 47 | m/z 378 (M + H)+ |
| 102 | 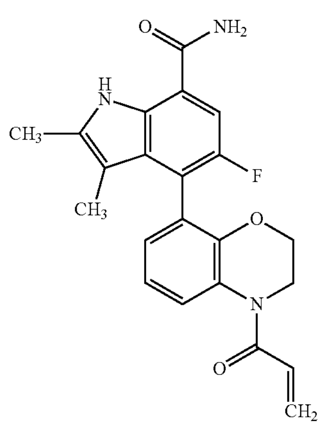 [SMILES: C=CC(=O)N1CCOc2c(-c3c(F)cc(C(N)=O)c4[nH]c(C)c(C)c34)cccc21] | Intermediate 49 | m/z 394 (M + H)+ |

Example 103

(RS)-2,3-Dimethyl-4-((1-propioloylpyrrolidin-3-yl)amino)-1H-indole-7-carboxamide

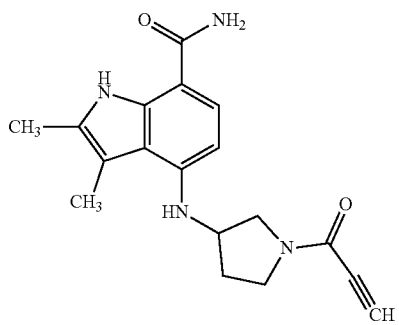
(103)

A solution of (RS)-2,3-dimethyl-4-(pyrrolidin-3-ylamino)-1H-indole-7-carboxamide [Intermediate 19] (35 mg, 0.096 mmol), HATU (73 mg, 0.19 mmol), DIEA (51 μL, 0.29 mmol) and propiolic acid (7.4 mg, 0.11 mmol) in DMF (1.4 mL) was stirred at room temperature. After 4 h, the mixture was filtered and purified by preparative reverse-phase HPLC to provide (RS)-2,3-dimethyl-4-((1-propioloylpyrrolidin-3-yl)amino)-1H-indole-7-carboxamide (7.1 mg, 23% yield). Mass spectrum m/z 325 (M+H)+. 1H NMR (500 MHz, DMSO-$d_6$) δ 10.44 (s, 1H), 7.64 (br. s., 1H), 7.44 (d, J=8.5 Hz, 1H), 6.88 (br. s., 1H), 6.15 (dd, J=18.9, 7.9 Hz, 1H), 5.20 (br. s., 1H), 4.52-4.40 (m, 1H), 4.29-4.17 (m, 1H), 4.11 (br. s., 1H), 3.83-3.51 (m, 3H), 2.38-2.19 (m, 7H), 2.12-1.98 (m, 1H).

Example 104

(RS)-4-(1-(But-2-ynoyl)piperidin-3-yl)-3-methyl-1H-indole-7-carboxamide

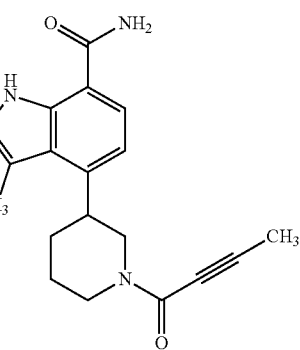
(104)

A solution of (RS)-3-methyl-4-(piperidin-3-yl)-1H-indole-7-carboxamide [Intermediate 39] (10.0 mg, 0.039 mmol), BOP (20.6 mg, 0.047 mmol), DIEA (68 μL, 0.39 mmol) and but-2-ynoic acid (6.5 mg, 0.078 mmol) in THF (2 mL) was stirred at room temperature. After 2 h, the mixture was filtered and purified by preparative reverse-phase HPLC to provide (RS)-4-(1-(but-2-ynoyl)piperidin-3-yl)-3-methyl-1H-indole-7-carboxamide (2.8 mg, 21% yield). Mass spectrum m/z 324 (M+H)+. 1H NMR (500 MHz, DMSO-$d_6$) δ 10.84 (d, J=15.3 Hz, 1H), 7.99 (br. s., 1H), 7.63 (t, J=8.5 Hz, 1H), 7.28 (br. s., 1H), 7.12 (d, J=12.8 Hz, 1H), 6.96 (dd, J=19.8, 7.6 Hz, 1H), 4.50-4.39 (m, 2H), 4.36 (t, J=11.3 Hz, 2H), 3.37 (br. s., 1H), 3.32-3.25 (m, 1H), 3.24-3.15 (m, 1H), 2.81-2.70 (m, 2H), 2.05 (s, 3H), 1.92 (s, 3H).

Additional Examples which were prepared by procedures described in Examples 103 and 104 or similar procedures, using the indicated starting material and the appropriate carboxylic acid, are shown in Table 4.

TABLE 4

| Example | Structure | Starting Material | Mass Spectrum |
|---|---|---|---|
| 105 | 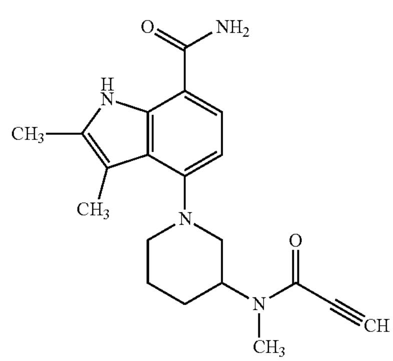 [SMILES: C#CC(=O)N(C)C1CCCN(c2ccc(C(N)=O)c3[nH]c(C)c(C)c23)C1] | Intermediate 35 | m/z 353 (M + H)+ |

TABLE 4-continued

| Example | Structure | Starting Material | Mass Spectrum |
|---|---|---|---|
| 106 | 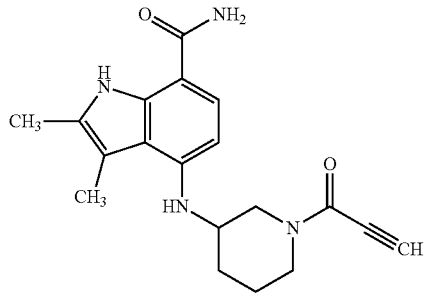 [SMILES: C#CC(=O)N1CCCC(Nc2ccc(C(N)=O)c3[nH]c(C)c(C)c23)C1] | Intermediate 25 | m/z 339 (M + H)+ |
| 107 | 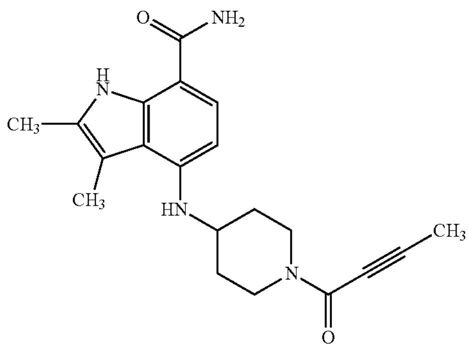 [SMILES: CC#CC(=O)N1CCC(Nc2ccc(C(N)=O)c3[nH]c(C)c(C)c23)CC1] | Intermediate 17 | m/z 353 (M + H)+ |
| 108 | 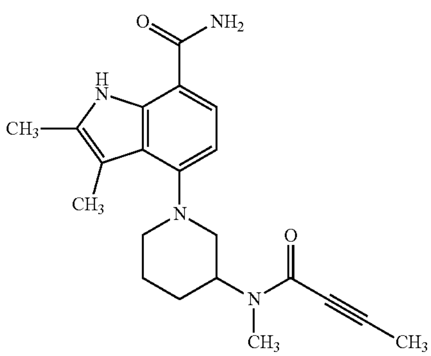 [SMILES: CC#CC(=O)N(C)C1CCCN(c2ccc(C(N)=O)c3[nH]c(C)c(C)c23)C1] | Intermediate 35 | m/z 367 (M + H)+ |
| 109 | 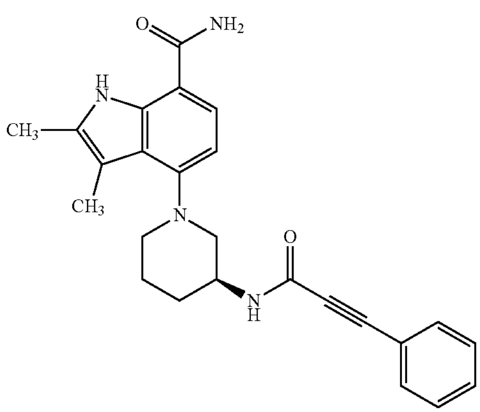 [SMILES: Cc1[nH]c2c(C(N)=O)ccc(N3CCC[C@H](NC(=O)C#Cc4ccccc4)C3)c2c1C] | Intermediate 13 | m/z 414 (M + H)+ |

TABLE 4-continued

| Example | Structure | Starting Material | Mass Spectrum |
|---------|-----------|-------------------|---------------|
| 110 | 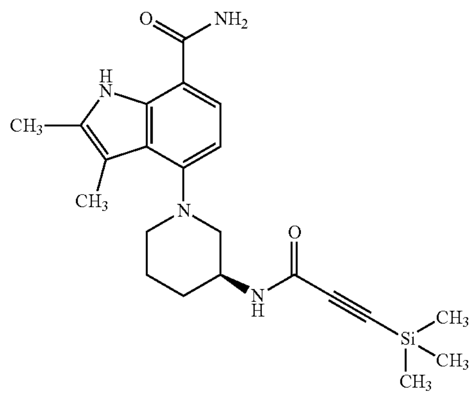 | Intermediate 13 | m/z 411 (M + H)+ |
| 111 | 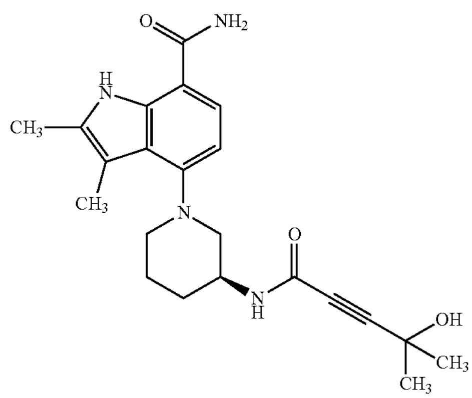 [SMILES: Cc1[nH]c2c(C(N)=O)ccc(N3CCC[C@H](NC(=O)C#CC(C)(C)O)C3)c2c1C] | Intermediate 13 | m/z 397 (M + H)+ |
| 112 | 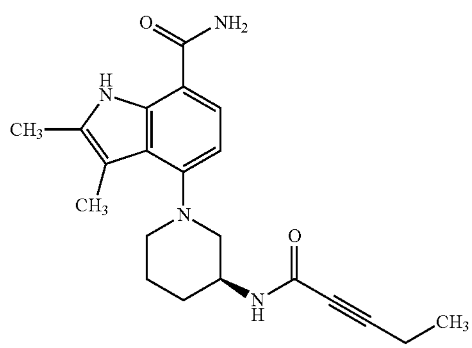 [SMILES: CCC#CC(=O)N[C@H]1CCCN(c2ccc(C(N)=O)c3[nH]c(C)c(C)c23)C1] | Intermediate 13 | m/z 367 (M + H)+ |
| 113 | 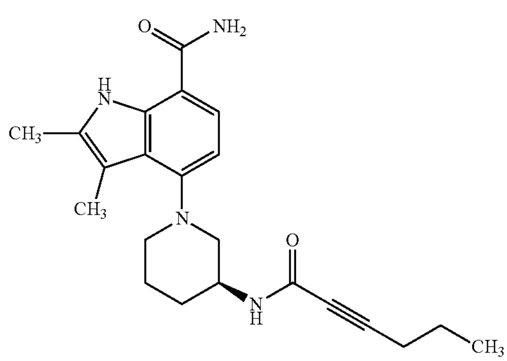 [SMILES: CCCC#CC(=O)N[C@H]1CCCN(c2ccc(C(N)=O)c3[nH]c(C)c(C)c23)C1] | Intermediate 13 | m/z 381 (M + H)+ |

TABLE 4-continued

| Example | Structure | Starting Material | Mass Spectrum |
|---|---|---|---|
| 114 | (2,3-dimethyl-1H-indole-7-carboxamide with 4-aminopiperidine N-propioloyl) | Intermediate 17 | m/z 339 (M + H)+ |
| 115 | (2,3-dimethyl-1H-indole-7-carboxamide with 3-propiolamido piperidine) | Intermediate 13 | m/z 339 (M + H)+ |
| 116 | (2,3-dimethyl-1H-indole-7-carboxamide with 3-(but-2-ynamido)piperidine) | Intermediate 13 | m/z 353 (M + H)+ |
| 117 | (2,3-dimethyl-1H-indole-7-carboxamide with 3-propiolamido piperidine) | Intermediate 14 | m/z 339 (M + H)+ |

TABLE 4-continued

| Example | Structure | Starting Material | Mass Spectrum |
|---|---|---|---|
| 118 | 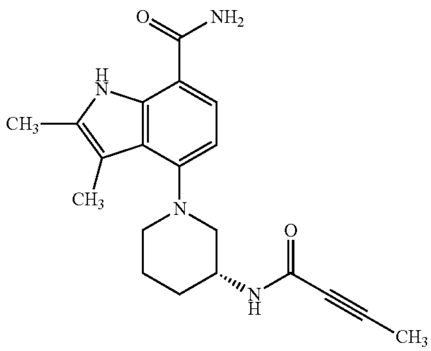 [SMILES: CC#CC(=O)N[C@@H]1CCCN(c2ccc(C(N)=O)c3[nH]c(C)c(C)c23)C1] | Intermediate 14 | m/z 353 (M + H)+ |
| 119 | 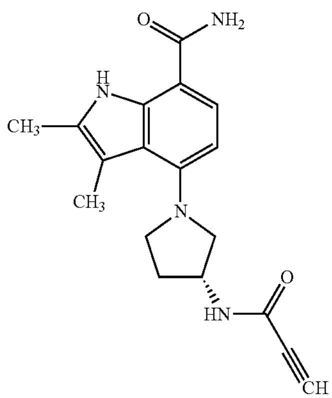 [SMILES: C#CC(=O)N[C@@H]1CCN(c2ccc(C(N)=O)c3[nH]c(C)c(C)c23)C1] | Intermediate 23 | m/z 325 (M + H)+ |
| 120 | 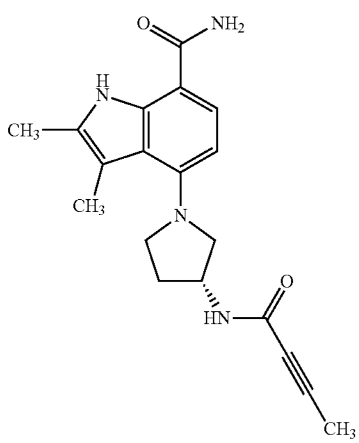 [SMILES: CC#CC(=O)N[C@@H]1CCN(c2ccc(C(N)=O)c3[nH]c(C)c(C)c23)C1] | Intermediate 23 | m/z 339 (M + H)+ |
| 121 | 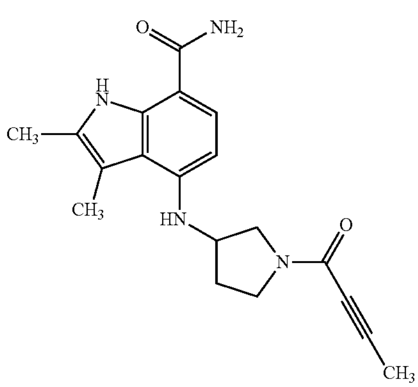 [SMILES: CC#CC(=O)N1CCC(Nc2ccc(C(N)=O)c3[nH]c(C)c(C)c23)C1] | Intermediate 19 | m/z 339 (M + H)+ |

TABLE 4-continued

| Example | Structure | Starting Material | Mass Spectrum |
|---------|-----------|-------------------|---------------|
| 122 | 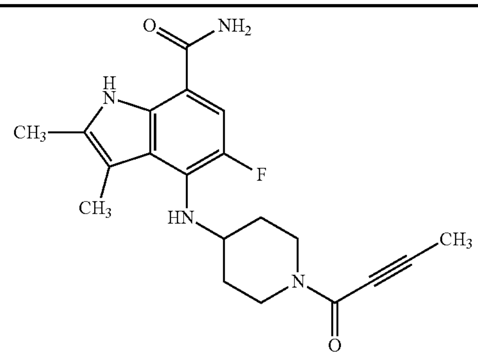 | Intermediate 18 | m/z 371 (M + H)+ |
| 124 | 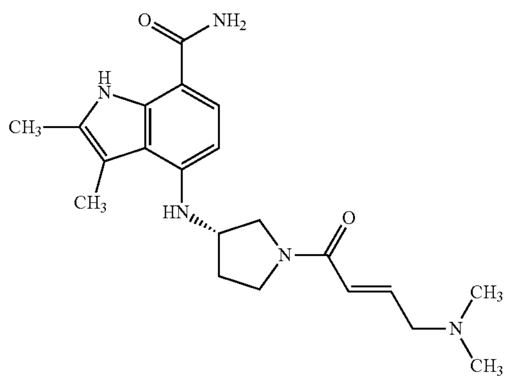 | Intermediate 26 | m/z 384 (M + H)+ |
| 125 | 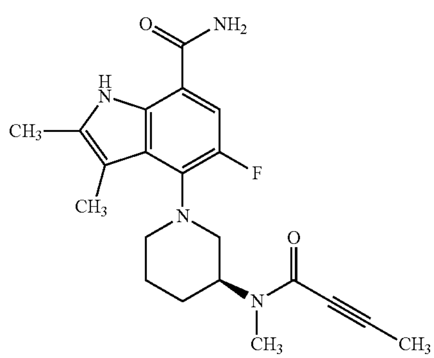 [SMILES: CC#CC(=O)N(C)[C@H]1CCCN(c2c(F)cc(C(N)=O)c3[nH]c(C)c(C)c23)C1] | Intermediate 36 | m/z 385 (M + H)+ |
| 126 | 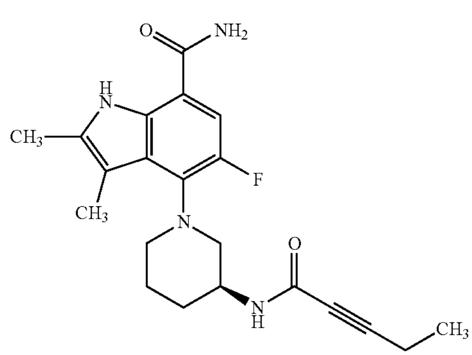 [SMILES: CCC#CC(=O)N[C@H]1CCCN(c2c(F)cc(C(N)=O)c3[nH]c(C)c(C)c23)C1] | Intermediate 16 | m/z 385 (M + H)+ |

TABLE 4-continued
| Example | Structure | Starting Material | Mass Spectrum |
|---|---|---|---|
| 127 | 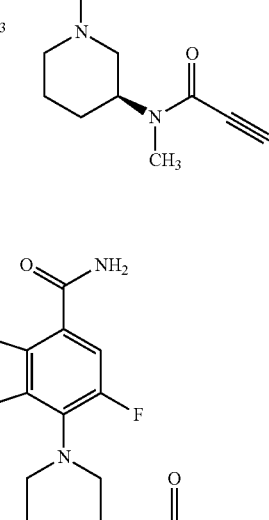 | Intermediate 36 | m/z 399 (M + H)+ |
| 128 | 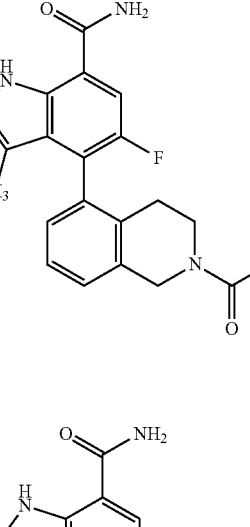 | Intermediate 16 | m/z 399 (M + H)+ |
| 129 | 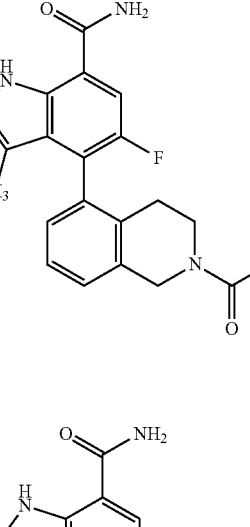 | Intermediate 42 | m/z 404 (M + H)+ |
| 130 | 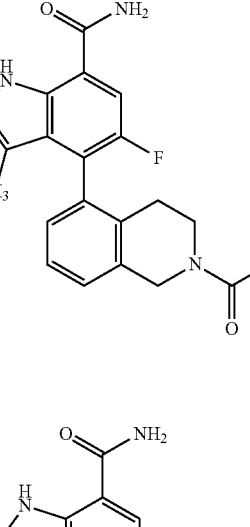 | Intermediate 33 | m/z 399 (M + H)+ |

TABLE 4-continued

| Example | Structure | Starting Material | Mass Spectrum |
|---|---|---|---|
| 131 | 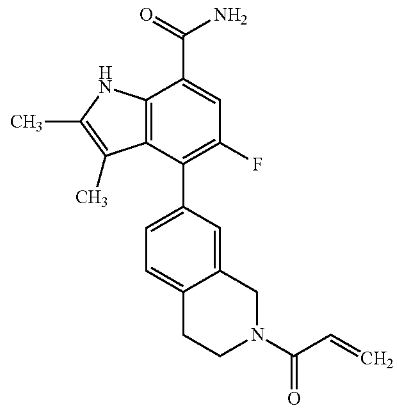 [SMILES: C=CC(=O)N1CCc2ccc(-c3c(F)cc(C(N)=O)c4[nH]c(C)c(C)c34)cc2C1] | Intermediate 44 | m/z 392 (M + H)+ |
| 132 | 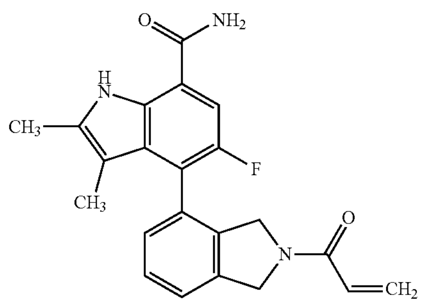 [SMILES: C=CC(=O)N1Cc2cccc(-c3c(F)cc(C(N)=O)c4[nH]c(C)c(C)c34)c2C1] | Intermediate 45 | m/z 378 (M + H)+ |
| 133 | 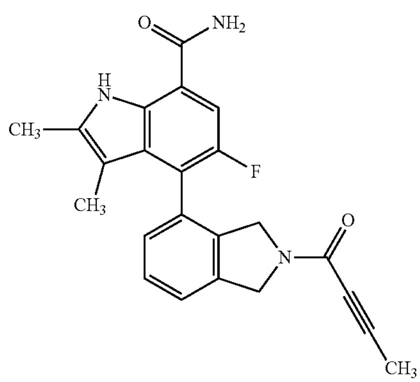 [SMILES: CC#CC(=O)N1Cc2cccc(-c3c(F)cc(C(N)=O)c4[nH]c(C)c(C)c34)c2C1] | Intermediate 45 | m/z 390 (M + H)+ |
| 134 | 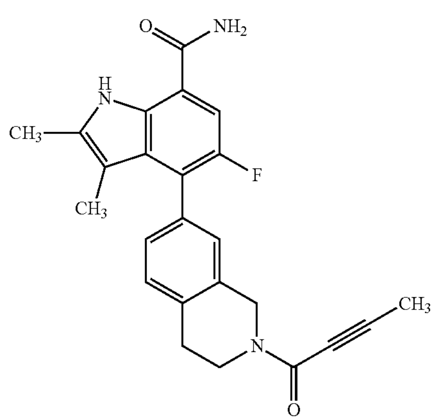 [SMILES: CC#CC(=O)N1CCc2ccc(-c3c(F)cc(C(N)=O)c4[nH]c(C)c(C)c34)cc2C1] | Intermediate 44 | m/z 404 (M + H)+ |

TABLE 4-continued

| Example | Structure | Starting Material | Mass Spectrum |
|---|---|---|---|
| 135 | 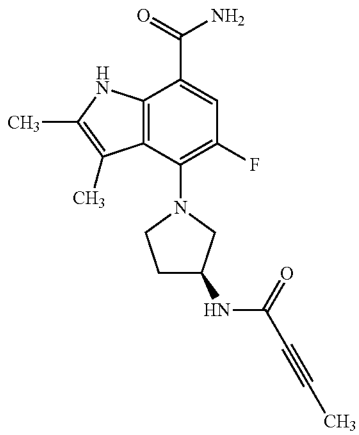 [SMILES: CC#CC(=O)N[C@H]1CCN(c2c(F)cc(C(N)=O)c3[nH]c(C)c(C)c23)C1] | Intermediate 24 | m/z 357 (M + H)+ |
| 136 | 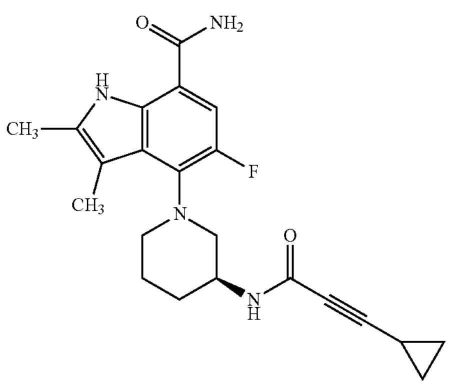 [SMILES: Cc1[nH]c2c(C(N)=O)cc(F)c(N3CCC[C@H](NC(=O)C#CC4CC4)C3)c2c1C] | Intermediate 16 | m/z 397 (M + H)+ |
| 137 | 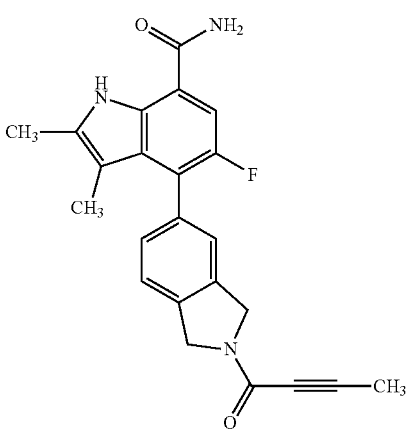 [SMILES: CC#CC(=O)N1Cc2ccc(-c3c(F)cc(C(N)=O)c4[nH]c(C)c(C)c34)cc2C1] | Intermediate 47 | m/z 390 (M + H)+ |

Example 138

(RS)-2,3-Dimethyl-4-(3-(N-methylvinylsulfonamido)piperidin-1-yl)-1H-indole-7-carboxamide

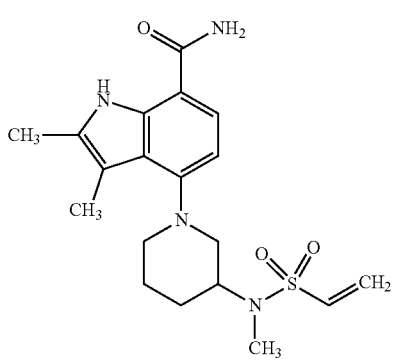

(138)

A solution of (RS)-2,3-dimethyl-4-(3-(methylamino)piperidin-1-yl)-1H-indole-7-carboxamide [Intermediate 35] (60 mg, 0.11 mmol) in 1:1 DCM-THF (2.08 mL) was cooled to −20° C. and treated with DIEA (40 µL, 0.23 mmol). A solution of 2-chloroethanesulfonyl chloride (21 µL, 0.21 mmol) in DCM (296 µL) was added slowly and the mixture was stirred at 0° C. After 1 h the mixture was concentrated. The residue was subjected to column chromatography on silica gel (4 g), eluting with EtOAc-hexanes (gradient from 25-50%), to provide (RS)-2,3-dimethyl-4-(3-(N-methylvinylsulfonamido) piperidin-1-yl)-1H-indole-7-carboxamide as a solid (20 mg, 44% yield). Mass spectrum m/z 391 (M+H)$^+$. $^1$H NMR (400 MHz, DMSO-d$_6$) δ 10.61 (s, 1H), 7.81 (br. s., 1H), 7.48 (d, J=8.1 Hz, 1H), 7.12 (br. s., 1H), 6.84 (dd, J=16.4, 10.0 Hz, 1H), 6.59 (d, J=7.9 Hz, 1H), 6.14-5.99 (m, 2H), 4.00-3.84 (m, 1H), 3.21 (d, J=10.8 Hz, 2H), 2.74 (s, 4H), 2.55 (br. s., 1H), 2.33 (d, J=12.3 Hz, 6H), 1.88-1.58 (m, 4H).

Additional Examples which were prepared by procedure described in Example 138 or similar procedures, using the indicated starting materials, are shown in Table 5.

TABLE 5

| Example | Structure | Starting Material | Mass Spectrum |
|---|---|---|---|
| 139 | 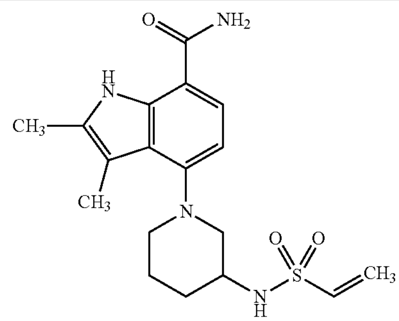 [SMILES: C=CS(=O)(=O)NC1CCCN(c2ccc(C(N)=O)c3[nH]c(C)c(C)c23)C1] | Intermediate 15 | m/z 377 (M + H)$^+$ |
| 140 | 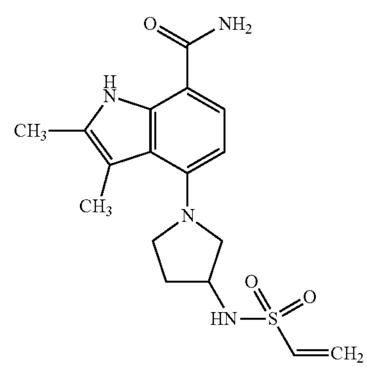 [SMILES: C=CS(=O)(=O)NC1CCN(c2ccc(C(N)=O)c3[nH]c(C)c(C)c23)C1] | Intermediate 22 | m/z 363 (M + H)$^+$ |
| 141 | 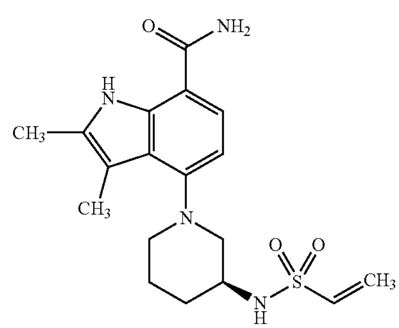 [SMILES: C=CS(=O)(=O)N[C@H]1CCCN(c2ccc(C(N)=O)c3[nH]c(C)c(C)c23)C1] | Intermediate 13 | m/z 377 (M + H)$^+$ |

TABLE 5-continued

| Example | Structure | Starting Material | Mass Spectrum |
|---|---|---|---|
| 142 | (structure) | Intermediate 23 | m/z 363 (M + H)+ |
| 143 | (structure) | Intermediate 14 | m/z 377 (M + H)+ |
| 143 | (structure) | Intermediate 19 | m/z 363 (M + H)+ |
| 144 | (structure) | Intermediate 34 | m/z 363 (M + H)+ |

TABLE 5-continued

| Example | Structure | Starting Material | Mass Spectrum |
|---|---|---|---|
| 145 | (structure) | Intermediate 16 | m/z 395 (M + H)+ |
| 34* | (structure) | Intermediate 41 | m/z 384 (M + H)+ |

*Alternative preparation of Example 34.

Example 147

(S)-4-((1-Cyanopyrrolidin-3-yl)amino)-5-fluoro-2,3-dimethyl-1H-indole-7-carboxamide (147)

A mixture of (S)-5-fluoro-2,3-dimethyl-4-(pyrrolidin-3-ylamino)-1H-indole-7-carboxamide [Intermediate 21] (0.041 g, 0.127 mmol) and $Cs_2CO_3$ (0.166 g, 0.508 mmol) in DMF (1.5 mL) was cooled to 0° C. and treated with 5 M cyanogen bromide in acetonitrile (0.028 mL, 0.140 mmol). The mixture was stirred at 0° C. for 60 min., then at room temperature overnight. The mixture was diluted with water and extracted with EtOAc. The organic layer was washed twice with 10% aqueous LiCl, then with brine. The combined aqueous layers were extracted with EtOAc, and the combined organic layers were dried and concentrated. The residue was subjected to column chromatography on silica gel, eluting with EtOAc-hexanes (gradient from 50-75%), to give (S)-4-((1-cyanopyrrolidin-3-yl)amino)-5-fluoro-2,3-dimethyl-1H-indole-7-carboxamide as a yellow solid (0.007 g, 17% yield). Mass spectrum m/z 316 (M+H)+.

Additional Examples which were prepared by procedures described in Example 147 or similar procedures, using the indicated starting material, are shown in Table 6.

TABLE 6

| Example | Structure | Starting Material | Mass Spectrum |
|---|---|---|---|
| 148 | (structure) | Intermediate 38 | m/z 297 (M + H)+ |
| 149 | (structure) | Intermediate 40 | m/z 283 (M + H)+ |

TABLE 6-continued

| Example | Structure | Starting Material | Mass Spectrum |
|---|---|---|---|
| 150 | 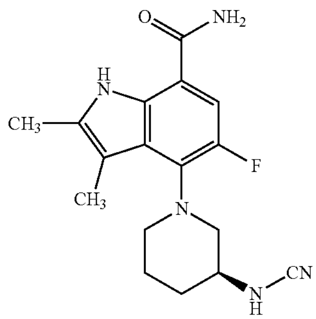 [SMILES: Cc1[nH]c2c(C(N)=O)cc(F)c(N3CCC[C@H](NC#N)C3)c2c1C] | Intermediate 16 | m/z 330 (M + H)+ |
| 151 | 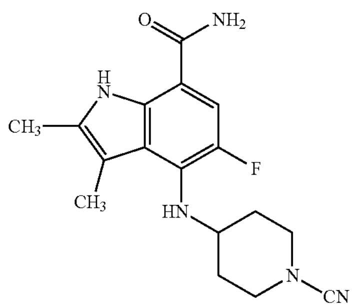 [SMILES: Cc1[nH]c2c(C(N)=O)cc(F)c(NC3CCN(C#N)CC3)c2c1C] | Intermediate 18 | m/z 330 (M + H)+ |
| 152 | 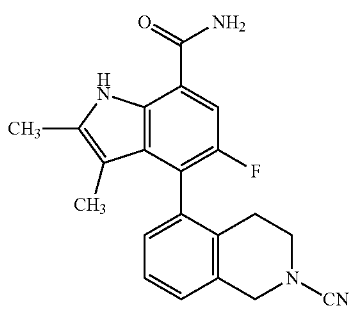 [SMILES: Cc1[nH]c2c(C(N)=O)cc(F)c(-c3cccc4c3CCN(C#N)C4)c2c1C] | Intermediate 42 | m/z 363 (M + H)+ |

Examples 153 and 154

4-(2-Acryloyl-1,2,3,4-tetrahydroisoquinolin-5-yl)-5-fluoro-2,3-dimethyl-1H-indole-7-carboxamide (single enantiomers)

(153 and 154)

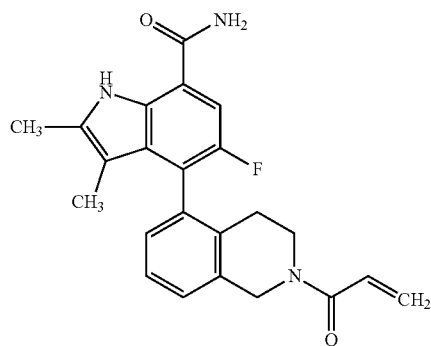

A sample of (RS)-4-(2-acryloyl-1,2,3,4-tetrahydroisoquinolin-5-yl)-5-fluoro-2,3-dimethyl-1H-indole-7-carboxamide [Example 95] (42 mg) was separated by chiral supercritical fluid chromatography (Column: IC (3×25 cm, 5 µm); mobile phase: $CO_2$-MeOH (55:45) at 150 mL/min; sample preparation: 5.83 mg/mL in MeOH-DCM (4:1); injection: 2 mL).

The first peak eluting from the column provided one enantiomer of 4-(2-acryloyl-1,2,3,4-tetrahydroisoquinolin-5-yl)-5-fluoro-2,3-dimethyl-1H-indole-7-carboxamide [Example 153] as a pale yellow solid (18 mg). Mass spectrum m/z 392 (M+H)+. 1H NMR (500 MHz, DMSO-$d_6$) δ 10.83 (s, 1H), 8.08 (br. s., 1H), 7.53 (d, J=10.7 Hz, 1H), 7.48 (br. s., 1H), 7.33-7.28 (m, 2H), 7.15-7.10 (m, 1H), 6.93 (dd, J=16.7, 10.5 Hz, 0.4H), 6.80 (dd, J=16.6, 10.5 Hz, 0.6H), 6.14 (d, J=16.6 Hz, 1H), 5.73 (d, J=10.7 Hz, 0.4H), 5.67 (dd, J=10.5, 1.9 Hz, 0.6H), 4.87 (s, 1H), 4.77 (d, J=3.8 Hz, 1H), 3.78-3.62 (m, 1H), 3.60-3.52 (m, 1H), 2.44-2.31 (m, 2H), 2.31-2.24 (m, 3H), and 1.43-1.38 (m, 3H).

The second peak eluting from the column provided the other enantiomer of 4-(2-acryloyl-1,2,3,4-tetrahydroisoquinolin-5-yl)-5-fluoro-2,3-dimethyl-1H-indole-7-carboxamide [Example 154] (18 mg). Mass spectrum m/z 392 (M+H)+. NMR: same as Example 153.

The absolute stereochemistries of Examples 153 and 154 have not been assigned.

Alternative Preparation of 4-(2-Acryloyl-1,2,3,4-tetrahydroisoquinolin-5-yl)-5-fluoro-2,3-dimethyl-1H-indole-7-carboxamide (Single enantiomer) [Example 153]

Following the procedure used to prepare Example 78, a single enantiomer of 5-fluoro-2,3-dimethyl-4-(1,2,3,4-tetrahydroisoquinolin-5-yl)-1H-indole-7-carboxamide [Intermediate 105] (20 mg, 0.059 mmol) was converted into a single enantiomer of 4-(2-acryloyl-1,2,3,4-tetrahydroisoquinolin-5-yl)-5-fluoro-2,3-dimethyl-1H-indole-7-carboxamide in 91% yield.

Alternative Preparation of 4-(2-Acryloyl-1,2,3,4-tetrahydroisoquinolin-5-yl)-5-fluoro-2,3-dimethyl-1H-indole-7-carboxamide (Single enantiomer) [Example 154]

Following the procedure used to prepare Example 78, a single enantiomer of 5-fluoro-2,3-dimethyl-4-(1,2,3,4-tetrahydroisoquinolin-5-yl)-1H-indole-7-carboxamide [Intermediate 106] (2.85 g, 8.45 mmol) was converted into a single enantiomer of 4-(2-acryloyl-1,2,3,4-tetrahydroisoquinolin-5-yl)-5-fluoro-2,3-dimethyl-1H-indole-7-carboxamide in 78% yield.

Examples 155 and 156

4-(4-Acryloyl-3,4-dihydro-2H-benzo[b][1,4]oxazin-8-yl)-5-fluoro-2,3-dimethyl-1H-indole-7-carboxamide (Single enantiomers)

(155 and 156)

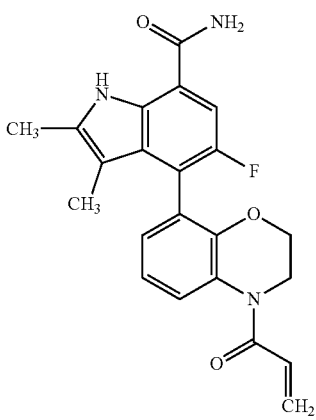

A sample of (RS)-4-(4-acryloyl-3,4-dihydro-2H-benzo[b][1,4]oxazin-8-yl)-5-fluoro-2,3-dimethyl-1H-indole-7-carboxamide [Example 102] (25 mg) was separated by chiral super-critical fluid chromatography (Column: CHIRALPAKR IC, 3×25 cm, 5 µm; mobile phase: $CO_2$-MeOH 55:45 at 150 mL/min, 35° C.; sample preparation: dissolved in 1:1 MeOH-DCM; injection 1.0 mL).

The first peak eluting from the column provided one enantiomer of 4-(4-acryloyl-3,4-dihydro-2H-benzo[b][1,4]oxazin-8-yl)-5-fluoro-2,3-dimethyl-1H-indole-7-carboxamide [Example 155] as an off-white solid (10.4 mg). Mass spectrum m/z 394 (M+H)$^+$. $^1$H NMR (400 MHz, DMSO-$d_6$) δ 10.73 (s, 1H), 8.04 (br. s., 1H), 7.60-7.38 (m, 3H), 7.08-6.95 (m, 2H), 6.82 (dd, J=16.8, 10.4 Hz, 1H), 6.30 (dd, J=16.8, 2.1 Hz, 1H), 5.91-5.80 (m, 1H), 4.17 (t, J=4.6 Hz, 2H), 4.08-3.95 (m, 1H), 3.83 (dt, J=13.6, 4.9 Hz, 1H), 2.29 (s, 3H), 1.57 (s, 3H).

The second peak eluting from the column provided the other enantiomer of 4-(4-acryloyl-3,4-dihydro-2H-benzo[b][1,4]oxazin-8-yl)-5-fluoro-2,3-dimethyl-1H-indole-7-carboxamide [Example 156] (11 mg). Mass spectrum m/z 394 (M+H)$^+$. $^1$H NMR (400 MHz, DMSO-$d_6$) δ 10.73 (s, 1H), 8.04 (br. s., 1H), 7.57-7.35 (m, 3H), 7.05-6.95 (m, 2H), 6.82 (dd, J=16.7, 10.3 Hz, 1H), 6.30 (dd, J=16.9, 2.0 Hz, 1H), 5.90-5.80 (m, 1H), 4.17 (t, J=4.6 Hz, 2H), 4.01 (dt, J=13.7, 4.4 Hz, 1H), 3.83 (dt, J=13.5, 4.9 Hz, 1H), 2.29 (s, 3H), 1.57 (s, 3H).

The absolute stereochemistries of Examples 155 and 156 have not been assigned.

Examples 157 and 158

4-(2-Cyano-1,2,3,4-tetrahydroisoquinolin-5-yl)-5-fluoro-2,3-dimethyl-1H-indole-7-carboxamide (Single enantiomers)

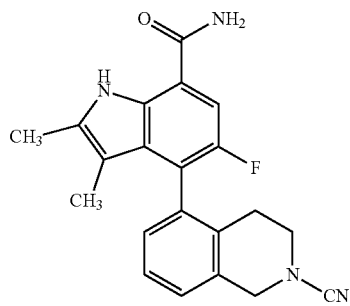

(157 and 158)

A sample of (RS)-4-(2-cyano-1,2,3,4-tetrahydroisoquinolin-5-yl)-5-fluoro-2,3-dimethyl-1H-indole-7-carboxamide [Example 152] (25 mg) was separated by chiral super-critical fluid chromatography (Column: AD-H (3×25 cm, 5 µm); mobile phase: $CO_2$-MeOH (65:35) at 150 mL/min; 100 bar, 40° C.; sample preparation: 4.39 mg/mL in MeOH; injection: 1 mL).

The first peak eluting from the column provided one enantiomer of 4-(2-cyano-1,2,3,4-tetrahydroisoquinolin-5-yl)-5-fluoro-2,3-dimethyl-1H-indole-7-carboxamide [Example 157] as an off-white solid (11 mg). Mass spectrum m/z 363 (M+H)+. $^1$H NMR (500 MHz, DMSO-$d_6$) δ 10.84 (s, 1H), 8.08 (br. s., 1H), 7.54 (d, J=10.7 Hz, 1H), 7.49 (br. s., 1H), 7.34-7.29 (m, 1H), 7.23 (d, J=7.0 Hz, 1H), 7.15 (d, J=7.3 Hz, 1H), 4.52 (s, 2H), 3.38 (t, J=6.3 Hz, 2H), 2.39 (t, J=5.9 Hz, 2H), 2.29 (s, 3H), and 1.43 (s, 3H).

The second peak eluting from the column provided the other enantiomer of 4-(2-cyano-1,2,3,4-tetrahydroisoquinolin-5-yl)-5-fluoro-2,3-dimethyl-1H-indole-7-carboxamide [Example 158] (18 mg). Mass spectrum m/z 363 (M+H)+. NMR: same as Example 157.

The absolute stereochemistries of Examples 157 and 158 have not been assigned.

Examples 159 and 160 cis-4-(1-Acryloylhexahydro-1H-pyrrolo[3,4-b]pyridin-6(2H)-yl)-5-fluoro-2,3-dimethyl-1H-indole-7-carboxamide (Single enantiomers)

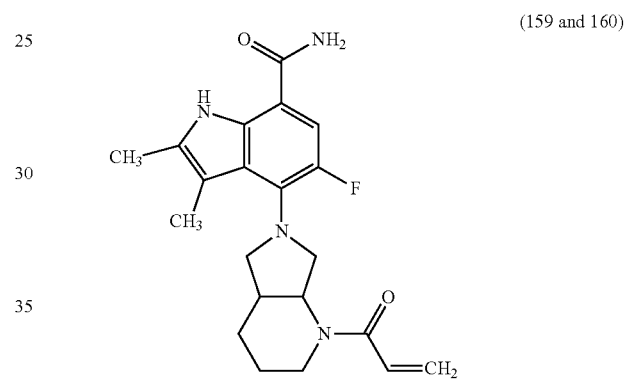

(159 and 160)

Example 159A: (RS)-cis-4-(1-Acryloylhexahydro-1H-pyrrolo[3,4-b]pyridin-6(2H)-yl)-5-fluoro-2,3-dimethyl-1H-indole-7-carboxamide Following the procedures used to prepare Example 78, 5-fluoro-4-(hexahydro-1H-pyrrolo[3,4-b]pyridin-6(2H)-yl)-2,3-dimethyl-1H-indole-7-carboxamide [Intermediate 29] was converted into (RS)-cis-4-(1-acryloylhexahydro-1H-pyrrolo[3,4-b]pyridin-6(2H)-yl)-5-fluoro-2,3-dimethyl-1H-indole-7-carboxamide as a yellow solid in 57% yield. Mass spectrum m/z 385 (M+H)$^+$. $^1$H NMR (500 MHz, MeOH-$d_4$) complex due to a mixture of rotamers. At 60° C.: δ 7.36 (d, J=13.6 Hz, 1H), 6.80 (br. s., 1H), 6.18 (d, J=16.5 Hz, 1H), 5.75 (br. s., 1H), 2.43 (s, 3H), 2.36 (s, 3H). Methylene and methine protons complex but consistent with expected structure.

Examples 159 and 160

A sample of (RS)-cis-4-(1-acryloylhexahydro-1H-pyrrolo[3,4-b]pyridin-6(2H)-yl)-5-fluoro-2,3-dimethyl-1H-indole-7-carboxamide (30 mg) was separated by chiral super-critical fluid chromatography (Column: OJ (3×25 cm, 5 µm); mobile phase: $CO_2$-MeOH (85:15) at 170 mL/min; 100 bar, 40° C.; sample preparation: 2.5 mg/mL in MeOH-DCM).

The first peak eluting from the column provided one enantiomer of cis-4-(1-acryloylhexahydro-1H-pyrrolo[3,4-b]pyridin-6(2H)-yl)-5-fluoro-2,3-dimethyl-1H-indole-7-carboxamide [Example 159] as an off-white solid (10.7 mg). The second peak eluting from the column provided the other enantiomer of cis-4-(1-acryloylhexahydro-1H-pyrrolo[3,4-b]pyridin-6(2H)-yl)-5-fluoro-2,3-dimethyl-1H-indole-7-carboxamide [Example 160] as an off-white solid (11.8 mg). Mass spectra and NMR spectra for both enantiomers were the same as those observed for the racemic mixture.

The absolute stereochemistries of Examples 159 and 160 have not been assigned.

Examples 161 to 164 cis-4-(3-Acryloyl-1a,2,3,7b-tetrahydro-H-cyclopropa[c]quinolin-7-yl)-5-fluoro-2,3-dimethyl-1H-indole-7-carboxamide (Single diastereomers)

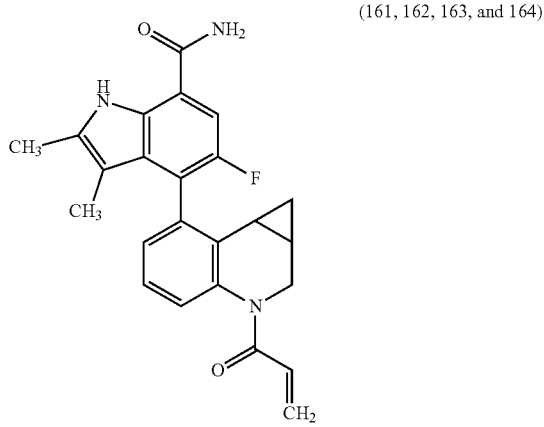 [SMILES: C=CC(=O)N1CC2CC2c2c(-c3c(F)cc(C(N)=O)c4[nH]c(C)c(C)c34)cccc21]

(161, 162, 163, and 164)

Example 161A: cis-4-(3-Acryloyl-1a,2,3,7b-tetrahydro-1H-cyclopropa[c]quinolin-7-yl)-5-fluoro-2,3-dimethyl-1H-indole-7-carboxamide (Mixture of Four diastereomers)

Following the procedures used to prepare Example 78, (RS-cis)-5-fluoro-2,3-dimethyl-4-(1a,2,3,7b-tetrahydro-1H-cyclopropa[c]quinolin-7-yl)-1H-indole-7-carboxamide TFA salt [Intermediate 48] was converted into cis-4-(3-acryloyl-1a,2,3,7b-tetrahydro-1H-cyclopropa[c]quinolin-7-yl)-5-fluoro-2,3-dimethyl-1H-indole-7-carboxamide, a mixture of four diastereomers, as a gum in 86% yield. Mass spectrum m/z 404 (M+H)+.

Examples 161 Through 164

A sample of cis-4-(3-acryloyl-1a,2,3,7b-tetrahydro-1H-cyclopropa[c]quinolin-7-yl)-5-fluoro-2,3-dimethyl-1H-indole-7-carboxamide, mixture of four diastereomers (29 mg) was separated by chiral super-critical fluid chromatography (Column: AS-H, 5×25 cm, 5 μm; mobile phase: $CO_2$-MeOH (72:28) at 280 mL/min, 100 bar; sample preparation: 2.9 mg/mL in MeOH).

The first peak eluting from the column was subjected to column chromatography on silica gel, eluting with 10% MeOH/EtOAc-hexanes (gradient from 0-100%), to provide one diastereomer of cis-4-(3-acryloyl-1a,2,3,7b-tetrahydro-1H-cyclopropa[c]quinolin-7-yl)-5-fluoro-2,3-dimethyl-1H-indole-7-carboxamide [Example 161] (1.09 mg).

The second peak eluting from the column provided a second diastereomer of cis-4-(3-acryloyl-1a,2,3,7b-tetrahydro-1H-cyclopropa[c]quinolin-7-yl)-5-fluoro-2,3-dimethyl-1H-indole-7-carboxamide [Example 162] (5.46 mg).

The third peak eluting from the column provided a third diastereomer of cis-4-(3-acryloyl-1a,2,3,7b-tetrahydro-H-cyclopropa[c]quinolin-7-yl)-5-fluoro-2,3-dimethyl-1H-indole-7-carboxamide [Example 163] (5.72 mg).

The fourth peak eluting from the column provided a fourth diastereomer of cis-4-(3-acryloyl-1a,2,3,7b-tetrahydro-1H-cyclopropa[c]quinolin-7-yl)-5-fluoro-2,3-dimethyl-1H-indole-7-carboxamide [Example 164] (5.37 mg).

The absolute stereochemistries of Examples 161 through 164 have not been assigned. The mass spectra for all four were the same as that of Example 161A.

Additional Examples which were prepared by procedures described for Examples 159 through 164 or similar procedures, using the indicated starting material, are shown in Table 7.

TABLE 7

| Example | Structure | Starting Material | Mass Spectrum |
|---|---|---|---|
| 165 (peak 1) | 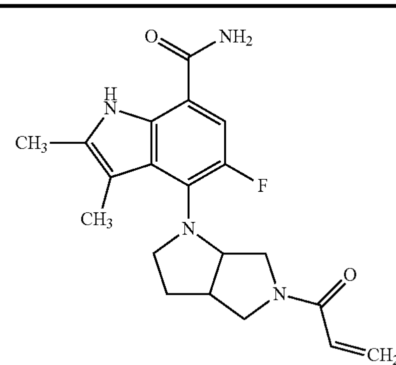 | Intermediate 30 | m/z 371 (M + H)+ |

TABLE 7-continued

| Example | Structure | Starting Material | Mass Spectrum |
|---|---|---|---|
| 166 (peak 2) | 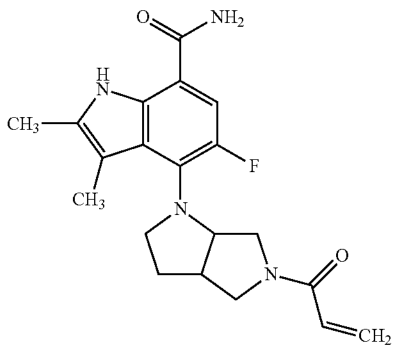 [SMILES: C=CC(=O)N1CC2CCN(c3c(F)cc(C(N)=O)c4[nH]c(C)c(C)c34)C2C1] | Intermediate 30 | m/z 371 (M + H)+ |
| 167 (peak 1) | 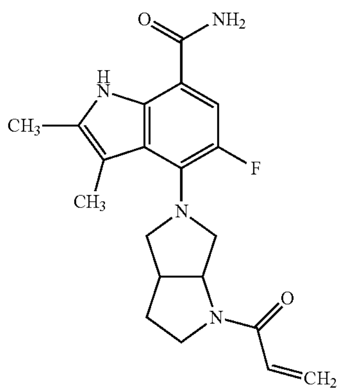 [SMILES: C=CC(=O)N1CCC2CN(c3c(F)cc(C(N)=O)c4[nH]c(C)c(C)c34)CC21] | Intermediate 31 | m/z 371 (M + H)+ |
| 168 (peak 2) | 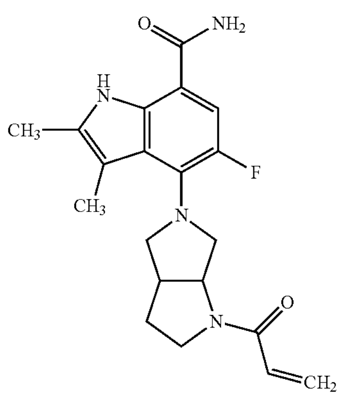 [SMILES: C=CC(=O)N1CCC2CN(c3c(F)cc(C(N)=O)c4[nH]c(C)c(C)c34)CC21] | Intermediate 31 | m/z 371 (M + H)+ |
| 169 (peak 1) | 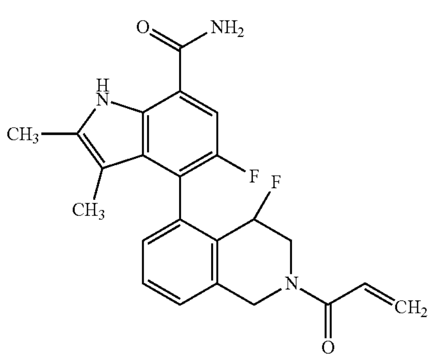 [SMILES: C=CC(=O)N1Cc2cccc(-c3c(F)cc(C(N)=O)c4[nH]c(C)c(C)c34)c2C(F)C1] | Intermediate 50 | m/z 410 (M + H)+ |

TABLE 7-continued
| Example | Structure | Starting Material | Mass Spectrum |
|---|---|---|---|
| 170 (peak 2) | 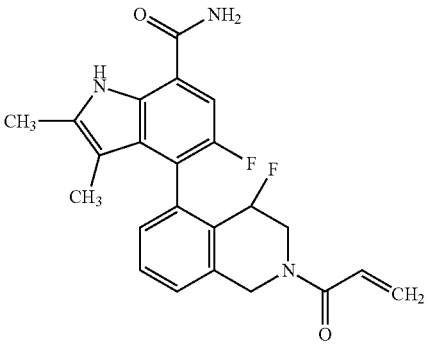 [SMILES: C=CC(=O)N1Cc2cccc(-c3c(F)cc(C(N)=O)c4[nH]c(C)c(C)c34)c2C(F)C1] | Intermediate 50 | m/z 410 (M + H)+ |
| 171 (peak 3) | 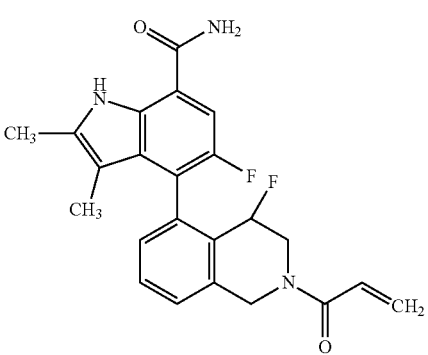 [SMILES: C=CC(=O)N1Cc2cccc(-c3c(F)cc(C(N)=O)c4[nH]c(C)c(C)c34)c2C(F)C1] | Intermediate 50 | m/z 410 (M + H)+ |
| 172 (peak 4) | 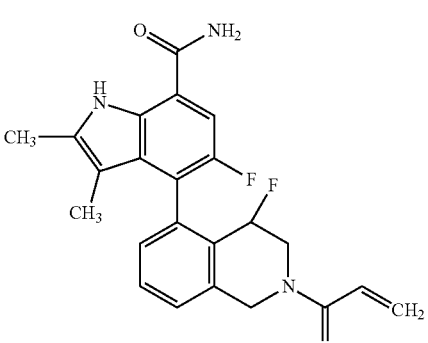 | Intermediate 50 | m/z 410 (M + H)+ |

Examples 173 and 174 cis-4-(1-(But-2-ynoyl)hexahydro-1H-pyrrolo[3,4-b]pyridin-6(2H)-yl)-5-fluoro-2,3-dimethyl-1H-indole-7-carboxamide (Single enantiomers)

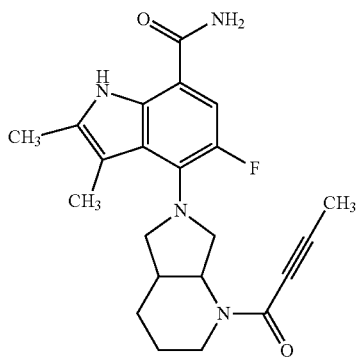

(173 and 174)

Example 173A: (RS)-cis-4-(1-(But-2-ynoyl)hexahydro-1H-pyrrolo[3,4-b]pyridin-6(2H)-yl)-5-fluoro-2,3-dimethyl-1H-indole-7-carboxamide Following the procedures used to prepare Example 103 but substituting but-2-ynoic acid for propiolic acid, 5-fluoro-4-(hexahydro-1H-pyrrolo[3,4-b]pyridin-6(2H)-yl)-2,3-dimethyl-1H-indole-7-carboxamide [Intermediate 29] was converted into (RS)-cis-4-(1-(but-2-ynoyl)hexahydro-1H-pyrrolo[3,4-b]pyridin-6(2H)-yl)-5-fluoro-2,3-dimethyl-1H-indole-7-carboxamide as a yellow gum in 75% yield. Mass spectrum m/z 397 (M+H)$^+$. $^1$H NMR (500 MHz, MeOH-$d_4$) complex due to mixture of rotamers.

Examples 173 and 174

A sample of (RS)-cis-4-(1-(but-2-ynoyl)hexahydro-1H-pyrrolo[3,4-b]pyridin-6(2H)-yl)-5-fluoro-2,3-dimethyl-1H-indole-7-carboxamide (32 mg) was separated by chiral super-critical fluid chromatography (Column: OJ-H (3×25 cm, 5 μm); mobile phase: $CO_2$-MeOH (85:15) at 150 mL/min; 40° C.; sample preparation: 3.2 mg/mL in MeOH).

The first peak eluting from the column provided one enantiomer of cis-4-(1-(but-2-ynoyl)hexahydro-1H-pyrrolo[3,4-b]pyridin-6(2H)-yl)-5-fluoro-2,3-dimethyl-1H-indole-7-carboxamide [Example 173] as a white solid (9.2 mg). The second peak eluting from the column provided the other enantiomer of cis-4-(1-(but-2-ynoyl)hexahydro-1H-pyrrolo[3,4-b]pyridin-6(2H)-yl)-5-fluoro-2,3-dimethyl-1H-indole-7-carboxamide [Example 174] as an off-white solid (9.8 mg). Mass spectra and NMR spectra for both enantiomers were the same as those observed for the racemic mixture.

The absolute stereochemistries of Examples 173 and 174 have not been assigned.

Additional Examples which were prepared by procedures described for Examples 173 and 174 or similar procedures, using the indicated starting material, are shown in Table 8.

TABLE 8

| Example | Structure | Starting Material | Mass Spectrum |
|---|---|---|---|
| 175 (peak 1) | 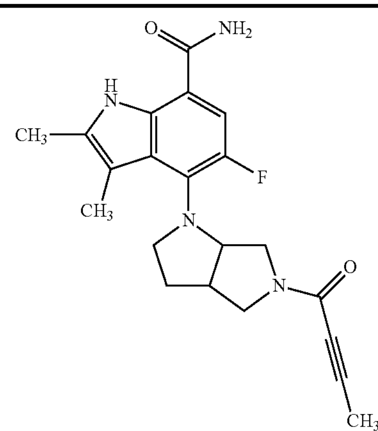 | Intermediate 30 | m/z 383 (M + H)$^+$ |

TABLE 8-continued

| Example | Structure | Starting Material | Mass Spectrum |
|---|---|---|---|
| 176 (peak 2) | 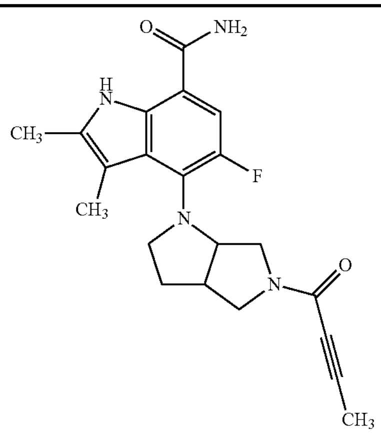 | Intermediate 30 | m/z 383 (M + H)+ |
| 177 (peak 1) | 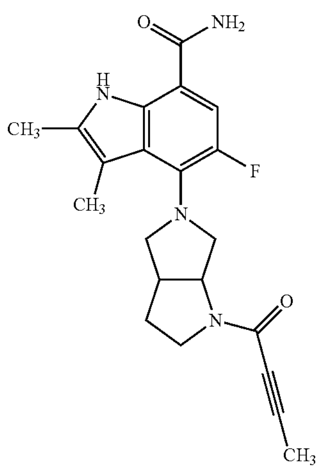 [SMILES: CC#CC(=O)N1CCC2CN(c3c(F)cc(C(N)=O)c4[nH]c(C)c(C)c34)CC21] | Intermediate 31 | m/z 383 (M + H)+ |
| 178 (peak 2) | 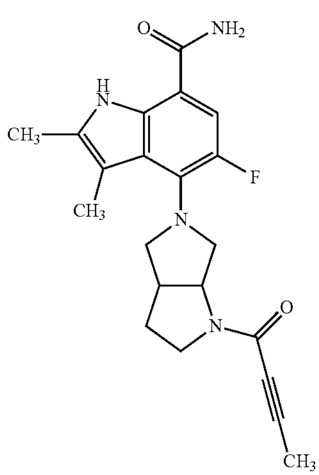 [SMILES: CC#CC(=O)N1CCC2CN(c3c(F)cc(C(N)=O)c4[nH]c(C)c(C)c34)CC21] | Intermediate 31 | m/z 383 (M + H)+ |

Examples 179 and 180 cis-4-(1-Cyanohexahydro-1H-pyrrolo[3,4-b]pyridin-6(2H)-yl)-5-fluoro-2,3-dimethyl-1H-indole-7-carboxamide (Single enantiomers)

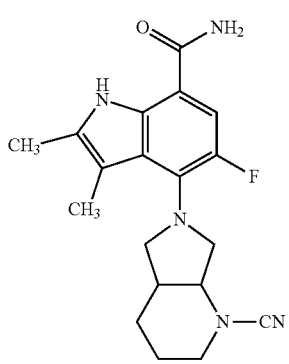

(179 and 180)

Example 179A: (RS)-cis-4-(1-Cyanohexahydro-1H-pyrrolo[3,4-b]pyridin-6(2H)-yl)-5-fluoro-2,3-dimethyl-1H-indole-7-carboxamide Following the procedures used to prepare Example 147, (RS-cis)-5-fluoro-4-(hexahydro-1H-pyrrolo[3,4-b]pyridin-6(2H)-yl)-2,3-dimethyl-1H-indole-7-carboxamide [Intermediate 29] was converted into (RS)-cis-4-(1-cyanohexahydro-1H-pyrrolo[3,4-b]pyridin-6(2H)-yl)-5-fluoro-2,3-dimethyl-1H-indole-7-carboxamide as a brown gum in 34% yield. Mass spectrum m/z 356 (M+H)$^+$.

Examples 179 and 180

A sample of (RS)-cis-4-(1-cyanohexahydro-1H-pyrrolo[3,4-b]pyridin-6(2H)-yl)-5-fluoro-2,3-dimethyl-1H-indole-7-carboxamide (12 mg) was separated by chiral supercritical fluid chromatography (Column: CHIRALPAKR AS-H 5×25 cm, 5 µm; mobile phase CO$_2$-MeOH 75:25 at 280 mL/min, 30° C.; sample preparation: dissolved in MeOH; injection: 1 mL).

The first peak eluting from the column provided one enantiomer of cis-4-(1-cyanohexahydro-1H-pyrrolo[3,4-b]pyridin-6(2H)-yl)-5-fluoro-2,3-dimethyl-1H-indole-7-carboxamide [Example 179] as a white solid (4.2 mg). Mass spectrum m/z 356 (M+H)$^+$. The second peak eluting from the column provided the other enantiomer of cis-4-(1-cyanohexahydro-1H-pyrrolo[3,4-b]pyridin-6(2H)-yl)-5-fluoro-2,3-dimethyl-1H-indole-7-carboxamide [Example 180] as a white solid (4.5 mg). Mass spectrum m/z 356 (M+H)$^+$.

The absolute stereochemistries of Examples 179 and 180 have not been assigned.

Example 181

5-Fluoro-2,3-dimethyl-4-((6-vinylpyridin-3-yl)methyl)-1H-indole-7-carboxamide, TFA Salt

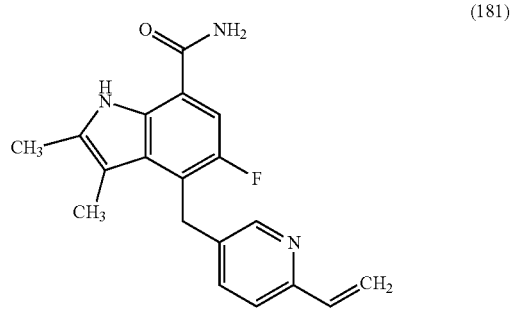 [SMILES: C=Cc1ccc(Cc2c(F)cc(C(N)=O)c3[nH]c(C)c(C)c23)cn1]

(181)

Example 181A: 4-Bromo-5-fluoro-2,3-dimethyl-1-((2-(trimethylsilyl)ethoxy)methyl)-1H-indole-7-carbonitrile

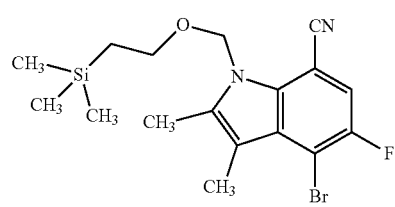

(181A)

A solution of 4-bromo-5-fluoro-2,3-dimethyl-1H-indole-7-carbonitrile [Intermediate 12] (1.50 g, 5.62 mmol) in THF (15 mL) at −78° C. was treated with 1.0 M lithium bis(trimethylsilyl)amide in THF (6.74 mL, 6.74 mmol) and the mixture was stirred at −78° C. for 15 min. (2-(Chloromethoxy)ethyl)trimethylsilane (0.983 g, 5.90 mmol) was added and the mixture was stirred at room temperature for 2 h. The mixture was diluted with EtOAc (45 mL), washed sequentially with saturated aqueous NaHCO$_3$ (2×45 mL) and 1.0 M aqueous HCl (45 mL), dried and concentrated. The residue was subjected to column chromatography on silica gel, eluting with EtOAc-hexanes (gradient from 0-30%), to provide 4-bromo-5-fluoro-2,3-dimethyl-1-((2-(trimethylsilyl)ethoxy) methyl)-1H-indole-7-carbonitrile as a white solid (1.92 g, 82% yield). $^1$H NMR (400 MHz, CDCl$_3$) δ 7.24 (d, J=8.4 Hz, 1H), 5.77 (s, 2H), 3.68-3.60 (m, 2H), 2.52 (d, J=0.5 Hz, 3H), 2.43 (s, 3H), 0.95 (dd, J=8.7, 7.7 Hz, 2H), −0.01 (s, 9H).

Example 181B: 4-((6-Chloropyridin-3-yl)methyl)-5-fluoro-2,3-dimethyl-1-((2-(trimethylsilyl)ethoxy)methyl)-1H-indole-7-carbonitrile

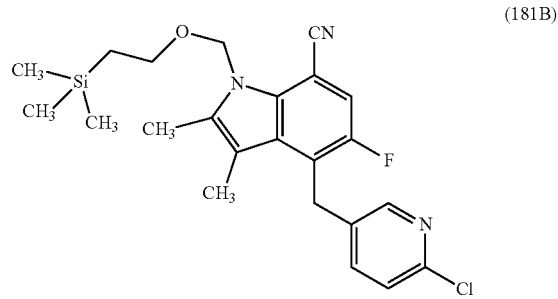 [SMILES: Cc1c(C)n(COCC[Si](C)(C)C)c2c(C#N)cc(F)c(Cc3ccc(Cl)nc3)c12]

(181B)

A suspension of 4-bromo-5-fluoro-2,3-dimethyl-1-((2-(trimethylsilyl)ethoxy) methyl)-1H-indole-7-carbonitrile (238 mg, 0.599 mmol) in THF (5.0 mL) was treated with 0.5 M (2-chloro-5-pyridyl)methylzinc chloride in THF (1.32 mL, 0.659 mmol) and tetrakis(triphenylphosphine)palladium (25.6 mg, 0.022 mmol) and the mixture was stirred at reflux for 18 h. The mixture was diluted with EtOAc (15 mL), washed twice with saturated aqueous NaHCO₃, dried and concentrated. The residue was subjected to column chromatography on silica gel, eluting with EtOAc-hexanes (gradient from 0-60%), to provide 4-((6-chloropyridin-3-yl)methyl)-5-fluoro-2,3-dimethyl-1-((2-(trimethylsilyl)ethoxy) methyl)-1H-indole-7-carbonitrile as a colorless gum (201 mg, 72% yield). Mass spectrum m/z 444, 446 (M+H)⁺. ¹H NMR (400 MHz, CDCl₃) δ 8.24 (d, J=2.1 Hz, 1H), 7.31-7.25 (m, 2H), 7.23-7.18 (m, 1H), 5.78 (s, 2H), 4.44 (s, 2H), 3.73-3.59 (m, 2H), 2.41 (s, 3H), 2.26 (d, J=0.4 Hz, 3H), 0.97 (dd, J=8.6, 7.6 Hz, 2H), −0.01 (s, 9H).

Example 181C: 4-((6-Chloropyridin-3-yl)methyl)-5-fluoro-2,3-dimethyl-1H-indole-7-carbonitrile

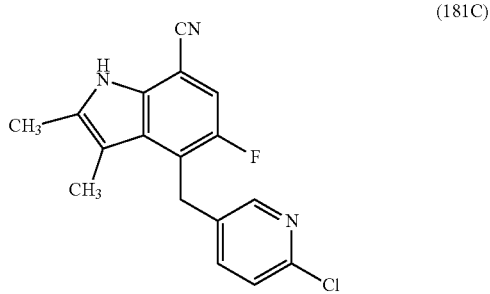 [SMILES: Cc1[nH]c2c(C#N)cc(F)c(Cc3ccc(Cl)nc3)c2c1C]

(181C)

A solution of 4-((6-chloropyridin-3-yl)methyl)-5-fluoro-2,3-dimethyl-1-((2-(trimethylsilyl)ethoxy)methyl)-1H-indole-7-carbonitrile (200 mg, 0.450 mmol) in THF (2.0 mL) was treated with a solution of 1.0 M tetra-n-butylammonium fluoride in THF (4.50 mL, 4.50 mmol), and the mixture was heated at reflux for 18 h. The cooled mixture was diluted with EtOAc and washed twice with saturated aqueous NaHCO₃, dried and concentrated. The residue was subjected to column chromatography on silica gel, eluting with EtOAc-hexanes (gradient from 0-30%), to provide 4-((6-chloropyridin-3-yl)methyl)-5-fluoro-2,3-dimethyl-1H-indole-7-carbonitrile as a white solid (90 mg, 61% yield). Mass spectrum m/z 314, 316 (M+H)⁺. ¹H NMR (400 MHz, CDCl₃) δ 8.37 (br. s., 1H), 8.25 (d, J=2.3 Hz, 1H), 7.33 (ddd, J=8.2, 2.5, 0.6 Hz, 1H), 7.25-7.16 (m, 2H), 4.43 (s, 2H), 2.41 (s, 3H), 2.26 (d, J=0.4 Hz, 3H).

Example 181D: 5-Fluoro-2,3-dimethyl-4-((6-vinylpyridin-3-yl)methyl)-1H-indole-7-carbonitrile

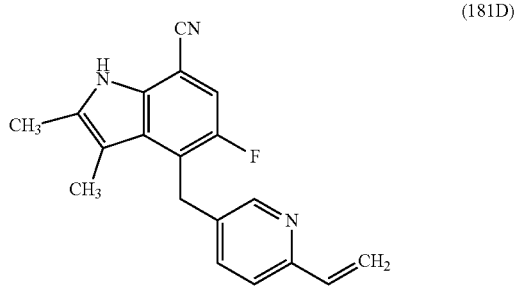 [SMILES: C=Cc1ccc(Cc2c(F)cc(C#N)c3[nH]c(C)c(C)c23)cn1]

(181D)

A mixture of 4-((6-chloropyridin-3-yl)methyl)-5-fluoro-2,3-dimethyl-1H-indole-7-carbonitrile (28 mg, 0.089 mmol), tri-n-butyl(vinyl)stannane (85 mg, 0.268 mmol), LiCl (11.4 mg, 0.268 mmol) and tetrakis(triphenylphosphine)palladium (10.3 mg, 8.92 mol) in DMF (1.0 mL) under a nitrogen atmosphere was heated at 90° C. for 18 h. The cooled mixture was diluted with EtOAc, washed twice with saturated aqueous NaHCO₃, dried and concentrated. The residue was subjected to column chromatography on silica gel, eluting with EtOAc-hexanes (gradient from 0-30%) to provide 5-fluoro-2,3-dimethyl-4-((6-vinylpyridin-3-yl)methyl)-1H-indole-7-carbonitrile as a white solid (22 mg, 77% yield). Mass spectrum m/z 306 (M+H)⁺. ¹H NMR (400 MHz, CDCl₃) δ 8.44 (d, J=2.0 Hz, 1H), 8.38 (br. s., 1H), 7.32 (dd, J=8.1, 1.7 Hz, 1H), 7.25-7.22 (m, 1H), 7.20 (d, J=9.5 Hz, 1H), 6.79 (dd, J=17.5, 10.9 Hz, 1H), 6.15 (dd, J=17.5, 1.2 Hz, 1H), 5.44 (dd, J=10.8, 1.3 Hz, 1H), 4.45 (s, 2H), 2.40 (s, 3H), 2.26 (d, J=0.2 Hz, 3H).

Example 181

5-Fluoro-2,3-dimethyl-4-((6-vinylpyridin-3-yl)methyl)-1H-indole-7-carbonitrile (22 mg, 0.072 mmol) was cooled in an ice-bath and treated with chlorotrimethylsilane (921 µL, 7.20 mmol), then with water (65 µl, 3.60 mmol) and the mixture was stirred at room temperature for 18 h. The supernatant was removed and the residue was dissolved in DMF and purified by preparative HPLC, eluting with MeOH-water containing 0.1% TFA (gradient from 20-100%). The appropriate effluent fractions were lyophilized from 1:1 water-acetonitrile (10 mL) to provide 5-fluoro-2,3-dimethyl-4-((6-vinylpyridin-3-yl)methyl)-1H-indole-7-carboxamide, TFA salt, as an off-white powder (15.8 mg, 48% yield). Mass spectrum m/z 324 (M+H)⁺. ¹H NMR (400 MHz, MeOH-d₄) δ 8.43 (d, J=1.3 Hz, 1H), 8.25-8.16 (m, 1H), 8.14-8.07 (m, 1H), 7.43 (d, J=11.0 Hz, 1H), 6.95 (dd, J=17.6, 11.2 Hz, 1H), 6.48 (d, J=17.6 Hz, 1H), 6.01 (d, J=11.2 Hz, 1H), 4.67 (s, 2H), 2.38 (s, 3H), 2.26 (s, 3H).

Example 182

5-Fluoro-2,3-dimethyl-4-((6-(prop-1-yn-1-yl)pyridin-3-yl)methyl)-1H-indole-7-carboxamide, TFA Salt

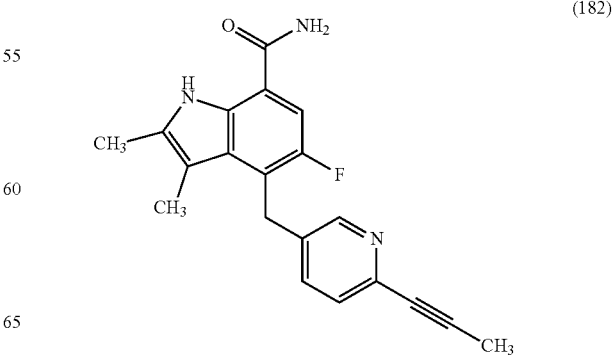

(182)

Example 182A: 5-Fluoro-2,3-dimethyl-4-((6-(prop-1-yn-1-yl)pyridin-3-yl)methyl)-1H-indole-7-carbonitrile

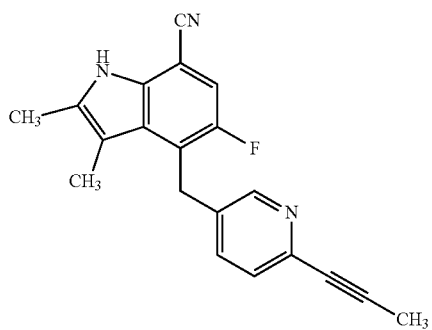

(182A)

Following the procedure used to prepare Example 181D but substituting tri-n-butyl(prop-1-yn-1-yl)stannane for tri-n-butyl(vinyl)stannane, 4-((6-chloropyridin-3-yl)methyl)-5-fluoro-2,3-dimethyl-1H-indole-7-carbonitrile [Example 181C] was converted into 5-fluoro-2,3-dimethyl-4-((6-(prop-1-yn-1-yl)pyridin-3-yl)methyl)-1H-indole-7-carbonitrile in 44% yield. Mass spectrum m/z 318 (M+H)+. $^1$H NMR (400 MHz, CDCl$_3$) δ 8.46-8.37 (m, 2H), 7.25 (d, J=1.3 Hz, 2H), 7.20 (d, J=9.4 Hz, 1H), 4.44 (d, J=1.6 Hz, 2H), 2.40 (s, 3H), 2.24 (d, J=0.4 Hz, 3H), 2.07 (s, 3H).

Example 182

Following the procedure used to convert Example 181D into Example 181, 5-fluoro-2,3-dimethyl-4-((6-(prop-1-yn-1-yl)pyridin-3-yl)methyl)-1H-indole-7-carbonitrile was converted into 5-fluoro-2,3-dimethyl-4-((6-(prop-1-yn-1-yl)pyridin-3-yl)methyl)-1H-indole-7-carboxamide, TFA salt, in 48% yield. Mass spectrum m/z 336 (M+H)$^+$. $^1$H NMR (400 MHz, MeOH-d$_4$) δ 8.41 (d, J=1.6 Hz, 1H), 8.00 (dd, J=8.3, 2.1 Hz, 1H), 7.76 (d, J=8.3 Hz, 1H), 7.43 (d, J=11.0 Hz, 1H), 4.64 (s, 2H), 2.39 (s, 3H), 2.25 (s, 3H), 2.19 (s, 3H).

Examples 183 and 184

5-Fluoro-2,3-dimethyl-4-(1-(6-vinylpyridin-3-yl)ethyl)-1H-indole-7-carboxamide, TFA salt (Single enantiomers)

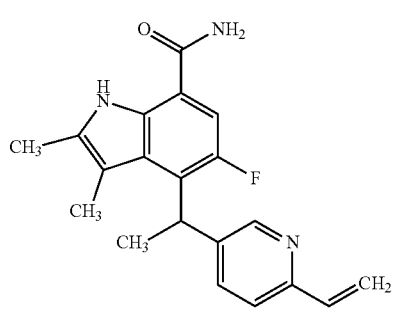

(183 and 184)

Example 183A: (RS)-4-(1-(6-Chloropyridin-3-yl)ethyl)-5-fluoro-2,3-dimethyl-1-((2-(trimethylsilyl)ethoxy)methyl)-1H-indole-7-carbonitrile

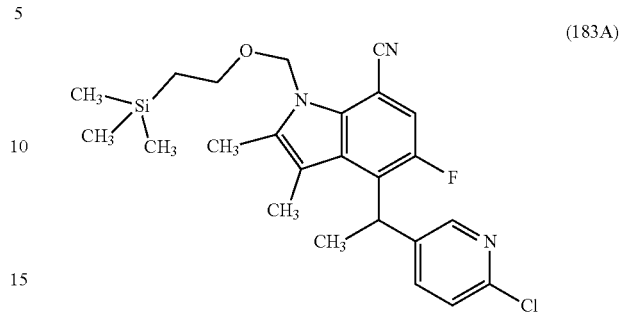

(183A)

A solution of 4-((6-chloropyridin-3-yl)methyl)-5-fluoro-2,3-dimethyl-1-((2-(trimethylsilyl)ethoxy)methyl)-1H-indole-7-carbonitrile [Example 181B] (91 mg, 0.205 mmol) in THF (5.0 mL) at −78° C. was treated with 1.0 M potassium bis(trimethylsilyl) amide in THF (0.615 mL, 0.615 mmol), then with iodomethane (0.038 mL, 0.615 mmol). The mixture was stirred at −78° C. for 1 h, then was warmed to room temperature, diluted with EtOAc, washed with saturated aqueous NaHCO$_3$, dried and concentrated. The residue was subjected to column chromatography on silica gel, eluting with EtOAc-hexanes (gradient from 0-30%), to provide (RS)-4-(1-(6-chloropyridin-3-yl)ethyl)-5-fluoro-2,3-dimethyl-1-((2-(trimethylsilyl)ethoxy)methyl)-1H-indole-7-carbonitrile as a colorless gum (90 mg, 91% yield). Mass spectrum m/z 458, 460 (M+H)$^+$. $^1$H NMR (400 MHz, CDCl$_3$) δ 8.30 (d, J=2.2 Hz, 1H), 7.53 (ddd, J=8.3, 1.7, 0.9 Hz, 1H), 7.25 (d, J=8.3 Hz, 1H), 7.14 (d, J=11.1 Hz, 1H), 5.79 (s, 2H), 5.15 (q, J=6.9 Hz, 1H), 3.75-3.62 (m, 2H), 2.46 (s, 3H), 2.45 (s, 3H), 1.82 (dd, J=7.2, 1.5 Hz, 3H), 0.97 (dd, J=8.7, 7.8 Hz, 2H), 0.00 (s, 9H).

Example 183B: (RS)-5-Fluoro-2,3-dimethyl-4-(1-(6-vinylpyridin-3-yl)ethyl)-1H-indole-7-carbonitrile

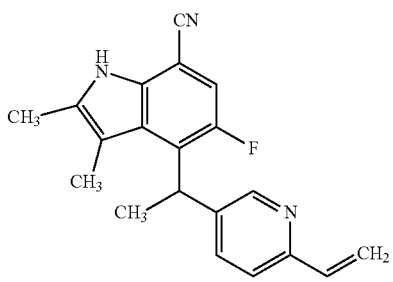

(183B)

Following the procedures used to convert Example 181B into Example 181D, (RS)-4-(1-(6-chloropyridin-3-yl)ethyl)-5-fluoro-2,3-dimethyl-1-((2-(trimethylsilyl) ethoxy) methyl)-1H-indole-7-carbonitrile was converted into (RS)-5-fluoro-2,3-dimethyl-4-(1-(6-vinylpyridin-3-yl)ethyl)-1H-indole-7-carbonitrile in 65% yield (two steps). Mass spectrum m/z 320 (M+H)+.

Examples 183 and 184

A sample of (RS)-4-(1-(6-chloropyridin-3-yl)ethyl)-5-fluoro-2, 3-dimethyl-1-((2-(trimethylsilyl)ethoxy)methyl)-1H-indole-7-carbonitrile (45 mg) was separated by chiral super-critical fluid chromatography (Column: AD-H, 3×25 cm, 5 m; mobile phase: CO$_2$-MeOH (70:30) at 150 mL/min; 35° C., 100 bar; sample preparation: 4.5 mg/mL; injection: 2.0 mL).

Concentration of the first peak eluting from the column provided a residue (14 mg) which was converted into one enantiomer of 5-fluoro-2,3-dimethyl-4-(1-(6-vinylpyridin-3-yl)ethyl)-1H-indole-7-carboxamide, TFA salt, as a white powder [Example 183] (11.6 mg) by following the procedure used to convert Example 181D to Example 181. Mass spectrum m/z 338 (M+H)+. $^1$H NMR (400 MHz, MeOH-d$_4$) δ 8.58 (s, 1H), 8.41 (dd, J=8.6, 2.0 Hz, 1H), 8.17 (d, J=8.6 Hz, 1H), 7.31 (d, J=12.7 Hz, 1H), 7.00 (dd, J=17.6, 11.2 Hz, 1H), 6.52 (d, J=17.6 Hz, 1H), 6.06 (d, J=11.2 Hz, 1H), 5.37 (q, J=6.8 Hz, 1H), 2.48 (s, 3H), 2.45 (s, 3H), 1.92 (dd, J=7.2, 1.0 Hz, 3H).

Concentration of the second peak eluting from the column provided a residue (14 mg) which likewise was converted into the other enantiomer of 5-fluoro-2,3-dimethyl-4-(1-(6-vinylpyridin-3-yl)ethyl)-1H-indole-7-carboxamide, TFA salt, as a white powder [Example 184] (10.6 mg) by following the procedure used to convert Example 181D to Example 181. Mass spectrum and NMR: same as those of Example 183.

Example 185

5-Fluoro-2,3-dimethyl-4-((2-vinylpyridin-4-yl)methyl)-1H-indole-7-carboxamide

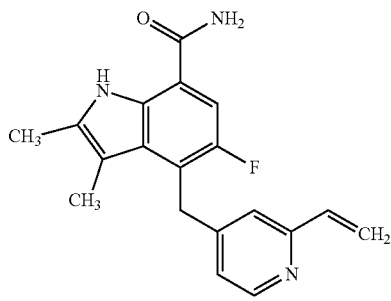

(185)

Example 185A: 4-((6-Chloropyridin-3-yl)methyl)-5-fluoro-2,3-dimethyl-1-((2-(trimethylsilyl)ethoxy)methyl)-1H-indole-7-carbonitrile

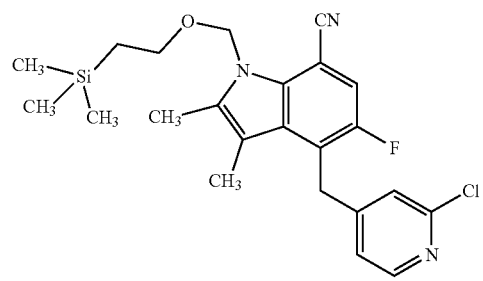

(185A)

Chlorotrimethylsilane (2.7 μL, 0.021 mmol) and 1,2-dibromoethane (3.2 μL, 0.043 mmol) were added to a suspension of zinc (84 mg, 1.28 mmol) in THF (1.5 mL) and the mixture was stirred at 65° C. for 20 min. The mixture was cooled to 0° C., treated dropwise with a solution of 2-chloro-4-(chloromethyl)pyridine (139 mg, 0.856 mmol) in THF (0.5 mL) and stirred for 20 min. A solution of 4-bromo-5-fluoro-2,3-dimethyl-1-((2-(trimethylsilyl)ethoxy)methyl)-1H-indole-7-carbonitrile [Example 181A] (170 mg, 0.428 mmol) and 1,1'-bis(di-tert-butylphosphino)ferrocene palladium(II) chloride (27.9 mg, 0.043 mmol) was added and the mixture was slowly warmed to room temperature and stirred for 1 h. The mixture was heated at 60° C. overnight, then was cooled to room temperature and filtered through a pad of CELITE®. The filtrate was diluted with DCM, washed sequentially with saturated aqueous NaHCO$_3$ and water, and dried and concentrated. The residue was subjected to column chromatography on silica gel, eluting with EtOAc-hexanes (gradient from 0-50%), to provide 4-((2-chloropyridin-4-yl)methyl)-5-fluoro-2,3-dimethyl-1-((2-(trimethylsilyl)ethoxy)methyl)-1H-indole-7-carbonitrile as a yellow glassy solid (168.5 mg, 75% yield). Mass spectrum m/z 444, 446 (M+H)$^+$.

Example 185B: 4-((2-Chloropyridin-4-yl)methyl)-5-fluoro-2,3-dimethyl-1H-indole-7-carbonitrile

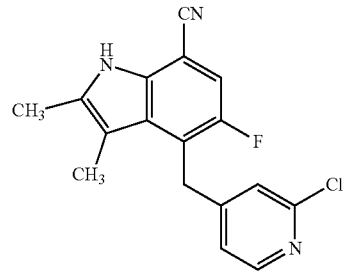

(185B)

A mixture of 4-((2-chloropyridin-4-yl)methyl)-5-fluoro-2,3-dimethyl-1-((2-(trimethylsilyl)ethoxy)methyl)-1H-indole-7-carbonitrile (130 mg, 0.293 mmol) and tetra-n-butylammonium fluoride (1 M in THF) (2.93 mL, 2.93 mmol) in THF (1 mL) was stirred at 70° C. for 3 h. The mixture was diluted with EtOAc, washed twice with saturated aqueous NaHCO$_3$, dried and concentrated. The residue was subjected to column chromatography on silica gel, eluting with EtOAc-hexanes (gradient from 0-100%) to provide 4-((2-chloropyridin-4-yl)methyl)-5-fluoro-2,3-dimethyl-1H-indole-7-carbonitrile as a yellow solid (38 mg, 29% yield). Mass spectrum m/z 314, 316 (M+H)$^+$.

Example 185C: 4-((2-Chloropyridin-4-yl)methyl)-5-fluoro-2,3-dimethyl-1H-indole-7-carboxamide, TFA Salt

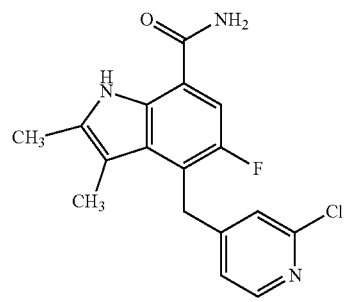

(185C)

A mixture of 4-((2-chloropyridin-4-yl)methyl)-5-fluoro-2,3-dimethyl-1H-indole-7-carbonitrile (45 mg, 0.143 mmol), chlorotrimethylsilane (2.5 mL, 19.6 mmol) and water (1 mL, 55.5 mmol) was stirred at room temperature overnight. The top layer was removed by decantation and the lower aqueous layer was concentrated. The residue was purified using preparative reverse-phase HPLC to provide 4-((2-chloropyridin-4-yl)methyl)-5-fluoro-2,3-dimethyl-1H-indole-7-carboxamide, TFA salt, as a white solid (18.7 mg, 29% yield). Mass spectrum m/z 332, 334 (M+H)$^+$. $^1$H NMR (400 MHz, MeOH-d$_4$) δ 8.21 (d, J=5.1 Hz, 1H), 7.41 (d, J=11.0 Hz, 1H), 7.17-7.07 (m, 2H), 4.51 (s, 2H), 2.37 (s, 3H), 2.19 (s, 3H).

Example 185

Following the procedure used to convert Example 181C to Example 181D, 4-((2-chloropyridin-4-yl)methyl)-5-fluoro-2,3-dimethyl-1H-indole-7-carboxamide, TFA salt, was converted into 5-fluoro-2,3-dimethyl-4-((2-vinylpyridin-4-yl)methyl)-1H-indole-7-carboxamide in 74% yield. Mass spectrum m/z 324 (M+H)$^+$. $^1$H NMR (400 MHz, MeOH-d$_4$) δ 8.31 (d, J=5.3 Hz, 1H), 7.41 (d, J=10.9 Hz, 1H), 7.27 (s, 1H), 6.98 (dd, J=5.3, 1.1 Hz, 1H), 6.74 (dd, J=17.6, 11.0 Hz, 1H), 6.05 (dd, J=17.6, 1.1 Hz, 1H), 5.45 (dd, J=11.0, 1.0 Hz, 1H), 4.51 (s, 2H), 2.36 (s, 3H), 2.19 (d, J=0.2 Hz, 3H).

Additional Examples which were prepared by procedures described above, using the starting material(s) and procedures indicated, are shown in Table 9.

TABLE 9

| Example | Structure | Starting Materials | Procedures | Mass Spectrum |
|---|---|---|---|---|
| 186 (racemic) | 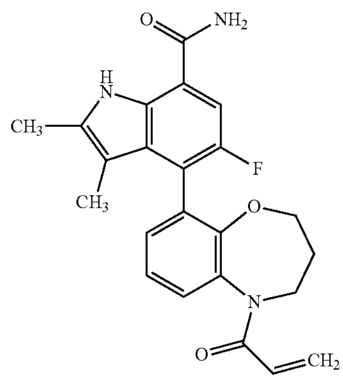 [SMILES: C=CC(=O)N1CCCOc2c(-c3c(F)cc(C(N)=O)c4[nH]c(C)c(C)c34)cccc21] | Intermediate 84 | (a) | m/z 408 (M + H)$^+$ |
| 187 single enantiomer (peak 1) | 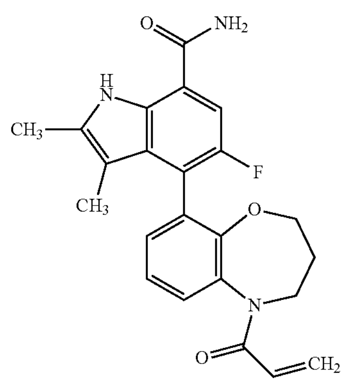 [SMILES: C=CC(=O)N1CCCOc2c(-c3c(F)cc(C(N)=O)c4[nH]c(C)c(C)c34)cccc21] | Example 186 | (b) | m/z 408 (M + H)$^+$ |
| 188 single enantiomer (peak 2) | 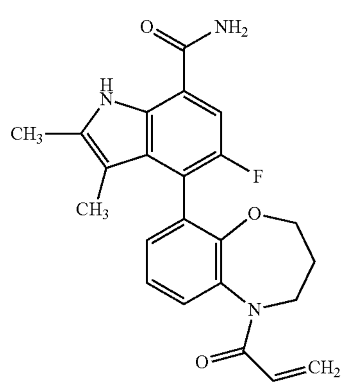 [SMILES: C=CC(=O)N1CCCOc2c(-c3c(F)cc(C(N)=O)c4[nH]c(C)c(C)c34)cccc21] | Example 186 | (b) | m/z 408 (M + H)$^+$ |

TABLE 9-continued

| Example | Structure | Starting Materials | Procedures | Mass Spectrum |
|---|---|---|---|---|
| 189 (racemic) | 2-methyl-3-methyl-4-(5-fluoro-7-fluoro-2-acryloyl-1,2,3,4-tetrahydroisoquinolin-5-yl)-1H-indole-7-carboxamide | Intermediate 85 | (a) | m/z 410 (M + H)+ |
| 190 single enantiomer (peak 1) | 2-methyl-3-methyl-4-(5-fluoro-7-fluoro-2-acryloyl-1,2,3,4-tetrahydroisoquinolin-5-yl)-1H-indole-7-carboxamide | Example 189 | (b) | m/z 410 (M + H)+ |
| 191 single enantiomer (peak 2) | 2-methyl-3-methyl-4-(5-fluoro-7-fluoro-2-acryloyl-1,2,3,4-tetrahydroisoquinolin-5-yl)-1H-indole-7-carboxamide | Example 189 | (b) | m/z 410 (M + H)+ |
| 192 | 2-methyl-3-methyl-4-(5-fluoro-2-acryloyl-1,2,3,4-tetrahydroisoquinolin-6-yl)-1H-indole-7-carboxamide | Intermediate 86 | (a) | m/z 392 (M + H)+ |

TABLE 9-continued
| Example | Structure | Starting Materials | Procedures | Mass Spectrum |
|---|---|---|---|---|
| 193 racemic | 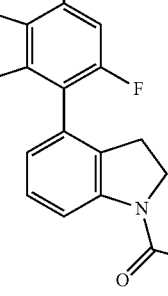 | Intermediate 87 | (a) | m/z 378 (M + H)+ |
| 194 racemic | 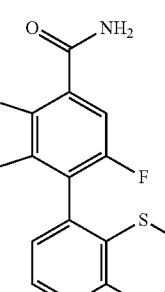 | Intermediate 88 | (a) | m/z 410 (M + H)+ |
| 195 single enantiomer (peak 1) | 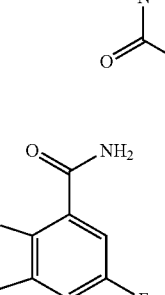 | Example 194 | (b) | m/z 410 (M + H)+ |
| 196 single enantiomer (peak 2) | 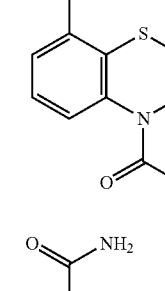 | Example 194 | (b) | m/z 410 (M + H)+ |

TABLE 9-continued

| Example | Structure | Starting Materials | Procedures | Mass Spectrum |
|---|---|---|---|---|
| 197 racemic | 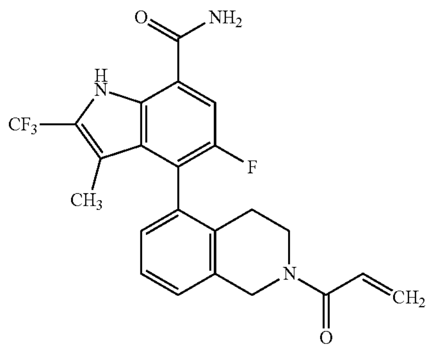 [SMILES: C=CC(=O)N1CCc2c(cccc2-c2c(F)cc(C(N)=O)c3[nH]c(C(F)(F)F)c(C)c23)C1] | Intermediate 92 | (a) | m/z 446 (M + H)+ |
| 198 single enantiomer (peak 1) | 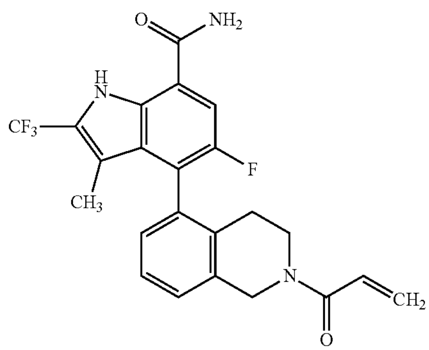 [SMILES: C=CC(=O)N1CCc2c(cccc2-c2c(F)cc(C(N)=O)c3[nH]c(C(F)(F)F)c(C)c23)C1] | Example 197 | (b) | m/z 446 (M + H)+ |
| 199 single enantiomer (peak 2) | 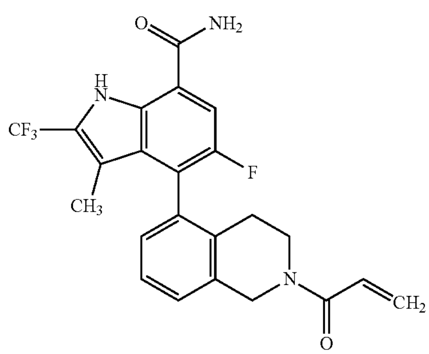 [SMILES: C=CC(=O)N1CCc2c(cccc2-c2c(F)cc(C(N)=O)c3[nH]c(C(F)(F)F)c(C)c23)C1] | Example 197 | (b) | m/z 446 (M + H)+ |
| 200 | 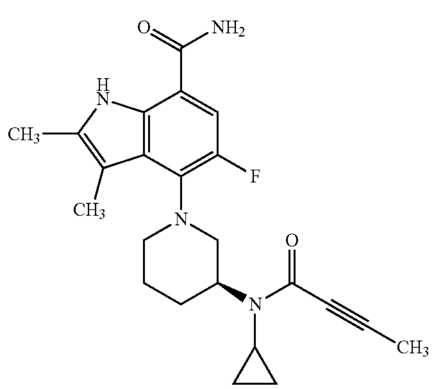 [SMILES: CC#CC(=O)N(C1CC1)[C@H]1CCCN(c2c(F)cc(C(N)=O)c3[nH]c(C)c(C)c23)C1] | Intermediate 89 | (c) | m/z 411 (M + H)+ |

TABLE 9-continued

| Example | Structure | Starting Materials | Procedures | Mass Spectrum |
|---|---|---|---|---|
| 201 | 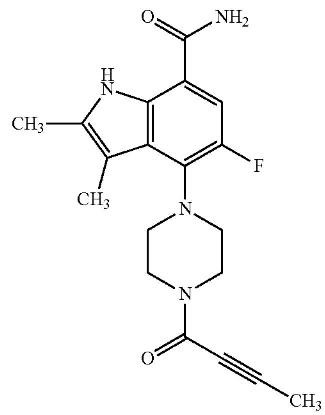 [SMILES: CC#CC(=O)N1CCN(c2c(F)cc(C(N)=O)c3[nH]c(C)c(C)c23)CC1] | Intermediate 90 | (c) | m/z 357 (M + H)+ |
| 202 | 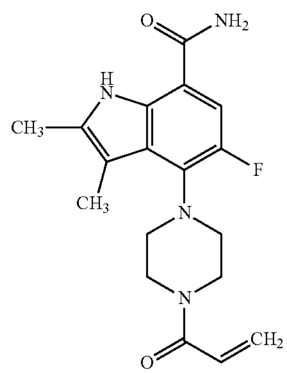 [SMILES: C=CC(=O)N1CCN(c2c(F)cc(C(N)=O)c3[nH]c(C)c(C)c23)CC1] | Intermediate 90 | (a) | m/z 345 (M + H)+ |
| 203 | 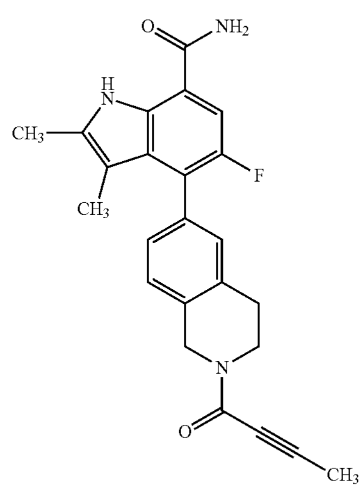 [SMILES: CC#CC(=O)N1CCc2cc(-c3c(F)cc(C(N)=O)c4[nH]c(C)c(C)c34)ccc2C1] | Intermediate 86 | (c) | m/z 404 (M + H)+ |
| 204 racemic | 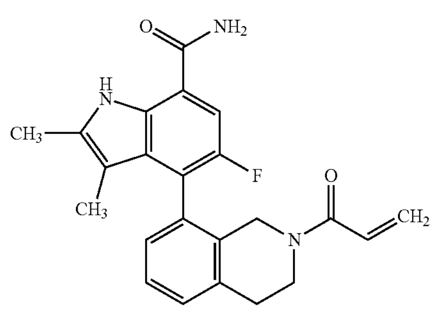 [SMILES: C=CC(=O)N1CCc2cccc(-c3c(F)cc(C(N)=O)c4[nH]c(C)c(C)c34)c2C1] | Intermediate 93 | (a) | m/z 392 (M + H)+ |

TABLE 9-continued

| Example | Structure | Starting Materials | Procedures | Mass Spectrum |
|---|---|---|---|---|
| 205 single enantiomer (peak 1) | 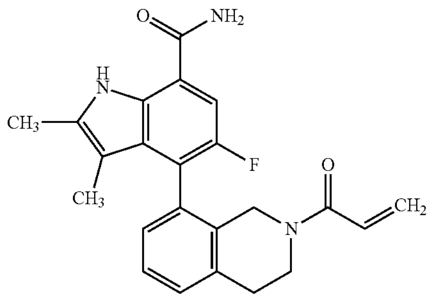 [SMILES: C=CC(=O)N1CCc2cccc(-c3c(F)cc(C(N)=O)c4[nH]c(C)c(C)c34)c2C1] | Example 204 | (b) | m/z 392 (M + H)+ |
| 206 single enantiomer (peak 2) | 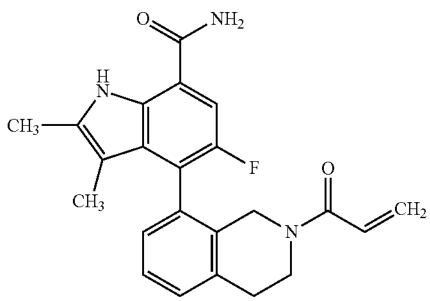 [SMILES: C=CC(=O)N1CCc2cccc(-c3c(F)cc(C(N)=O)c4[nH]c(C)c(C)c34)c2C1] | Example 204 | (b) | m/z 392 (M + H)+ |
| 207 | 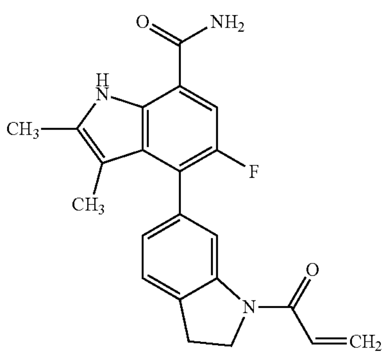 [SMILES: C=CC(=O)N1CCc2ccc(-c3c(F)cc(C(N)=O)c4[nH]c(C)c(C)c34)cc21] | Intermediate 94 | (a) | m/z 378 (M + H)+ |
| 208 | 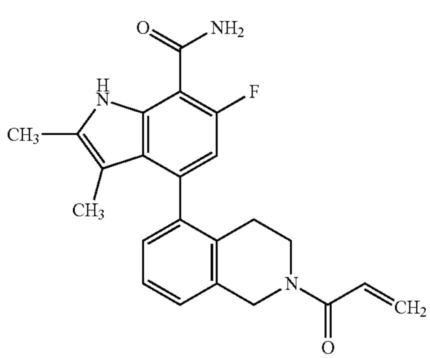 [SMILES: C=CC(=O)N1CCc2c(cccc2-c2cc(F)c(C(N)=O)c3[nH]c(C)c(C)c23)C1] | Intermediate 96 | (a) | m/z 392 (M + H)+ |

TABLE 9-continued

| Example | Structure | Starting Materials | Procedures | Mass Spectrum |
|---|---|---|---|---|
| 209 racemic | 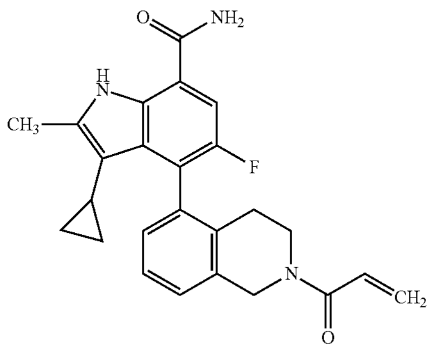 [SMILES: C=CC(=O)N1CCc2c(cccc2-c2c(F)cc(C(N)=O)c3[nH]c(C)c(C4CC4)c23)C1] | Intermediate 98 | (a) | m/z 418 (M + H)+ |
| 210 single enantiomer (peak 1) | 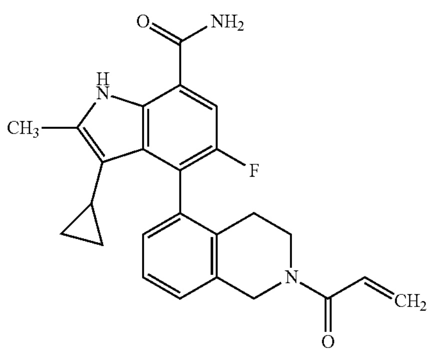 [SMILES: C=CC(=O)N1CCc2c(cccc2-c2c(F)cc(C(N)=O)c3[nH]c(C)c(C4CC4)c23)C1] | Example 209 | (b) | m/z 418 (M + H)+ |
| 211 single enantiomer (peak 1) | 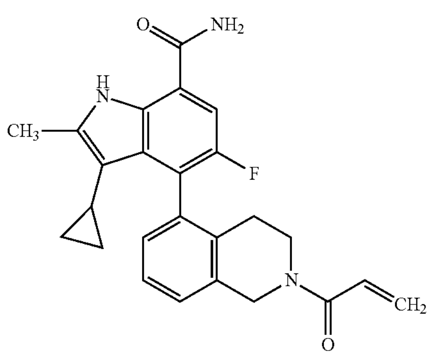 [SMILES: C=CC(=O)N1CCc2c(cccc2-c2c(F)cc(C(N)=O)c3[nH]c(C)c(C4CC4)c23)C1] | Example 209 | (b) | m/z 418 (M + H)+ |
| 212 racemic | 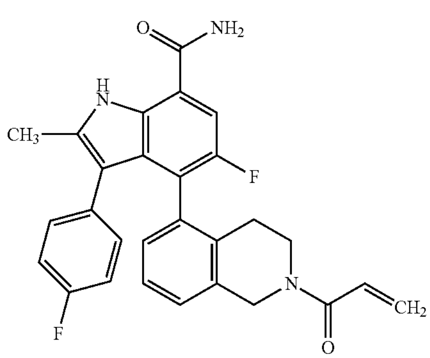 [SMILES: C=CC(=O)N1CCc2c(cccc2-c2c(F)cc(C(N)=O)c3[nH]c(C)c(-c4ccc(F)cc4)c23)C1] | Intermediate 100 | (a) | m/z 472 (M + H)+ |

TABLE 9-continued

| Example | Structure | Starting Materials | Procedures | Mass Spectrum |
|---|---|---|---|---|
| 213 single enantiomer (peak 1) | 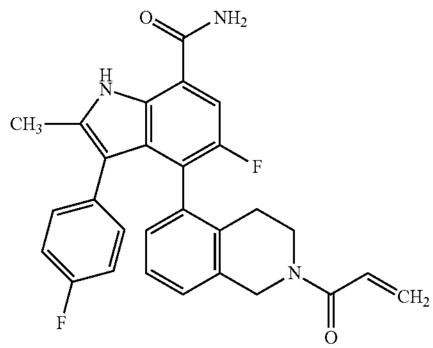 [SMILES: C=CC(=O)N1CCc2c(cccc2-c2c(F)cc(C(N)=O)c3[nH]c(C)c(-c4ccc(F)cc4)c23)C1] | Example 212 | (b) | m/z 472 (M + H)+ |
| 214 single enantiomer (peak 2) | 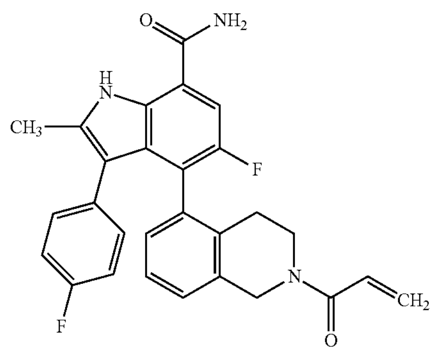 [SMILES: C=CC(=O)N1CCc2c(cccc2-c2c(F)cc(C(N)=O)c3[nH]c(C)c(-c4ccc(F)cc4)c23)C1] | Example 212 | (b) | m/z 472 (M + H)+ |
| 215 racemic | 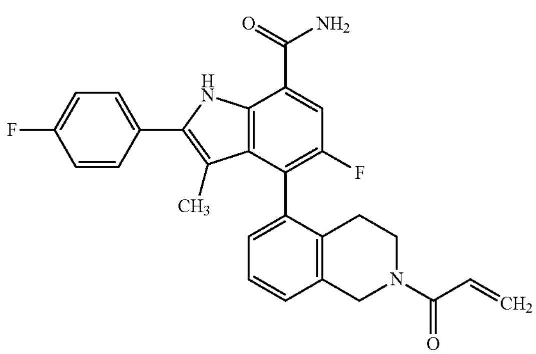 [SMILES: C=CC(=O)N1CCc2c(cccc2-c2c(F)cc(C(N)=O)c3[nH]c(-c4ccc(F)cc4)c(C)c23)C1] | Intermediate 102 | (a) | m/z 472 (M + H)+ |
| 216 | 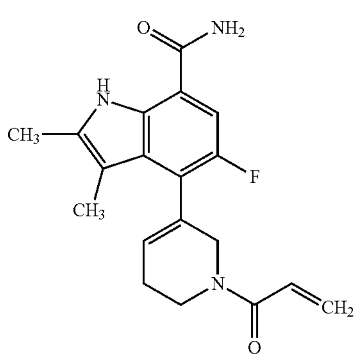 [SMILES: C=CC(=O)N1CCC=C(c2c(F)cc(C(N)=O)c3[nH]c(C)c(C)c23)C1] | Intermediate 103 | (a) | m/z 342 (M + H)+ |

TABLE 9-continued

| Example | Structure | Starting Materials | Procedures | Mass Spectrum |
|---|---|---|---|---|
| 217 racemic | (indole with 2-CH₃, 3-CH₃, 5-F, 7-carboxamide, 4-(1-acryloylpiperidin-3-yl)) | Intermediate 104 | (a) | m/z 344 (M + H)⁺ |
| 218 single enantiomer (peak 1) | (same as 217) | Example 217 | (b) | m/z 344 (M + H)⁺ |
| 219 single enantiomer (peak 2) | (same as 217) | Example 217 | (b) | m/z 344 (M + H)⁺ |
| 220 racemic | (indole with 2-CH₃, 3-CH₃, 5-F, 7-carboxamide, 4-(1-(but-2-ynoyl)piperidin-3-yl)) | Intermediate 104 | (c) | m/z 356 (M + H)⁺ |

(a) Prepared following the procedure used to prepare Example 78 or similar procedures.
(b) Prepared by super-critical fluid chromatography of the racemic compound. Absolute configuration was not assigned.
(c) Prepared following the procedure used to prepare Example 103 or similar procedures.

Example 221

5-Fluoro-2,3-dimethyl-4-((6-vinylpyridin-2-yl)methyl)-1H-indole-7-carboxamide

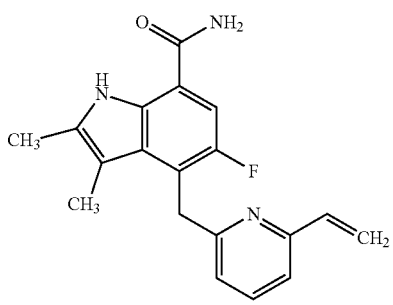

(221)

Example 221A: 5-Fluoro-2,3-dimethyl-4-(4,4,5,5-tetramethyl-1,3,2-dioxaborolan-2-yl)-1-((2-(trimethylsilyl)ethoxy)methyl)-1H-indole-7-carbonitrile

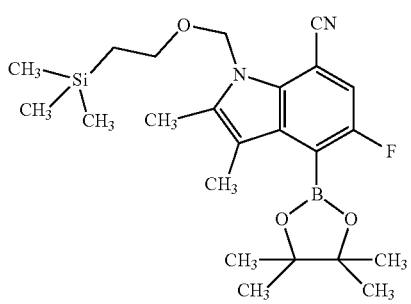

(221A)

Following the procedure used to prepare Intermediate 9, 4-bromo-5-fluoro-2,3-dimethyl-1-((2-(trimethylsilyl)ethoxy)methyl)-1H-indole-7-carbonitrile [Example 181A] was converted into 5-fluoro-2,3-dimethyl-4-(4,4,5,5-tetramethyl-1,3,2-dioxaborolan-2-yl)-1-((2-(trimethylsilyl)ethoxy)methyl)-1H-indole-7-carbonitrile as a white solid in 45% yield. Mass spectrum m/z 445 (M+H)⁺. ¹H NMR (400 MHz, CDCl₃) δ 7.15 (d, J=8.6 Hz, 1H), 5.76 (s, 2H), 3.58 (dd, J=8.6, 7.6 Hz, 2H), 2.41 (s, 3H), 2.26 (s, 3H), 1.45 (s, 12H), 0.95-0.88 (m, 2H), −0.03 (s, 9H).

Example 221B: 4-((6-Chloropyridin-2-yl)methyl)-5-fluoro-2,3-dimethyl-1-((2-(trimethylsilyl)ethoxy)methyl)-1H-indole-7-carbonitrile

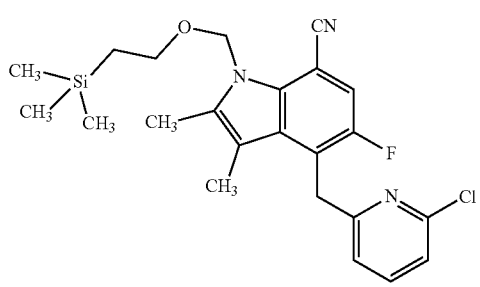

(221B)

A mixture of 2-(bromomethyl)-6-chloropyridine hydrochloride (19.1 mg, 0.079 mmol), 5-fluoro-2,3-dimethyl-4-(4,4,5,5-tetramethyl-1,3,2-dioxaborolan-2-yl)-1-((2-(trimethylsilyl)ethoxy)methyl)-1H-indole-7-carbonitrile (35 mg, 0.079 mmol), 1,1'-bis(di-tert-butylphosphino)ferrocene palladium dichloride (2.6 mg, 3.94 μmol) and K₃PO₄ (67 mg, 0.315 mmol) in THF (300 μL) and water (150 μL) was stirred at room temperature under nitrogen. After 18 h, the mixture was diluted with EtOAc (2 mL), dried and concentrated. The residue was subjected to column chromatography on silica gel, eluting with EtOAc-hexanes (gradient from 0-30%) to provide 4-((6-chloropyridin-2-yl)methyl)-5-fluoro-2,3-dimethyl-1-((2-(trimethylsilyl)ethoxy)methyl)-1H-indole-7-carbonitrile as a colorless gum (29 mg, 79% yield). Mass spectrum m/z 444, 446 (M+H)⁺. ¹H NMR (400 MHz, CDCl₃) δ 7.47 (t, J=7.8 Hz, 1H), 7.29-7.24 (m, 1H), 7.16 (dd, J=7.9, 0.6 Hz, 1H), 6.73 (d, J=7.6 Hz, 1H), 5.76 (s, 2H), 4.62 (d, J=1.3 Hz, 2H), 3.69-3.62 (m, 2H), 2.38 (s, 3H), 2.25 (s, 3H), 1.00-0.91 (m, 2H), −0.02 (s, 9H).

Example 221C: 5-Fluoro-2,3-dimethyl-1-((2-(trimethylsilyl)ethoxy)methyl)-4-((6-vinylpyridin-2-yl)methyl)-1H-indole-7-carbonitrile

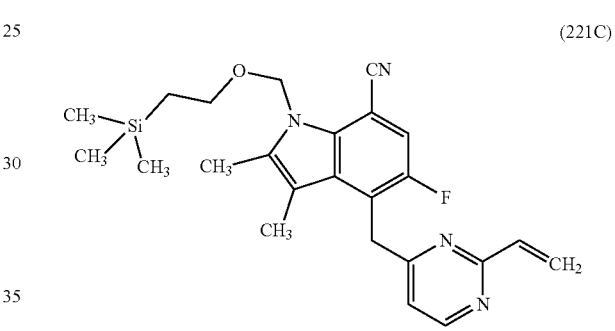

(221C)

Following the procedure used to convert Example 181C to Example 181D, 4-((6-chloropyridin-2-yl)methyl)-5-fluoro-2,3-dimethyl-1-((2-(trimethylsilyl)ethoxy)methyl)-1H-indole-7-carbonitrile was converted into 5-fluoro-2,3-dimethyl-1-((2-(trimethylsilyl)ethoxy)methyl)-4-((6-vinylpyridin-2-yl)methyl)-1H-indole-7-carbonitrile as a colorless gum in 74% yield. Mass spectrum m/z 436 (M+H)⁺. ¹H NMR (400 MHz, CDCl₃) δ 7.49 (t, J=7.8 Hz, 1H), 7.31-7.24 (m, 1H), 7.17 (d, J=7.6 Hz, 1H), 6.82 (dd, J=17.5, 10.8 Hz, 1H), 6.76 (d, J=7.8 Hz, 1H), 6.19 (dd, J=17.5, 1.5 Hz, 1H), 5.78 (s, 2H), 5.47 (dd, J=10.8, 1.3 Hz, 1H), 4.65 (d, J=1.7 Hz, 2H), 3.71-3.61 (m, 2H), 2.40 (s, 3H), 2.33 (s, 3H), 1.03-0.92 (m, 2H), −0.01 (s, 9H).

Example 221D: 5-Fluoro-2,3-dimethyl-4-((6-vinylpyridin-2-yl)methyl)-1H-indole-7-carbonitrile

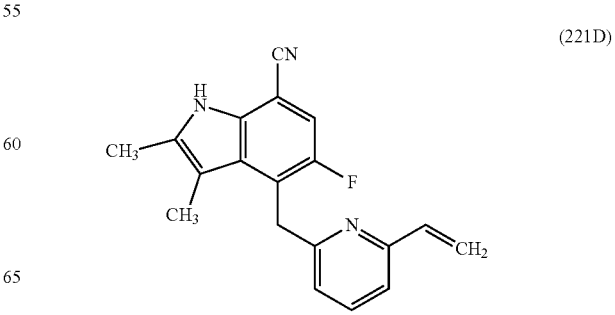

(221D)

Following the procedure used to convert Example 181B to Example 181C, 5-fluoro-2,3-dimethyl-1-((2-(trimethylsilyl)ethoxy)methyl)-4-((6-vinylpyridin-2-yl)methyl)-1H-indole-7-carbonitrile was converted into 5-fluoro-2,3-dimethyl-4-((6-vinylpyridin-2-yl)methyl)-1H-indole-7-carbonitrile as a white solid in 49% yield. Mass spectrum m/z 306 (M+H)$^+$.

Example 221

Following the procedure used to convert Example 181D to Example 181, 5-fluoro-2,3-dimethyl-4-((6-vinylpyridin-2-yl)methyl)-1H-indole-7-carbonitrile was converted into 5-fluoro-2,3-dimethyl-4-((6-vinylpyridin-2-yl)methyl)-1H-indole-7-carboxamide as a white powder in 30% yield. Mass spectrum m/z 324 (M+H)$^+$. $^1$H NMR (400 MHz, CDCl$_3$) δ 9.94 (br. s., 1H), 7.47 (t, J=7.8 Hz, 1H), 7.17 (d, J=7.7 Hz, 1H), 7.10 (d, J=10.4 Hz, 1H), 6.85 (dd, J=17.5, 10.9 Hz, 1H), 6.78 (d, J=7.8 Hz, 1H), 6.22 (dd, J=17.5, 1.3 Hz, 1H), 5.49 (dd, J=10.8, 1.3 Hz, 1H), 4.67 (d, J=1.6 Hz, 2H), 2.37 (s, 3H), 2.30 (s, 3H).

Example 222

5-Fluoro-4-((5-fluoro-6-vinylpyridin-3-yl)methyl)-2,3-dimethyl-1H-indole-7-carboxamide

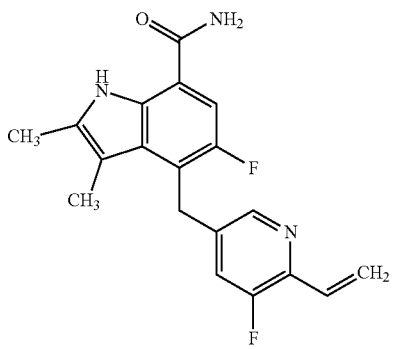

(222)

Example 222A: 4-((6-Chloro-5-fluoropyridin-3-yl)methyl)-5-fluoro-2,3-dimethyl-1H-indole-7-carboxamide

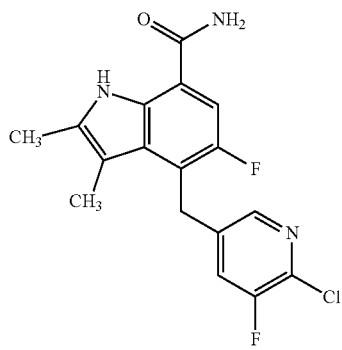

(222A)

Following the procedure used to convert Example 221A into Example 221B, 5-fluoro-2,3-dimethyl-4-(4,4,5,5-tetramethyl-1,3,2-dioxaborolan-2-yl)-1H-indole-7-carboxamide [Intermediate 83] and 5-(bromomethyl)-2-chloro-3-fluoropyridine [prepared according to the procedure of U.S. Pat. No. 8,188,292, Example VII step 1] were converted into 4-((6-chloro-5-fluoropyridin-3-yl)methyl)-5-fluoro-2,3-dimethyl-1H-indole-7-carboxamide as a colorless gum in 60% yield. Mass spectrum m/z 350, 352 (M+H)$^+$.

Example 222

Following the procedure used to convert Example 181C to Example 181D, 4-((6-chloro-5-fluoropyridin-3-yl)methyl)-5-fluoro-2,3-dimethyl-1H-indole-7-carboxamide was converted into 5-fluoro-4-((5-fluoro-6-vinylpyridin-3-yl)methyl)-2,3-dimethyl-1H-indole-7-carboxamide as a white powder in 22% yield. Mass spectrum m/z 342 (M+H)$^+$. $^1$H NMR (400 MHz, CDCl$_3$) δ 8.18 (s, 1H), 7.43 (d, J=11.0 Hz, 1H), 7.20 (d, J=11.2 Hz, 1H), 6.94 (ddd, J=17.5, 11.2, 1.1 Hz, 1H), 6.29 (dd, J=17.5, 1.7 Hz, 1H), 5.57 (dd, J=11.2, 1.5 Hz, 1H), 4.54 (s, 2H), 2.39 (s, 3H), 2.26 (s, 3H).

Example 223

(S)-4-(3-(But-2-ynamido)piperidin-1-yl)-5-fluoro-2,3-dimethyl-1H-indole-7-carboxamide

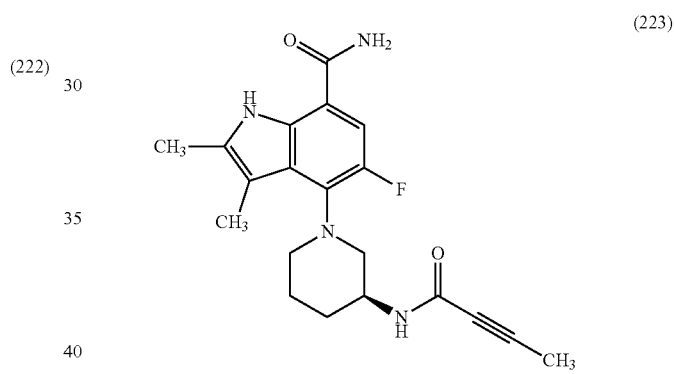

(223)

Intermediate 223A: 4-Bromo-5-fluoro-2,3-dimethyl-1H-indole-7-carbonitrile

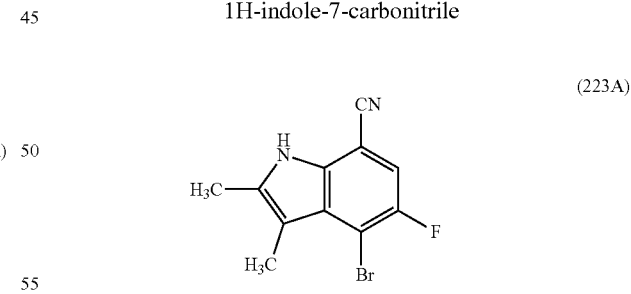

(223A)

To a homogeneous solution of 4-bromo-5-fluoro-2,3-dimethyl-1H-indole-7-carboxamide (3.43 g, 12.0 mmol) in tetrahydrofuran (25 mL) at room temperature was added phosphoryl trichloride (2.24 mL, 24.1 mmol) dropwise via syringe. The reaction mixture was stirred for 3.5 days. The heterogeneous reaction mixture was concentrated under reduced pressure. The residue was diluted with ethyl acetate, and the resulting solid was collected by vacuum filtration, washed with ethyl acetate, and dried to give 4-bromo-5-fluoro-2,3-dimethyl-1H-indole-7-carbonitrile (2.56 g, 9.58 mmol, 80% yield) as a yellow solid. The product had a UPLC ret. time=1.31 min.—Column: PHENOMENEX® Kinetex C18 2.1×50 mm (1.5 min. gradient); Solvent A=10% AcCN, 90% H₂O, 0.1% TFA; Solvent B=90% AcCN, 10% H₂O, 0.1% TFA. LC/MS M+1=268.2.

Intermediate 223B: (S)-Benzyl (1-(7-cyano-5-fluoro-2,3-dimethyl-1H-indol-4-yl) piperidin-3-yl) carbamate

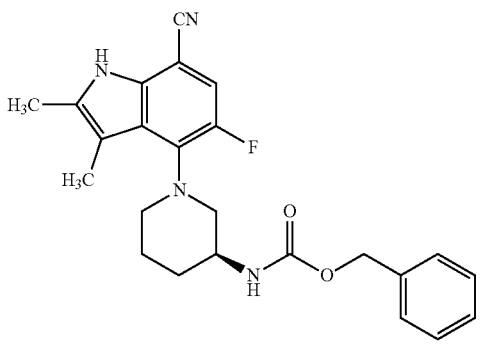

(223B)

A mixture of 4-bromo-5-fluoro-2,3-dimethyl-1H-indole-7-carbonitrile (2.37 g, 8.86 mmol), (S)-benzyl piperidin-3-ylcarbamate (2.49 g, 10.6 mmol), and (S)-benzyl piperidin-3-ylcarbamate (2.49 g, 10.6 mmol) in dioxane (50 mL) was degassed with vacuum and nitrogen (3×). BINAP (0.276 g, 0.443 mmol) was added followed by Pd₂(dba)₃ (0.405 g, 0.443 mmol), and the mixture was degassed (3×). The reaction mixture was immersed in an oil bath at 103° C. and stirred for ~36 h. After cooling to room temperature, the reaction mixture was diluted with ethyl acetate, washed with water, and washed with brine. The organic layer was collected, and the aqueous layers were sequentially extracted with ethyl acetate (2×). The combined organic layers were dried over anhydrous sodium sulfate and concentrated under reduced pressure. The residue was purified by flash silica gel chromatography using a mixture of ethyl acetate in hexane to give (S)-benzyl (1-(7-cyano-5-fluoro-2,3-dimethyl-1H-indol-4-yl)piperidin-3-yl)carbamate (1.08 g, 2.57 mmol, 29% yield) as a pale yellow solid. The product had a UPLC ret. time=1.40 min.—Column: PHENOMENEX® Kinetex C18 2.1×50 mm (1.5 min. gradient); Solvent A=10% MeCN, 90% H₂O, 0.1% TFA; Solvent B=90% MeCN, 10% H₂O, 0.1% TFA. LC/MS M+1=421.5.

Intermediate 223C: (S)-4-(3-Aminopiperidin-1-yl)-5-fluoro-2,3-dimethyl-1H-indole-7-carboxamide

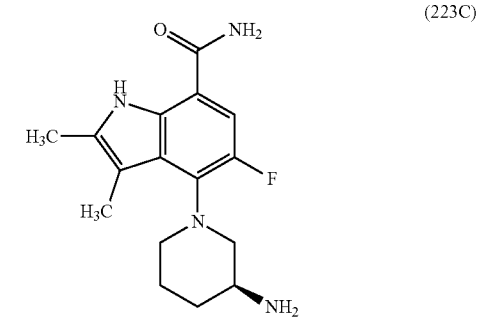 [SMILES: Cc1[nH]c2c(C(N)=O)cc(F)c(N3CCC[C@H](N)C3)c2c1C]

(223C)

A mixture of (S)-benzyl (1-(7-cyano-5-fluoro-2,3-dimethyl-1H-indol-4-yl) piperidin-3-yl)carbamate (1.00 g, 2.38 mmol) and 90% aqueous sulfuric acid (14.1 ml, 238 mmol) was immersed in an oil bath at 60° C. and stirred for 60 min. To the reaction mixture, cooled to 0° C., was added sodium hydroxide (10M) (47.6 ml, 476 mmol) dropwise with stirring. A few additional drops of the sodium hydroxide solution was added until the pH was ~7. The mixture was extracted with ethyl acetate, resulting in a suspension. The mixture was filtered under reduced pressure, and the solid was washed well with water. Drying under reduced pressure provided (S)-4-(3-aminopiperidin-1-yl)-5-fluoro-2,3-dimethyl-1H-indole-7-carboxamide (0.724 g, 2.37 mmol, 99% yield) as a tan solid. The product had a UPLC ret. time=0.767 min.—Column: PHENOMENEX® Kinetex C18 2.1×50 mm (1.5 min. gradient); Solvent A=10% AcCN, 90% H₂O, 0.1% TFA; Solvent B=90% AcCN, 10% H₂O, 0.1% TFA. LC/MS M+1=305.2.

Example 223

A mixture of (S)-4-(3-aminopiperidin-1-yl)-5-fluoro-2,3-dimethyl-1H-indole-7-carboxamide (0.171 g, 0.562 mmol), but-2-ynoic acid (0.094 g, 1.124 mmol), HATU (0.470 g, 1.24 mmol), and Hunig's Base (0.343 mL, 1.97 mmol) in N,N-dimethylformamide (5.0 mL) was stirred at room temperature for 60 min. HPLC analysis indicated that the reaction was complete. The mixture was diluted with ethyl acetate, washed with water, washed with 10% aqueous lithium chloride (2×), washed with brine and dried over anhydrous sodium sulfate. Concentration under reduced pressure followed by purification by flash silica gel chromatography using a mixture of ethyl acetate in hexane afforded (S)-4-(3-(but-2-ynamido)piperidin-1-yl)-5-fluoro-2,3-dimethyl-1H-indole-7-carboxamide (0.130 g, 0.351 mmol, 63% yield) as a white solid. The product had a UPLC ret. time=1.00 min.—Column: PHENOMENEX® Kinetex C18 2.1×50 mm (1.5 min. gradient); Solvent A=10% MeCN, 90% H₂O, 0.1% TFA; Solvent B=90% MeCN, 10% H₂O, 0.1% TFA. LC/MS M+1=371.4. ¹H NMR (500 MHz, DMSO-d₆) δ 10.61 (s, 1H), 8.46 (d, J=6.3 Hz, 1H), 7.90 (br. s., 1H), 7.42-7.37 (m, 1H), 7.31 (br. s., 1H), 3.96-3.84 (m, 1H), 3.13 (d, J=7.6 Hz, 1H), 3.05-2.93 (m, 2H), 2.80 (br. s., 1H), 2.36 (s, 3H), 2.33-2.29 (m, 3H), 1.93 (s, 3H), 1.87 (d, J=8.5 Hz, 1H), 1.71 (br. s., 2H), and 1.32 (br. s., 1H).

Alternative Preparation of Example 223

Intermediate 223D: 4-Bromo-5-fluoro-2,3-dimethyl-1H-indole-7-carbonitrile

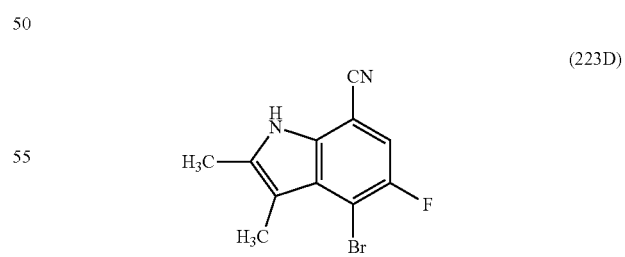

(223D)

To a 100 mL 3-neck flask was added 4-bromo-5-fluoro-2,3-dimethyl-1H-indole-7-carboxamide (40.4 g, 142 mmol) and dichloromethane (810 mL). To the resulting heterogeneous mixture was added pyridine (50 g, 2.5 eq) and phosphoryl trichloride (19.8 ml, 213 mmol) dropwise at room temperature over 2 minutes. The reaction mixture was stirred for 20 min. The solvent was removed under reduced pressure, water was added to the residue, and the mixture was stirred for 30 min. The precipitate was collected by filtration and dried to give 4-bromo-5-fluoro-2,3-dimethyl-1H-indole-7-carbonitrile (35 g, 131 mmol, 92% yield) as a tan solid.

Intermediate 223E: (S)-tert-Butyl (1-(7-cyano-5-fluoro-2,3-dimethyl-1H-indol-4-yl) piperidin-3-yl) carbamate

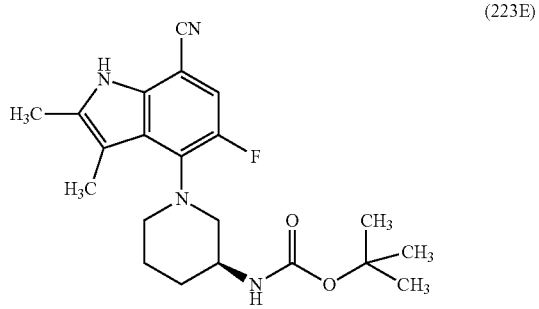 [SMILES: Cc1[nH]c2c(C#N)cc(F)c(N3CCC[C@H](NC(=O)OC(C)(C)C)C3)c2c1C]

(223E)

A mixture of (S)-tert-butyl piperidin-3-ylcarbamate (33.9 g, 169 mmol), 4-bromo-5-fluoro-2,3-dimethyl-1H-indole-7-carbonitrile (41.13 g, 154 mmol), cesium carbonate (100 g, 308 mmol), and BINAP (9.59 g, 15.40 mmol) in 1,4-dioxane (1380 ml) was degassed by bubbling nitrogen for 5 min. To the mixture was added Pd$_2$(dba)$_3$ (7.05 g, 7.70 mmol), and the reaction mixture was stirred at reflux for 24 h. The reaction mixture was diluted with ethyl acetate (750 mL) and washed with water (1000 mL), washed with brine (100 mL), and dried over anhydrous sodium sulfate. Concentration under reduced pressure afforded the crude product as a brown solid, which was passed through a pad (5") of silica gel with ethyl acetate (900 mL) to remove any inorganics. The reddish crude product was then purified by recrystallization from acetonitrile to give two crops of (S)-tert-butyl (1-(7-cyano-5-fluoro-2,3-dimethyl-1H-indol-4-yl)piperidin-3-yl)carbamate (53 g, 108 mmol, 86% yield).

Intermediate 223F: (S)-4-(3-Aminopiperidin-1-yl)-5-fluoro-2,3-dimethyl-1H-indole-7-carboxamide

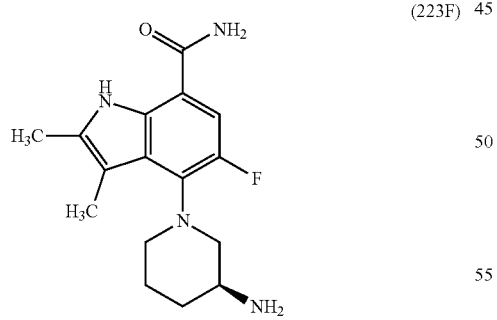

(223F)

To a 100 mL 3-neck flask was added sulfuric acid (90 g). The solution was heated to 60° C. (S)-tert-Butyl (1-(7-cyano-5-fluoro-2,3-dimethyl-1H-indol-4-yl) piperidin-3-yl) carbamate (21 g, 54.3 mmol) was added portionwise over a period of 1.5 h. The reaction mixture was stirred at 60° C. for 1 h. The reaction mixture was added to ice and warmed to room temperature with stirring. The water phase was extracted with dichloromethane (3×) to remove organic impurities. The water phase was adjusted to pH 8, and the solution was extracted with ethyl acetate (2×). The combined organic layers were washed with brine (500 mL), dried over anhydrous sodium sulfate, and concentrated under reduced pressure to give (S)-4-(3-aminopiperidin-1-yl)-5-fluoro-2,3-dimethyl-1H-indole-7-carboxamide (13.6 g, 44.7 mmol, 82% yield) as a yellow solid.

Example 223

To a 500 mL 3-neck flask were added (S)-4-(3-aminopiperidin-1-yl)-5-fluoro-2,3-dimethyl-1H-indole-7-carboxamide (33.2 g, 109 mmol) in N,N-dimethylformamide (364 mL), but-2-ynoic acid (11.9 g, 142 mmol), HATU (62.2 g, 164 mmol), and Hunig's Base (38.1 ml, 218 mmol) (temperature rose to 35° C.). The resulting solution was stirred at room temperature for 1.5 h. The mixture was diluted with ethyl acetate (250 mL) and washed with water (500 mL). The organic phase was separated, and the aqueous layer was extracted with ethyl acetate (2×250 mL) (layer separation was helped by adding small amount of NaCl). The combined organic extracts were washed with water (with small amount of NaCl) (4×500 mL), washed with brine (500 mL), and dried over anhydrous sodium sulfate. Concentration under reduced pressure afforded the crude product, which was purified by recrystallization from ethyl acetate to give (S)-4-(3-(but-2-ynamido)piperidin-1-yl)-5-fluoro-2,3-dimethyl-1H-indole-7-carboxamide (31 g, 83 mmol, 76% yield) as a white solid.

Example 224

4-(2-Acryloyl-1,2,3,4-tetrahydroisoquinolin-5-yl)-5-iodo-2,3-dimethyl-1H-indole-7-carboxamide

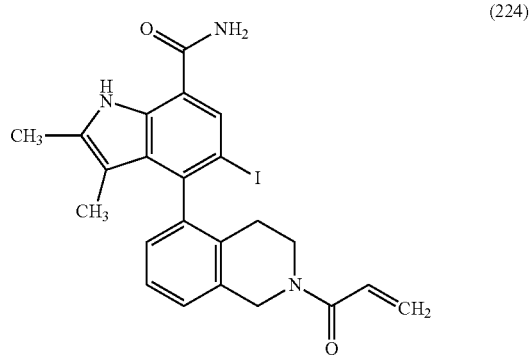 [SMILES: C=CC(=O)N1CCc2c(cccc2-c2c(I)cc(C(N)=O)c3[nH]c(C)c(C)c23)C1]

(224)

Intermediates 224A-1 and 224A-2: Mixture of tert-butyl 5-((2R,3R)-7-carbamoyl-2,3-dimethylindolin-4-yl)-3,4-dihydroisoquinoline-2(1H)-carboxylate and tert-butyl 5-((2R,3S)-7-carbamoyl-2,3-dimethyl-indolin-4-yl)-3,4-dihydroisoquinoline-2(1H)-carboxylate

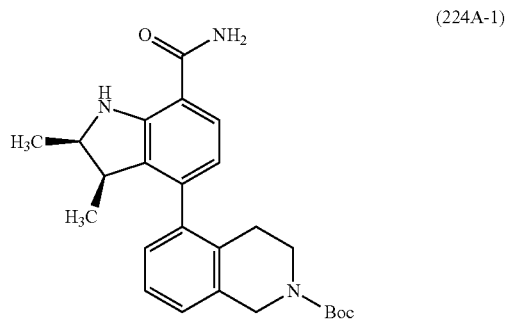

(224A-1)

(224A-2)

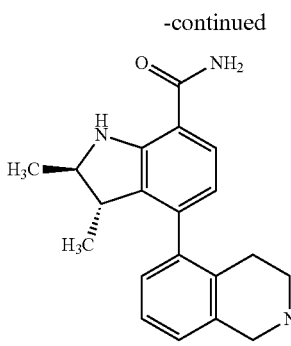

To a solution of tert-butyl 5-(7-carbamoyl-2,3-dimethyl-1H-indol-4-yl)-3,4-dihydroisoquinoline-2(1H)-carboxylate (650 mg, 1.549 mmol) in dichloromethane (20 mL) was added sodium cyanoborohydride (487 mg, 7.75 mmol) and acetic acid (1.77 mL, 31.0 mmol). The resulted mixture was stirred at room temperature for 12 h. Purification by reverse-phase preparative HPLC afforded tert-butyl 5-((2R,3R)-7-carbamoyl-2,3-dimethylindolin-4-yl)-3,4-dihydroisoquinoline-2(1H)-carboxylate (350 mg, 53.6% yield) and tert-butyl 5-((2R,3S)-7-carbamoyl-2,3-dimethylindolin-4-yl)-3,4-dihydroisoquinoline-2(1H)-carboxylate (250 mg, 38.3% yield) as white solids.

The cis product had a UPLC ret. time=1.17 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. MS (E+) m/z: 546.2 (M+H). $^1$H NMR (400 MHz, chloroform-d) δ 7.27-7.18 (m, 3H), 7.15-7.02 (m, 2H), 4.73 (dd, J=16.7, 5.8 Hz, 2H), 4.58 (d, J=16.8 Hz, 1H), 3.95-3.84 (m, 2H), 3.69-3.58 (m, 1H), 3.46-3.22 (m, 2H), 3.02-2.92 (m, 1H), 2.90-2.78 (m, 1H), 2.67 (dd, J=6.8, 5.3 Hz, 1H), 2.62-2.40 (m, 2H), 2.01-1.89 (m, 2H), 1.40-1.24 (m, 5H), 0.86 (d, J=6.8 Hz, 2H), and 0.76 (d, J=7.0 Hz, 2H).

The trans product had a UPLC ret. time=1.23 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. MS (E+) m/z: 546.2 (M+H). $^1$H NMR (400 MHz, chloroform-d) δ 7.27-7.17 (m, 3H), 7.14-7.02 (m, 2H), 6.57 (dd, J=8.0, 2.3 Hz, 2H), 4.73 (dd, J=16.7, 6.2 Hz, 2H), 4.58 (d, J=16.9 Hz, 2H), 3.72-3.60 (m, 2H), 3.02-2.93 (m, 1H), 2.68 (d, J=1.5 Hz, 1H), 2.62-2.42 (m, 2H), 1.40-1.34 (m, 3H), 1.32 (d, J=6.4 Hz, 2H), 0.86 (d, J=6.8 Hz, 2H), and 0.76 (d, J=7.0 Hz, 2H).

Intermediate 224B: tert-Butyl 5-(7-carbamoyl-5-iodo-2,3-dimethyl-1H-indol-4-yl)-3,4-dihydroisoquinoline-2(1H)-carboxylate (224B)

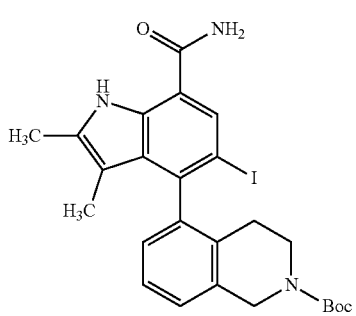

To a suspension of tert-butyl 5-((2R,3R)-7-carbamoyl-2,3-dimethylindolin-4-yl)-3,4-dihydroisoquinoline-2(1H)-carboxylate (350 mg, 0.830 mmol) in tetrahydrofuran (5 mL) was added N-iodosuccinimide (280 mg, 1.25 mmol) and a drop of pyridine (0.201 mL, 2.49 mmol). The resulting mixture was stirred at 70° C. for 1 h. Purification by reverse-phase preparative HPLC afforded tert-butyl 5-(7-carbamoyl-5-iodo-2,3-dimethyl-1H-indol-4-yl)-3,4-dihydroisoquinoline-2(1H)-carboxylate (150 mg, 0.275 mmol, 33% yield) as a white solid. The product had a UPLC ret. time=1.38 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. MS (E+) m/z: 546.2 (M+H). $^1$H NMR (400 MHz, chloroform-d) δ 7.82 (s, 1H), 7.31 (t, J=7.5 Hz, 1H), 7.25 (d, J=7.3 Hz, 1H), 7.02 (d, J=7.3 Hz, 1H), 4.69 (s, 2H), 3.57 (br. s., 2H), 2.49-2.23 (m, 5H), 1.50 (br. s., 9H), and 1.43-1.35 (m, 3H).

Intermediate 224B: Alternative Preparation

To a suspension of tert-butyl 5-((2R,3S)-7-carbamoyl-2,3-dimethylindolin-4-yl)-3,4-dihydroisoquinoline-2(1H)-carboxylate (300 mg, 0.712 mmol) in tetrahydrofuran (5 mL) was added N-iodosuccinimide (240 mg, 1.07 mmol) and a drop of pyridine (0.20 mL, 2.49 mmol). The resulting mixture was stirred at room temperature for 1 h, and then DDQ (188 mg, 0.830 mmol) was added, kept stirring for another 1 h. Purification by reverse-phase preparative HPLC afforded tert-butyl 5-(7-carbamoyl-5-iodo-2,3-dimethyl-1H-indol-4-yl)-3,4-dihydroisoquinoline-2(1H)-carboxylate (100 mg, 0.183 mmol, 26% yield) as a white solid. The product had a UPLC ret. time=1.38 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. MS (E+) m/z: 546.2 (M+H).

Intermediates 224C-1 and 224C-2: tert-Butyl 5-(7-carbamoyl-5-iodo-2,3-dimethyl-1H-indol-4-yl)-3,4-dihydroisoquinoline-2(1H)-carboxylate (Atropisomers 1 and 2)

Atropiosmer 1

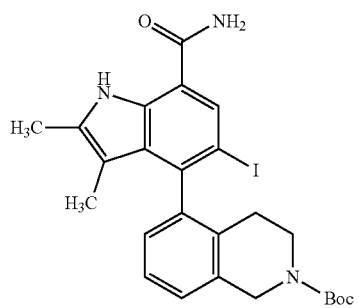

Atropiosmer 2

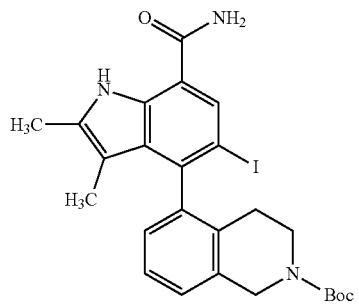

tert-Butyl 5-(7-carbamoyl-5-iodo-2,3-dimethyl-1H-indol-4-yl)-3,4-dihydroisoquinoline-2(1H)-carboxylate (70 mg, dissolved in 12 mL 9:1 MeOH/CH$_2$Cl$_2$) was resolved into its corresponding enantiomers using chiral supercritical fluid chromatography (SFC) with the following conditions. Column, CHIRALPAK®-IC, 3 cm×25 cm, 5 μM; mobile phase, 45% MeOH/CO$_2$; flow rate, 120 mL/min; detection, UV (220 nM). Column temperature: 35° C., pressure: 100 bars BPR.

Example 224-Atropisomer 1

A solution of tert-butyl 5-(7-carbamoyl-5-iodo-2,3-dimethyl-1H-indol-4-yl)-3,4-dihydroisoquinoline-2(1H)-carboxylate (Atropisomer 1; 10 mg, 0.018 mmol) in trifluoroacetic acid (0.5 mL, 6.49 mmol) was stirred at room temperature for 10 min. The trifluoroacetic acid was removed under reduced pressure. The resulting mixture was dissolved in tetrahydrofuran (1 mL), and to the solution was added DIEA (9.61 μl, 0.055 mmol) and acryloyl chloride (1.99 mg, 0.022 mmol). The reaction mixture was stirred at room temperature for another 10 min. Purification by reverse-phase preparative HPLC afforded 4-(2-acryloyl-1,2,3,4-tetrahydroisoquinolin-5-yl)-5-iodo-2,3-dimethyl-1H-indole-7-carboxamide (Atropisomer 1; 6 mg, 66% yield) as a white solid. The product had a UPLC ret. time=1.08 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. MS (E+) m/z: 500.2 (M+H). $^1$H NMR (400 MHz, methanol-d$_4$) δ 8.07 (s, 1H), 7.43-7.28 (m, 2H), 7.07-6.99 (m, 1H), 6.78 (dd, J=16.8, 10.6 Hz, 1H), 6.33-6.21 (m, 1H), 5.87-5.68 (m, 1H), 3.86-3.68 (m, 3H), 2.57-2.27 (m, 5H), 1.96-1.83 (m, 1H), and 1.43-1.31 (m, 3H).

Example 224-Atropisomer 2

The title compound was prepared in a manner similar to that of the preparation of the Example 1. The product had a UPLC ret. time=1.08 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. MS (E+) m/z: 500.2 (M+H). $^1$H NMR (400 MHz, methanol-d$_4$) δ 8.07 (s, 1H), 7.43-7.27 (m, 2H), 7.07-6.98 (m, 1H), 6.78 (dd, J=16.8, 10.6 Hz, 1H), 6.26 (d, J=16.8 Hz, 1H), 5.89-5.69 (m, 1H), 4.95-4.89 (m, 1H), 3.78 (q, J=6.2 Hz, 2H), 2.56-2.27 (m, 6H), and 1.45-1.33 (m, 3H).

Example 225

4-(2-Acryloyl-1,2,3,4-tetrahydroisoquinolin-5-yl)-2,3-dimethyl-1H-pyrrolo[2,3-c]pyridine-7-carboxamide

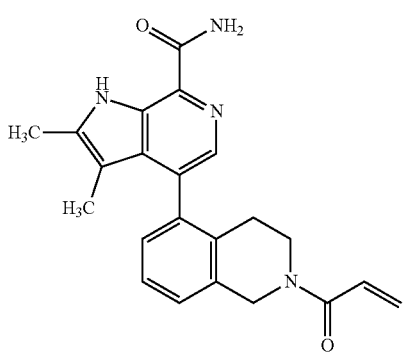

(225)

Intermediate 225A: 4-Bromo-7-chloro-2,3-dimethyl-1H-pyrrolo[2,3-c]pyridine

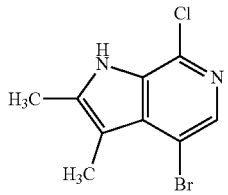

(225A)

A 0.5M tetrahydrofuran solution of (E)-but-2-en-2-yl-magnesium bromide (295 ml, 147 mmol) was added at −70° C. to a stirred solution of 5-bromo-2-chloro-3-nitropyridine (10 g, 42.1 mmol) in tetrahydrofuran (80 mL). The reaction mixture was allowed to come to −35° C. over 30 min. and then quenched with a saturated aqueous solution of ammonium chloride, extracted with ethyl acetate, and dried over magnesium sulfate. The crude product was purified ISCO flash chromatography (silica gel/hexane-EtOAc 100:0 to 0:100 gradient) followed by trituration with hexanes-ether to afford 4-bromo-7-chloro-2,3-dimethyl-1H-pyrrolo[2,3-c]pyridine (1 g, 3.85 mmol, 9.2% yield) as a pink solid. LC/MS M+1=261.1 and 263.1.

Intermediate 225B: 5-(7-Chloro-2,3-dimethyl-1H-pyrrolo[2,3-c]pyridin-4-yl)-3,4-dihydroisoquinoline-2(1H)-carboxylate

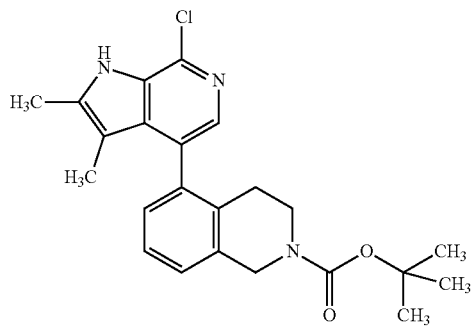

(225B)

A mixture of 4-bromo-7-chloro-2,3-dimethyl-1H-pyrrolo[2,3-c]pyridine (0.500 g, 1.927 mmol), tert-butyl 5-(4,4,5,5-tetramethyl-1,3,2-dioxaborolan-2-yl)-3,4-dihydroisoquinoline-2(1H)-carboxylate (0.831 g, 2.31 mmol), tripotassium phosphate (2 M in water) (2.89 mL, 5.78 mmol), and tetrahydrofuran (10 mL) was degassed with vacuum and nitrogen (3×). 1,1'-Bis(di-tert-butylphosphino)ferrocene palladium dichloride (0.063 g, 0.096 mmol) was added, and the reaction mixture was degassed (2×). The mixture was stirred at room temperature overnight. The reaction mixture was diluted with ethyl acetate, washed with water, washed with brine, and dried over anhydrous sodium sulfate. Concentration under reduced pressure followed by purification purified by ISCO flash chromatography (40 g column; gradient: 0%-100% ethyl acetate in hexane) afforded tert-butyl 5-(7-chloro-2,3-dimethyl-1H-pyrrolo[2,3-c]pyridin-4-yl)-3,4-dihydroisoquinoline-2(1H)-carboxylate (0.681 g, 1.65 mmol, 86% yield) as a yellow solid. The product had a UPLC ret. time=1.17 min. Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. LC/MS M+1=412.5 and 414.5.

Intermediate 225C: tert-Butyl 5-(7-cyano-2,3-dimethyl-1H-pyrrolo[2,3-c]pyridin-4-yl)-3,4-dihydroisoquinoline-2(1H)-carboxylate

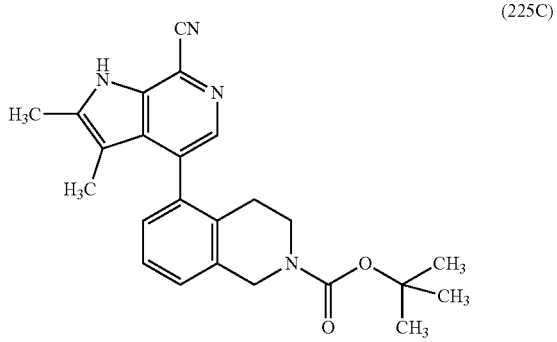 [SMILES: Cc1[nH]c2c(C#N)ncc(-c3cccc4c3CCN(C(=O)OC(C)(C)C)C4)c2c1C]

(225C)

A mixture of tert-butyl 5-(7-chloro-2,3-dimethyl-1H-pyrrolo[2,3-c]pyridin-4-yl)-3,4-dihydroisoquinoline-2(1H)-carboxylate (0.300 g, 0.728 mmol), zinc cyanide (0.051 g, 0.437 mmol), zinc (5.71 mg, 0.087 mmol), and 1,1'-bis(diphenylphosphine)ferrocene (DPPF) (0.048 g, 0.087 mmol) in N,N-dimethylacetamide (4 mL) was degassed well with vacuum and nitrogen (3×). To the mixture was added tris(dibenzylideneacetone) dipalladium(0) (0.040 g, 0.044 mmol), with degassing, and the reaction mixture was immersed in an oil bath at 130° C. for 6.5 h. The reaction was then cooled and stirred at room temperature overnight. The mixture was diluted with ethyl acetate, washed with 10% aqueous lithium chloride (2×), and washed with brine. The organic layer was collected, and the aqueous layers were sequentially extracted with ethyl acetate (2×). The combined organic layers were dried over anhydrous sodium sulfate. Concentration under reduced pressure followed by purification by ISCO flash chromatography (24 g column; gradient: 0%-100% ethyl acetate in hexane) afforded tert-butyl 5-(7-cyano-2,3-dimethyl-1H-pyrrolo[2,3-c]pyridin-4-yl)-3,4-dihydroisoquinoline-2(1H)-carboxylate (0.153 g, 0.380 mmol, 52% yield) as a yellow film. The product had a UPLC with a ret. time=1.29 min. Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=403.5.

Intermediate 225D: 2,3-Dimethyl-4-(1,2,3,4-tetrahydroisoquinolin-5-yl)-1H-pyrrolo[2,3-c]pyridine-7-carboxamide

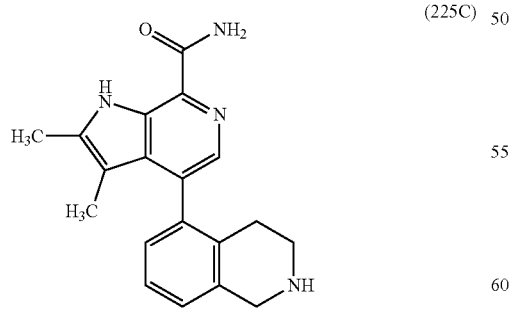

(225C)

A mixture of tert-butyl 5-(7-cyano-2,3-dimethyl-1H-pyrrolo[2,3-c]pyridin-4-yl)-3,4-dihydroisoquinoline-2(1H)-carboxylate (0.152 g, 0.378 mmol) and 90% aqueous sulfuric acid (4.47 ml, 76 mmol) was immersed in an oil bath at 60° C. and stirred for 60 min. To the reaction mixture, cooled to 0° C., was added an aqueous solution of sodium hydroxide (10M) (15.1 mL, 151 mmol) dropwise with stirring. A few additional drops of the sodium hydroxide solution were added until the pH was ~9. The resulting suspension was stirred overnight. The precipitate was collected by vacuum filtration and washed well with water and dried to give 2,3-dimethyl-4-(1,2,3,4-tetrahydroisoquinolin-5-yl)-1H-pyrrolo[2,3-c]pyridine-7-carboxamide (0.097 g, 0.288 mmol, 76% yield) as a tan solid. The product had a UPLC ret. time=0.698 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=324.2.

The filtrate was extracted with dichloromethane (3×), and the organic layer was dried over anhydrous sodium sulfate to give 2,3-dimethyl-4-(1,2,3,4-tetrahydroisoquinolin-5-yl)-1H-pyrrolo[2,3-c]pyridine-7-carboxamide (0.024 g, 0.074 mmol, 20% yield) as a pale yellow solid.

Example 225

To a mixture of 2,3-dimethyl-4-(1,2,3,4-tetrahydroisoquinolin-5-yl)-1H-pyrrolo[2,3-c]pyridine-7-carboxamide (0.097 g, 0.303 mmol) and Hunig's Base (0.212 mL, 1.21 mmol) in tetrahydrofuran (2.0 mL) at room temperature was added acryloyl chloride (0.025 mL, 0.303 mmol). The reaction mixture was stirred for 20 min. The reaction mixture was diluted with dichloromethane, washed with water, and dried over anhydrous sodium sulfate. Concentration under reduced pressure followed by purification by ISCO flash chromatography (12 g column; gradient: 0%-5% methanol in dichloromethane) provided 4-(2-acryloyl-1,2,3,4-tetrahydroisoquinolin-5-yl)-2,3-dimethyl-1H-pyrrolo[2,3-c]pyridine-7-carboxamide (0.039 g, 0.103 mmol, 34% yield) as a pale yellow solid. The product had a UPLC ret. time=0.807 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=375.1. $^1$H NMR (500 MHz, DMSO-$d_6$) δ 11.27 (s, 1H), 8.16 (d, J=2.0 Hz, 1H), 7.82 (s, 1H), 7.60 (d, J=1.8 Hz, 1H), 7.32 (d, J=7.2 Hz, 2H), 7.18-7.11 (m, 1H), 6.96-6.73 (m, 1H), 6.13 (d, J=16.6 Hz, 1H), 5.76-5.63 (m, 1H), 4.93-4.81 (m, 1H), 4.77 (s, 1H), 3.76-3.55 (m, 2H), 2.45-2.38 (m, 1H), 2.37 (s, 3H), 2.33 (br. s., 1H), and 1.56-1.49 (m, 3H).

Example 226

4-(2-Acryloyl-1,2,3,4-tetrahydroisoquinolin-5-yl)-2,3,5-trimethyl-1H-pyrrolo[2,3-c]pyridine-7-carboxamide (Mixture of atropisomers)

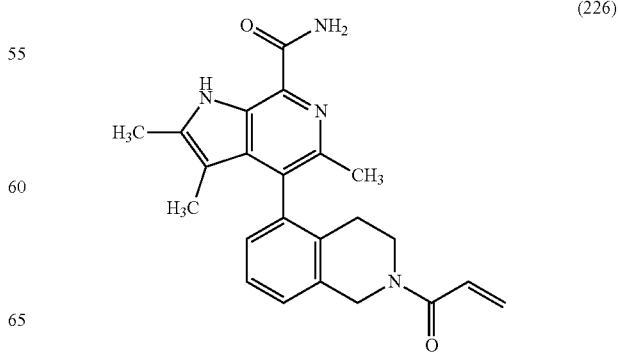

(226)

Intermediate 226A: 4-Bromo-7-chloro-2,3,5-trimethyl-1H-pyrrolo[2,3-c]pyridine

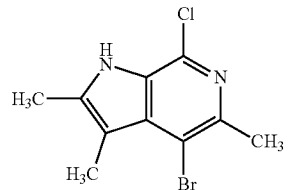

(226A)

To a stirred solution of 3-bromo-6-chloro-2-methyl-5-nitropyridine (2.00 g, 7.95 mmol) in tetrahydrofuran (16 mL) at −78° C. was added (E)-but-2-en-2-ylmagnesium bromide (0.5M in THF) (55.7 mL, 27.8 mmol). The reaction mixture was allowed to warm to ~−35° C. over 30 min. and was then quenched with a saturated aqueous solution of ammonium chloride. The mixture was diluted with ethyl acetate, washed with a saturated aqueous solution of ammonium chloride, washed with brine, and dried over anhydrous sodium sulfate. The organic layer was collected, and the aqueous layers were sequentially washed extracted with ethyl acetate (2×). The combined organic layers were dried over anhydrous sodium sulfate, and the resulting residue was purified by ISCO flash silica gel chromatography (24 g column; gradient: 0%-100 ethyl acetate in hexane) to give 4-bromo-7-chloro-2,3,5-trimethyl-1H-pyrrolo[2,3-c]pyridine (0.402 g, 1.47 mmol, 19% yield) as a yellow solid. The product had a UPLC ret. time=1.14 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=273.2 and 275.2.

Intermediate 226B: tert-Butyl 5-(7-chloro-2,3,5-trimethyl-1H-pyrrolo[2,3-c]pyridin-4-yl)-3,4-dihydroisoquinoline-2(1H)-carboxylate

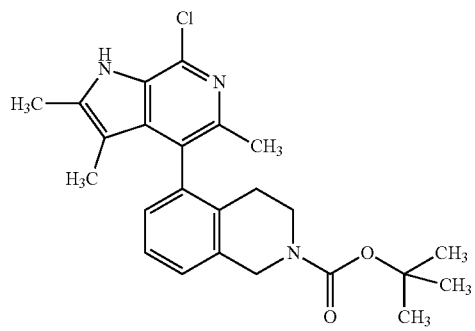

(226B)

A mixture of 4-bromo-7-chloro-2,3,5-trimethyl-1H-pyrrolo[2,3-c]pyridine (0.400 g, 1.46 mmol), tert-butyl 5-(4,4,5,5-tetramethyl-1,3,2-dioxaborolan-2-yl)-3,4-dihydroisoquinoline-2(1H)-carboxylate (0.630 g, 1.76 mmol), tripotassium phosphate (2M in water) (2.19 mL, 4.39 mmol), and tetrahydrofuran (8 mL) was degassed with vacuum and nitrogen (3×). 1,1'-Bis(di-tert-butylphosphino) ferrocene palladium dichloride (0.048 g, 0.073 mmol) was added, and the reaction mixture was degassed (2×). The reaction mixture was stirred at room temperature overnight. The mixture was diluted with ethyl acetate, washed with water, washed with brine, and dried over anhydrous sodium sulfate. Concentration under reduced pressure followed by purification purified by ISCO flash chromatography (40 g column; gradient: 0%-100% ethyl acetate in hexane) afforded tert-butyl 5-(7-chloro-2,3,5-trimethyl-1H-pyrrolo[2,3-c]pyridin-4-yl)-3,4-dihydroisoquinoline-2(1H)-carboxylate (0.331 g, 0.777 mmol, 53% yield) as a yellow solid. The product had a UPLC ret. time=1.09 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=426.5 and 428.4.

Intermediate 226C: tert-Butyl 5-(7-cyano-2,3,5-trimethyl-1H-pyrrolo[2,3-c]pyridin-4-yl)-3,4-dihydroisoquinoline-2(1H)-carboxylate

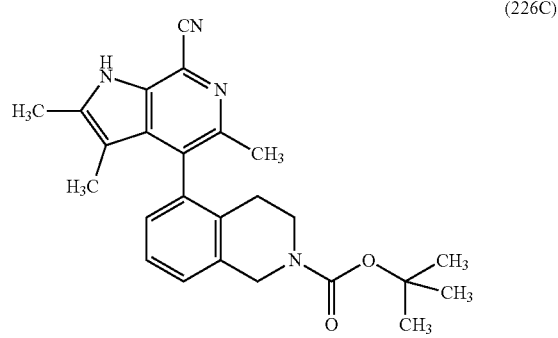 [SMILES: Cc1nc(C#N)c2[nH]c(C)c(C)c2c1-c1cccc2c1CCN(C(=O)OC(C)(C)C)C2]

(226C)

A mixture of tert-butyl 5-(7-chloro-2,3,5-trimethyl-1H-pyrrolo[2,3-c]pyridin-4-yl)-3,4-dihydroisoquinoline-2(1H)-carboxylate (0.331 g, 0.777 mmol), zinc cyanide (0.055 g, 0.466 mmol), zinc (6.10 mg, 0.093 mmol), and 1,1'-bis(diphenylphosphine) ferrocene (DPPF) (0.052 g, 0.093 mmol) in N,N-dimethylacetamide (4 mL) was degassed well with vacuum and nitrogen (3×). To the mixture was added tris(dibenzylideneacetone)dipalladium(0) (0.043 g, 0.047 mmol), with degassing, and the reaction mixture was immersed in an oil bath at 130° C. for 6 h. The mixture was then stirred overnight at room temperature. The reaction mixture was diluted with ethyl acetate, washed with 10% aqueous lithium chloride (2×), and washed with brine. The organic layer was collected, and the aqueous layers were sequentially extracted with ethyl acetate (2×). The combined organic layers were dried over anhydrous sodium sulfate. Concentration under reduced pressure followed by purification by ISCO flash chromatography (24 g column; gradient: 0%-100% ethyl acetate in hexane) afforded tert-butyl 5-(7-cyano-2,3,5-trimethyl-1H-pyrrolo[2,3-c]pyridin-4-yl)-3,4-dihydroisoquinoline-2(1H)-carboxylate (0.164 g, 0.394 mmol, 51% yield) as a yellow film. The product had a UPLC ret. time=1.21 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=417.5.

287

Intermediate 226D: 2,3,5-Trimethyl-4-(1,2,3,4-tetra-hydroisoquinolin-5-yl)-1H-pyrrolo[2,3-c]pyridine-7-carboxamide

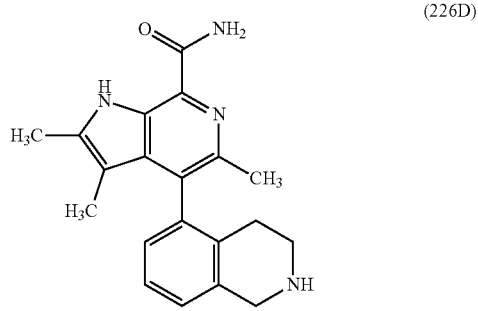 [SMILES: Cc1nc(C(N)=O)c2[nH]c(C)c(C)c2c1-c1cccc2c1CCNC2]

(226D)

A mixture of tert-butyl 5-(7-cyano-2,3,5-trimethyl-1H-pyrrolo[2,3-c]pyridin-4-yl)-3,4-dihydroisoquinoline-2(1H)-carboxylate (0.164 g, 0.394 mmol) and 90% aqueous sulfuric acid (4.66 ml, 79 mmol) was immersed in an oil bath at 60° C. and stirred for 60 min. UPLC and LCMS indicated that the reaction was complete. To the reaction mixture cooled to 0° C. was added sodium hydroxide (10M) (15.8 ml, 157 mmol) dropwise with stirring. A few additional drops of the sodium hydroxide solution were added until the pH was ~9. The resulting solid was collected by vacuum filtration and washed with water, washed with ethyl acetate, and dried to give 2,3,5-trimethyl-4-(1,2,3,4-tetrahydroisoquinolin-5-yl)-1H-pyrrolo[2,3-c]pyridine-7-carboxamide (0.043 g, 0.129 mmol, 33% yield as a yellow solid. The ethyl acetate layer was collected and washed with brine. The organic layer was collected, and the aqueous layers were sequentially extracted with ethyl acetate. The combined organic layers were dried over anhydrous sodium sulfate and concentrated to give 2,3,5-trimethyl-4-(1,2,3,4-tetrahydroisoquinolin-5-yl)-1H-pyrrolo[2,3-c]pyridine-7-carboxamide (0.026 g, 0.078 mmol, 20% yield) as a pale yellow solid. The product had a UPLC ret. time=0.708 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=335.4.

Example 226

To a mixture of 2,3,5-trimethyl-4-(1,2,3,4-tetrahydroisoquinolin-5-yl)-1H-pyrrolo[2,3-c]pyridine-7-carboxamide (0.043 g, 0.129 mmol) and Hunig's Base (0.090 mL, 0.514 mmol) in tetrahydrofuran (1 mL) at room temperature was added acryloyl chloride (0.686 mL, 8.45 mmol). The reaction mixture was stirred for 30 min. The reaction mixture was diluted with ethyl acetate, washed with water, washed with brine, and dried over anhydrous sodium sulfate. The product mixture was concentrated under reduced pressure, and the residue was purified by ISCO flash chromatography (4 g column; gradient: 0%-5% methanol in dichloromethane) to give 4-(2-acryloyl-1,2,3,4-tetrahydroisoquinolin-5-yl)-2,3,5-trimethyl-1H-pyrrolo[2,3-c]pyridine-7-carboxamide (0.025 g, 0.064 mmol, 50% yield) as a pale yellow solid. The product had a UPLC ret. time=0.798 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=389.6.

288

Examples 227 and 228

4-(2-Acryloyl-1,2,3,4-tetrahydroisoquinolin-5-yl)-2,3,5-trimethyl-1H-pyrrolo[2,3-c]pyridine-7-carboxamide (Mixture of atropisomers)

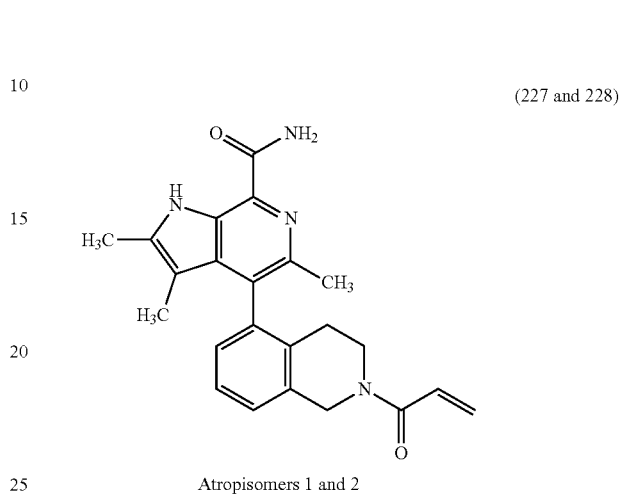

(227 and 228)

Atropisomers 1 and 2

A sample of 4-(2-acryloyl-1,2,3,4-tetrahydroisoquinolin-5-yl)-2,3,5-trimethyl-1H-pyrrolo[2,3-c]pyridine-7-carboxamide (Intermediate 2E, mixture of two atropisomers) was separated by chiral super-critical fluid chromatography using the following preparative conditions to give two isolated and stable atropisomers.

Preparative Chromatographic Conditions: Instrument: Thar350; Column: Cellulose-4 (3×25 cm; 5 m); BPR pressure: 100 bars; Temperature: 35° C.; Flow rate: 150 mL/min; mobile phase: $CO_2$/MeOH (55/45); detector wavelength: 220 nm; injection: 2.5 mL; sample preparation: 21 mg/7 mL MeOH, 3 mg/mL.

Atropisomer 1 (Peak 1): The product was >99% pure by UPLC with a ret. time=0.793 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=389.4. $^1$H NMR (400 MHz, DMSO-$d_6$) δ 11.05 (s, 1H), 8.03 (d, J=2.8 Hz, 1H), 7.58 (d, J=2.8 Hz, 1H), 7.32 (d, J=5.7 Hz, 2H), 7.09-7.05 (m, 1H), 6.93 (dd, J=16.3, 10.4 Hz, 0.4H), 6.78 (dd, J=16.8, 10.4 Hz, 0.6H), 6.13 (d, J=16.8 Hz, 1H), 5.76-5.63 (m, 1H), 4.88 (br. s., 1H), 4.77 (s, 1H), 3.74-3.57 (m, 2H), 2.31 (s, 3H), 3.32 (s, 3H), 2.29-2.21 (m, 2H), and 2.19 (s, 2H).

Atropisomer 2 (Peak 2): The product had a UPLC ret. time=0.803 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=389.3. $^1$H NMR (400 MHz, DMSO-$d_6$) δ 11.05 (s, 1H), 8.03 (d, J=2.6 Hz, 1H), 7.58 (d, J=2.7 Hz, 1H), 7.36-7.27 (m, 2H), 7.10-7.04 (m, 1H), 6.93 (dd, J=16.6, 10.6 Hz, 0.4H), 6.78 (dd, J=16.6, 10.5 Hz, 0.6H), 6.13 (d, J=16.6 Hz, 1H), 5.76-5.63 (m, 1H), 4.88 (br. s., 1H), 4.77 (s, 1H), 3.74-3.58 (m, 2H), 3.30 (s, 3H), 2.31 (s, 3H), 2.28-2.22 (m, 2H), and 2.19 (s, 3H).

Example 229

4-(2-Acryloyl-1,2,3,4-tetrahydroisoquinolin-5-yl)-5-cyano-2,3-dimethyl-1H-indole-7-carboxamide

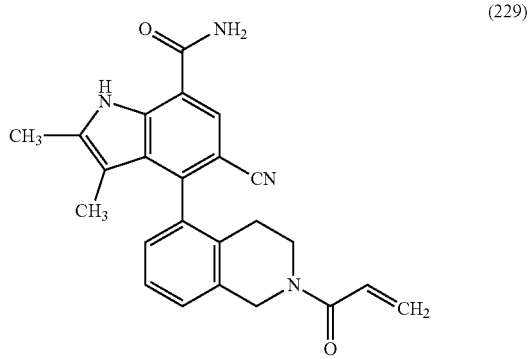 [SMILES: C=CC(=O)N1CCc2c(cccc2-c2c(C#N)cc(C(N)=O)c3[nH]c(C)c(C)c23)C1]

(229)

Intermediate 229A: tert-Butyl 5-(7-carbamoyl-5-cyano-2,3-dimethyl-1H-indol-4-yl)-3,4-dihydroisoquinoline-2(1H)-carboxylate

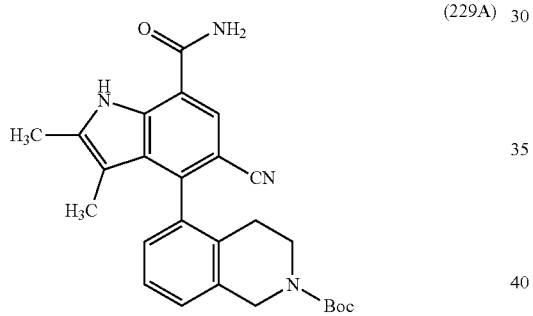

(229A)

A mixture of tert-butyl 5-(7-carbamoyl-5-iodo-2,3-dimethyl-1H-indol-4-yl)-3,4-dihydroisoquinoline-2(1H)-carboxylate (25 mg, 0.046 mmol) and zinc cyanide (5.38 mg, 0.046 mmol) in N,N-dimethylformamide (1 mL) was degassed well with vacuum and nitrogen (3×). To the mixture was added Pd(Ph₃P)₄ (5.30 mg, 4.58 µmol), the yellow heterogeneous solution was degassed (3×), immersed in an oil bath at 100° C., and stirred for 12 h. During the reaction, the mixture changed from a yellow heterogeneous solution to a dark homogeneous solution. Purification by reverse-phase preparative HPLC afforded 5-(7-carbamoyl-5-cyano-2,3-dimethyl-1H-indol-4-yl)-3,4-dihydroisoquinoline-2(1H)-carboxylate (15 mg, 0.034 mmol, 74% yield) as a white solid. The product had a UPLC ret. time=1.24 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. MS (E+) m/z: 445.3 (M+H).

Example 229

A solution of tert-butyl 5-(7-carbamoyl-5-cyano-2,3-dimethyl-1H-indol-4-yl)-3,4-dihydroisoquinoline-2(1H)-carboxylate (10 mg, 0.022 mmol) in trifluoroacetic acid (0.5 mL, 6.49 mmol) was stirred at room temperature for 10 min., and then concentrated under vacuum to remove TFA. Further dried on vacuum pump. The resulted mixture was dissolved in tetrahydrofuran (1 mL), and to the solution was added DIEA (0.012 mL, 0.067 mmol), BOP (11.9 mg, 0.027 mmol), and but-2-ynoic acid (2.27 mg, 0.027 mmol). The reaction mixture was stirred at room temperature for another 10 min. Purification by reverse-phase preparative HPLC afforded 4-(2-acryloyl-1,2,3,4-tetrahydroisoquinolin-5-yl)-5-cyano-2,3-dimethyl-1H-indole-7-carboxamide (6.4 mg, 71% yield) as a white solid. The product had a UPLC ret. time=0.980 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. MS (E+) m/z: 399.3 (M+H). $^1$H NMR (400 MHz, methanol-d$_4$) δ 7.82 (s, 1H), 7.43-7.27 (m, 2H), 7.09-7.01 (m, 1H), 6.78 (dd, J=16.8, 10.6 Hz, 1H), 6.28 (m, 1H), 5.89-5.69 (m, 1H), 4.95-4.89 (m, 1H), 3.78 (q, J=6.2 Hz, 2H), 2.55-2.27 (m, 6H), and 1.44-1.32 (m, 3H).

Example 230

4-((1-Acryloylpiperidin-4-yl)methyl)-5-fluoro-3-methyl-2-(trifluoromethyl)-1H-indole-7-carboxamide

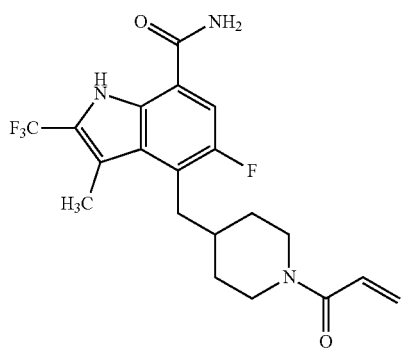

(230)

Intermediate 230A: tert-Butyl 4-((7-carbamoyl-5-fluoro-3-methyl-2-(trifluoromethyl)-1H-indol-4-yl)methylene)piperidine-1-carboxylate

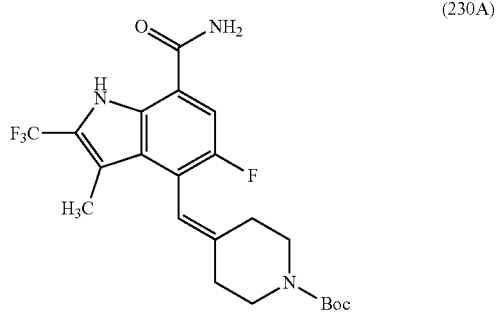 [SMILES: Cc1c(C(F)(F)F)[nH]c2c(C(N)=O)cc(F)c(C=C3CCN(C(=O)OC(C)(C)C)CC3)c12]

(230A)

A mixture of 4-bromo-5-fluoro-3-methyl-2-(trifluoromethyl)-1H-indole-7-carboxamide (100 mg, 0.295 mmol), tert-butyl 4-methylenepiperidine-1-carboxylate (116 mg, 0.590 mmol), 1,1'-bis(di-tert-butylphosphino)ferrocene palladium dichloride (19.22 mg, 0.029 mmol), N,N-dicyclohexylmethylamine (0.094 mL, 0.442 mmol) and tetrabutylammonium chloride (8.20 mg, 0.029 mmol) in degassed DMA (2.0 mL) under nitrogen was stirred in a seal vial at 80° C. for 18 hr. The mixture was diluted with EtOAc (15 mL) and was washed with a solution of aqueous saturated sodium bicarbonate (2×15 mL). The ethyl acetate layer was dried over sodium sulfate and concentrated. The crude product was purified by prep-HPLC (PHENOMENEX®, Luna 5 30×250 mm, flow rate=30 ml/min., gradient=20% A to 100% B in 30 min., A=H$_2$O/MeOH/TFA (90:10:0.1), B=H$_2$O/MeOH/TFA (10:90:0.1)). Yield tert-butyl 4-((7-carbamoyl-5-fluoro-3-methyl-2-(trifluoromethyl)-1H-indol-4-yl)methylene)piperidine-1-carboxylate (108 mg, 0.225 mmol, 76% yield) as white solid. $^1$H NMR (400 MHz, methanol-d$_4$) δ 7.75-7.65 (m, 1H), 6.89-6.72 (m, 1H), 3.86-3.70 (m, 1H), 3.51-3.39 (m, 1H), 3.25-3.03 (m, 2H), 2.61 (d, J=1.6 Hz, 4H), 2.49-2.39 (m, 1H), 1.96-1.81 (m, 1H), 1.76-1.60 (m, 1H), 1.51 (s, 9H). LCMS: 1.21 min., M+H 456.

Example 230

To a solution of tert-butyl 4-((7-carbamoyl-5-fluoro-3-methyl-2-(trifluoromethyl)-1H-indol-4-yl)methylene)piperidine-1-carboxylate (15 mg, 0.033 mmol) and triethyl silane (0.263 mL, 1.647 mmol) in DCM (1.0 mL) was added TFA (0.254 mL, 3.29 mmol), the mixture was stirred at room temperature for 30 min. The mixture was concentrated to give crude 5-fluoro-3-methyl-4-(piperidin-4-ylmethyl)-2-(trifluoromethyl)-1H-indole-7-carboxamide, TFA salt.

To a solution of 5-fluoro-3-methyl-4-(piperidin-4-ylmethyl)-2-(trifluoromethyl)-1H-indole-7-carboxamide, TFA salt and TEA (0.023 mL, 0.165 mmol) in DMF (0.3 mL) and DCM (1.0 mL) was added a solution of acryloyl chloride (2.68 µl, 0.033 mmol) in DCM (0.3 mL), the mixture was stirred at room temperature for 30 min. The mixture was concentrated. The crude product was purified by prep-HPLC (PHENOMENEX®, Luna 5µ 30×250 mm, flow rate=30 ml/min., gradient=20% A to 100% B in 30 min., A=H$_2$O/MeOH/TFA (90:10:0.1), B=H$_2$O/MeOH/TFA (10:90:0.1)). Yield 4-((1-acryloylpiperidin-4-yl)methyl)-5-fluoro-3-methyl-2-(trifluoromethyl)-1H-indole-7-carboxamide (3.8 mg, 8.78 µmol, 26.6% yield). $^1$H NMR (500 MHz, DMSO-d$_6$) δ 11.12 (br. s., 1H), 8.27 (br. s., 1H), 7.81 (d, J=10.9 Hz, 1H), 7.70 (br. s., 1H), 6.79 (dd, J=16.7, 10.5 Hz, 1H), 6.08 (dd, J=16.7, 2.2 Hz, 1H), 5.65 (dd, J=10.5, 2.2 Hz, 1H), 4.40 (d, J=13.5 Hz, 1H), 4.02 (d, J=12.7 Hz, 1H), 3.06-2.86 (m, 3H), 1.84 (br. s., 1H), 1.64 (d, J=12.5 Hz, 2H), 1.32-1.10 (m, 3H). LCMS: 0.93 min., M+H 412.

Examples 231 and 232 (atropisomers)

4-(2-Acryloyl-4,4-difluoro-1,2,3,4-tetrahydroisoquinolin-5-yl)-5-fluoro-2,3-dimethyl-1H-indole-7-carboxamide

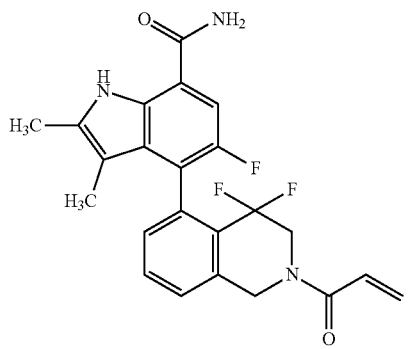

(231 and 232)

Intermediate 231A: Ethyl 2-(2-chloro-6-methylphenyl)-2,2-difluoroacetate

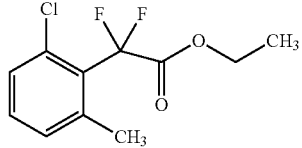

(231A)

To a suspension of copper (1.057 g, 16.63 mmol) and 1-chloro-2-iodo-3-methylbenzene (1.50 g, 5.94 mmol) in DMSO (5.0 mL) was added ethyl 2-bromo-2,2-difluoroacetate (1.206 g, 5.94 mmol), the mixture was stirred at 55° C. for 18 hr. The mixture was poured into a cold solution of saturated NH$_4$Cl in water (100 mL) and was extracted with EtOAc (70 mL). The EtOAc was then washed with a solution of 1.0 N aqueous HCl (2×50 mL). The ethyl acetate layer was dried over sodium sulfate and concentrated. The crude product was subjected to ISCO flash chromatography (silica gel/hexane-EtOAc 100:0 to 70:30 gradient). Yield ethyl 2-(2-chloro-6-methylphenyl)-2,2-difluoroacetate (1.26 g, 4.81 mmol, 81% yield) as clear oil. $^1$H NMR (400 MHz, chloroform-d) δ 7.33-7.24 (m, 2H), 7.23-7.11 (m, 1H), 4.39 (q, J=7.2 Hz, 2H), 2.58 (t, J=5.9 Hz, 3H), 1.41-1.30 (m, 3H).

Intermediate 231B: Ethyl 2-(2-(bromomethyl)-6-chlorophenyl)-2,2-difluoroacetate

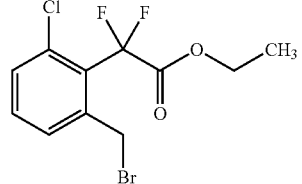

(231B)

A mixture of ethyl 2-(2-chloro-6-methylphenyl)-2,2-difluoroacetate (1.26 g, 5.07 mmol), NBS (0.947 g, 5.32 mmol), and benzoyl peroxide (0.123 g, 0.507 mmol) in CCl$_4$ (15 mL) was stirred at reflux for 4 hr. The mixture was cooled to room temperature. The precipitate was filtered off and the filtrate was concentrated. Crude yield ethyl 2-(2-(bromomethyl)-6-chlorophenyl)-2,2-difluoroacetate (1.81 g, 4.42 mmol, 87% yield) as light brown gum. $^1$H NMR (400 MHz, chloroform-d) δ 7.45-7.39 (m, 2H), 7.33-7.26 (m, 1H), 4.74 (t, J=2.1 Hz, 2H), 4.43-4.37 (m, 2H), 1.37-1.33 (m, 3H).

Intermediate 231C: Ethyl 2-(2-(azidomethyl)-6-chlorophenyl)-2,2-difluoroacetate

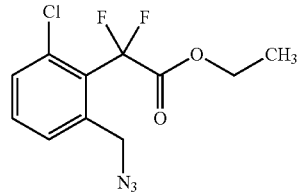

(231C)

A mixture of ethyl 2-(2-(bromomethyl)-6-chlorophenyl)-2,2-difluoroacetate (1.81 g, 5.53 mmol) and sodium azide (0.718 g, 11.05 mmol) in DMF (15 mL) was stirred at room temperature for 18 hr. The mixture was diluted with EtOAc (35 mL) and was washed with a solution of aqueous saturated sodium bicarbonate (2×35 mL) and aqueous 1.0 M HCl (35 mL). The ethyl acetate layer was dried over sodium sulfate and concentrated. The crude product was subjected to ISCO flash chromatography (silica gel/hexane-EtOAc 100:0 to 0:100 gradient). Yield ethyl 2-(2-(azidomethyl)-6-chlorophenyl)-2,2-difluoroacetate (1.36 g, 4.46 mmol, 81% yield) as clear gum. $^1$H NMR (400 MHz, chloroform-d) δ 7.51-7.41 (m, 3H), 4.69 (t, J=3.1 Hz, 2H), 4.44-4.34 (m, 2H), 1.39-1.30 (m, 3H).

Intermediate 231D: 5-Chloro-4,4-difluoro-1,2-dihydroisoquinolin-3(4H)-one

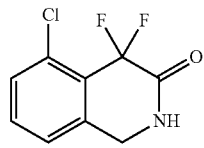

(231D)

A mixture of ethyl 2-(2-(azidomethyl)-6-chlorophenyl)-2,2-difluoroacetate (1.25 g, 4.32 mmol) and platinum(IV) oxide (0.098 g, 0.432 mmol) in MeOH (10 mL) was hydrogenated at 1 atm of hydrogen for 2 hr. Platinum was filtered off and the filtrate was concentrated. Yield 5-chloro-4,4-difluoro-1,2-dihydroisoquinolin-3(4H)-one (950 mg, 4.15 mmol, 96% yield) as white solid. $^1$H NMR (400 MHz, methanol-d$_4$) δ 7.59-7.52 (m, 2H), 7.35 (d, J=4.6 Hz, 1H), 4.70 (t, J=3.5 Hz, 2H).

Intermediate 231E: tert-Butyl 5-chloro-4,4-difluoro-3,4-dihydroisoquinoline-2(1H)-carboxylate

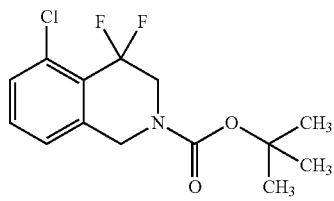

(231E)

To a solution of 5-chloro-4,4-difluoro-1,2-dihydroisoquinolin-3(4H)-one (950 mg, 4.37 mmol) in THF (5.0 mL) was added 1.0M borane tetrahydrofuran complex in THF (24.01 mL, 24.01 mmol), the mixture was stirred reflux for 2 hr. The mixture was cooled to room temperature and the mixture was quenched with a solution of 1.0 M aqueous HCl (17.46 mL, 17.46 mmol). The mixture was stirred at reflux for 2 hr and cooled to room temperature. The mixture was concentrated. The mixture was washed with ethyl ether (2×80 mL). A solution of aqueous 10 N NaOH was added until pH 10 and was extracted with EtOAc (2×50 mL). The ethyl acetate layer was dried over sodium sulfate and concentrated to give 5-chloro-4,4-difluoro-1,2,3,4-tetrahydroisoquinoline.

To a solution of 5-chloro-4,4-difluoro-1,2,3,4-tetrahydroisoquinoline in THF (15 mL) was added BOC$_2$O (1.014 mL, 4.37 mmol), the mixture was stirred at room temperature for 60 min. The mixture was concentrated. The crude product was subjected to ISCO flash chromatography (silica gel/hexane-EtOAc 100:0 to 0:100 gradient). Yield tert-butyl 5-chloro-4,4-difluoro-3,4-dihydroisoquinoline-2(1H)-carboxylate (960 mg, 3.00 mmol, 68.8% yield) as clear gum. $^1$H NMR (400 MHz, chloroform-d) δ 7.36 (d, J=12.8 Hz, 2H), 7.17-7.07 (m, 1H), 4.68 (br. s., 2H), 4.06 (t, J=12.0 Hz, 2H), 1.51 (s, 9H).

Intermediate 231F: tert-Butyl 4,4-difluoro-5-(4,4,5,5-tetramethyl-1,3,2-dioxaborolan-2-yl)-3,4-dihydroisoquinoline-2(1H)-carboxylate

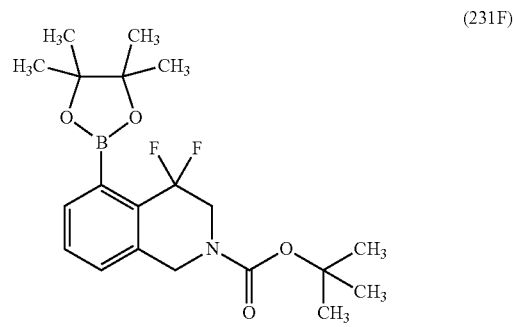 [SMILES: CC(C)(C)OC(=O)N1Cc2cccc(B3OC(C)(C)C(C)(C)O3)c2C(F)(F)C1]

(231F)

A mixture of bis(pinacolato) diboron (881 mg, 3.47 mmol), tert-butyl 5-chloro-4,4-difluoro-3,4-dihydroisoquinoline-2(1H)-carboxylate (527 mg, 1.735 mmol), potassium acetate (511 mg, 5.21 mmol) and 1,1'-bis(di-tert-butylphosphino)ferrocene palladium dichloride (56.5 mg, 0.087 mmol) in dioxane (6.0 mL) under nitrogen was stirred at 90° C. for 18 hr. The mixture was diluted with EtOAc (15 mL) and was washed with a solution of aqueous saturated sodium bicarbonate (15 mL). The ethyl acetate layer was dried over sodium sulfate and concentrated. The crude product was subjected to ISCO flash chromatography (silica gel/hexane-EtOAc 100:0 to 70:30 gradient). Yield tert-butyl 4,4-difluoro-5-(4,4,5,5-tetramethyl-1,3,2-dioxaborolan-2-yl)-3,4-dihydroisoquinoline-2(1H)-carboxylate (160 mg, 0.385 mmol, 22.16% yield) as light brown gum.

Intermediate 231G: tert-Butyl 5-(7-carbamoyl-5-fluoro-2,3-dimethyl-1H-indol-4-yl)-4,4-difluoro-3,4-dihydroisoquinoline-2(1H)-carboxylate

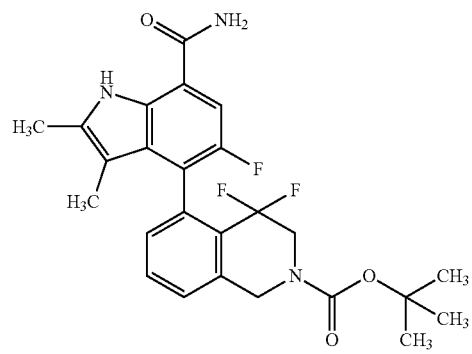

(I-231G)

A mixture of tert-butyl 4,4-difluoro-5-(4,4,5,5-tetramethyl-1,3,2-dioxaborolan-2-yl)-3,4-dihydroisoquinoline-2

(1H)-carboxylate (160 mg, 0.405 mmol), 4-bromo-5-fluoro-2,3-dimethyl-1H-indole-7-carboxamide (115 mg, 0.405 mmol), 1,1'-bis(di-tert-butylphosphino)ferrocene palladium dichloride (13.19 mg, 0.020 mmol) and potassium phosphate tribasic (258 mg, 1.214 mmol) in THF (3.0 mL) and water (1.500 mL) was stirred at 50° C. in a seal vial under nitrogen for 4 hr. EtOAc (5.0 mL) was added to extract the product. The EtOAc layer was dried over sodium sulfate and concentrated. The crude product was subjected to ISCO flash chromatography (silica gel/hexane-10% MeOH/EtOAc 100:0 to 50:50 gradient). Yield tert-butyl 5-(7-carbamoyl-5-fluoro-2,3-dimethyl-1H-indol-4-yl)-4,4-difluoro-3,4-dihydroisoquinoline-2(1H)-carboxylate (125 mg, 0.238 mmol, 58.7% yield) as light brown foam. Mass spectrum m/z 474 (M+H)+.

Examples 231 and 232

A mixture of tert-butyl 5-(7-carbamoyl-5-fluoro-2,3-dimethyl-1H-indol-4-yl)-4,4-difluoro-3,4-dihydroisoquinoline-2(1H)-carboxylate (125 mg, 0.264 mmol) in DCM (1.0 mL) and TFA (1.0 mL) was stirred at room temperature for 30 min. The mixture was then concentrated to give 4-(4,4-difluoro-1,2,3,4-tetrahydroisoquinolin-5-yl)-5-fluoro-2,3-dimethyl-1H-indole-7-carboxamide.

To a solution of 4-(4,4-difluoro-1,2,3,4-tetrahydroisoquinolin-5-yl)-5-fluoro-2,3-dimethyl-1H-indole-7-carboxamide and TEA (0.110 mL, 0.792 mmol) in DCM (3.0 mL) at 0° C. was added a solution of acryloyl chloride (23.89 mg, 0.264 mmol) in DCM (0.30 mL), the mixture was stirred at 0° C. for 30 min. The mixture was diluted with DCM (5 mL) and was washed with a solution of aqueous saturated sodium bicarbonate (5 mL). The DCM layer was dried over sodium sulfate and concentrated. The crude product was subjected to ISCO flash chromatography (silica gel/hexane-10% MeOH/EtOAc 100:0 to 0:100 gradient). Yield 4-(2-acryloyl-4,4-difluoro-1,2,3,4-tetrahydroisoquinolin-5-yl)-5-fluoro-2,3-dimethyl-1H-indole-7-carboxamide (76 mg, 0.169 mmol, 64.0% yield) as light brown gum.

4-(2-Acryloyl-4,4-difluoro-1,2,3,4-tetrahydroisoquinolin-5-yl)-5-fluoro-2,3-dimethyl-1H-indole-7-carboxamide was separated by chiral super-critical fluid chromatography (CHIRALCEL® OJ (3×25 cm, 5 µm); mobile phase: 20% MeOH in $C_{O2}$ at 120 mL/min; 100 bar, 30° C.; sample preparation: 76 mg in 7 mL MeOH. The first peak eluting from the column provided one enantiomer of 4-(2-acryloyl-4,4-difluoro-1,2,3,4-tetrahydroisoquinolin-5-yl)-5-fluoro-2,3-dimethyl-1H-indole-7-carboxamide [Intermediate 1] as a white powder (33 mg). The second peak eluting from the column provided the other enantiomer of 4-(2-acryloyl-4,4-difluoro-1,2,3,4-tetrahydroisoquinolin-5-yl)-5-fluoro-2,3-dimethyl-1H-indole-7-carboxamide as a white powder (30 mg).

Additional Examples were prepared by procedures described above or similar procedures to those known in the art, using the appropriate starting materials, are shown in Table 10.

TABLE 10

| Ex. No. | Structure | Name | Starting Intermediate | Mass Spectrum |
|---|---|---|---|---|
| 233 | 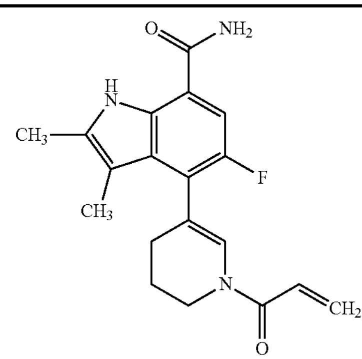 | 4-(1-acryloyl-1,4,5,6-tetrahydropyridin-3-yl)-5-fluoro-2,3-dimethyl-1H-indole-7-carboxamide | 108 | m/z 342 (M + H)+ |
| 234 | 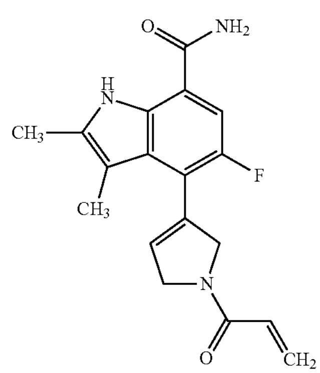 [SMILES: C=CC(=O)N1CC=C(c2c(F)cc(C(N)=O)c3[nH]c(C)c(C)c23)C1] | 4-(1-acryloyl-2,5-dihydro-1H-pyrrol-3-yl)-5-fluoro-2,3-dimethyl-1H-indole-7-carboxamide | 2 | m/z 328 (M + H)+ |

TABLE 10-continued

| Ex. No. | Structure | Name | Starting Intermediate | Mass Spectrum |
|---|---|---|---|---|
| 235 | 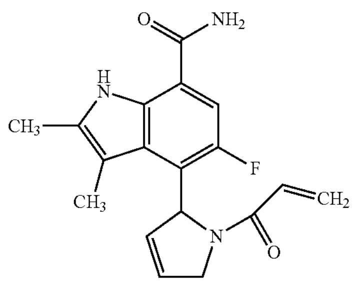 [SMILES: C=CC(=O)N1CC=CC1c1c(F)cc(C(N)=O)c2[nH]c(C)c(C)c12] | 4-(1-acryloyl-2,5-dihydro-1H-pyrrol-2-yl)-5-fluoro-2,3-dimethyl-1H-indole-7-carboxamide | 2 | m/z 328 (M + H)+ |
| 236 | 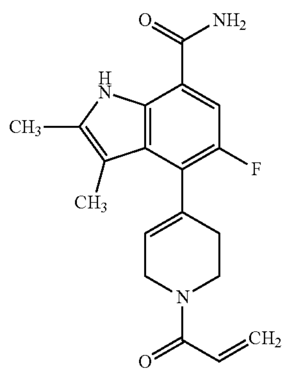 [SMILES: C=CC(=O)N1CC=C(c2c(F)cc(C(N)=O)c3[nH]c(C)c(C)c23)CC1] | 4-(1-acryloyl-1,2,3,6-tetrahydropyridin-4-yl)-5-fluoro-2,3-dimethyl-1H-indole-7-carboxamide | 2 | m/z 342 (M + H)+ |
| 237 | 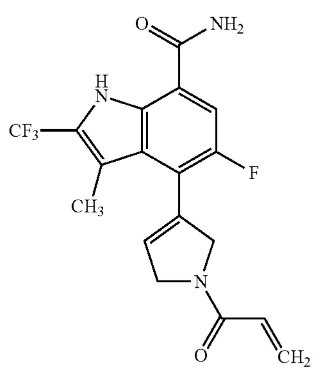 [SMILES: C=CC(=O)N1CC=C(c2c(F)cc(C(N)=O)c3[nH]c(C(F)(F)F)c(C)c23)C1] | 4-(1-acryloyl-2,5-dihydro-1H-pyrrol-3-yl)-5-fluoro-3-methyl-2-(trifluoromethyl)-1H-indole-7-carboxamide | 91 | m/z 382 (M + H)+ |
| 238 | 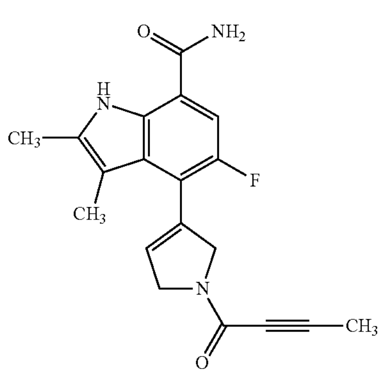 [SMILES: CC#CC(=O)N1CC=C(c2c(F)cc(C(N)=O)c3[nH]c(C)c(C)c23)C1] | 4-(1-(but-2-ynoyl)-2,5-dihydro-1H-pyrrol-3-yl)-5-fluoro-2,3-dimethyl-1H-indole-7-carboxamide | 2 | m/z 340 (M + H)+ |

TABLE 10-continued

| Ex. No. | Structure | Name | Starting Intermediate | Mass Spectrum |
|---|---|---|---|---|
| 239 | 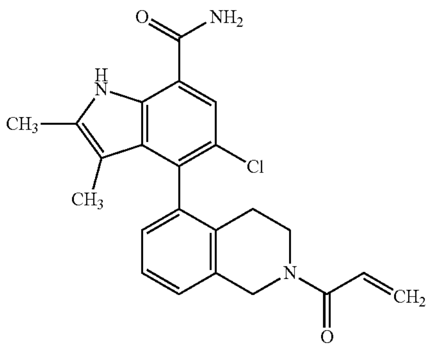 | 4-(2-acryloyl-1,2,3,4-tetrahydroisoquinolin-5-yl)-5-chloro-2,3-dimethyl-1H-indole-7-carboxamide, racemate | 3 | m/z 408, 410 (M + H)+ |
| 240 | 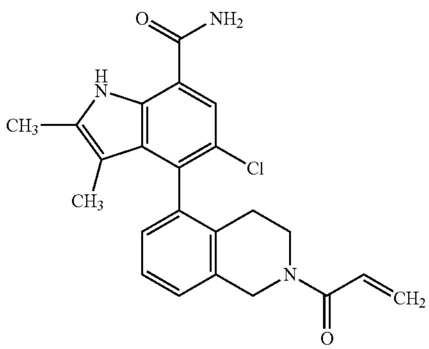 [SMILES: C=CC(=O)N1CCc2c(cccc2-c2c(Cl)cc(C(N)=O)c3[nH]c(C)c(C)c23)C1] | 4-(2-acryloyl-1,2,3,4-tetrahydroisoquinolin-5-yl)-5-chloro-2,3-dimethyl-1H-indole-7-carboxamide, atropisomer A | 3 | m/z 408, 410 (M + H)+ |
| 241 | 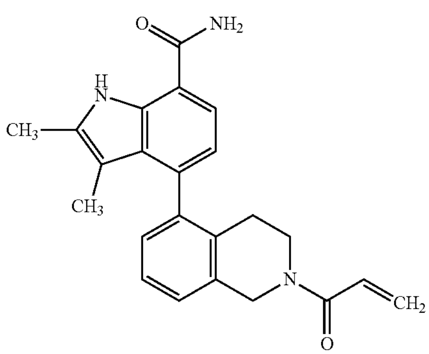 [SMILES: C=CC(=O)N1CCc2c(cccc2-c2ccc(C(N)=O)c3[nH]c(C)c(C)c23)C1] | 4-(2-acryloyl-1,2,3,4-tetrahydroisoquinolin-5-yl)-2,3-dimethyl-1H-indole-7-carboxamide | 1 | m/z 374 (M + H)+ |
| 242 | 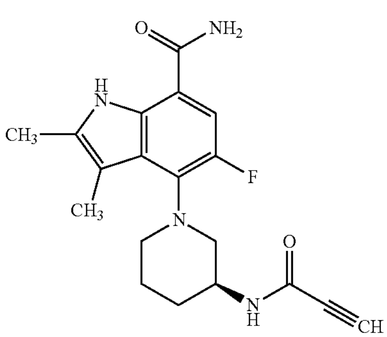 [SMILES: C#CC(=O)N[C@H]1CCCN(c2c(F)cc(C(N)=O)c3[nH]c(C)c(C)c23)C1] | (S)-5-fluoro-2,3-dimethyl-4-(3-propiolamidopiperidin-1-yl)-1H-indole-7-carboxamide | 16 | m/z 357 (M + H)+ |

TABLE 10-continued

| Ex. No. | Structure | Name | Starting Intermediate | Mass Spectrum |
|---|---|---|---|---|
| 243 | 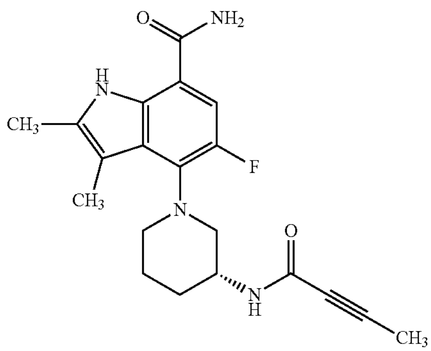 [SMILES: CC#CC(=O)N[C@@H]1CCCN(c2c(F)cc(C(N)=O)c3[nH]c(C)c(C)c23)C1] | (R)-4-(3-(but-2-ynamido)piperidin-1-yl)-5-fluoro-2,3-dimethyl-1H-indole-7-carboxamide | 12 | m/z 371 (M + H)+ |
| 244 | 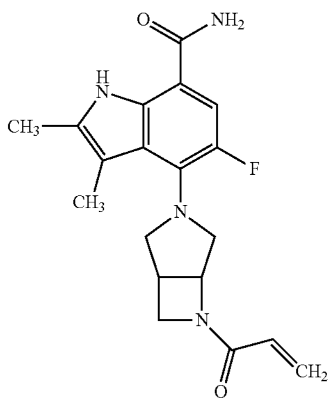 [SMILES: C=CC(=O)N1CC2CN(c3c(F)cc(C(N)=O)c4[nH]c(C)c(C)c34)CC21] | 4-(6-acryloyl-3,6-diazabicyclo[3.2.0]heptan-3-yl)-5-fluoro-2,3-dimethyl-1H-indole-7-carboxamide | 12 | m/z 357 (M + H)+ |
| 245 | 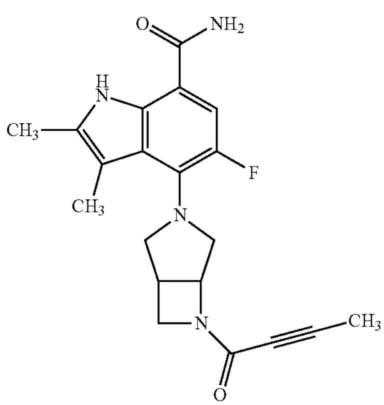 [SMILES: CC#CC(=O)N1CC2CN(c3c(F)cc(C(N)=O)c4[nH]c(C)c(C)c34)CC21] | 4-(6-(but-2-ynoyl)-3,6-diazabicyclo[3.2.0]heptan-3-yl)-5-fluoro-2,3-dimethyl-1H-indole-7-carboxamide | 12 | m/z 369 (M + H)+ |
| 246 | 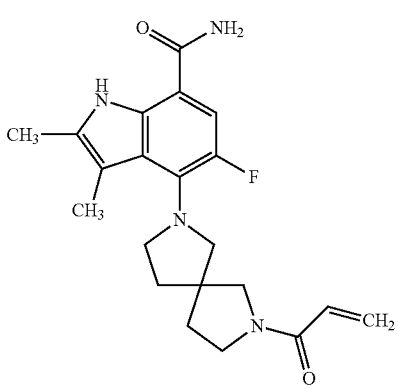 [SMILES: C=CC(=O)N1CCC2(CCN(c3c(F)cc(C(N)=O)c4[nH]c(C)c(C)c34)C2)C1] | 4-(7-acryloyl-2,7-diazaspiro[4.4]nonan-2-yl)-5-fluoro-2,3-dimethyl-1H-indole-7-carboxamide | 107 | m/z 385 (M + H)+ |

TABLE 10-continued

| Ex. No. | Structure | Name | Starting Intermediate | Mass Spectrum |
|---|---|---|---|---|
| 247 | 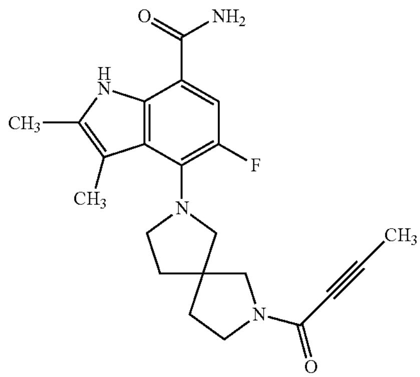 [SMILES: CC#CC(=O)N1CCC2(CCN(c3c(F)cc(C(N)=O)c4[nH]c(C)c(C)c34)C2)C1] | 4-(7-(but-2-ynoyl)-2,7-diazaspiro[4.4]nonan-2-yl)-5-fluoro-2,3-dimethyl-1H-indole-7-carboxamide | 107 | m/z 397 (M + H)+ |
| 248 | 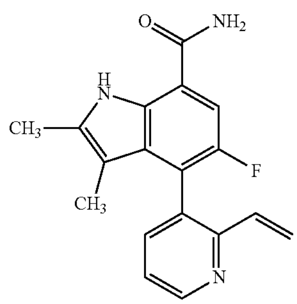 [SMILES: C=Cc1ncccc1-c1c(F)cc(C(N)=O)c2[nH]c(C)c(C)c12] | 5-fluoro-2,3-dimethyl-4-(2-vinylpyridin-3-yl)-1H-indole-7-carboxamide | 2 | m/z 310 (M + H)+ |
| 249 | 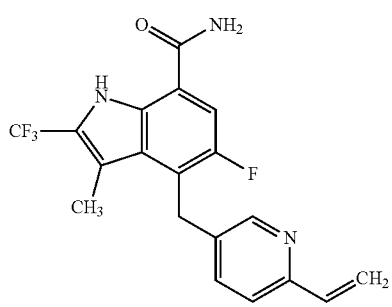 [SMILES: C=Cc1ccc(Cc2c(F)cc(C(N)=O)c3[nH]c(C(F)(F)F)c(C)c23)cn1] | 5-fluoro-3-methyl-2-(trifluoromethyl)-4-((6-vinylpyridin-3-yl)methyl)-1H-indole-7-carboxamide | 91 | m/z 378 (M + H)+ |
| 250 | 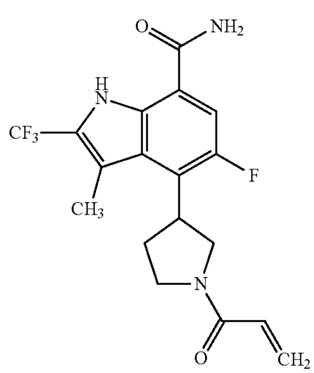 [SMILES: C=CC(=O)N1CCC(c2c(F)cc(C(N)=O)c3[nH]c(C(F)(F)F)c(C)c23)C1] | 4-(1-acryloylpyrrolidin-3-yl)-5-fluoro-3-methyl-2-(trifluoromethyl)-1H-indole-7-carboxamide | 91 | m/z 384 (M + H)+ |

TABLE 10-continued

| Ex. No. | Structure | Name | Starting Intermediate | Mass Spectrum |
|---|---|---|---|---|
| 251 | 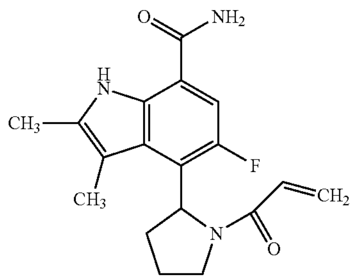 [SMILES: C=CC(=O)N1CCCC1c1c(F)cc(C(N)=O)c2[nH]c(C)c(C)c12] | 4-(1-acryloylpyrrolidin-2-yl)-5-fluoro-2,3-dimethyl-1H-indole-7-carboxamide | 2 | m/z 330 (M + H)+ |
| 252 | 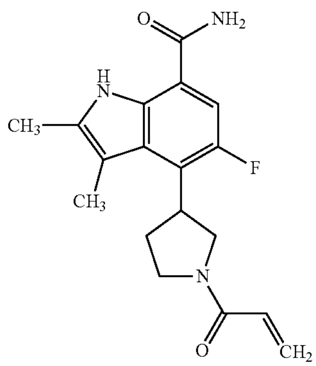 [SMILES: C=CC(=O)N1CCC(c2c(F)cc(C(N)=O)c3[nH]c(C)c(C)c23)C1] | 4-(1-acryloylpyrrolidin-3-yl)-5-fluoro-2,3-dimethyl-1H-indole-7-carboxamide | 2 | m/z 33042 (M + H)+ |
| 253 | 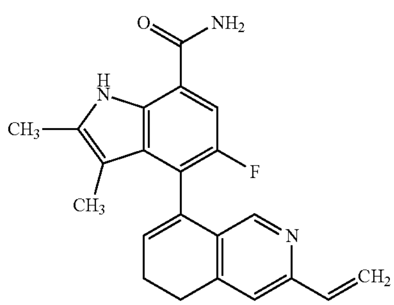 [SMILES: C=Cc1cc2c(cn1)C(c1c(F)cc(C(N)=O)c3[nH]c(C)c(C)c13)=CCC2] | 5-fluoro-2,3-dimethyl-4-(3-vinyl-5,6-dihydroisoquinolin-8-yl)-1H-indole-7-carboxamide | 2 | m/z 362 (M + H)+ |
| 254 | 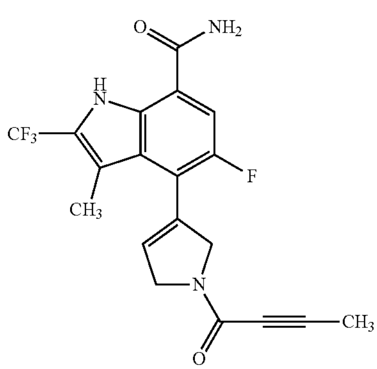 [SMILES: CC#CC(=O)N1CC=C(c2c(F)cc(C(N)=O)c3[nH]c(C(F)(F)F)c(C)c23)C1] | 4-(1-(but-2-ynoyl)-2,5-dihydro-1H-pyrrol-3-yl)-5-fluoro-3-methyl-2-(trifluoromethyl)-1H-indole-7-carboxamide | 109 | m/z 394 (M + H)+ |

TABLE 10-continued

| Ex. No. | Structure | Name | Starting Intermediate | Mass Spectrum |
|---|---|---|---|---|
| 255 | 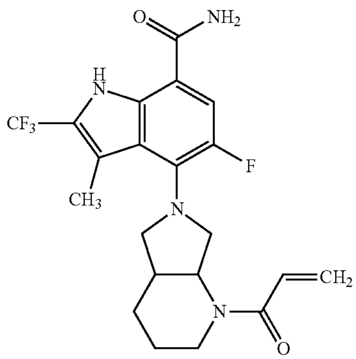 [SMILES: C=CC(=O)N1CCCC2CN(c3c(F)cc(C(N)=O)c4[nH]c(C(F)(F)F)c(C)c34)CC21] | 4-(1-acryloyloctahydro-6H-pyrrolo[3,4-b]pyridin-6-yl)-5-fluoro-3-methyl-2-(trifluoromethyl)-1H-indole-7-carboxamide | 109 | m/z 439 (M + H)+ |
| 256 | 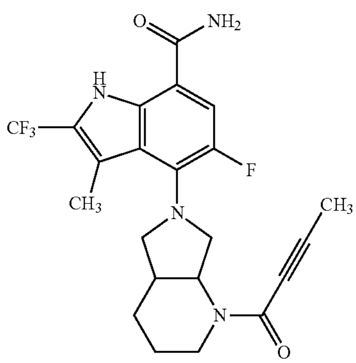 [SMILES: CC#CC(=O)N1CCCC2CN(c3c(F)cc(C(N)=O)c4[nH]c(C(F)(F)F)c(C)c34)CC21] | 4-(1-(but-2-ynoyl)octahydro-6H-pyrrolo[3,4-b]pyridin-6-yl)-5-fluoro-3-methyl-2-(trifluoromethyl)-1H-indole-7-carboxamide | 109 | m/z 451 (M + H)+ |

Additional Examples were prepared by procedures described above or similar procedures to those known in the art, using the appropriate starting materials, are shown in Table 11.

TABLE 11

| Ex. No. | Structure | Name | Mass Spectrum |
|---|---|---|---|
| 257 | 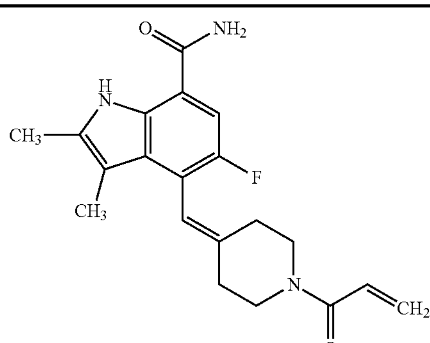 | 4-((1-acryloylpiperidin-4-ylidene)methyl)-5-fluoro-2,3-dimethyl-1H-indole-7-carboxamide | m/z 356 (M + H)+ |

TABLE 11-continued

| Ex. No. | Structure | Name | Mass Spectrum |
|---|---|---|---|
| 258 | 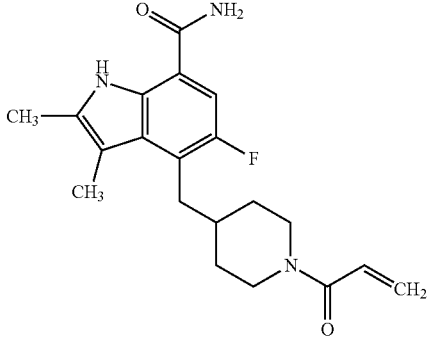 [SMILES: C=CC(=O)N1CCC(Cc2c(F)cc(C(N)=O)c3[nH]c(C)c(C)c23)CC1] | 4-((1-acryloylpiperidin-4-yl)methyl)-5-fluoro-2,3-dimethyl-1H-indole-7-carboxamide | m/z 358 (M + H)+ |
| 259 | 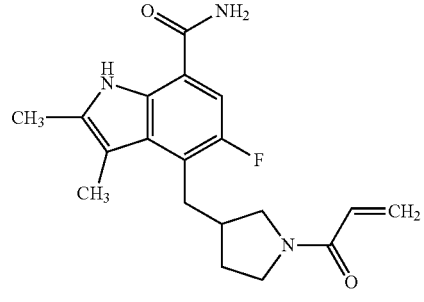 [SMILES: C=CC(=O)N1CCC(Cc2c(F)cc(C(N)=O)c3[nH]c(C)c(C)c23)C1] | 4-((1-acryloylpyrrolidin-3-yl)methyl)-5-fluoro-2,3-dimethyl-1H-indole-7-carboxamide | m/z 344 (M + H)+ |
| 260 | 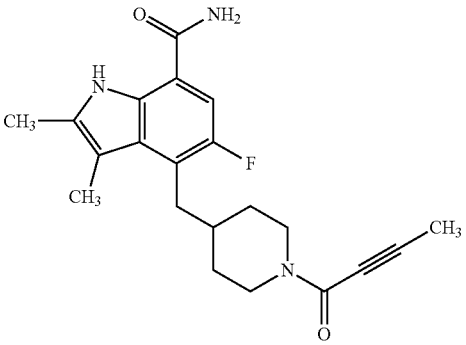 [SMILES: CC#CC(=O)N1CCC(Cc2c(F)cc(C(N)=O)c3[nH]c(C)c(C)c23)CC1] | 4-((1-(but-2-ynoyl)piperidin-4-yl)methyl)-5-fluoro-2,3-dimethyl-1H-indole-7-carboxamide | m/z 370 (M + H)+ |
| 261 | 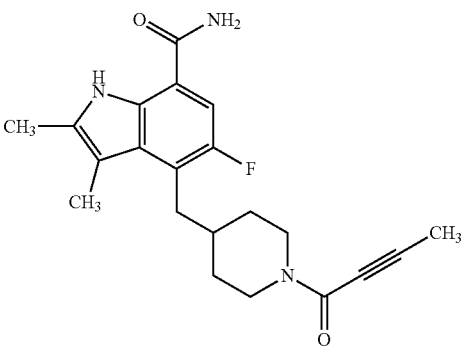 [SMILES: CC#CC(=O)N1CCC(Cc2c(F)cc(C(N)=O)c3[nH]c(C)c(C)c23)CC1] | 4-((1-(but-2-ynoyl)piperidin-4-ylidene)methyl)-5-fluoro-2,3-dimethyl-1H-indole-7-carboxamide | m/z 368 (M + H)+ |

TABLE 11-continued

| Ex. No. | Structure | Name | Mass Spectrum |
|---|---|---|---|
| 262 | 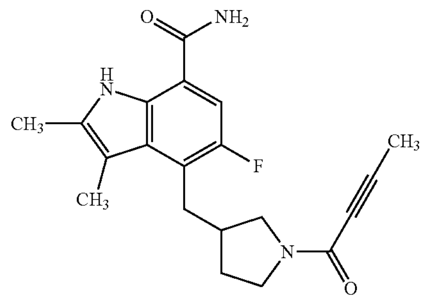 [SMILES: CC#CC(=O)N1CCC(Cc2c(F)cc(C(N)=O)c3[nH]c(C)c(C)c23)C1] | 4-((1-(but-2-ynoyl)pyrrolidin-3-yl)methyl)-5-fluoro-2,3-dimethyl-1H-indole-7-carboxamide | m/z 356 (M + H)+ |
| 263 | 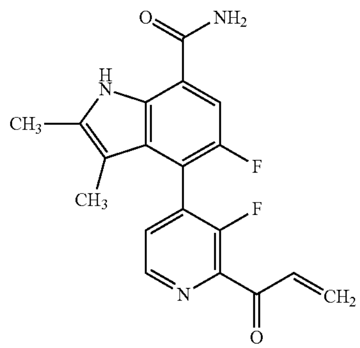 | 5-fluoro-4-(3-fluoro-2-vinylpyridin-4-yl)-2,3-dimethyl-1H-indole-7-carboxamide | m/z 328 (M + H)+ |
| 264 | 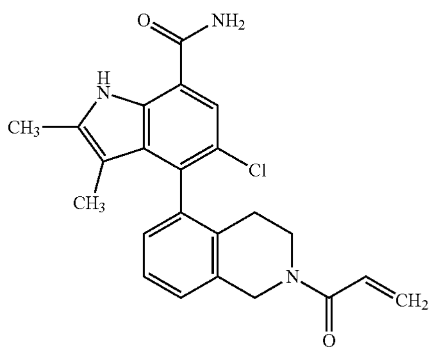 [SMILES: C=CC(=O)N1CCc2c(cccc2-c2c(Cl)cc(C(N)=O)c3[nH]c(C)c(C)c23)C1] | 4-(2-acryloyl-1,2,3,4-tetrahydroisoquinolin-5-yl)-5-chloro-2,3-dimethyl-1H-indole-7-carboxamide, atropisomer B | m/z 408 (M + H)+ |
| 265 | 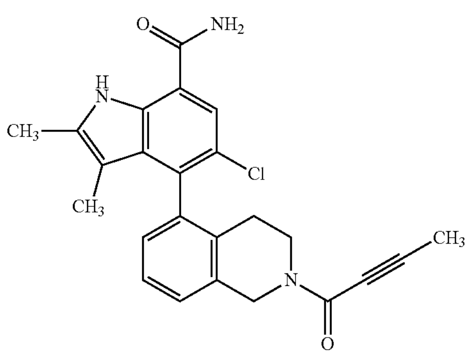 | 4-(2-(but-2-ynoyl)-1,2,3,4-tetrahydroisoquinolin-5-yl)-5-chloro-2,3-dimethyl-1H-indole-7-carboxamide | m/z 420 (M + H)+ |

Biological Assays

The pharmacological properties of the compounds of this invention may be confirmed by a number of biological assays. The exemplified biological assays, which follow, have been carried out with compounds of the invention.

Human Recombinant Btk Enzyme Assay

To V-bottom 384-well plates were added test compounds, human recombinant Btk (1 nM, Invitrogen Corporation), fluoresceinated peptide (1.5 µM), ATP (20 µM), and assay buffer (20 mM HEPES pH 7.4, 10 mM MgCl$_2$, 0.015% Brij 35 surfactant and 4 mM DTT in 1.6% DMSO), with a final volume of 30 µL. After incubating at room temperature for 60 min., the reaction was terminated by adding 45 µL of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to control reactions with no enzyme (for 100% inhibition) and controls with no inhibitor (for 0% inhibition). Dose response curves were generated to determine the concentration required for inhibiting 50% of Btk activity ($IC_{50}$). Compounds were dissolved at 10 mM in DMSO and evaluated at eleven concentrations.

Ramos FLIPR Assay

Ramos RA1 B cells (ATCC CRL-1596) at a density of $2 \times 10^6$ cells/mL in RPMI minus phenol red (Invitrogen 11835-030) and 50 mM HEPES (Invitrogen 15630-130) containing 0.1% BSA (Sigma A8577) were added to one half volume of calcium loading buffer (BD bulk kit for probenecid sensitive assays, #640177) and incubated at room temperature in the dark for 1 hr. Dye-loaded cells were pelleted (Beckmann GS-CKR, 1200 rpm, room temperature, 5 min) and resuspended at room temperature in RPMI minus phenol red with 50 mM HEPES and 10% FBS to a density of $1 \times 10^6$ cells/mL. 150 µL aliquots (150,000 cells/well) were plated into 96 well poly-D-lysine coated assay plates (BD 35 4640) and briefly centrifuged (Beckmann GS-CKR 800 rpm, 5 min., without brake). Next, 50 µL compound dilutions in 0.4% DMSO/RPMI minus phenol red+50 mM HEPES+10% FBS were added to the wells and the plate was incubated at room temperature in the dark for 1 hr. The assay plate was briefly centrifuged as above prior to measuring calcium levels. Using the FLIPR1 (Molecular Devices), cells were stimulated by adding goat anti-human IgM (Invitrogen AHI0601) to 2.5 µg/mL. Changes in intracellular calcium concentrations were measured for 180 seconds and percent inhibition was determined relative to peak calcium levels seen in the presence of stimulation only.

Table 12 below lists the Btk and the Ramos $IC_{50}$ values for the following Examples of this invention measured in the human recombinant Btk enzyme assay and the Ramos FLIPR assay. The compounds of the present invention, as exemplified by the following Examples, showed Btk $IC_{50}$ values of less than 700 nM.

TABLE 12

| Example | Btk $IC_{50}$ value (nM) | Ramos $IC_{50}$ value (nM) |
|---|---|---|
| 1 | 1.2 | 15 |
| 2 | 0.6 | 51 |
| 3 | 0.49 | 91 |
| 4 | 0.080 | 6.4 |
| 5 | 0.38 | 9.2 |
| 6 | 13 | 1300 |
| 7 | 0.31 | 34 |
| 8 | 15 | 9200 |
| 9 | 63 | 5300 |
| 10 | 120 | 6600 |
| 11 | 60 | 7600 |
| 12 | 510 | 11000 |
| 13 | 74 | 990 |
| 14 | 110 | 1300 |
| 15 | 52 | 850 |
| 16 | 0.98 | 38 |
| 17 | 36 | 1000 |
| 18 | 16 | 750 |
| 19 | 130 | 5600 |
| 20 | 0.59 | 61 |
| 21 | 66 | 1000 |
| 22 | 0.21 | 16 |
| 23 | 0.11 | 26 |
| 24 | 0.14 | 11 |
| 25 | 0.070 | 63 |
| 26 | 0.50 | 35 |
| 27 | 0.33 | 39 |
| 28 | 0.25 | 63 |
| 29 | 0.23 | 170 |
| 30 | 1.7 | 290 |
| 31 | 0.30 | 16 |
| 32 | 0.42 | 81 |
| 33 | 0.12 | 98 |
| 34 | 0.14 | 23 |
| 35 | 17 | 380 |
| 36 | 49 | 4100 |
| 37 | 87 | 4300 |
| 38 | 0.66 | 42 |
| 39 | 16 | 30 |
| 40 | 0.25 | 66 |
| 41 | 5.0 | 580 |
| 42 | 2.2 | 480 |
| 43 | 1.7 | 24 |
| 44 | 640 | >300 |
| 45 | 1.1 | 57 |
| 46 | 3.3 | 450 |
| 47 | 29 | 500 |
| 48 | 14 | 910 |
| 49 | 12 | 890 |
| 50 | 15 | 450 |
| 51 | 48 | 860 |
| 52 | 400 | — |
| 53 | 310 | — |
| 54 | 220 | — |
| 55 | 250 | — |
| 56 | 390 | — |
| 57 | 300 | — |
| 58 | 170 | — |
| 59 | 92 | >2000 |
| 60 | 81 | >2000 |
| 61 | 120 | >2000 |
| 62 | 130 | >2000 |
| 63 | 34 | (35% @2000) |
| 64 | 150 | >2000 |
| 65 | 160 | >2000 |
| 66 | 100 | (26% @2000) |
| 67 | 13 | 250 |
| 68 | 15 | 410 |
| 69 | 550 | — |
| 70 | 11 | >300 |
| 71 | 74 | 900 |
| 72 | 19 | 1500 |
| 73 | 92 | 1200 |
| 74 | 38 | >2000 |
| 75 | 260 | >2000 |
| 76 | 29 | (22% @2000) |
| 77 | 0.38 | 24 |
| 78 | 1.8 | 81 |
| 79 | 3.3 | 43 |
| 80 | 1.1 | 54 |
| 81 | 20 | 310 |
| 82 | 4.2 | 270 |
| 83 | 3.3 | 100 |
| 84 | 53 | 320 |
| 85 | 9.9 | 360 |
| 86 | 4.6 | 13 |
| 87 | 8.4 | >300 |
| 88 | 3.3 | 5.2 |
| 89 | 1.0 | 29 |
| 90 | 12 | 130 |
| 91 | 59 | >300 |
| 92 | 1.7 | 22 |
| 93 | 3.5 | 20 |
| 94 | 1.2 | 46 |
| 95 | 0.13 | 23 |
| 96 | 1.0 | 20 |
| 97 | 0.12 | 77 |
| 98 | 1.6 | 220 |
| 99 | 0.19 | 22 |
| 100 | 1.0 | 120 |
| 101 | 13 | >300 |
| 102 | 0.17 | 14 |
| 103 | 2.4 | 9.4 |
| 104 | 33 | (32% @300) |
| 105 | 0.64 | 26 |
| 106 | 29 | >300 |

TABLE 12-continued

| Example | Btk IC$_{50}$ value (nM) | Ramos IC$_{50}$ value (nM) |
|---|---|---|
| 107 | 260 | >300 |
| 108 | 3.1 | 160 |
| 109 | 0.95 | 63 |
| 110 | 0.39 | 3.9 |
| 111 | 8.8 | (48% @300) |
| 112 | 1.1 | 24 |
| 113 | 1.1 | 17 |
| 114 | 0.85 | 16 |
| 115 | 0.14 | 5.4 |
| 116 | 0.52 | 40 |
| 117 | 1.4 | 26 |
| 118 | 5.6 | 70 |
| 119 | 6.5 | 7.2 |
| 120 | 4.5 | 36 |
| 121 | 60 | (33% @300) |
| 122 | 84 | >300 |
| 123 | 0.09 | 8.0 |
| 124 | 92 | (30% @300) |
| 125 | 0.14 | 9.8 |
| 126 | 0.06 | 2.8 |
| 127 | 0.17 | 24 |
| 128 | 0.06 | 10 |
| 129 | 14 | (32% @300) |
| 130 | 0.21 | 25 |
| 131 | 0.47 | 73 |
| 132 | 0.15 | 28 |
| 133 | 71 | >300 |
| 134 | 150 | >300 |
| 135 | 0.30 | 27 |
| 136 | 0.050 | 5.8 |
| 137 | 46 | >300 |
| 138 | 0.93 | 65 |
| 139 | 1.2 | 30 |
| 140 | 3.5 | 170 |
| 141 | 0.72 | 18 |
| 142 | 2.7 | — |
| 143 | 1.2 | 28 |
| 144 | 1.0 | 22 |
| 145 | 0.29 | 8.2 |
| 146 | 0.20 | 5.0 |
| 147 | 3.0 | 46 |
| 148 | 22 | (24% @300) |
| 149 | 60 | (35% @300) |
| 150 | 11 | 63 |
| 151 | 560 | >300 |
| 152 | 76 | (21% @300) |
| 153 | 5.0 | 230 |
| 154 | 0.10 | 4.7 |
| 155 | 0.15 | 0.20 |
| 156 | 3.1 | 3.1 |
| 157 | 620 | — |
| 158 | 49 | — |
| 159 | 0.09 | 3.7 |
| 160 | 0.10 | 13 |
| 161 | 3.3 | — |
| 162 | 280 | >300 |
| 163 | 720 | >300 |
| 164 | 2.6 | 25% @300 |
| 165 | 0.17 | 90 |
| 166 | 8.8 | >300 |
| 167 | 0.37 | 58 |
| 168 | 0.04 | 3.3 |
| 169 | 61 | >300 |
| 170 | 0.080 | 6.1 |
| 171 | 2.2 | 150 |
| 172 | 0.74 | 17 |
| 173 | 0.66 | 130 |
| 174 | 0.09 | 74 |
| 175 | 110 | >300 |
| 176 | 15 | >300 |
| 177 | 2.8 | >300 |
| 178 | 1.9 | 290 |
| 179 | 92 | >300 |
| 180 | 20 | 13% @300 |
| 181 | 0.40 | 51 |
| 182 | 2.9 | >300 |
| 183 | 0.29 | 26 |

TABLE 12-continued

| Example | Btk IC$_{50}$ value (nM) | Ramos IC$_{50}$ value (nM) |
|---|---|---|
| 184 | 3.5 | 110 |
| 185 | 0.13 | 12 |
| 186 | 0.80 | 20 |
| 187 | 40 | >300 |
| 188 | 0.60 | 5.1 |
| 189 | 0.16 | 21 |
| 190 | 38 | >300 |
| 191 | 0.13 | 12 |
| 192 | 2.8 | (23% @300) |
| 193 | 0.14 | 17 |
| 194 | 0.23 | 35 |
| 195 | 0.12 | 15 |
| 196 | 2.7 | — |
| 197 | 0.54 | 36 |
| 198 | 150 | — |
| 199 | 0.24 | — |
| 200 | 0.27 | 34 |
| 201 | 260 | (22% @300) |
| 202 | 120 | >300 |
| 203 | 31 | — |
| 204 | 0.33 | — |
| 205 | 16 | >300 |
| 206 | 0.040 | 57 |
| 207 | 0.094 | — |
| 208 | 0.32 | 6.5 |
| 209 | 0.24 | 73 |
| 210 | 6.4 | >300 |
| 211 | 0.20 | 41 |
| 212 | 0.50 | 40 |
| 213 | 0.29 | 51 |
| 214 | 29 | >300 |
| 215 | 0.76 | 55 |
| 216 | 0.20 | 1.9 |
| 217 | 0.19 | 11 |
| 218 | 5.8 | (40% @300) |
| 219 | 0.052 | 4.8 |
| 220 | 39 | (28% @300) |
| 221 | 11 | >300 |
| 222 | 2.6 | >300 |
| 223 | 0.11 | 11 |
| 224 | 0.2 | ND |
| 225 | 0.6 | 53 |
| 226 | 0.4 | 84 |
| 227 | 0.3 | 34 |
| 228 | 1181.4 | ND |
| 229 | 0.9 | ND |
| 230 | 51.4 | ND |
| 231 | 3.4 | 78 |
| 232 | 0.1 | 1 |
| 233 | 0.1 | 4 |
| 234 | 0.2 | 18 |
| 235 | 0.3 | 14 |
| 236 | 0.3 | 45% at 0.3 μM |
| 237 | 0.9 | 81 |
| 238 | 3.5 | 0 |
| 239 | 0.5 | 44 |
| 240 | 0.2 | 6 |
| 241 | 0.6 | ND |
| 242 | 0.1 | ND |
| 243 | 0.2 | 4 |
| 244 | 0.3 | ND |
| 245 | 0.7 | 37 |
| 246 | 0.4 | ND |
| 247 | 0.3 | ND |
| 248 | 3.6 | ND |
| 249 | 5.2 | ND |
| 250 | 8.5 | ND |
| 251 | 2.0 | ND |
| 252 | 2.7 | ND |
| 253 | 2.7 | 277 |
| 254 | 35.6 | ND |
| 255 | pending | ND |
| 256 | pending | ND |
| 257 | 0.4 | ND |
| 258 | 5.6 | ND |
| 259 | 2.3 | 40% Ramos at 0.3 μM |
| 260 | 233.0 | ND |

TABLE 12-continued

| Example | Btk IC$_{50}$ value (nM) | Ramos IC$_{50}$ value (nM) |
|---|---|---|
| 261 | 46.9 | ND |
| 262 | 14.2 | ND |
| 263 | 146.0 | ND |
| 264 | 43.2 | ND |

The compounds of the present invention possess activity as inhibitors of Btk, and therefore, may be used in the treatment of diseases associated with Btk activity.

Collagen-Induced Arthritis in Mice:

DBA/1 male mice (8-10 wk of age; Harlan) were immunized subcutaneously at the base of the tail on Day 0 and again on Day 21 with 200 μg bovine type II collagen mixed with reconstituted Sigma Adjuvant System (SAS; Sigma-Aldrich). Daily oral (PO) dosing was immediately initiated with Example 223 or methotrexate (1 mg/kg) in PEG400: water (80:20) and continued to the end of the study (38 days).

Following the booster immunization, mice were monitored three times per week for the development and severity of paw inflammation. Each paw was visually scored by the following scheme: +0=normal; +1=one (or more) joints inflamed on digits; +2=mild-moderate inflammation of plantar surface of paw and paw thickness modestly increased; +3=moderate-severe inflammation of plantar surface of paw and paw thickness significantly increased; +4=ankylosis of ankle joint (significantly reduced joint motion on flexion/extension). Clinical paw scores for all four paws were summed for each mouse, and the mean was calculated for each treatment group.

Results:

Treatment with Example 223 provided dose-responsive inhibition of clinically evident disease, with 21%, 83%, and 93% inhibition of mean clinical scores at the end of the study at doses of 0.1, 0.5, and 2.5 mg/kg orally QD, respectively. In contrast, treatment with methotrexate at 1 mg/kg, the standard of care in rheumatoid arthritis, showed only 58% inhibition of clinical scores.

NZB/W Lupus-Prone Mice:

Female NZB/WF1 mice, age 24 weeks were dosed by oral gavage, once daily, for 16 weeks and included the following treatment groups: Example 223 at 0.2, 0.5 and 1.5 mg/kg in vehicle (80:20 PEG400:water), vehicle alone, or prednisolone at 10 mg/kg. Proteinuria was measured using a colorimetric assay for albumin (Siemens Albustix Reagent Strips for Urinalysis).

At the end of the study, kidneys were collected in 10% Neutral Buffered Formalin for histological evaluation. Fixed kidney tissues were routinely processed and paraffin embedded. Kidney sections were stained with periodic acid Schiff and hematoxylin (PASH) and hematoxylin and eosin (H&E) for the evaluation of nephritis severity. Blinded to treatment group, severity of nephritis was evaluated using the following criteria. For glomerular damage: 1-Mesangial matrix thickening and/or mesangial cell proliferation; 2—Crescent formation—Cellular deposits/casts in Bowman's space; 3-Cellular infiltration—composed of mononuclear cells in glomerular tufts; 4—Fibrosis of Bowman's capsule. For tubular damage: 1—Infiltration of mononuclear cells; 2—Severity of tubular epithelial cell damage; 3-Protein casts. For tubulo-interstitial damage: 1-Fibrosis; 2—Infiltration of mononuclear cells. Each subcategory was assigned a score from 0 to 4. The total score for each mouse was the sum of the above 9 subcategories.

Results:

Treatment with Example 223 showed dose dependent inhibition of severe proteinuria, a measure of the underlying nephritis, at the end of the study, with 42%, 17%, and 8% of the mice showing severe proteinuria (>300 mg/dL) at doses of 0.2, 0.5 and 1.5 mg/kg, respectively. In comparison, 75% of the vehicle control animals showed severe proteinuria. Histological evaluation of the kidneys from vehicle control mice showed advanced nephritis, with mesangial hypertrophy of the glomeruli, prominent cellular casts/crescents and capsular fibrosis. Tubular epithelial cells were frequently damaged and protein casts were numerous. In addition, there was a prominent mononuclear cell infiltrate present in the interstitium of many of the kidneys examined. The results of the present study show that the Total Nephritis Histology Severigy Scores for the three groups of mice treated with 0.2, 0.5 and 1.5 mg/kg of Example 223 were 6.4, 7.5, and 5.0, respectively. In comparison, the groups of mice treated with either prednisolone or vehicle only had Total Nephritis Histology Severigy Scores of 7.8 and 21.0, respectively. In summary, the results of the present study indicates that treatment with Example 223 at all doses provided protection against tubulo-interstitial and glomerular nephritis as well as inflammatory infiltration.

TABLE 13

Effect of Example 223 on Nephritis in NZB/W Lupus-Prone Mice

| Treatment | Glomerular Nephritis Severity Score (Group Mean) | Tubulo-Interstitial Nephritis Severity Score (Group Mean) | Total Nephritis Histology Severity Score (Group Mean) |
|---|---|---|---|
| None (Vehicle) | 9.0 | 12.0 | 21.0 |
| 0.2 mg/kg Example 223 | 2.4 | 4.0 | 6.4 |
| 0.5 mg/kg Example 223 | 3.7 | 3.8 | 7.5 |
| 1.5 mg/kg Example 223 | 2.2 | 2.8 | 5.0 |
| 10 mg/kg Prednisolone | 4.5 | 3.3 | 7.8 |

The invention claimed is:

1. A compound of Formula (I):

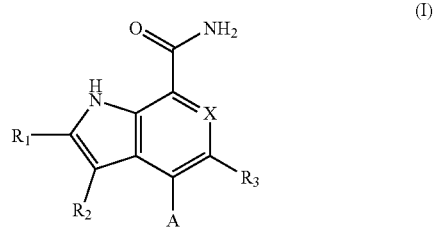

wherein:
X is CR$_4$;
A is

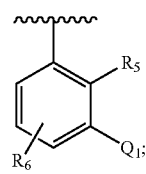

Q$_1$ is —NR$_7$Q$_2$, —CR$_{10}$R$_{10}$NR$_7$Q$_2$, —C(O)NR$_7$(C$_{1-4}$ alkyl substituted with zero or 1 R$_{11}$), —CH=CH$_2$, —CH=C(CN)S(O)$_2$CH$_3$, —S(O)$_2$CH=CR$_{10}$R$_{10}$, —NR$_7$(dichlorotriazinyl), —NR$_7$(quinazolin-4-yl substituted with zero or 1 R$_{11}$), 3-methylenepyrrolidin-2-on-1-yl, or a cyclic group selected from 1H-pyrrol-2(5H)-on-1-yl, isoindolin-1-on-2-yl, quinazolin-4(3H)-on-3-yl, and quinazoline-2,4(1H, 3H)-dion-3-yl, each cyclic group substituted with zero to two substituents independently selected from F, Cl, —CH$_3$, —CN, and —OCH$_3$;

Q$_2$ is —CN, —C(O)(C$_{1-4}$ alkyl substituted with zero or 1 R$_{11}$), —C(O)(C$_{3-6}$ cycloalkyl substituted with zero or 1 R$_{11}$), —C(O)(C$_{5-6}$ cycloalkenyl), —C(O)CR$_{10}$=CR$_{10}$R$_{10}$, —C(O)C(R$_{10}$)=CHCH$_2$N(CH$_3$)$_2$, —C(O)C≡CR$_7$, —C(O)C≡C(C$_{1-3}$ hydroxyalkyl), —C(O)C≡C(phenyl), —C(O)C≡CSi(CH$_3$)$_3$, or —S(O)$_2$CH=CHR$_{10}$;

R$_1$ is H, —CH$_3$, —CF$_3$, or phenyl substituted with zero or 1 R$_{12}$;

R$_2$ is H, —CH$_3$, cyclopropyl, or phenyl substituted with zero or 1 R$_{12}$, provided that zero or one of R$_1$ and R$_2$ is phenyl substituted with zero or 1 R$_{11}$;

R$_3$ is F, Cl, or I;
R$_4$ is H, F, —OH, or —OCH$_3$;
R$_5$ is H, F, Cl, or —CH$_3$;
R$_6$ is H, F, Cl, —CF$_3$, or C$_{1-3}$ alkoxy;
R$_7$ is H, C$_{1-4}$ alkyl, or cyclopropyl;
R$_{10}$, at each occurrence, is independently H or —CH$_3$;
R$_{11}$ is F, Cl, —CN, —CF$_3$, or C$_{1-3}$ alkoxy; and
R$_{12}$ is F, Cl, —CN, —CF$_3$, or C$_{1-3}$ alkoxy.

2. The compound according to claim 1 wherein:
R$_1$ is H or —CH$_3$;
R$_2$ is H, —CH$_3$, or cyclopropyl;
R$_3$ is F or Cl;
R$_4$ is H or F; and
R$_6$ is H, F, or Cl.

3. The compound according to claim 2 wherein R$_3$ is F.

4. The compound according to claim 2 wherein:
R$_3$ is Cl.

5. The compound according to claim 2 wherein:
R$_5$ is H; and
R$_6$ is H.

6. The compound according to claim 2 wherein:
Q$_1$ is —N(CH$_3$)C(O)CH=CH$_2$, —N(CH$_3$)S(O)$_2$CH=CH$_2$, or

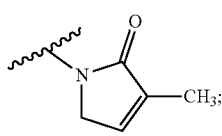 [SMILES: *N1CC=C(C)C1=O]

R$_1$ is —CH$_3$;
R$_2$ is —CH$_3$;
R$_3$ is F or Cl;
R$_4$ is H;
R$_5$ is H; and
R$_6$ is H.

7. The compound according to claim 1 having the structure:

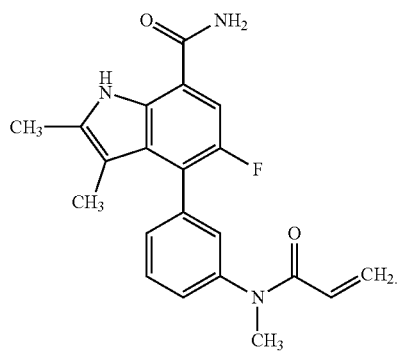 [SMILES: C=CC(=O)N(C)c1cccc(-c2c(F)cc(C(N)=O)c3[nH]c(C)c(C)c23)c1]

8. The compound according to claim 1 having the structure:

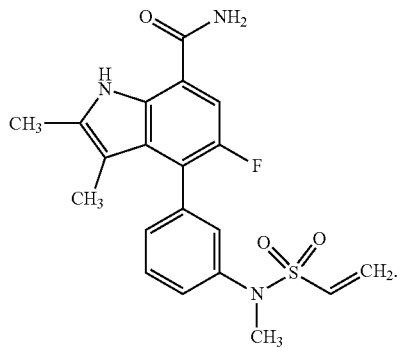 [SMILES: C=CS(=O)(=O)N(C)c1cccc(-c2c(F)cc(C(N)=O)c3[nH]c(C)c(C)c23)c1]

9. The compound according to claim 1 having the structure:

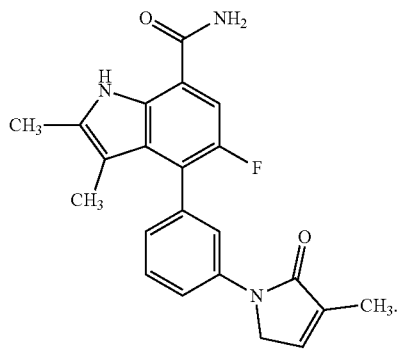 [SMILES: CC1=CCN(c2cccc(-c3c(F)cc(C(N)=O)c4[nH]c(C)c(C)c34)c2)C1=O]

10. A pharmaceutical composition comprising a compound according to claim 1 or a pharmaceutically-acceptable salt thereof; and a pharmaceutically acceptable carrier.

11. A method for treating a disease comprising the administration to a subject in need thereof a therapeutically-effective amount of at least one compound according to claim or a pharmaceutically-acceptable salt thereof, wherein said disease is systemic lupus erythematosus (SLE).

12. A method for treating a disease comprising the administration to a subject in need thereof a therapeutically-effective amount of at least one compound according to claim 1 or a pharmaceutically-acceptable salt thereof, wherein said disease is rheumatoid arthritis.

13. A method for treating a disease comprising the administration to a subject in need thereof a therapeutically-effective amount of at least one compound according to claim 1 or a pharmaceutically-acceptable salt thereof, wherein said disease is multiple sclerosis (MS).

14. A method for treating a disease comprising the administration to a subject in need thereof a therapeutically-effective amount of at least one compound according to claim 1 or a pharmaceutically-acceptable salt thereof, wherein said disease is Sjögren's syndrome.

* * * * *

UNITED STATES PATENT AND TRADEMARK OFFICE
CERTIFICATE OF CORRECTION

PATENT NO. : 10,604,504 B2  
APPLICATION NO. : 16/396879  
DATED : March 31, 2020  
INVENTOR(S) : Liu et al.

Page 1 of 1

It is certified that error appears in the above-identified patent and that said Letters Patent is hereby corrected as shown below:

In the Specification

Column 1, Line 8, delete "Mary" and insert -- May --.

In the Claims

Claim 11, Column 320, Line 63, after "claim" insert -- 1 --.

Signed and Sealed this  
First Day of December, 2020

Andrei Iancu  
*Director of the United States Patent and Trademark Office*